(12) United States Patent
Bouvier et al.

(10) Patent No.: US 9,018,395 B2
(45) Date of Patent: Apr. 28, 2015

(54) PYRAZOLOPYRIDINE AND PYRAZOLOPYRIMIDINE DERIVATIVES AS MELANOCORTIN-4 RECEPTOR MODULATORS

(75) Inventors: Michel Bouvier, Montreal (CA); Anne Marinier, Kirkland, CA (US); Réjean Ruel, Saint-Lambert, CA (US); Patricia René, Montreal (CA); Yves Chantigny, Pincourt, CA (US); Philippe Dagneau, St-Laurent, CA (US); Stéphane Gingras, Montreal (CA)

(73) Assignee: Université de Montréal, Montreal (CA)

( * ) Notice: Subject to any disclaimer, the term of this patent is extended or adjusted under 35 U.S.C. 154(b) by 0 days.

(21) Appl. No.: 13/981,834

(22) PCT Filed: Jan. 26, 2012

(86) PCT No.: PCT/CA2012/000089
§ 371 (c)(1),
(2), (4) Date: Nov. 15, 2013

(87) PCT Pub. No.: WO2012/100342
PCT Pub. Date: Aug. 2, 2012

(65) Prior Publication Data
US 2014/0057894 A1    Feb. 27, 2014

Related U.S. Application Data

(60) Provisional application No. 61/436,727, filed on Jan. 27, 2011.

(51) Int. Cl.
| | | |
|---|---|---|
| C07D 231/56 | (2006.01) | |
| C07D 487/00 | (2006.01) | |
| C07D 471/04 | (2006.01) | |
| C07D 487/04 | (2006.01) | |
| G01N 33/74 | (2006.01) | |
| G01N 33/50 | (2006.01) | |

(52) U.S. Cl.
CPC ............ C07D 471/04 (2013.01); C07D 487/04 (2013.01); G01N 33/74 (2013.01); G01N 2333/72 (2013.01); G01N 2500/04 (2013.01); G01N 2500/10 (2013.01); G01N 33/5008 (2013.01)

(58) Field of Classification Search
USPC ..................................................... 548/360.1
See application file for complete search history.

(56) References Cited

U.S. PATENT DOCUMENTS

| 5,731,408 | A | 3/1998 | Hadley et al. |
|---|---|---|---|
| 6,054,556 | A | 4/2000 | Huby et al. |
| 6,060,589 | A | 5/2000 | Stark et al. |
| 6,613,874 | B1 | 9/2003 | Mazur et al. |
| 6,638,927 | B2 | 10/2003 | Renhowe et al. |
| 6,699,873 | B1 | 3/2004 | Maguire et al. |
| 6,979,691 | B2 | 12/2005 | Yu et al. |
| 7,622,479 | B2 | 11/2009 | Oda et al. |
| 2003/0158209 | A1 | 8/2003 | Dyck et al. |
| 2003/0162819 | A1 | 8/2003 | Eisinger et al. |
| 2003/0176425 | A1 | 9/2003 | Eisinger et al. |
| 2003/0186992 | A1 | 10/2003 | Nakazato et al. |
| 2004/0082590 | A1 | 4/2004 | Briner et al. |
| 2004/0147567 | A1 | 7/2004 | Nakazato et al. |
| 2008/0085898 | A1 | 4/2008 | Lu et al. |

FOREIGN PATENT DOCUMENTS

| CA | 2604161 | 10/2006 |
|---|---|---|
| CA | 2610860 | 12/2006 |
| CA | 2669686 | 5/2009 |
| CA | 2732950 | 2/2010 |
| JP | 2011136925 A2 | 7/2011 |
| WO | 9955679 | 11/1999 |
| WO | 9964002 | 12/1999 |

(Continued)

OTHER PUBLICATIONS

Richardson et al., "Synthesis and Structure-Activity Relationships of Novel Arylpipererazines as Potent and Selective Agonists of the Melanocortin Subtype-4 Receptor," Journal of Medicinal Chemistry (2204) 47:744-755.
International Search Report of International Application No. PCT/CA2012/000089, filed Jan. 26, 2012.
Anthes et al., "An Improved Synthesis of a Selective Serotonin Reuptake Inhibitor," Organic Process Research & Development (2008) 12:178-182.
Bednarek et al., "Ligands of the melanocortin receptors, 2002-2003 update," Expert Opin. Ther. Patents (2004) 14(3):327-336.
Biebermann et al., "Autosomal-Dominant Mode of Inheritance of a Melanocortin-4 Receptor Mutation in a Patient wit Severe Early-Onset Obesity Is Due to a Dominant-Negative Effect Caused by Receptor Dimerization," Diabetes (2003) 52:2984-2988.

(Continued)

*Primary Examiner* — Jeffrey H Murray
*Assistant Examiner* — Oluwafemi Masha
(74) *Attorney, Agent, or Firm* — Volpe and Koenig, P.C.

(57) ABSTRACT

Disclosed herein is a compound of Formula I: wherein X, $R^1$, $R^2$, and $R^3$ are as defend herein, or a pharmaceutically acceptable salt thereof to allow the drug to penetrate the cell membrane; or a prodrug, or the compound is labeled with a detectable label or an affinity tag thereof. Also disclosed is a pharmaceutical composition, a method of treating a disorder mediated by melanocortin-4 receptors, and a method of treating obesity using the compounds described.

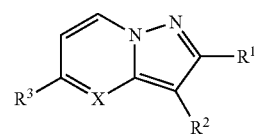

I

12 Claims, No Drawings

(56) References Cited

FOREIGN PATENT DOCUMENTS

| WO | 0218382 | 3/2002 |
|---|---|---|
| WO | 02062766 | 8/2002 |
| WO | 02067869 | 9/2002 |
| WO | 02068387 | 9/2002 |
| WO | 02070511 | 9/2002 |
| WO | 02079146 | 10/2002 |
| WO | 03007949 | 1/2003 |
| WO | 03009847 | 2/2003 |
| WO | 03009850 | 2/2003 |
| WO | 03031410 | 4/2003 |
| WO | 03061660 | 7/2003 |
| WO | 03066587 | 8/2003 |
| WO | 03066597 | 8/2003 |
| WO | 03068738 | 8/2003 |
| WO | 03072056 | 9/2003 |
| WO | 03092690 | 11/2003 |
| WO | 03093234 | 11/2003 |
| WO | 03094918 | 11/2003 |
| WO | 2004075823 | 9/2004 |
| WO | 2004085409 A2 | 10/2004 |
| WO | 2004089951 | 10/2004 |
| WO | 2005056533 | 6/2005 |
| WO | 2006010811 | 2/2006 |
| WO | 2009080291 | 7/2009 |
| WO | 2009115321 | 9/2009 |
| WO | 2010034500 | 4/2010 |
| WO | 2010037081 | 4/2010 |
| WO | 2010056022 | 5/2010 |
| WO | 2010065799 | 6/2010 |
| WO | 2010065800 | 6/2010 |
| WO | 2010065801 | 6/2010 |
| WO | 2010065802 | 6/2010 |
| WO | 2010081666 | 7/2010 |
| WO | 2010144344 | 12/2010 |
| WO | 2011051452 A1 | 5/2011 |
| WO | 2011054285 | 5/2011 |

OTHER PUBLICATIONS

Blondet et al., "Characterization of Cell Lines Stably Expressing Human Normal or Mutated EGFP-Tagged MC4R," J Biochem (2004) 135(4):541-546.

Branson et al., "Binge Eating as a Major Phenotype of Melanocortin 4 Receptor Gene Mutations," N. Engl. J. Med. (2003) 348(12):1096-1103.

Bull et al., "Convenient One-Pot Synthesis of (E)-β-Aryl Vinyl Halides from Benzyl Bromides and Dihalomethanes," Organic Letters (2008) 10(23):5485-5488.

Chen et al., "Pharmacological and pharmacokinetic characterization of 2-piperazine-α-isopropyl benzylamine derivatives as melanocortin-4 receptor antagonists," Bioorganic & Medicinal Chemistry (2008) 16:5606-5618.

Cheung et al., "Preparation of human Melanocortin-4 receptor agonist libraries: Linear peptides X-Y-DPhe7-Arg8-Trp (or 2-Nal)9-Z-NH2," Bioorganic & Medicinal Chemistry Letters (2005) 15:5504-5508.

Cole et al., "2-Benzimidazolyl-9-(chroman-4-yl)-purinone derivatives as JAK3 inhibitors," Bioorganic & Medicinal Chemistry Letters (2009) 19:6788-6792.

Conde-Frieboes et al., "Serendipitous discovery of a new class of agonists for the melanocortin 1 and 4 receptors and a new class of cyclophanes," Bioorganic & Medicinal Chemistry Letters (2011) 21:1459-1463.

Crowley et al., "Obesity Therapy: Altering the Energy Intake-and-Expenditure Balance Sheet," Nature Reviews/Drug Discovery (2002) 1:276-286.

DeBoer et al., "Update on melanocortin interventions for cachexia: Progress toward clinical application," Nutrition (2010) 16:146-151.

Drazen et al., "Peripheral signals in the control of satiety and hunger," Current Opinion in Clinical Nutrition and Metabolic Care (2003) 6:621-629.

Emmerson et al., "Melanocortin-4 Receptor Agonists for the Treatment of Obesity," Current Topics in Medicinal Chemistry (2007) 7:1121-1130.

Farooqi et al., "Clinical Spectrum of Obesity and Mutations in the Melanocortin 4 Receptor Gene," N Engl J Med (2003) 348(12):1085-1095.

Farooqi et al., "New Advances in the genetics of early onset obesity," International Journal of Obesity (2005) 29:1149-1152.

Farooqi et al., "Monogenic Obesity in Humans," Annu. Rev. Med. (2005) 56:443-458.

Govaerts et al., "Obesity-associated mutations in the melanocortin 4 receptor provide novel insights into its function," Peptides (2005) 26:1909-1919.

Graham et al., "Overexpression of Agrt leads to obesity in transgenic mice," Nature Genetics (1997) 17:273-274.

Greszler et al., "Synthesis of Pyrazolo[1,5-a]Pyridines via Azirines: Preparation of 2-(3-Bromophenyl)-6-(Trifluoromethyl)Pyrazolo[1,5-a]Pyridine," Org. Synth (2009) 86:18-27.

Grieco et al., "Structure-Activity Studies of the Melanocortin Peptides: Discovery of Potent and Selective Affinity Antagonists for the hMC4 Receptors," J. Med. Chem. (2002) 45:5287-5294.

Grieco et al., "Sturcture-activity studies of new melanocortin peptides containing an aromatic amino acid at the N-terminal position," Peptides (2006) 27:472-481.

Gu et al., "Identification and Functional Analysis of Novel Human Melanocortin-4 Receptor Variants," Diabetes (1999) 48:635-639.

Guo et al., "Synthesis and SAR of potent and orally bioavailable tert-butylpyrrolidine archetype derived melanocortin subtype-4 receptor modulators," Bioorganic & Medicinal Chemistry Letters (2008) 18:3242-3247.

He et al., "Discovery of highly potent and efficacious MC4R agonists with spiroindane N-Me-1,2,4-triazole privileges structures for the treatment of obesity," Bioorganic & Medicinal Chemistry Letters (2010) 20:6524-6532.

Hong et al., "Discovery of a piperazine urea based compound as a potent, selective, orally bioavailable melanocortin subtype-4 receptor partial agonist," Bioorganic & Medicinal Chemistry Letters (2011) 21:2330-2334.

Hsiung et al., "A Novel and Selective 11-Melanocyte-Stimulating Hormone-Derived Peptide Agonist for Melanocortin 4 Receptor Potently Decreased Food Intake and Body Weight Gain in Diet-Induced Obese Rats," Endocrinology (2005) 146(12):5257-5266.

Jones, Dan, "Novel pharmacotherapies for obesity poised to enter market," Nature Reviews/Drug Discovery (2009) 8:833-834.

Legault et al., "Highly Efficient Synthesis of O-(2,4-Dinitrophenyl)hydroxylamine. Application to the Synthesis of Substituted N-Benzoyliminopyridinium Ylides," J. Org. Chem (2003) 68:7119-7122.

McMinn et al., "Neuroendocrine mechanisms regulating food intake and body weight," Obesity reviews (2000) 1:37-46.

MacKenzie, Robert G., "Signaling in "Obesity Neurons"," Curr. Med. Chem.-Immun. Endoc. & Metab. Agents (2004) 4:113-117.

Marinkovic et al., "Structure-activity relationship studies on a series of piperazinebenzylalcohols and their ketone and amine analogs as melanocortin-4 receptor ligands," Bioorganic & Medicinal Chemistry Letters (2008) 18:4817-4822.

Markison et al., "Targeting melanocortin receptors for the treatment of obesity," Drug Discovery Today: Therapeutic Strategies, Nervous System Disorders (2006) 3(4):569-576.

Mayorov et al., "Cyclic lactam hybrid α-MSH/Agouti-related protein (AGRP) analogues with nanomolar range binding affinities at the human melanocortin receptors," Bioorganic & Medicinal Chemistry Letters (2011) 21:3099-3102.

Mousseau et al., "Synthesis of 2-Substituted Pyrazolo[1,5-a]pyridines through Cascase Direct Alkenylation/Cyclization Reactions," Organic Letters (2010) 12(3):516-519.

Nargund et al., "Melanocortin-4 Receptor (MC4R) Agonists for the Treatment of Obesity," J. Med. Chem. (2006) 49:4035-4043.

Nijenhuis et al., "Discovery and in vivo evaluation of new melanocortin-4 receptor-selective peptides," Peptides (2003) 24:271-280.

(56) References Cited

OTHER PUBLICATIONS

Nijenhuis et al., "Poor Cell Surface Expression of Human Melanocortin-4 Receptor Mutations Associated with Obesity," The Journal of Biological Chemistry (2003) 278(25):22939-22945.

Novinson et al., "Synthesis and Antifungal Properties of Certain 7-Alkylaminopyrazolo[1,5-a]pyrimidines," Journal of Medicinal Chemistry (1977) 20(2):296-299.

Nozawa et al., "Recent advances in the development of melanocortin-4 receptor ligands," Expert Opin. Ther. Patents (2008) 18(4):403-427.

Ollmann et al., "Antagonism of Central Melanocortin Receptors in Vitro and in Vivo by Agouti-Related Protein," Science (1997) 273:135-138.

Pontillo et al., "Piperazinebenzylamines as potent and selective antagoinists of the human melanocortin-4 receptor," Bioorganic & Medicinal Chemistry Letters (2004) 14:5605-5609.

Pontillo et al., "A potent and selective nonpeptide antagonist of the melancortin-4 receptor induces food intake in satiated mice," Bioorganic & Medicinal Chemistry Letters (2005) 15:2541-2546.

Pontillo et al., "Structure-activity relationship studies on a series of cyclohexylpiperazines bearing a phanylacetamide as ligands of the human melanocortin-4 receptor," Bioorganic & Medicinal Chemistry Letters (2005) 15:5237-5240.

Rene et al., "Pharmacological Chaperones Restore Function to MC4R Mutants Responsible for Severe Early-Onset Obesity," The Journal of Pharmacology and Experimental Therapeutics (2010) 335(3):520-532.

Roubert et al., "Novel pharmacological MC4R agonists can efficiently activate mutated MC4R from obese pateint with impaired endogenous agonist response," Journal of Endocrinology (2010) 207:177-183.

Sebhat et al., "Melanocortin subtype 4 receptor agonists: Structure-activity relationships about the 4-alkyl piperidine core," Bioorganic & Medicinal Chemistry Letters (2007) 17:5720-5723.

Singh et al., "Incorporation of a Bioactive Reverse-Turn Heterocycle into a Peptide Template Using Solid-Phase Synthesis to Probe Melanocortin Receptor Selectivity and Ligand Conformations by 2D1H NMR," Journal of Medicinal Chemistry (2011) 54:1379-1390.

Sun et al., "A predictive pharmacophore model of human melanocortin-4 receptor as derived from the solution structures of cyclic peptides," Bioorganic & Medicinal Chemistry (2004) 12:2671-2677.

Sutton et al., "A derivative of the melanocortin receptor antagonist SHU9119 (PG932) increases food intake when administered peripherally," Peptides (2008) 29:104-111.

Todorovic et al., "A review of melanocortin receptor small molecule ligands," Peptides (2005) 26:2026-2036.

Tran et al., "Syntheses of tetrahydrothiophenes and tetrahydrofurans and studies of their derivatives as melanocortin-4 receptor ligands," Bioorganic & Medicinal Chemistry Letters (2008) 18:1124-1130.

Tran et al., "Design and synthesis of 3-arylpyrrolidine-2-carboxamide derivatives as melanocortin-4 receptor ligands," Bioorganic & Medicinal Chemistry Letters (2008) 18:1931-1938.

Ujjainwalla et al., "Design and synthesis of melanocortin subtype-4 receptor agonists. Part 2: Discovery of the dihydropyridazinone motif," Bioorganic & Medicinal Chemistry Letters (2005) 15:4023-4028.

Yan et al., "Potent and selective MC-4 receptor agonists based on a novel disulfide scaffold," Bioorganic & Medicinal Chemistry Letters (2005) 15:4611-4614.

Yao et al., "Obesity Drug Update: The Lost Decade?," Pharmaceuticals (2010) 3:3494-3521.

Löber et al., "Rationally Based Efficacy Tuning of Selective Dopamine D4 Receptor Ligands Leading to the complete Antagonist 2-[4-4(4-Chlorophenyl)piperazin-1-ylmethyl]pyrazolo[1,5-a]pyridine (FAUC 213)," J. Med. Chem. (2001) 44:2691-2694.

PYRAZOLOPYRIDINE AND PYRAZOLOPYRIMIDINE DERIVATIVES AS MELANOCORTIN-4 RECEPTOR MODULATORS

This application is a 35 U.S.C. §371 national phase application of PCT/CA2012/000089, filed Jan. 26, 2012, which claims benefit of U.S. Provisional Patent Application No. 61/436,727, filed Jan. 27, 2011, the entire contents of which are incorporated herein by reference as if fully set forth.

TECHNICAL FIELD

The present concerns pyrazolopyridine and pyrazolopyrimidine derivatives, their compositions and method of using same to modulate the activity of melanocortin-4 receptors.

BACKGROUND

Obesity represents the most prevalent of body weight disorders, and it is the most important nutritional disorder in the Western world, with estimates of its prevalence ranging from 30% to 50% of the middle-aged population. The number of overweight and obese Americans has continued to increase since 1960, a trend that is not slowing down. Today, 64.5 percent of adult Americans (about 127 million) are categorized as being overweight or obese. Each year, obesity causes at least 300,000 deaths in the U.S., and healthcare costs of American adults with obesity amount to approximately $100 billion (American Obesity Association).

Obesity increases an individual's risk of developing conditions such as high blood pressure, diabetes (type 2), hyperlipidemia, heart disease, hypertension, stroke, gallbladder disease, and cancer of the breast, prostate, and colon (see, e.g., Nishina, P. M. et al, Metab. 1994, 43, 554; Grundy, S. M. & Barnett, J. P., Dis. Mon. 1990, 36, 641). In the U.S., the incidence of being overweight or obese occurs at higher rates in racial/ethnic minority populations such as African American and Hispanic Americans, compared with Caucasian Americans. Women and persons of low socioeconomic status within minority populations appear to particularly be affected by excess weight and obesity. This trend is not limited to adults. Approximately 30.3 percent of children (ages 6 to 11) are overweight and 15.3 percent are obese. For adolescents (ages 12 to 19), 30.4 percent are overweight and 15.5 percent are obese. Diabetes, hypertension and other obesity-related chronic diseases that are prevalent among adults have now become more common in children and young adults. Poor dietary habits and inactivity are reported to contribute to the increase of obesity in youth. Additionally, risk factors for developing childhood obesity include having overweight parents, or parents unconcerned about their child's weight, increased energy intake due to larger serving sizes, increased sedentary lifestyle and decreased transport-related activity (walking to school or to the bus stop), having a temperament with high levels of anger/frustration (which may cause parents to give their child extra food and calories to decrease tantrums), having Down's Syndrome, mother's pregnancy body mass index (BMI) and first born status (increased prevalence of obesity). One tool used for diagnosing obesity in adults is calculating an individual's BMI, which is a measure of body weight for height (Garrow & Webster, International Journal of Obesity 1985, 9, 147). A BMI of 25 to 29.9 indicates that an individual is overweight, while a BMI of 30 or above is indicative of obesity. For children, BMI is gender and age specific (Pietrobelli et al, Journal of Pediatrics 1998, 132, 204). Risk factors for developing obesity in adulthood include poor diet (high-calorie, low nutrients); lack of physical activity; working varied shifts; quitting smoking, having certain medical conditions such as rare hereditary diseases, and hormonal imbalances (such as hypothyroid, Cushing's disease and polycystic ovarian syndrome); certain medications (steroids and some antidepressants); being a racial or ethnic minority (especially a female minority); low socioeconomic status; age (increased risk from 20-55), pregnancy; and retirement (due to altered schedule).

Melanocortin 4 Receptor and Obesity

Melanocortin (MC) receptors are members of the seven-transmembrane-domain G protein-coupled receptor superfamily that activate generation of the second messenger cyclic AMP (cAMP). There are five MC receptors isolated to date: MC1R, MC2R, MC3R, MC4R and MC5R. Human MC4R is 332 amino acids in length. The melanocortin 4 receptor (MC4R) has been implicated in the regulation of body weight (Graham et al, Nat. Genetics 1997, 17, 273). MC4R is expressed in the brain, including the hypothalamus, which influences food intake (Markison & Foster, Drug Discovery Today, 2006, 3, 569).

Signaling via MC4R stimulates anorexigenic neural pathways. MC4R null mice develop late onset obesity with hyperglycemia and hyperinsulinemia. Mice lacking one MC4R allele (heterozygotes) have intermediate body weight between wild-type and homozygous null mice. Transgenic mice overexpressing an endogenous MC4R antagonist, i.e. agouti-related protein (AgRP), exhibited increased weight gain, food consumption, and body length compared with non-transgenic littermates (Oilman et al., Science 1997, 278 135). In humans, MC4R deficiency is the most common monogenic form of obesity (Farooqi et al., New Engl. J. Med. 2003 348, 1085). Numerous mutations affecting MC4R activity have been found and many are associated with obesity including early-onset (childhood) obesity (Nijenhuis et al., J. Biol. Chem. 2003, 278, 22939; Branson et al., New Eng. J. Med. 2003, 348, 1096; Gu et al., Diabetes 1999, 48, 635; Tao et al., Endocrinology 2003, 144, 4544). Recently, pharmacological restoration of mutant melanocortin-4 receptor signaling with cell permeable MC4R ligands has also been reported (René et al. J. Pharmacol. Exp Ther. 2010, 335, 520).

Several authors have now reviewed the recent advances in our understanding of the genetics of MC4R in early onset obesity (e.g., Farooqi I S & O'Rahilly S, Int J Obes (Lond), 2005 October, 29(10), 1149; Govaerts et al., Peptides, 2005 October, 26(10), 1909; Tao Y X, Mol Cell Endocrinol, 2005 M 15, 239(1-2), 1-14; Farooqi I S & O'Rahilly S, Annu Rev Med, 2005, 56, 443-58). For example, in one patient with severe early-onset obesity, an autosomal-dominant mode of inheritance of an MC4R mutation has been found to be due to a dominant-negative effect caused by receptor dimerization (Biebermann H et al. Diabetes, 2003 December, 52(12), 2984).

Natural agonists (ligands) of MC4R include [alpha]-MSH, ACTH, [beta]-MSH, and [gamma]-MSH (in order from highest to lowest affinity). Other MC4R ligands, including agonists and antagonists, which have been described to date are peptides (U.S. Pat. No. 6,060,589) and cyclic peptide analogs (U.S. Pat. No. 6,613,874 to Mazur et al.). Further, U.S. Pat. Nos. 6,054,556 and 5,731,408 describe families of agonists and antagonists for MC4R that are lactam heptapeptides having a cyclic structure. A series of MC4R peptide agonists have also been designed (Sun et al., Bioorg Med Chem 2004, 12(10):2671). In addition, Nijenhuis et al. (Peptides 2003, 24(2):271) described the development and evaluation of melanocortin antagonist compounds that were selective for the MC4R. One compound, designated Ac-Nle-Gly-Lys-D-Phe- Arg-Trp-Gly-NH(2) (SEQ ID NO:9), was found to be the most selective MC4R compound, with a 90- and 110-fold selectivity for the MC4R as compared to the MC3R and MC5R, respectively. Subsequent modification yielded compound Ac-Nle-Gly-Lys-D-Nal(2)-Arg-Trp-Gly-NH(2) (SEQ ID NO: 10), a selective MC4R antagonist with 34-fold MC4R/MC3R and 109-fold MC4R/MC5R selectivity. Both compounds were active in vivo, and crossed the blood-brain barrier. On the other hand, it was recently shown that the moderately selective peptide antagonist PG-932 (7-fold MC4R/MC3R selectivity) increased food intake in mice upon peripheral administration (Sutton et al. Peptides, 2008, 29, 104). A recent report also describes the activation of mutated MC4R by novel peptide agonists (Roubert et al., J. of Endocrinology, 2010, 207, 177).

Other high-affinity MC4R antagonists are described in Grieco et al. (J Med Chem 2002; 24:5287). These cyclic antagonists were designed based on the known high affinity antagonist SHU9119 (Ac-Nle4-[Asp5-His6-DNal(2')7-Arg8-Trp9-LyslO]-NH(2)) (SEQ ID NO: 11). The SHU9119 analogues were modified in position 6 (His) with non-conventional amino acids. One compound containing a Che substitution at position 6 is a high affinity MC4R antagonist (IC50=0.48 nM) with 100-fold selectivity over MC3R. Another compound with a Cpe substitution at position 6 also was a high affinity MC4R antagonist (IC50=0.51 nM) with a 200-fold selectivity over MC3R. Molecular modeling was used to examine the conformational properties of the cyclic peptides modified in position 6 with conformationally restricted amino acids. See also, Grieco et al., Peptides 2006, 27, 472. Several non-peptide MC4R ligands have also been disclosed in U.S. published patent applications 2003/0158209 to Dyck et al. and 2004/082590 to Briner et al. Also, U.S. Pat. No. 6,638,927 to Renhowe et al. describes small, low-molecular weight guanidobenzamides as specific MC4R agonists. Richardson et al., have described novel arylpiperizines that are agonists of MC4R (J Med Chem 2004; 47(3), 744). U.S. Pat. No. 6,979,691 to Yu et al. and U.S. Pat. No. 6,699,873 to Maguire also describe non-peptide compounds which bind selectively to MC4R. WO 99/55679 to Basu et al. discloses isoquinoline derivatives, small molecule non-peptide compounds, which show low (micromolar) affinities for the MC1R and MC4R, reduction of dermal inflammation induced by arachidonic acids, and reductions of body weight and food intake. WO 99/64002 to Nargund et al. also discloses spiropiperidine derivatives as melanocortin receptor agonists, useful for the treatment of diseases and disorders such as obesity, diabetes, and sexual dysfunction. A large number of MC4-receptor ligands developed recently are analogs of N-acylpiperidines or piperazines (Nozawa et al. Expert Opin. Ther. Patents, 2008, 18, 403).

Other non-peptide MC4R antagonists have been described. Thus, U.S. published patent applications 2003/0176425 and 2003/0162819 to Eisinger et al. disclose novel 1,2,4-thiadiazole and 1,2,4-thiadiazolium derivatives, respectively, as MC4R antagonists or agonists. These applications also disclose use of these compounds to treat obesity. Other MC4R binding compounds are described in the following: Singh et al. J. Med. Chem., 2011, 54, 1379; Mayorov et al., Bioorg. Med. Chem. Lett., 2011, 21, 3099; Conde-Frieboes et al., Bioorg. Med. Chem. Lett., 2011, 21, 1459; Hong et al., Bioorg. Med. Chem. Lett., 2011, 21, 3099; DeBoer, Nutrition, 2010, 26, 146. He et al. Bioorg. Med. Chem. Lett. 2010, 20, 6524. Emmerson et al., Curr. Top. Med. Chem. 2007, 7, 1121. Nargund et. al. J. Med. Chem. 2006, 49, 4035. Guo et al., Bioorg. Med. Chem. Lett. 2008, 18, 3242. Sebhat et al. Bioorg. Med. Chem. Lett. 2007, 17, 5720. Chen et al. Bioorg. Med. Chem. 2008, 16, 5606. Marinkovic et al. Bioorg. Med. Chem. Lett. 2008, 18, 4817. Tran et al., Bioorg. Med. Chem. Lett. 2008, 18, 1124. Tran et al. Bioorg. Med. Chem. Lett. 2008, 18, 1931. Bednarek & Fong, Exp Opn Ther Patents 2004, 14, 327; Ujjainwalla et al., Bioorg. Med. Chem. Lett. 2005, 15, 4023; WO11/054,285 (Zhang Ga); WO 10/144,344 (Palatin); WO 10/065,801 (Palatin); WO 10/037,081 (Palatin); WO 10/065,802 (Palatin); WO 10/065,801 (Palatin); WO 10/065,800 (Palatin); WO 10/065,799 (Palatin); WO 03/07949 (Merck); WO 10/081,666 (Santhera); WO 10/034,500 (Santhera); WO 09/080291 (Santhera); WO 09/115321 (Santhera); WO 04/075823 (Ipsen); WO 04/089951 (Ipsen); WO 05/056533 (Ipsen); WO 06/010811 (Ipsen); WO 03/61660 (Eli Lilly); WO 03/09847 (Amgen); WO 03/09850 (Amgen); WO 03/31410 (Neurocrine Biosciences); WO 03/94918 (Neurocrine Biosciences); WO 03/68738 (Neurocrine Biosciences); WO 03/92690 (Procter and Gamble); WO 03/93234 (Procter and Gamble); WO 03/72056 (Chiron); WO 03/66597 (Chiron); WO 03/66587 (Chiron); WO 03/66587 (Chiron); WO 02/67869 (Merck); WO 02/68387 (Merck); WO 02/00259 (Taisho); WO 02/92566 (Taisho); WO 02/070511 (Bristol-Myers Squibb); WO 02/079146 (Bristol-Myers Squibb); WO 10/056,022 (LG Life Sciences); Pontillo et al., Bioorg Med Chem. Lett. 2005, 15, 5237; Pontillo et al., Bioorg Med Chem. Lett. 2005, 15, 2541; Pontillo et al., Bioorg Med Chem. Lett. 2004, 14, 5605; Cheung et al., Bioorg Med Chem. Lett. 2005, 15, 5504; Yan et al., Bioorg Med Chem. Lett. 2004 15, 4611; Hsiung et al., Endocrinology. 2005, 146, 5257; and Todorovic et al., Peptides. 2005 October, 26(10), 2026.

Current Treatments

Current anti-obesity drugs have limited efficacy (Jones, Nat. Rev. Drug Discov. 2009, 8, 834. Yao & Mackenzie, Pharmaceuticals, 2010, 3, 3494) and numerous side effects (Crowley et al., Nat. Rev. Drug Discov. 2002; 1, 276). With obesity reaching epidemic proportions worldwide, there is a pressing need for the development of adequate therapeutics in this area. In recent years, hormones and neuropeptides involved in the regulation of appetite, body energy expenditure, and fat mass accumulation have emerged as potential anti-obesity drugs (McMinn, et al., Obes Rev 2000, 1, 37; Drazen, D. L. & Woods, S. C, Curr Opin Clin Nutr Metab Care 2003, 6, 621). At present, however, these peptides require parenteral administration. The prospect of daily injections to control obesity for extended periods of time (since obesity is a chronic condition) is not very encouraging and limits the use of these drugs.

Thus, there is a need for improved pharmacological agents that are useful to treat obesity in humans.

BRIEF SUMMARY

Accordingly, there is provided a compound of Formula I:

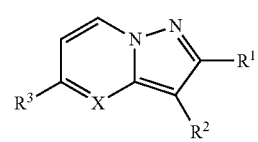

wherein
X=CH, or N;
$R^1$ is
1) halogen,
2) $C_1$-$C_6$ alkyl,

3) $C_3$-$C_7$ cycloalkyl,
4) aryl,
5) heteroaryl,
6) $NHR^4$,
7) $C(O)NHR^4$,
8) $C(O)$-aryl,
9) $C(O)$-heteroaryl, or
10) $C(O)$ heterocyclyl,
wherein the aryl and the heteroaryl are optionally substituted with one or more $R^7$ substituents;
$R^2$ is
1) $C_1$-$C_6$ alkyl-heterocyclyl,
2) $C_1$-$C_6$ alkyl-$NR^5R^6$,
3) $C_3$-$C_6$ alkenyl-heterocyclyl,
4) $C_3$-$C_6$ alkenyl-$NR^5R^6$,
5) $C_3$-$C_6$ alkynyl-heterocyclyl,
6) $C_3$-$C_6$ alkynyl-$NR^5R^6$,
7) aryl $C_1$-$C_3$ alkyl-heterocyclyl, or
8) $C(O)NH$ $C_2$-$C_6$ alkyl-heterocyclyl,
wherein the heterocyclyl is optionally substituted with one or more $C_1$-$C_6$ alkyl substituents, or one or more halo substituents, or one or more haloalkyl substituents;
$R^3$ is
1) $NR^8R^9$,
2) $C(O)NR^8R^9$,
3) $C(=NH)NR^8R^9$,
4) $C(=NC_1$-$C_6$ alkyl$)NR^8R^9$,
5) $C(S)NR^8R^9$,
6) $CH_2NR^8R^9$, or
7) $C(O)$heterocyclyl optionally substituted with a $C_1$-$C_6$ alkyl substituent;
$R^4$ is
1) aryl,
2) heteroaryl,
3) $C_1$-$C_6$ alkyl-aryl,
4) $C_1$-$C_6$ alkyl-heteroaryl,
5) $C_1$-$C_6$ alkyl-$NHC(O)C_1$-$C_6$ alkyl,
6) $C_1$-$C_6$ alkyl-$O$—$C_1$-$C_6$ alkyl, or
7) $C_1$-$C_6$ alkyl-heterocyclyl,
wherein the aryl, the heteroaryl and the heterocyclyl are optionally substituted with one or more $R^7$ substituents;
$R^5$ and $R^6$ are both or each independently,
1) H,
2) $C_1$-$C_6$ alkyl,
3) $C_1$-$C_6$ alkyl-aryl, or
4) heterocyclyl;
$R^7$ is
1) CN,
2) halogen,
3) haloalkyl,
4) $C_1$-$C_6$ alkyl,
5) $OC_1$-$C_6$ alkyl,
6) O-aryl,
7) O—$C_1$-$C_6$alkyl-aryl,
8) $C(O)OC_1$-$C_6$ alkyl,
9) $C(O)$ $C_1$-$C_6$ alkyl,
10) $C(O)$ aryl,
11) $C(O)$ heteroaryl,
12) $C(O)NH$ $C_1$-$C_6$ alkyl,
13) $NHC(O)$ $C_1$-$C_6$ alkyl,
14) $C(O)OH$,
15) $C(O)NH_2$,
16) $NO_2$,
17) heterocyclyl,
18) $C_1$-$C_6$ alkyl heterocyclyl,
19) heteroaryl,
20) aryl,
21) $NH_2$
22) OH,
23) $CH(OH)$ $C_1$-$C_6$ alkyl,
24) $C(OH)(C_1$-$C_6$ alkyl$)_2$,
25) $C(NH_2)=NH$,
26) $C(NH_2)=N$—OH, or
27) $C(NH_2)=N$—$OC(O)$ $C_1$-$C_6$ alkyl,
wherein the heteroaryl is optionally substituted with aryl, $C_1$-$C_6$ alkyl, haloalkyl, heteroaryll or $CH_2$-aryl-F; and
$R^8$ and $R^9$ are both or each independently
1) $C_3$-$C_7$-alkyl, or
2) $C_1$-$C_4$-alkyl-$C_3$-$C_6$-cycloalkyl,
or a pharmaceutically acceptable salt thereof to allow the drug to penetrate the cell membrane; or a prodrug, or the compound is labeled with a detectable label or an affinity tag thereof.

According to another aspect, there is provided a pharmaceutical composition comprising a compound of Formula I as described above and a pharmaceutically acceptable carrier.

According to another aspect, there is provided a method of making a pharmaceutical composition comprising mixing a compound of Formula I with a pharmaceutically acceptable carrier.

According to another aspect, there is provided a method of treating a disorder mediated by melanocortin-4 receptors, the method comprising administering to a subject in need thereof a therapeutically effective amount of a compound of Formula I so as to treat the disorder.

According to another aspect, there is provided a method of treating obesity in a subject, the method comprising: administering to the subject in need thereof, a pharmaceutically acceptable amount of a compound of Formula I, as described above, so as to treat the obesity.

According to another aspect, there is provided a method of modulating melanocortin-4 receptor activity, the method comprising: contacting the receptor with a compound of Formula I in an amount sufficient to modulate the receptor activity.

According to another aspect, there is provided an in vitro method of modulating melanocortin-4 receptor activity, the method comprising: contacting a cell with a compound of Formula I, as described above, in an amount sufficient to modulate the receptor activity.

According to one aspect, there is provided use of a compound, as described above, to treat a disorder mediated by melanocortin-4 receptors.

According to another aspect, there is provided use of a compound, as described above, to treat obesity.

According to another aspect, there is provided a method of screening for a compound's ability to modulate the stability, activity, and/or cell surface localization of an MC4R polypeptide, the method comprising:
    contacting a labeled or unlabeled test compound with a MC4R protein or a fragment thereof; and
    measuring the amount of the test compound bound to the MC4R protein or to the fragment.

According to another aspect, there is provided a method determining whether a test compound modulates the stability of the MC4R polypeptide, the method comprising:
    contacting a first cell with a test compound for a time sufficient to allow the cell to respond to the contact with the test compound;
    measuring the conformational stability, activity, and/or cell surface localization of a MC4R polypeptide or a fragment thereof; and
    comparing the stability, activity, and/or cell surface localization of the MC4R polypeptide measured to that of an MC4R polypeptide in a control cell that has not been contacted with the test compound; wherein a detectable change in the stability, activity, and/or cell surface localization of the MC4R polypeptide in the first cell in response to contact with the test compound compared to the stability level of the MC4R polypeptide in the control cell that has not been contacted with the test compound, indicates that the test compound modulates the stability of the MC4R polypeptide.

DETAILED DESCRIPTION

1) General Overview

We have discovered pyrazolopyridine and pyrazolopyrimidine derivatives that have beneficial pharmaceutical properties and that these compounds may be effective to treat melanocortin-4 mediated diseases such as obesity, cachexia, eating disorders, diabetes, metabolic diseases, erectile dysfunction and/or sexual disorders.

2) Compounds

Broadly speaking, the present concerns compounds represented by Formula I:

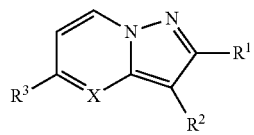

I wherein X, $R^1$, $R^2$ and $R^3$ are as defined hereinabove and hereinbelow, or a stable isotope or a prodrug or a pharmaceutically acceptable salt to allow the drug to penetrate the cell membrane; or the compound is labeled with a detectable label or an affinity tag thereof.

Further included within the scope of Formula I are compounds of Formula IA and IB:

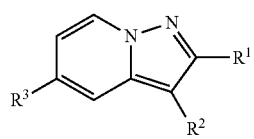

IA

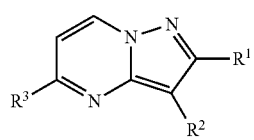

IB wherein $R^1$, $R^2$ and $R^3$ are as defined hereinabove and hereinbelow; or a prodrug or a pharmaceutically acceptable salt to allow the drug to penetrate the cell membrane; or the compound is labeled with a detectable label or an affinity tag thereof.

Further included within the scope of Formula IA are compounds of Formula IA1 through Formula IA50:

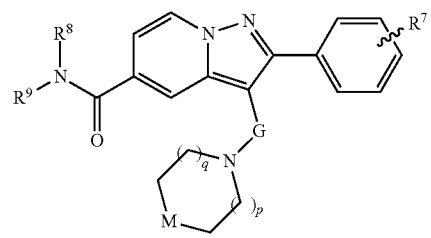

IA1

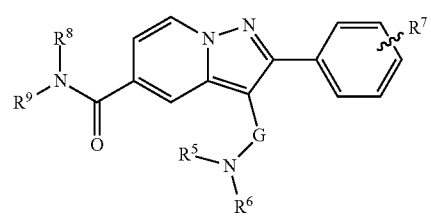

IA2

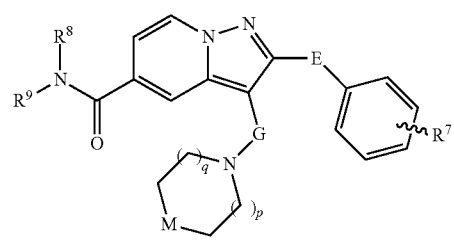

IA3

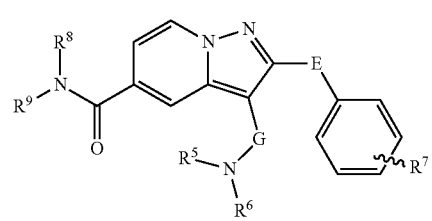

IA4

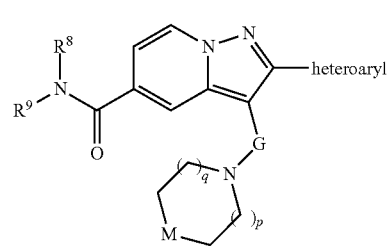

IA5

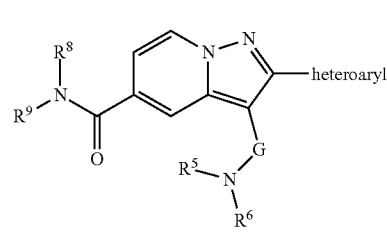

IA6

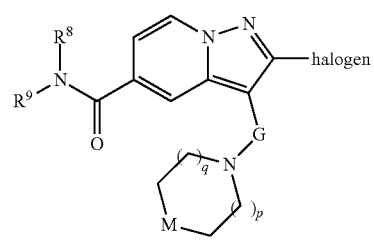

IA7

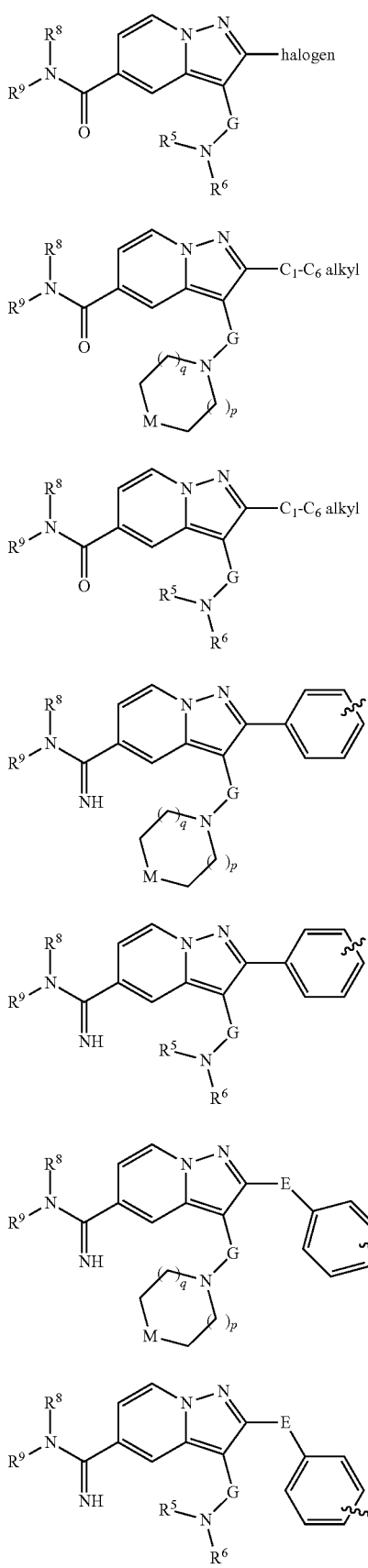
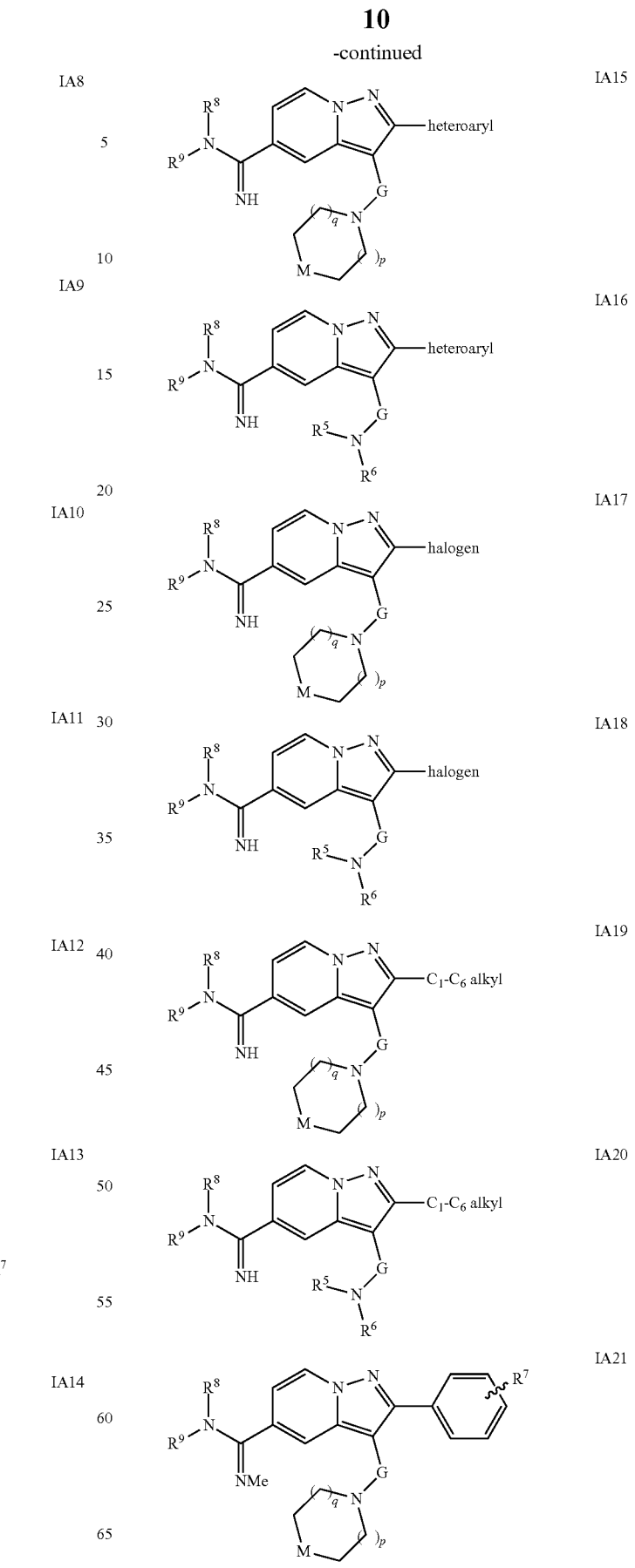

-continued
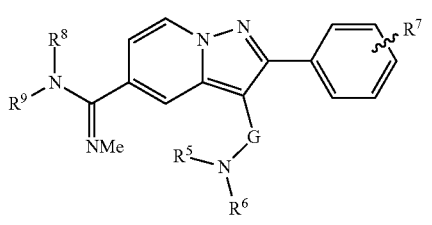
IA22
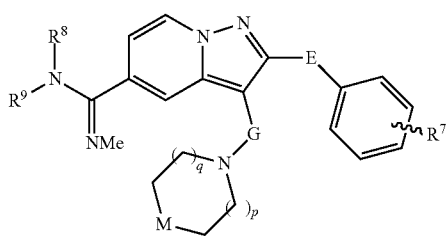
IA23
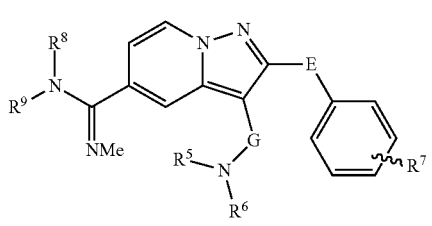
IA24
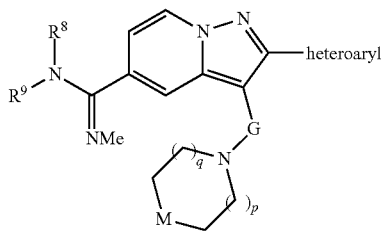
IA25
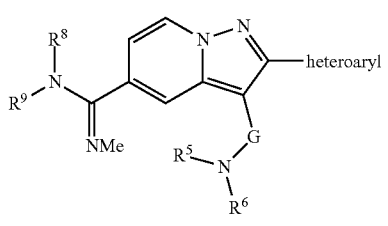
IA26
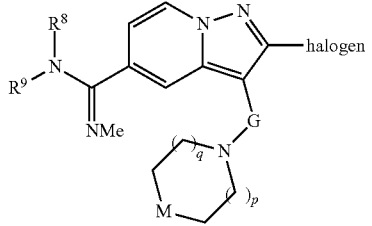
IA27
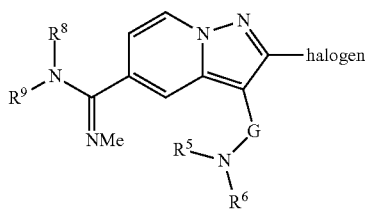
IA28
-continued
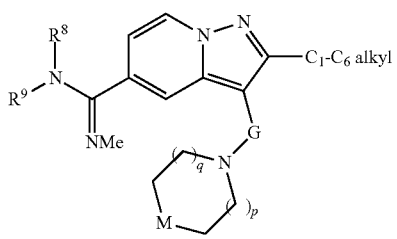
IA29
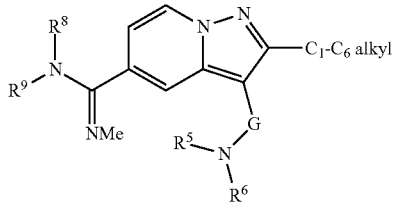
IA30
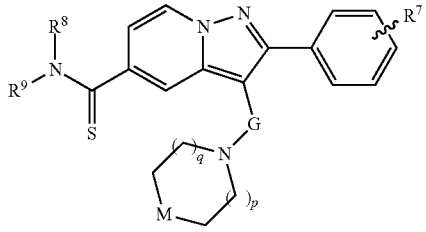
IA31
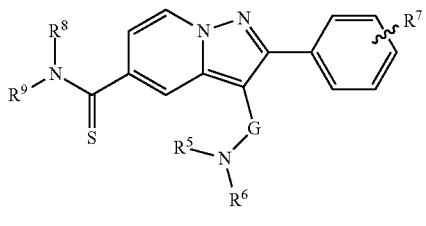
IA32
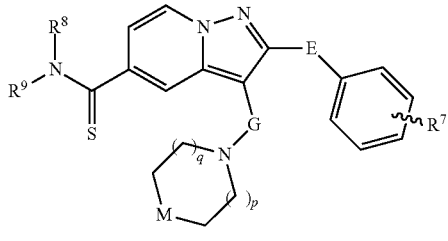
IA33
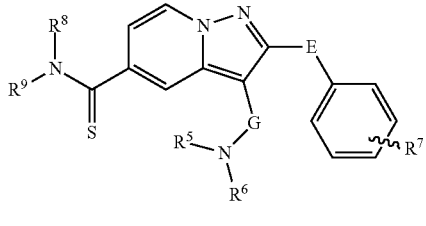
IA34
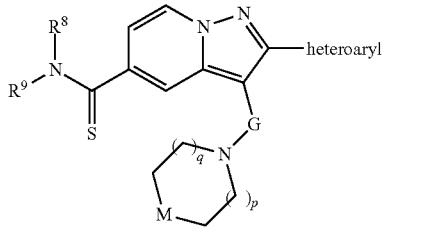
IA35

IA36
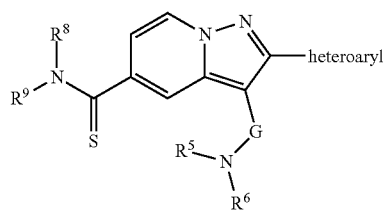
IA37
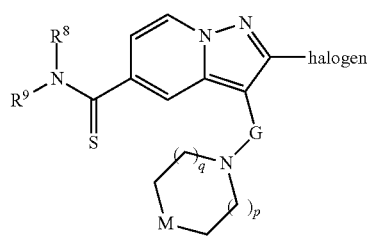
IA38
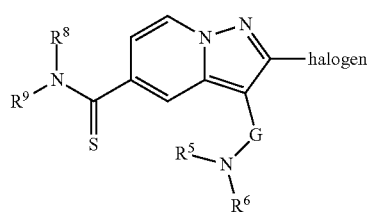
IA39
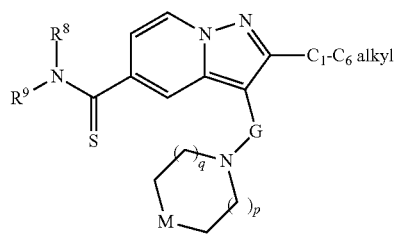
IA40
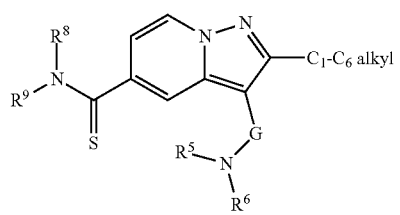
IA41
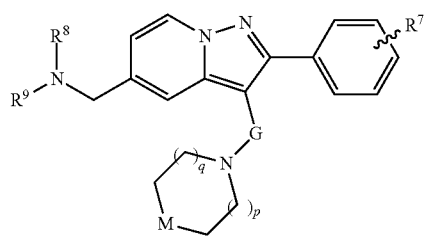
IA42
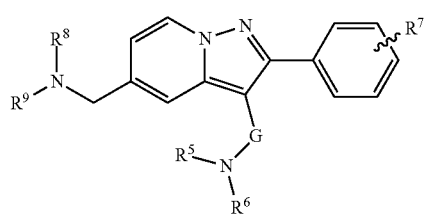
IA43
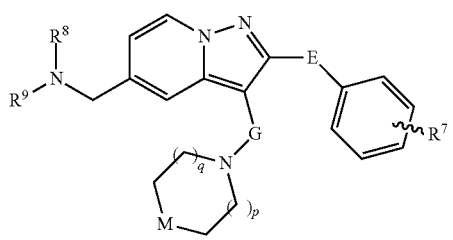
IA44
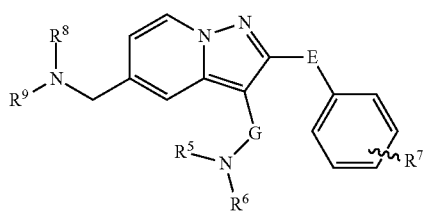
IA45
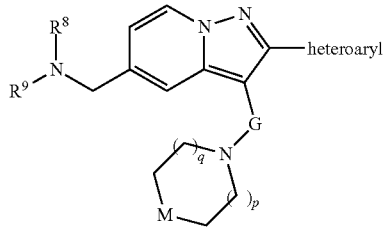
IA46
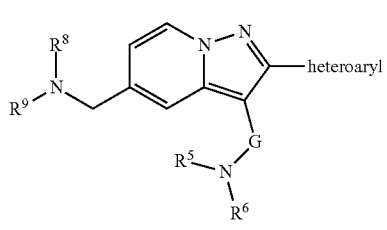
IA47
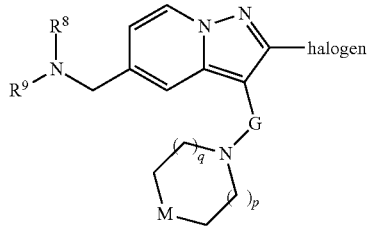
IA48
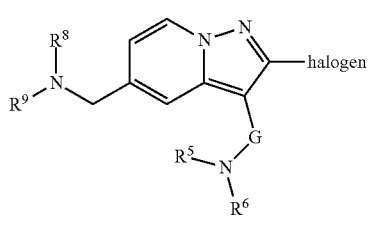
IA49
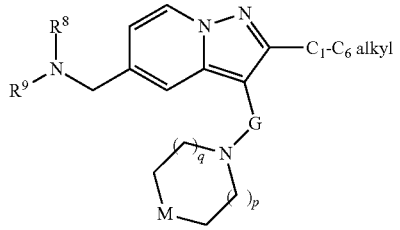

IA50
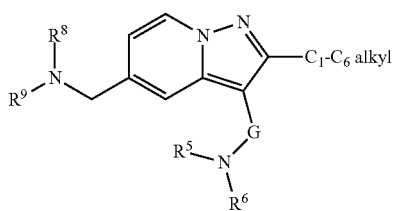

wherein G is $C_2$-$C_4$ alkyl, $C_2$-$C_4$ alkenyl, $C_2$-$C_4$ alkynyl, arylalkyl or C(O)NHalkyl, p is 0, 1 or 2; q is 0 or 1; M is $CH_2$, O, $CF_2$ or CH—$C_1$-$C_6$haloalkyl; E is NH or CONH, $R^5$, $R^6$, $R^7$, $R^8$, $R^9$, alkyl, alkenyl, alkynyl, heteroaryl and aryl are as defined hereinabove and hereinbelow, or a prodrug; or a pharmaceutically acceptable salt to allow the drug to penetrate the cell membrane; or the compound is labeled with a detectable label or an affinity tag thereof.

Alternatively, included within the scope of Formula IB are compounds of Formula IB1 through Formula IB50:

IB1
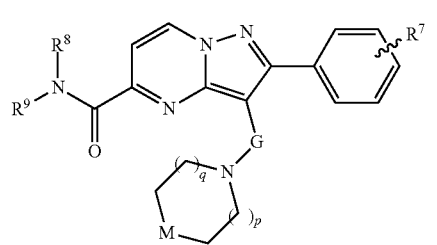

IB2
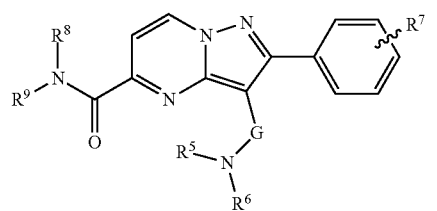

IB3
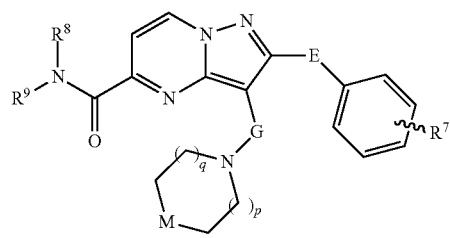

IB4
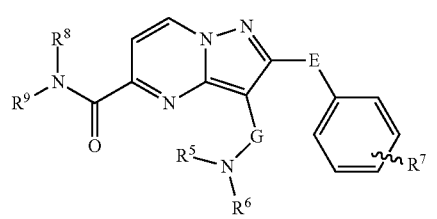

IB5
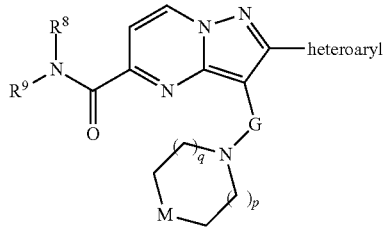

IB6
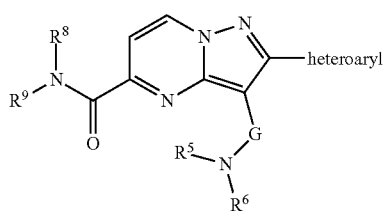

IB7
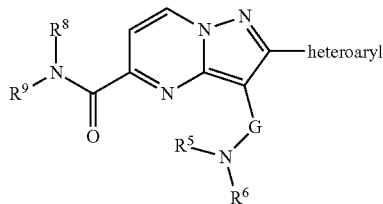

IB8
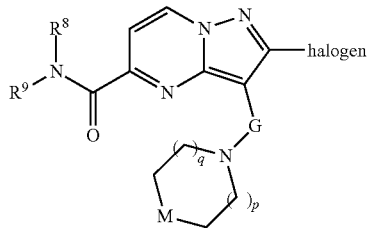

IB9
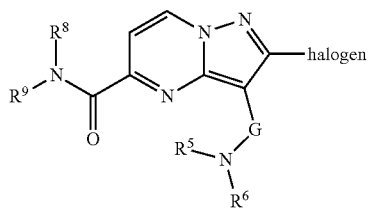

IB10
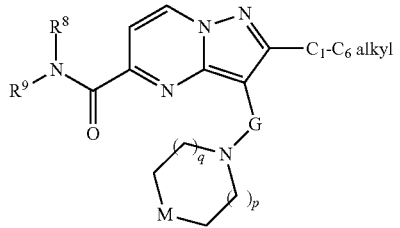

IB11
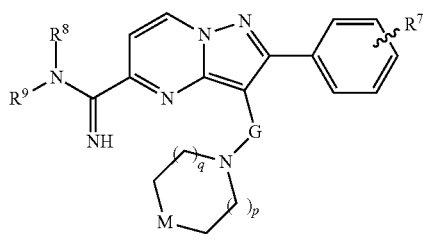

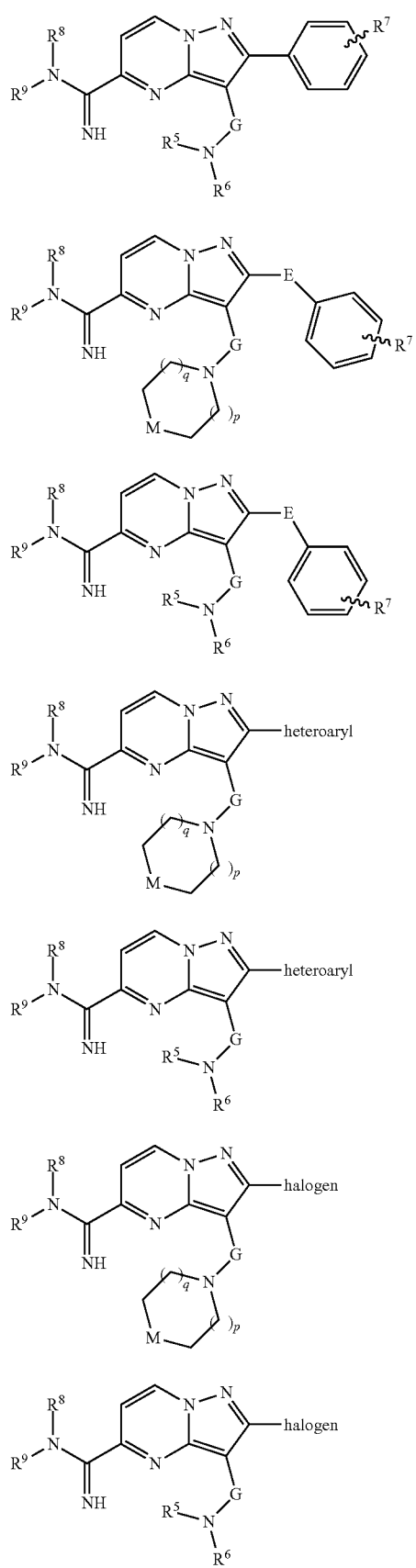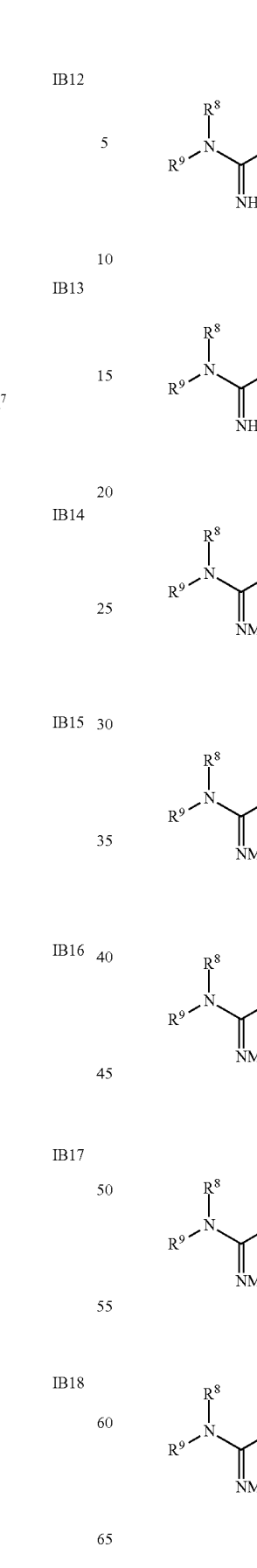

-continued
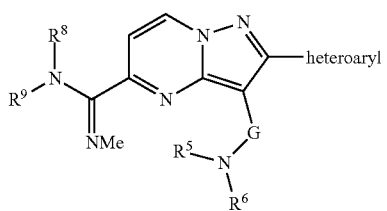
IB26
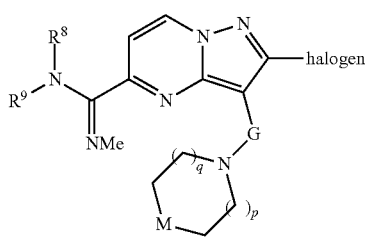
IB27
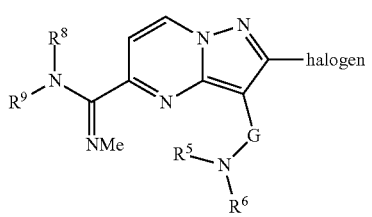
IB28
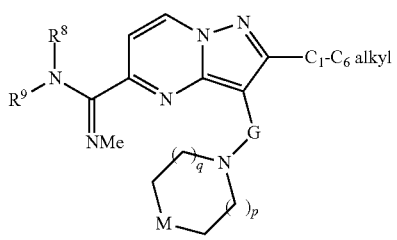
IB29
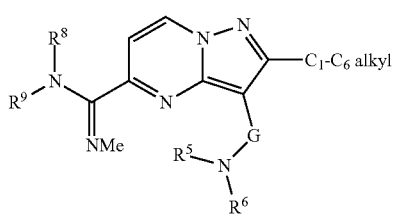
IB30
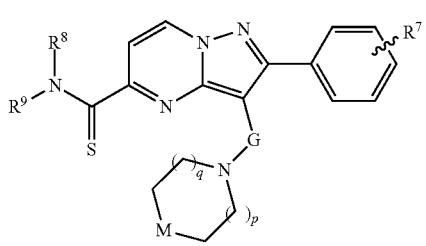
IB31
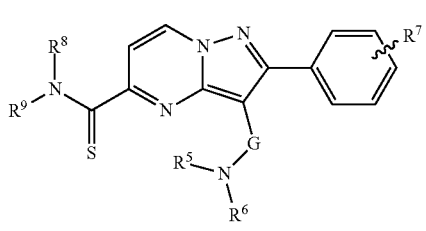
IB32
-continued
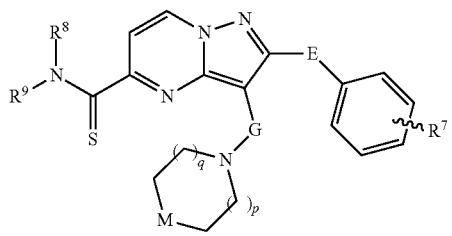
IB33
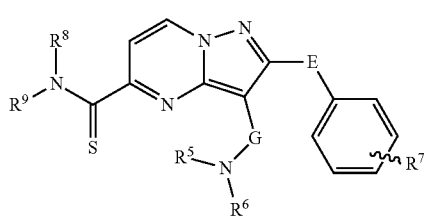
IB34
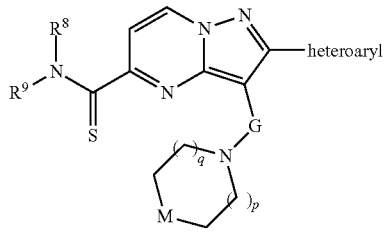
IB35
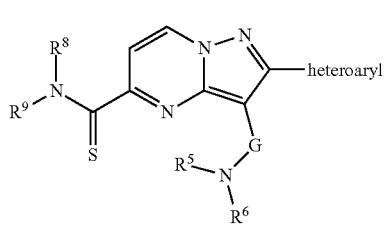
IB36
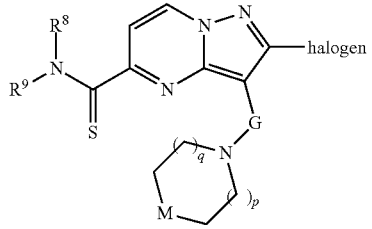
IB37
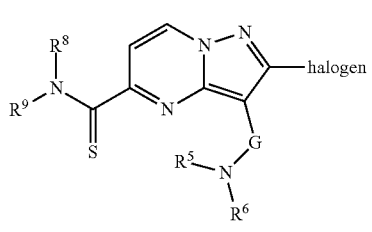
IB38
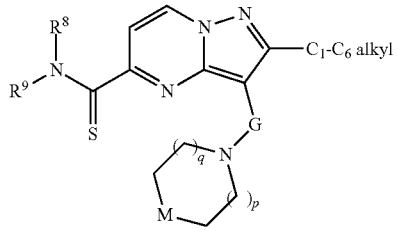
IB39

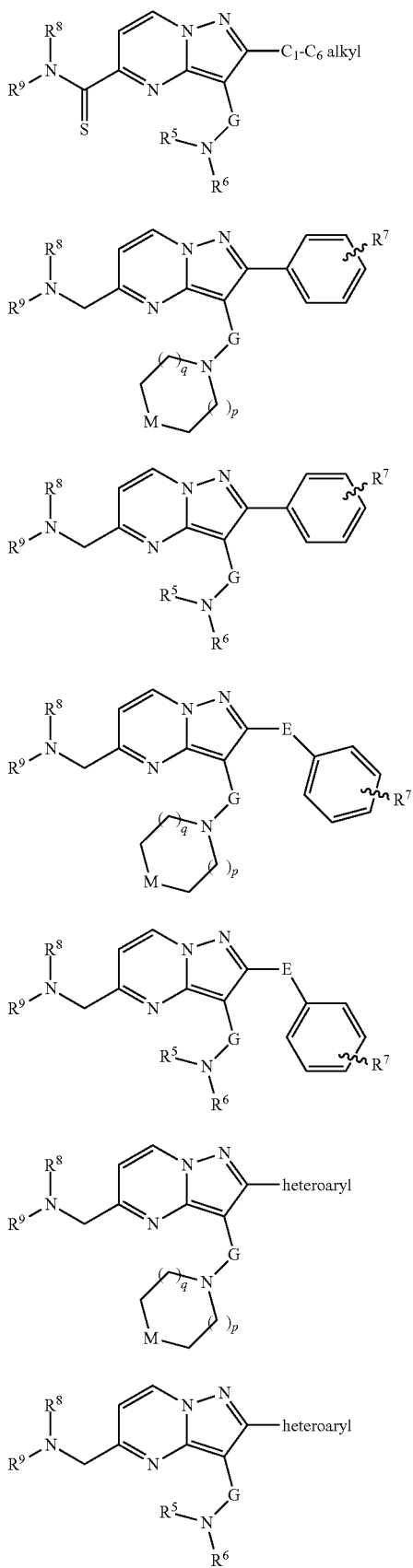

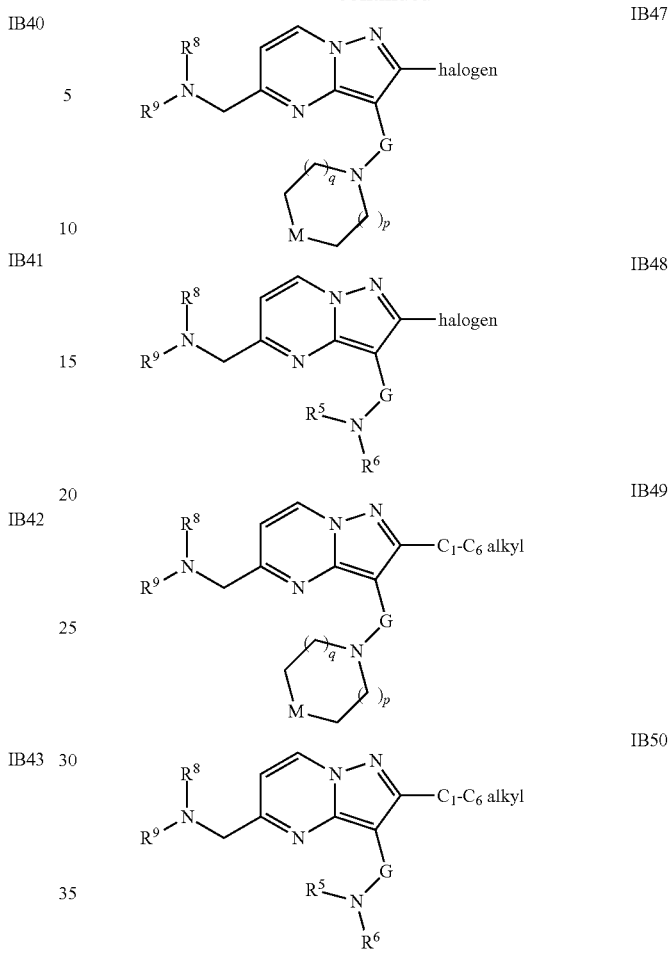

wherein G is $C_2$-$C_4$ alkyl, $C_2$-$C_4$ alkenyl, $C_2$-$C_4$ alkynyl, arylalkyl or C(O)NHalkyl, p is 0, 1 or 2; q is 0 or 1; M is $CH_2$, O, $CF_2$ or CH—$C_1$-$C_6$haloalkyl; E is NH or CONH, $R^5$, $R^6$, $R^7$, $R^8$, $R^9$, alkyl, alkenyl, alkynyl, heteroaryl and aryl are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA1, there is provided a compound of Formula IA1.1

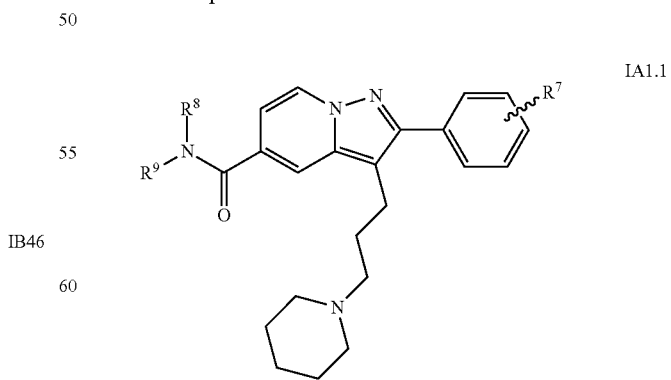

wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA1, there is provided a compound of Formula IA1.2

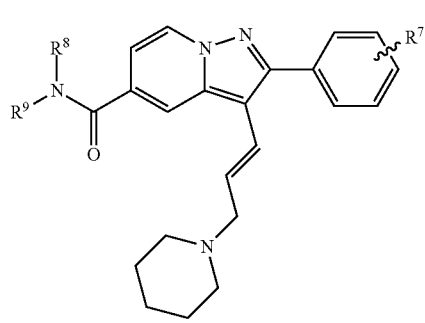

IA1.2 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA1, there is provided a compound of Formula IA1.3

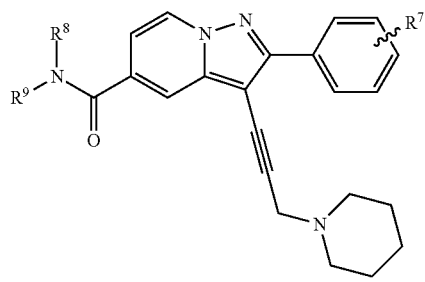

IA1.3 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA1, there is provided a compound of Formula IA1.4

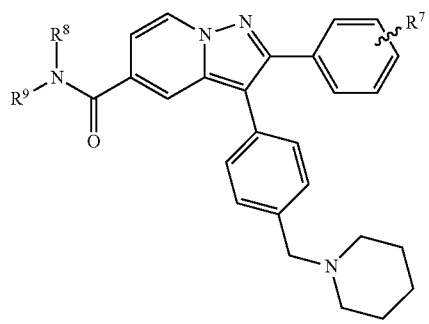

IA1.4 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA1, there is provided a compound of Formula IA1.5

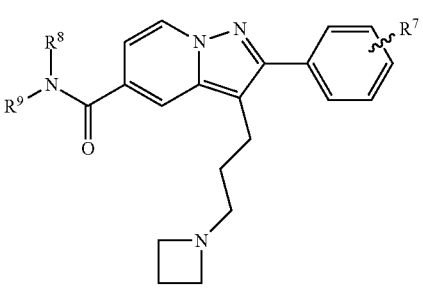

IA1.5 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA1, there is provided a compound of Formula IA1.6

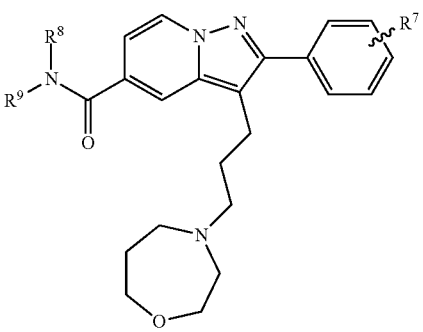

IA1.6 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA1, there is provided a compound of Formula IA1.7

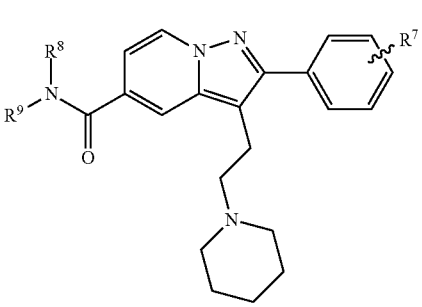

IA1.7 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA1, there is provided a compound of Formula IA1.8

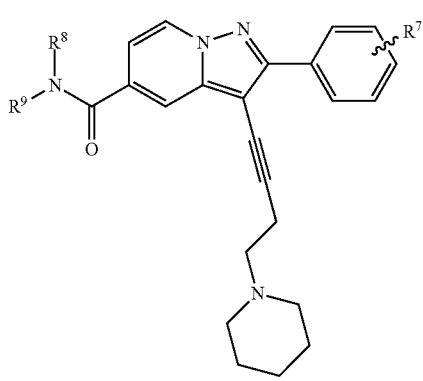

IA1.8 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA2, there is provided a compound of Formula IA2.1

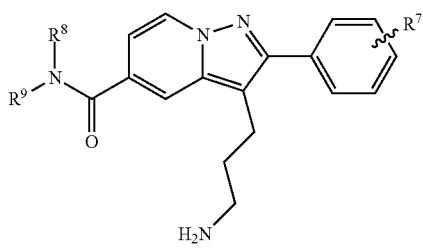

IA2.1 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA2, there is provided a compound of Formula IA2.2

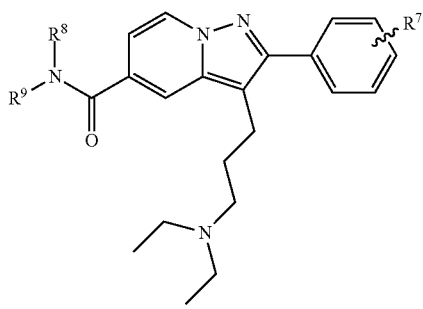

IA2.2 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA2, there is provided a compound of Formula IA2.3

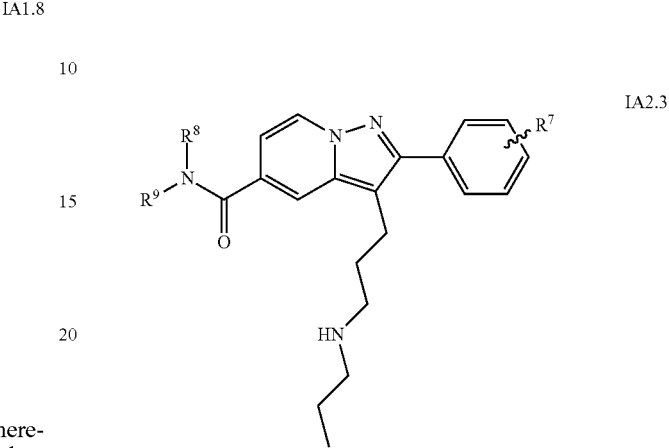

IA2.3 wherein $R^7$, $R^8$, and $R^9$ are as defined hereinabove and hereinbelow; or a prodrug; or a pharmaceutically acceptable salt to allow the drug to penetrate the cell membrane; or the compound is labeled with a detectable label or an affinity tag thereof.

In one subset of compounds of Formula IA2, there is provided a compound of Formula IA2.4

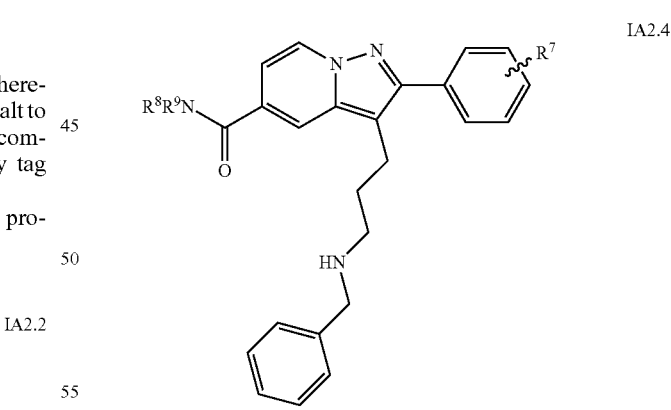

IA2.4 wherein $R^7$, $R^8$, and $R^9$ are as defined hereinabove and hereinbelow; or a prodrug; or a pharmaceutically acceptable salt to allow the drug to penetrate the cell membrane; or the compound is labeled with a detectable label or an affinity tag thereof.

In one subset of compounds of Formula IA2, there is provided a compound of Formula IA2.5

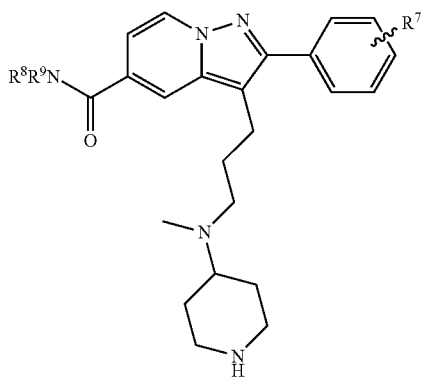

IA2.5 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA3, there is provided a compound of Formula IA3.1

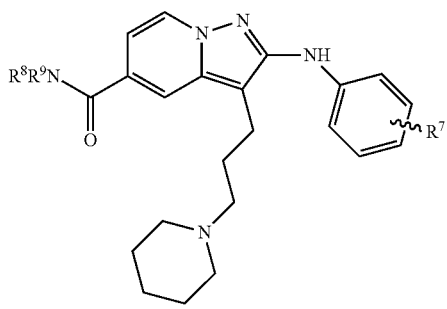

IA3.1 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA3, there is provided a compound of Formula IA3.2

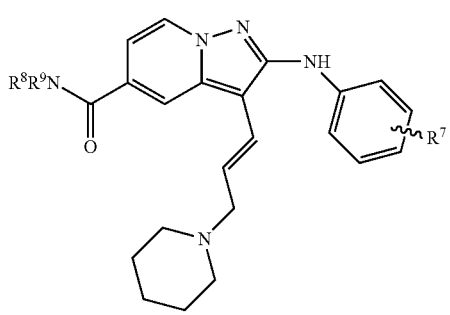

IA3.2 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA3, there is provided a compound of Formula IA3.3

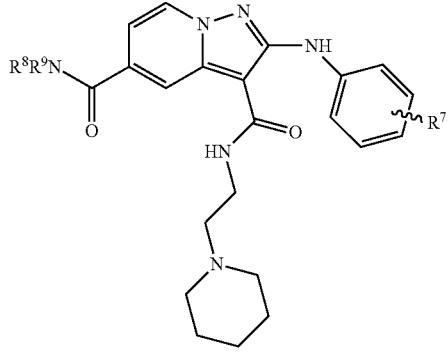

IA3.3 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA3, there is provided a compound of Formula IA3.4

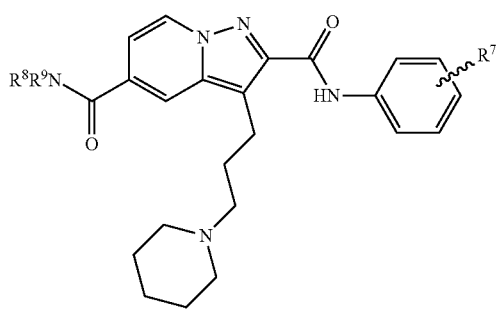

IA3.4 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA3, there is provided a compound of Formula IA3.5

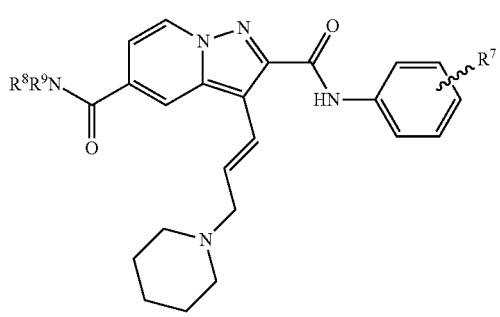

IA3.5 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA5, there is provided a compound of Formula IA5.1

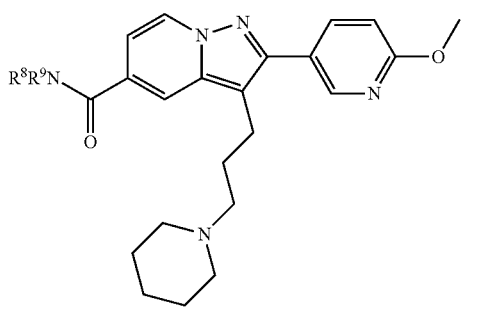

IA5.1 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA7, there is provided a compound of Formula IA7.1

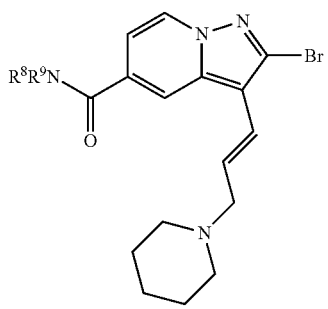

IA7.1 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA9, there is provided a compound of Formula IA9.1

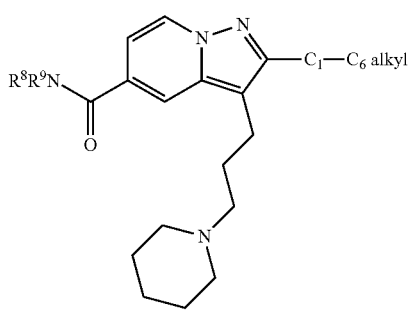

IA9.1

In one subset of compounds of Formula IA11, there is provided a compound of Formula IA11.1

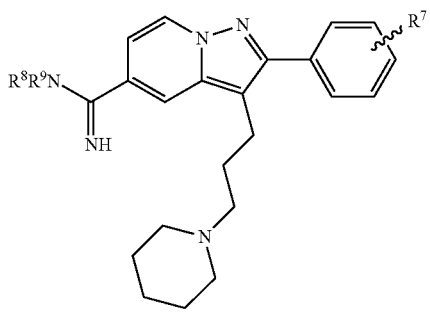

IA11.1 wherein $R^7$, $R^8$, and $R^9$ are as defined hereinabove and hereinbelow; or a prodrug; or a pharmaceutically acceptable salt to allow the drug to penetrate the cell membrane; or the compound is labeled with a detectable label or an affinity tag thereof.

In one subset of compounds of Formula IA21, there is provided a compound of Formula IA21.1

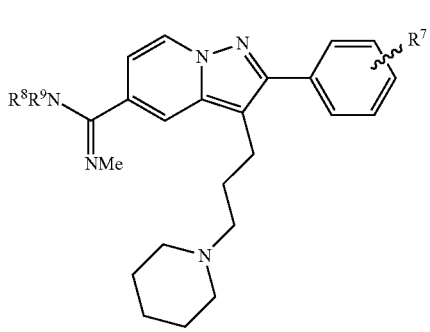

IA21.1 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA31, there is provided a compound of Formula IA31.1

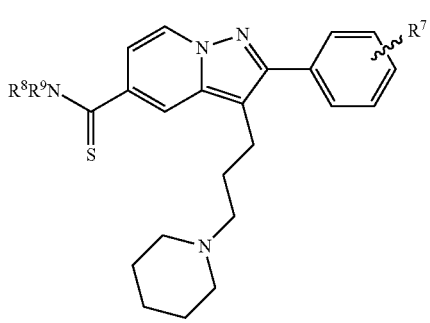

IA31.1 wherein $R^7$, $R^8$, and $R^9$ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IA41, there is provided a compound of Formula IA41.1

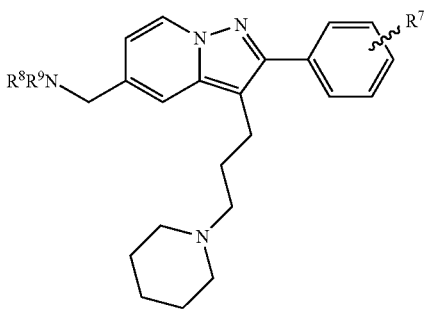

IA41.1 wherein R⁷, R⁸, and R⁹ are as defined hereinabove and hereinbelow; or a prodrug; or a pharmaceutically acceptable salt to allow the drug to penetrate the cell membrane; or the compound is labeled with a detectable label or an affinity tag thereof.

In one subset of compounds of Formula IB1, there is provided a compound of Formula IB1.1

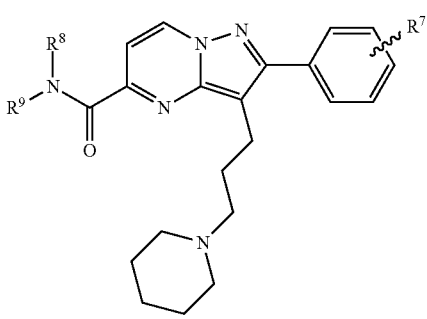

IB1.1 wherein R⁷, R⁸, and R⁹ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IB1, there is provided a compound of Formula IB1.2

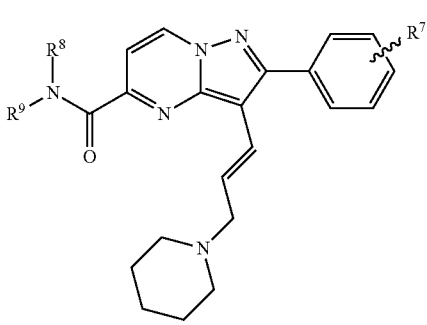

IB1.2 wherein R⁷, R⁸, and R⁹ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IB2, there is provided a compound of Formula IB2.1

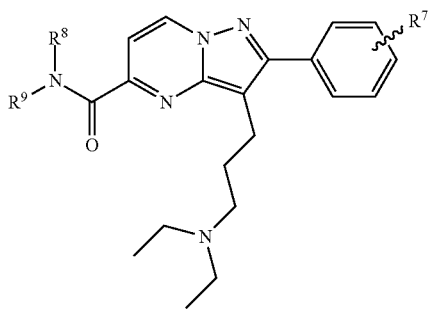

IB2.1 wherein R⁷, R⁸, and R⁹ are as defined hereinabove and hereinbelow, or a prodrug; or a pharmaceutically acceptable salt to allow the drug to penetrate the cell membrane; or the compound is labeled with a detectable label or an affinity tag thereof.

In one subset of compounds of Formula IB2, there is provided a compound of Formula IB2.2

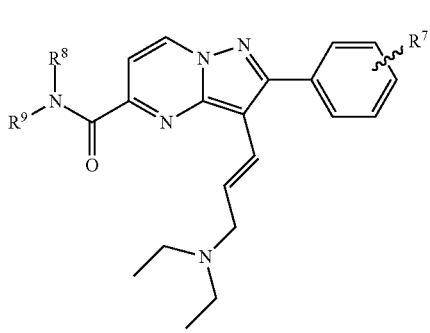

IB2.2 wherein R⁷, R⁸, and R⁹ are as defined hereinabove and hereinbelow, or a prodrug; or a pharmaceutically acceptable salt to allow the drug to penetrate the cell membrane; or the compound is labeled with a detectable label or an affinity tag thereof.

X:

In one subset of compounds, X is CH,

In another subset of compounds, X is N.

Any and each individual definition of X as set out herein may be combined with any and each individual definition of $R^1$, $R^2$ and $R^3$ as set out herein.

$R^1$:

In one subset of compounds, $R^1$ is aryl optionally substituted with one or more $R^7$ substituents.

In one example, $R^1$ is phenyl substituted with one $R^7$ substituent.

In another example, $R^1$ is phenyl substituted with two $R^7$ substituents.

In another example, $R^1$ is phenyl substituted with three $R^7$ substituents.

In another subset of compounds, $R^1$ is heteroaryl substituted with one $R^7$ substituent.

In another subset of compounds, $R^1$ is NH-aryl substituted with one $R^7$ substituent.

In another subset of compounds, $R^1$ is C(O)NH-aryl substituted with one $R^7$ substituent.

In another subset of compounds, $R^1$ is halogen.

In another subset of compounds, $R^1$ is $C_1$-$C_6$-alkyl.

Any and each individual definition of $R^1$ as set out herein may be combined with any and each individual definition of X, $R^2$ and $R^3$ as set out herein.

$R^2$:

In one subset of compounds, $R^2$ is $C_1$-$C_6$ alkyl-heterocyclyl, wherein the heterocyclyl is optionally substituted with one or more $C_1$-$C_6$ alkyl substituents, or one or more halo substituents, or one or more haloalkyl substituents.

In another subset of compounds, $R^2$ is $C_3$-$C_6$ alkenyl-heterocyclyl, wherein the heterocyclyl is optionally substituted with one or more $C_1$-$C_6$ alkyl substituents, or one or more halo substituents, or one or more haloalkyl substituents.

In another subset of compounds, $R^2$ is $C_3$-$C_6$ alkynyl-heterocyclyl, wherein the heterocyclyl is optionally substituted with one or more $C_1$-$C_6$ alkyl substituents, or one or more halo substituents, or one or more haloalkyl substituents.

In another subset of compounds, $R^2$ is aryl alkyl-heterocyclyl, wherein the heterocyclyl is optionally substituted with one or more $C_1$-$C_6$ alkyl substituents, or one or more halo substituents, or one or more haloalkyl substituents.

In another subset of compounds, $R^2$ is $C(O)NHC_2$-$C_6$ alkynyl-heterocyclyl, wherein the heterocyclyl is optionally substituted with one or more $C_1$-$C_6$ alkyl substituents, or one or more halo substituents, or one or more haloalkyl substituents.

Any and each individual definition of $R^2$ as set out herein may be combined with any and each individual definition of X, $R^1$ and $R^3$ as set out herein.

$R^3$:

In one subset of compounds, $R^3$ is $C(O)NR^8R^9$.

In another subset of compounds, $R^3$ is $C(=NH)NR^8R^9$.

In another subset of compounds, $R^3$ is $C(=NMe)NR^8R^9$.

In another subset of compounds, $R^3$ is $C(S)NR^8R^9$.

In another subset of compounds, $R^3$ is $CH_2NR^8R^9$.

Any and each individual definition of $R^3$ as set out herein may be combined with any and each individual definition of X, $R^1$ and $R^2$ as set out herein.

$R^4$:

In one subset of compounds $R^4$ is aryl substituted with one $R^7$ substituent.

In one subset of compounds, $R^4$ is aryl substituted with one O—$C_1$-$C_6$ alkyl substituent.

In one subset of compounds, $R^4$ is aryl substituted with one $C(O)OC_1$-$C_6$ alkyl substituent.

In another example, $R^4$ is aryl substituted with one $C(O)NH_2$ substituent.

In another example, $R^4$ is aryl substituted with one $C(O)OH$ substituent.

Any and each individual definition of $R^4$ as set out herein may be combined with any and each individual definition of X, $R^1$ and $R^2$ as set out herein.

$R^5$ and $R^6$:

In one subset of compounds, $R^5$ and $R^6$ are both hydrogen.

In another subset of compounds, $R^5$ is hydrogen and $R^6$ is $C_1$-$C_6$ alkyl.

In another subset of compounds, $R^5$ is hydrogen and $R^6$ is $C_1$-$C_6$ alkyl-aryl.

In another subset of compounds, $R^5$ and $R^6$ are both $C_1$-$C_6$ alkyl.

In another subset of compounds, $R^5$ is heterocyclyl and $R^6$ is $C_1$-$C_6$ alkyl.

Any and each individual definition of $R^5$ and $R^6$ as set out herein may be combined with any and each individual definition of X, $R^1$, $R^2$ and $R^3$ as set out herein.

$R^7$

In one subset of compounds, $R^7$ is

1) CN,
2) halogen,
3) $C_1$-$C_6$ alkyl,
4) $OC_1$-$C_6$ alkyl,
5) $C(O)OC_1$-$C_6$ alkyl.
6) $C(O)C_1$-$C_6$ alkyl,
7) C(O) heteroaryl,
8) C(O)OH,
9) $C(O)NH_2$,
10) heterocyclyl,
11) heteroaryl,
12) $C(OH) C_1$-$C_6$ alkyl,
13) $C(NH_2)=NH$,
14) $C(NH_2)=N—OH$, or
15) $C(NH_2)=N—OC(O) C_1$-$C_6$ alkyl.

Any and each individual definition of $R^7$ as set out herein may be combined with any and each individual definition of X, $R^1$, $R^2$ and $R^3$ asset out herein.

$R^8$ and $R^9$:

In one subset of compounds, both $R^8$ and $R^9$ are both $C_1$-$C_6$ alkyl.

In one subset of compounds, both $R^8$ and $R^9$ are both $C_1$-$C_4$ alkyl-$C_3$-$C_6$ cycloakyl.

In an alternative subset of compounds, $R^8$ is $C_3$-$C_6$ alkyl and $R^9$ is $C_1$-$C_4$ alkyl-$C_3$-$C_6$ cycloakyl.

Any and each individual definition of $R^8$ and $R^9$ as set out herein may be combined with any and each individual definition of X, $R^1$, $R^2$ and $R^3$ as set out herein.

DEFINITIONS

Unless otherwise specified, the following definitions apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein, the term "alkyl" is intended to include both branched and straight chain saturated aliphatic hydrocarbon groups having the specified number of carbon atoms, for example, $C_1$-$C_6$ as in $C_1$-$C_6$ alkyl is defined as including groups having 1, 2, 3, 4, 5 or 6 carbons in a linear or branched arrangement. Within this definition is, for example $C_1$-$C_4$ alkyl including groups having 1, 2, 3, or 4 carbons in a linear or branched arrangement. Examples of $C_1$-$C_6$ alkyl as defined above include, but are not limited to, methyl, ethyl, n-propyl, i-propyl, n-butyl, t-butyl, i-butyl, pentyl, and hexyl. The term "alkyl" also includes $C_3$-$C_7$ alkyl which is defined as including 3, 4, 5, 6 or 7 carbons in a linear or branched arrangement.

As used herein, the term "alkenyl" is intended to mean unsaturated straight or branched chain hydrocarbon groups having the specified number of carbon atoms therein, and in which at least two of the carbon atoms are bonded to each other by a double bond, and having either E or Z regeochemistry and combinations thereof. For example, $C_2$-$C_6$ as in $C_2$-$C_6$ alkenyl is defined as including groups having 1, 2, 3, 4, 5, or 6 carbons in a linear or branched arrangement, at least two of the carbon atoms being bonded together by a double bond. Examples of $C_2$-$C_6$ alkenyl include ethenyl (vinyl), 1-propenyl, 2-propenyl, 1-butenyl and the like.

As used herein, the term "alkynyl" is intended to mean unsaturated, straight chain hydrocarbon groups having the specified number of carbon atoms therein and in which at least two carbon atoms are bonded together by a triple bond. For example $C_2$-$C_6$ as in $C_2$-$C_6$ alkynyl is defined as including groups having 2, 3, 4, 5 or 6 carbon atoms in a chain, at least two of the carbon atoms being bonded together by a triple bond. Examples of such alkynyls include ethynyl, 1-propynyl, 2-propynyl and the like.

As used herein, the term "cycloalkyl" is intended to mean a monocyclic saturated aliphatic hydrocarbon group having the specified number of carbon atoms therein, for example, $C_3$-$C_7$ as in $C_3$-$C_7$ cycloalkyl is defined as including groups having 3, 4, 5, 6, or 7 carbons in a monocyclic arrangement. Within this definition is, for example, $C_3$-$C_6$ cycloalkyl including groups having 3, 4, 5, or 6 carbons in a monocyclic arrangement. Examples of $C_3$-$C_7$ cycloalkyl as defined above include, but are not limited to, cyclopropyl, cyclobutyl, cyclopentyl, cyclohexyl and cycloheptyl.

As used herein, the term "halo" or "halogen" is intended to mean fluorine, chlorine, bromine and iodine.

As used herein, the term "haloalkyl" is intended to mean an alkyl as defined above, in which each hydrogen atom may be successively replaced by a halogen atom. Examples of haloalkyls include, but are not limited to, $CH_2F$, $CHF_2$ and $CF_3$.

As used herein, the term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The aryls may be connected to another group either at a suitable position on the cycloalkyl ring or the aromatic ring.

As used herein, the term "heteroaryl" is intended to mean a monocyclic or bicyclic ring system of up to ten atoms, wherein at least one ring is aromatic, and contains from 1 to 4 hetero atoms selected from the group consisting of O, N, and S. The heteroaryl substituent may be attached either via a ring carbon atom or one of the heteroatoms. Examples of heteroaryl groups include, but are not limited to thienyl, benzimidazolyl, benzo[b]thienyl, furyl, benzofuranyl, pyranyl, isobenzofuranyl, chromenyl, xanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, napthyridinyl, quinoxalinyl, quinazolinyl, cinnolinyl, pteridinyl, isothiazolyl, isochromanyl, chromanyl, isoxazolyl, furazanyl, indolinyl, isoindolinyl, thiazolo[4,5-b]-pyridine, and fluoroscein derivatives.

As used herein, the term "heterocycle", "heterocyclic" or "heterocyclyl" is intended to mean a 5, 6, or 7 membered non-aromatic ring system containing from 1 to 4 heteroatoms selected from the group consisting of O, N and S. Examples of heterocycles include, but are not limited to pyrrolidinyl, tetrahydrofuranyl, piperidyl, pyrrolinyl, piperazinyl, imidazolidinyl, morpholinyl, imidazolinyl, pyrazolidinyl, pyrazolinyl.

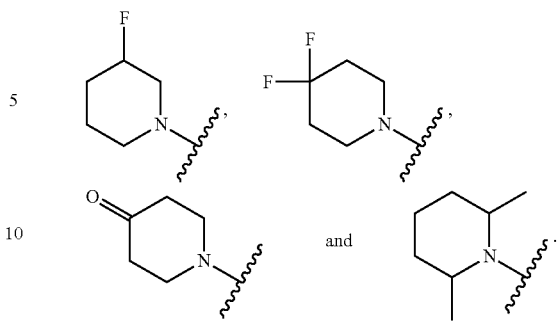

As used herein, the term "modulating the activity of melanocortin-4 receptor" is intended to mean a compound which, upon binding to the receptor, elicits a physiological response such as, but not limited to, regulation of food intake and energy expenditure. The compounds can be agonists, antagonists, partial agonists and inverse agonists. Generally, all diseases and disorders where the regulation of MC4R is involved can be treated with the compounds described herein.

As used herein, the term "detectable label" is intended to mean a group that may be linked to a compound of Formula I to produce a probe or to a melanocortin-4 receptor, such that when the probe is associated with the melanocortin-4 receptor, the label allows either direct or indirect recognition of the probe so that it may be detected, measured and quantified.

As used herein, the term "affinity tag" is intended to mean a ligand or group, which is linked to either a compound of Formula I or to a melanocortin-4 receptor to allow another compound to be extracted from a solution to which the ligand or group is attached.

As used herein, the term "probe" is intended to mean a compound of Formula I, which is labeled with either a detectable label or an affinity tag, and which is capable of binding, either covalently or non-covalently, to a melanocortin-4 receptor. When, for example, the probe is non-covalently bound, it may be displaced by a test compound. When, for example, the probe is bound covalently, it may be used to form cross-linked adducts, which may be quantified and inhibited by a test compound.

As used herein, the term "optionally substituted with one or more substituents" or its equivalent term "optionally substituted with at least one substituent" is intended to mean that the subsequently described event of circumstances may or may not occur, and that the description includes instances where the event or circumstance occurs and instances in which it does not. The definition is intended to mean from zero to five substituents.

If the substituents themselves are incompatible with the synthetic methods described herein, the substituent may be protected with a suitable protecting group (PG) that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (4th ed.), John Wiley & Sons, NY (2007), which is incorporated herein by reference in its entirety. Examples of protecting groups used throughout include, but are not limited to Fmoc, Bn, Boc, CBz and $COCF_3$. In some instances, a substituent may be specifically selected to be reactive under the reaction conditions used in the methods described herein. Under these circumstances, the reaction conditions convert the selected substituent into another substituent that is either useful in an intermediate compound in the methods described herein or is a desired substituent in a target compound.

As used herein, the term "prodrug" is intended to mean a compound that may be converted under physiological conditions or by solvolysis to a biologically active compound of Formula I. Thus, the term "prodrug" refers to a precursor of a compound of Formula I that is pharmaceutically acceptable. A prodrug may be inactive or display limited activity when administered to a subject in need thereof, but is converted in vivo to an active compound of Formula I. Typically, prodrugs are transformed in vivo to yield the compound of Formula I, for example, by hydrolysis in blood or other organs by enzymatic processing. The prodrug compound often offers advantages of solubility, tissue compatibility or delayed release in the subject (see, Bundgard, H., Design of Prodrugs (1985), pp. 7-9, 21-24 (Elsevier, Amsterdam). The definition of prodrug includes any covalently bonded carriers which release the active compound described herein in vivo when such prodrug is administered to a subject. Prodrugs of a compound of Formula I may be prepared by modifying functional groups present in the compound of Formula I in such a way that the modifications are cleaved, either in routine manipulation or in vivo, to a parent compound of Formula I.

As used herein, the term "pharmaceutically acceptable salt" is intended to mean both acid and base addition salts.

As used herein, the term "pharmaceutically acceptable acid addition salt" is intended to mean those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

As used herein, the term "pharmaceutically acceptable base addition salt" is intended to mean those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

The compounds of Formula I, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. The present is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of Formula I may exist as a mix of epimers. Epimers means diastereoisomers that have the opposite configuration at only one of two or more stereogenic centres present in the respective compound.

Certain compounds of Formula I may exist in Zwitterionic form and the present includes Zwitterionic forms of these compounds and mixtures thereof.

In addition, the compounds of Formula I also may exist in hydrated and anhydrous forms. Hydrates of the compound of any of the formulas described herein are included. In a further embodiment, the compound according to any of the formulas described herein is a monohydrate. In one embodiment, the compounds described herein comprise about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In another embodiment, the compounds described herein comprise, about 0.1% or more, about 0.5% or more, about 1% or more, about 2% or more, about 3% or more, about 4% or more, about 5% or more, or about 6% or more by weight of water.

As used herein, the term "isotopes" is intended to mean that the compounds of Formula I may exist in any isotopic composition, particularly deuterium analogs.

As used herein, the term "melanocortin-4 receptor" is intended to mean a G-protein coupled receptor encoded by the MC4R gene and that binds melanocortins, Agouti and Agouti-related protein.

As used herein, the term "therapeutically effective amount" is intended to mean an amount of a compound of Formula I which, when administered to a subject is sufficient to effect treatment for a disease-state mediated by a melanocortin-4 receptor. The amount of the compound of Formula I will vary depending on the compound, the condition and its severity, and the age of the subject to be treated, but can be determined routinely by one of ordinary skill in the art having regard to his own knowledge and to this disclosure.

As used herein, the term "treating" or "treatment" is intended to mean treatment of a disease-state mediated by a melanocortin-4 receptor, as disclosed herein, in a subject, and includes: (i) preventing a disease or condition mediated by a melanocortin-4 receptor from occurring in a subject, in particular, when such mammal is predisposed to the disease or condition but has not yet been diagnosed as having it; (ii) inhibiting a disease or condition mediated by a melanocortin-4 receptor, i.e., arresting its development; or (iii) relieving a disease/disorder or condition mediated by a melanocortin-4 receptor, i.e., causing regression of the condition.

As used herein, the term "treating obesity" is intended to mean the administration of a pharmaceutical composition described herein to a subject, preferably a human, which is afflicted with obesity to cause an alleviation of the obesity.

As used herein, the term "$IC_{50}$" is intended to mean an amount, concentration or dosage of a particular compound of Formula I that achieves a 50% inhibition of a maximal agonist response.

As used herein, the term "$EC_{50}$" is intended to mean an amount, concentration or dosage of a particular compound of Formula I that achieves a 50% of its maximal effect.

As used herein, the term "modulate" or "modulating" is intended to mean the treatment, prevention, suppression, enhancement or induction of a function or condition using the compounds as described herein. For example, the compounds as described herein can modulate melanocortin-4 receptor function in a subject, thereby altering or regulating the activity of melanocortin-4 receptor (MC4R) and consequently modifying physiological responses associated with MC4R such as, but not limited to, food intake and energy expenditure. In this context, compounds as described herein can elicit an effect useful for the treatment of cachexia, eating disorders, diabetes, metabolic diseases, erectile and/or sexual dysfunction.

3. Utilities

The compounds as described herein are useful as melanocortin-4 receptor modulating compounds and as such the compounds, compositions and methods described herein include application to the cells or subjects afflicted with or having a predisposition towards developing a particular disease state, which is mediated by a melanocortin-4 receptor. Thus, the compounds, compositions and methods are used to treat diseases/disorders, which include, but are not limited to, obesity, cachexia, eating disorders, diabetes, metabolic diseases, erectile and sexual dysfunction.

The treatment involves administration to a subject in need thereof a compound of Formula I or a pharmaceutically acceptable salt thereof, or a pharmaceutical composition comprising a pharmaceutical carrier and a therapeutically effective amount of a compound of Formula I, or a pharmaceutically acceptable salt thereof. In particular, the compounds, compositions and methods described herein are useful in the treatment of obesity, cachexia, eating disorders, diabetes, metabolic diseases, erectile and/or sexual dysfunction.

The compounds described herein, or their pharmaceutically acceptable salts or their prodrugs, may be administered in pure form or in an appropriate pharmaceutical composition, and can be carried out via any of the accepted modes of Galenic pharmaceutical practice.

The pharmaceutical compositions described herein can be prepared by mixing a compound of described herein with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral (subcutaneous injections, intravenous, intramuscular, intrasternal injection or infusion techniques), sublingual, ocular, rectal, vaginal, and intranasal. Pharmaceutical compositions described herein are formulated so as to allow the active ingredients contained therein to be bioavailable upon administration of the composition to a subject. Compositions that will be administered to a subject or patient take the form of one or more dosage units, where for example, a tablet may be a single dosage unit, and a container of a compound described herein in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound described herein, or a pharmaceutically acceptable salt thereof, for treatment of a disease-state as described above.

A pharmaceutical composition described herein may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example inhalatory administration.

For oral administration, the pharmaceutical composition is typically in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil such as soybean or vegetable oil.

The pharmaceutical composition may be in the form of a liquid, e.g., an elixir, syrup, solution, emulsion or suspension. The liquid may be for oral administration or for delivery by injection, as two examples. When used for oral administration, a typical composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions described herein, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; encapsulating agents such as cyclodextrins or functionalized cyclodextrins, including, but not limited to, α, β or δ-hydroxypropylcyclodextrins or Captisol; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is typically sterile.

A liquid pharmaceutical composition may be used for either parenteral or oral administration should contain an amount of a compound described herein such that a suitable dosage will be obtained. Typically, this amount is at least 0.01% of a compound described herein in the composition. When intended for oral administration, this amount may be varied to be between 0.1 and about 70% of the weight of the composition. For parenteral usage, compositions and preparations described herein are prepared so that a parenteral dosage unit contains between 0.01 to 10% by weight of the compound described herein. Pharmaceutical compositions may be further diluted at the time of administration; for example a parenteral formulation may be further diluted with a sterile, isotonic solution for injection such as 0.9% saline, 5 wt % dextrose (D5W), Ringer's solution, or others.

The pharmaceutical composition described herein may be used for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound described herein from about 0.1 to about 10% w/v (weight per unit volume).

The pharmaceutical composition described herein may be used for rectal administration of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition described herein may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition described herein in solid or liquid form may include an agent that binds to the compound described herein and thereby assists in the delivery of the compound. Suitable agents that may act in this capacity include, but are not limited to, a monoclonal or polyclonal antibody, a protein or a liposome.

The pharmaceutical composition described herein may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds described herein may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions described herein may be prepared by methodology well known in the pharmaceutical art. For example, a pharmaceutical composition intended to be administered by injection can be prepared by mixing a compound described herein with sterile, distilled water so as to form a solution. A surfactant may be added to facilitate the formation of a homogeneous solution or suspension. Surfactants are compounds that non-covalently interact with the compound described herein so as to facilitate dissolution or homogeneous suspension of the compound in the aqueous delivery system.

The compounds described herein, or their pharmaceutically acceptable salts, may be administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose may be from about 0.1 mg to about 40 mg/kg of body weight per day or twice per day of a compound described herein, or a pharmaceutically acceptable salt thereof.

4. Screening Assays

The compounds described herein may also be used in a method to screen for other compounds that bind to a melanocortin-4 receptor. Generally speaking, to use the compounds described herein in a method of identifying compounds that bind to a melanocortin-4 receptor, the receptor is bound to a support, and a compound described herein is added to the assay. Alternatively, the compound may be bound to the support and the receptor is added.

There are a number of ways in which to determine the binding of a compound described herein to the melanocortin-4 receptor. In one way, the compound, for example, may be fluorescently or radioactively labeled and binding determined directly. For example, this may be done by attaching the receptor to a solid support, adding a detectably labeled compound, washing off excess reagent, and determining whether the amount of the detectable label is that present on the solid support. Numerous blocking and washing steps may be used, which are known to those skilled in the art.

In some cases, only one of the components is labeled. For example, specific residues in the receptor may be labeled. Alternatively, more than one component may be labeled with different labels; for example, using $^{125}$I for the receptor, and a fluorescent label for the probe.

The compounds described herein may also be used as competitors to screen for additional drug candidates or test compounds. As used herein, the terms "drug candidate" or "test compounds" are used interchangeably and describe any molecule, for example, protein, oligopeptide, small organic molecule, polysaccharide, polynucleotide, and the like, to be tested for bioactivity. The compounds may be capable of directly or indirectly altering the melanocortin-4 receptor biological activity.

Drug candidates can include various chemical classes, although typically they are small organic molecules having a molecular weight of more than 100 and less than about 2,500 Daltons. Candidate agents typically include functional groups necessary for structural interaction with proteins, for example, hydrogen bonding and lipophilic binding, and typically include at least an amine, carbonyl, hydroxyl, ether, or carboxyl group. The drug candidates often include cyclical carbon or heterocyclic structures and/or aromatic or polyaromatic structures substituted with one or more functional groups.

Drug candidates can be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Competitive screening assays may be done by combining a melanocortin-4 receptor and a probe to form a probe: receptor complex in a first sample followed by adding a test compound from a second sample. The binding of the test is determined, and a change or difference in binding between the two samples indicates the presence of a test compound capable of binding to the receptor and potentially modulating the receptor's activity.

In one case, the binding of the test compound is determined through the use of competitive binding assays. In this example, the probe is labeled with a fluorescent label. Under certain circumstances, there may be competitive binding between the test compound and the probe. Test compounds which display the probe, resulting in a change in fluorescence as compared to control, are considered to bind to the melanocortin-4 receptor.

In one case, the test compound may be labeled. Either the test compound, or a compound described herein, or both, is added first to the melanocortin-4 receptor for a time sufficient to allow binding to form a complex.

Formation of the probe:receptor complex typically require incubations of between 4° C. and 40° C. for between 10 minutes to about 1 hour to allow for high-throughput screening. Any excess of reagents are generally removed or washed away. The test compound is then added, and the presence or absence of the labeled component is followed, to indicate binding to the receptor.

In one case, the probe is added first, followed by the test compound. Displacement of the probe is an indication the test compound is binding to the melanocortin-4 receptor and thus is capable of binding to, and potentially modulating, the activity of the receptor. Either component can be labeled. For example, the presence of a probe in the wash solution indicates displacement by the test compound. Alternatively, if the test compound is labeled, the presence of the probe on the support indicates displacement.

In one case, the test compound may be added first, with incubation and washing, followed by the probe. The absence of binding by the probe may indicate the test compound is bound to the melanocortin-4 receptor with a higher affinity. Thus, if the probe is detected on the support, coupled with a lack of test compound binding, may indicate the test compound is capable of binding to the receptor.

Modulation is tested by screening for a test compound's ability to modulate the activity of melanocortin-4 receptor and includes combining a test compound with the receptor, as described above, and determining an alteration in the biological activity of the receptor. Therefore in this case, the test compound should both bind to the receptor (although this may not be necessary), and after its biological activity as defined herein.

Positive controls and negative controls may be used in the assays. All control and test samples are performed multiple times to obtain statistically significant results. Following incubation, all samples are washed free of non-specifically bound material and the amount of bound probe determined. For example, where a radiolabel is employed, the samples may be counted in a scintillation counter to determine the amount of bound compound.

Typically, the signals that are detected in the assay may include fluorescence, resonance energy transfer, time resolved fluorescence, radioactivity, fluorescence polarization, plasma resonance, or chemiluminescence and the like, depending on the nature of the label. Detectable labels useful in performing screening assays described herein include a fluorescent label such as Fluorescein, Oregon green, dansyl, rhodamine, tetramethyl rhodamine, Texas Red, $Eu^{3+}$; a chemiluminescent label such as luciferase; colorimetric labels; enzymatic markers; or radioisotopes such as tritium, $I^{125}$ and the like Affinity tags, which may be useful in performing the screening assay described herein include biotin, polyhistidine and the like.

Synthesis and Methodology

General methods for the synthesis of the compounds are shown below and are disclosed merely for the purpose of illustration and are not meant to be interpreted as limiting the processes to make the compounds by any other methods. Those skilled in the art will appreciate that a number of methods are available for the preparation of compounds described herein.

Schemes 1 to 8 illustrate general synthetic procedures for the preparation of compounds described herein. Scheme 1 describes a general synthetic approach to the compounds 1-ix and 1-x as described herein. Ketone 1-iii is obtained by treatment of a 2-methyl pyridine compound 1-i and an alkyl benzoate 1-ii in the presence of a base such as lithium bis(trimethylsilyl)amide. Other methods known by those skilled in the art such as, but not limited to, the one described in *Org. Synth.* 2009, 86, 18 can be used to afford compounds related to 1-iii. Oxime intermediate 1-iv can be obtained by treating ketone 1-iii with hydroxylamine-hydrochloride in the presence of a base. Treatment of oxime 1-iv with trifluoroacetic anhydride in the presence of a base such as triethylamine affords the azirine intermediate 1-v which is converted to the pyrazolopyridine 1-vi upon heating in a microwave reactor using 1,2-dichloroethane as solvent in the presence of a base. Failure to add a base such as N,N-diisopropylethylamine in the conversion of 1-v to 1-vi typically results in bromide to chloride scrambling involving the participation of the solvent. It should be noted that other non-chlorinated solvents were found sub-optimal for this reaction. The reference cited above (i.e. *Org. Synth.* 2009, 86, 18) also describes a similar sequence to the one used herein for the preparation of pyrazolo[1,5-a]pyridines 1-vi from 1-iii (this reference provides examples of compounds with different substitution patterns by comparison to the compounds as described herein. Side-chain introduction leading to 1-vii can be accomplished with reagents such as (E)-3-dimethylamino acrylaldehyde and phosphoryl chloride. Other methods such as, but not limited to, Organic Process Research & Development 2008, 12, 178 can also be used. Compounds 1-viii are finally obtained by treatment of aldehydes 1-vii with amine nucleophiles $T^2H$ and a reducing reagent such as sodium triacetoxyborohydride. Various carbonylation methods known by those skilled in the art can be used to convert 1-viii into 1-ix which can be hydrogenated under standard conditions to provide 1-x. The compounds 1-x can be obtained from olefinic compounds 1-ix using alternative reduction methods such as diimide reduction or treatment with triethylsilane/trifluoroacetic acid.

This is required when, for example, the $R^7$ substituent in olefins 1-ix is reactive to the standard hydrogenation reaction conditions (e.g when $R^7$ is bromide or chloride). Alternatively the alkyl benzoate 1-ii can be replaced by an alkyl acetate such as methyl tert-butylacetate and, following the same reaction sequence, compound 1-x in which the phenyl group is replaced by a t-butyl is obtained.

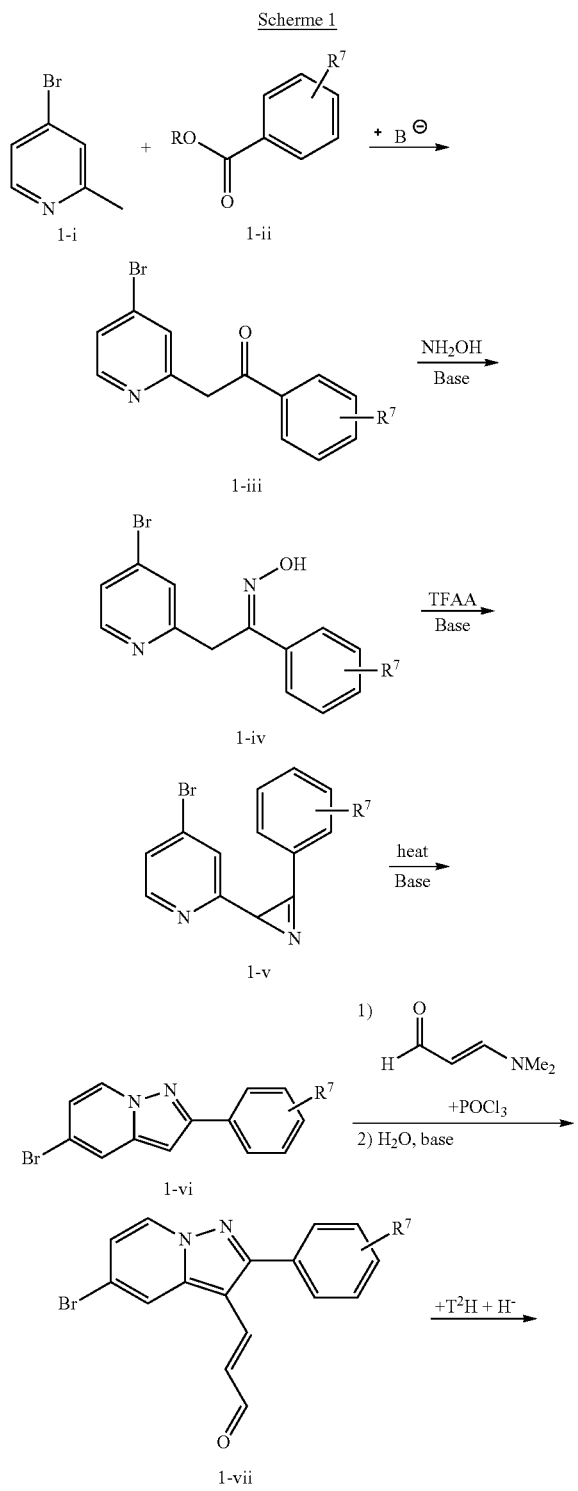

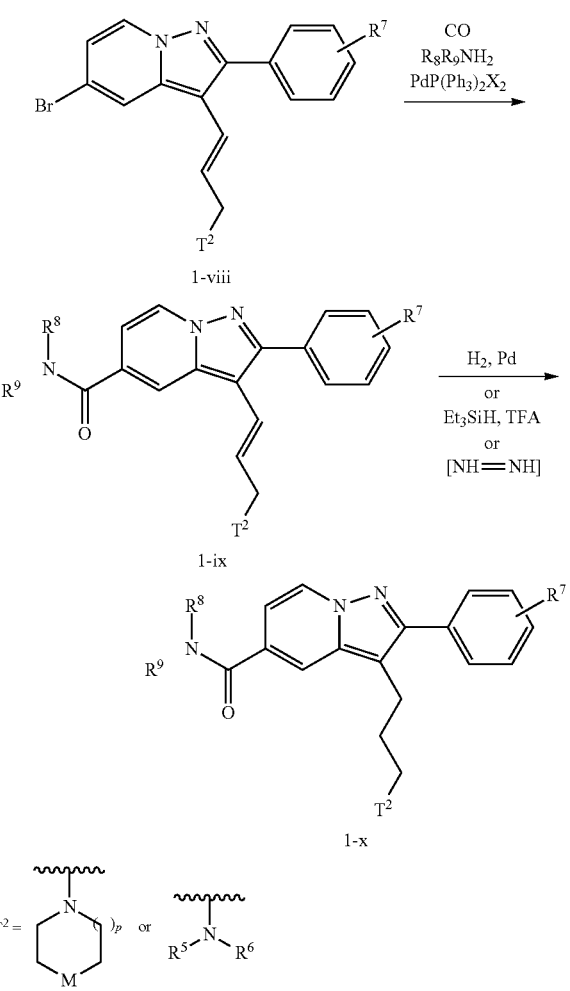

Scheme 2 describes another general synthetic approach to the compounds as described herein. Compounds 2-vii are prepared by the following sequence. Intermediates 2-i and 2-ii are reacted under the conditions described by A. B. Charette et. al in Organic Letters 2010, 12, 516 to provide the pyrazolopyridine compounds 2-iii. Simple methods known by those skilled in the art are used to introduce the amide side-chain in 2-iv from the ester 2-iii (R=alkyl). As described above in Scheme 1, side-chain introduction leading to 2-v can be accomplished with reagents such as (E)-3-dimethylamino acrylaldehyde and phosphoryl chloride. Compounds 2-vi are finally obtained by treatment of aldehydes 2-v with an amine nucleophiles ($T^2H$) and a reducing reagent such as sodium triacetoxyborohydride. The resulting compound 2-vi can be hydrogenated under standard conditions to provide 2-vii. The compounds 2-vii can be obtained using alternative methods such as diimide reduction when, for example, the $R^4$ substituent is reactive to the hydrogenation conditions. A subset of compounds, namely the bromides 2-vi ($R^7$=Br) can be reacted with tin reagent 2-viii in the presence of a palladium catalyst such as palladium tetrakis(triphenylphosphine) to afford, after hydrolysis, the methyl ketone 2-x. Similarly, a methyl ester 2-ix can be obtained from 2-vi ($R^7$=Br) with palladium catalyst such as palladium tetrakis(triphenylphosphine) and carbon monoxide in the presence of methanol.

Scheme 2
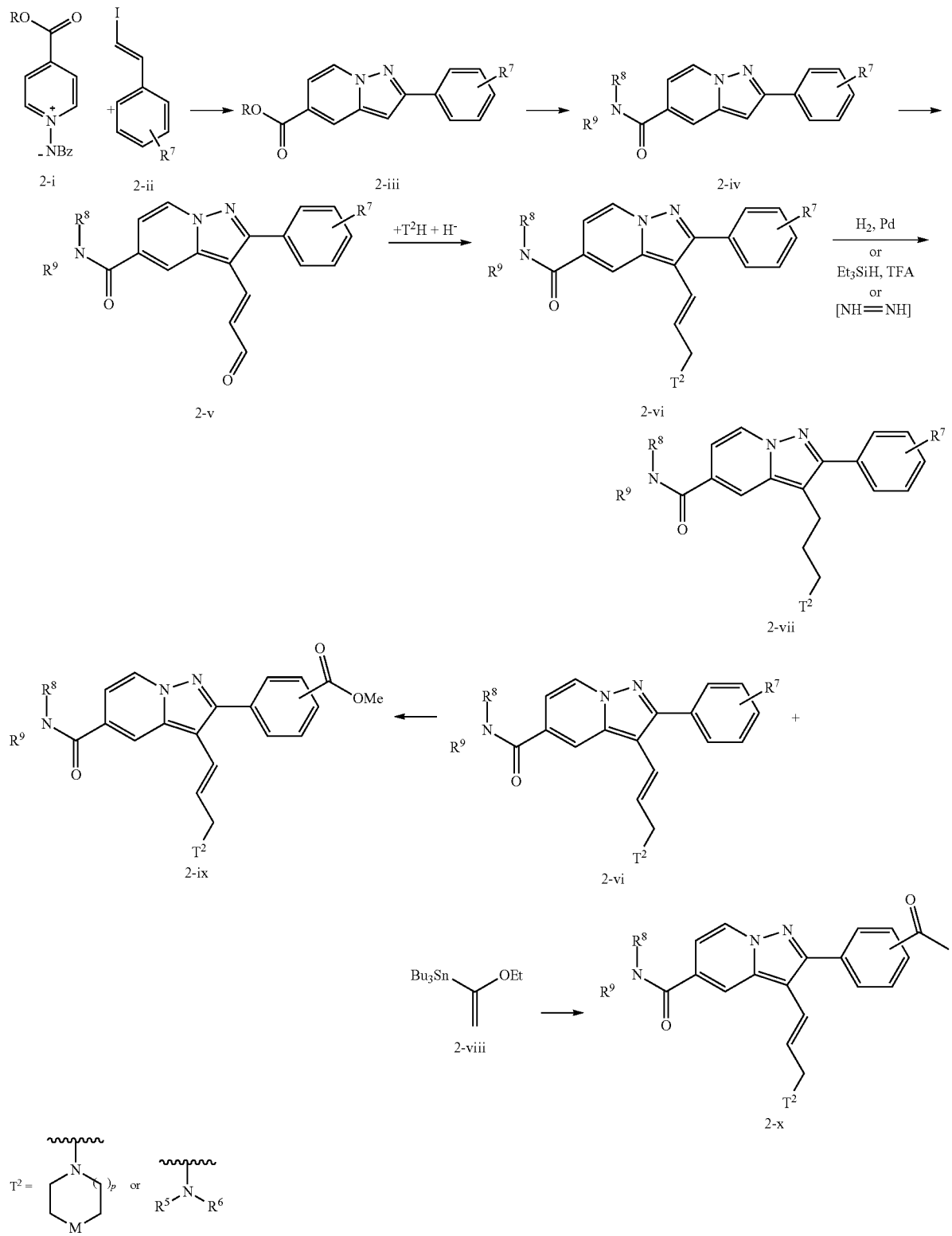
Scheme 3 describes another general synthetic approach to the pyrimidine compounds 3-xi and 3-xii described herein. First, the 3-aminopyrazole derivatives 3-iii are obtained via the condensation of ketonitriles 3-i and hydrazine (3-ii). According to a related procedure described in Journal of Medicinal Chemistry 1977, 20, 296, aminopyrazoles 3-iii are then treated with acetylenedicarboxylate 3-iv to provide compounds 3-v. Phosphoryl chloride (3-vi) is then used to convert the alcohols 3-v to chlorides 3-vii and a catalytic hydrogenation on the latter, under standard conditions, allows the formation of pyrazolopyrimidine 3-viii. As described for the preparation of intermediate 2-iv above, standard procedures are used to convert the alkyl ester 3-viii to the amides 3-ix. Similarly, procedures similar to those described above were used to prepare compounds 3-x and compounds as described herein 3-xi and 3-xii.

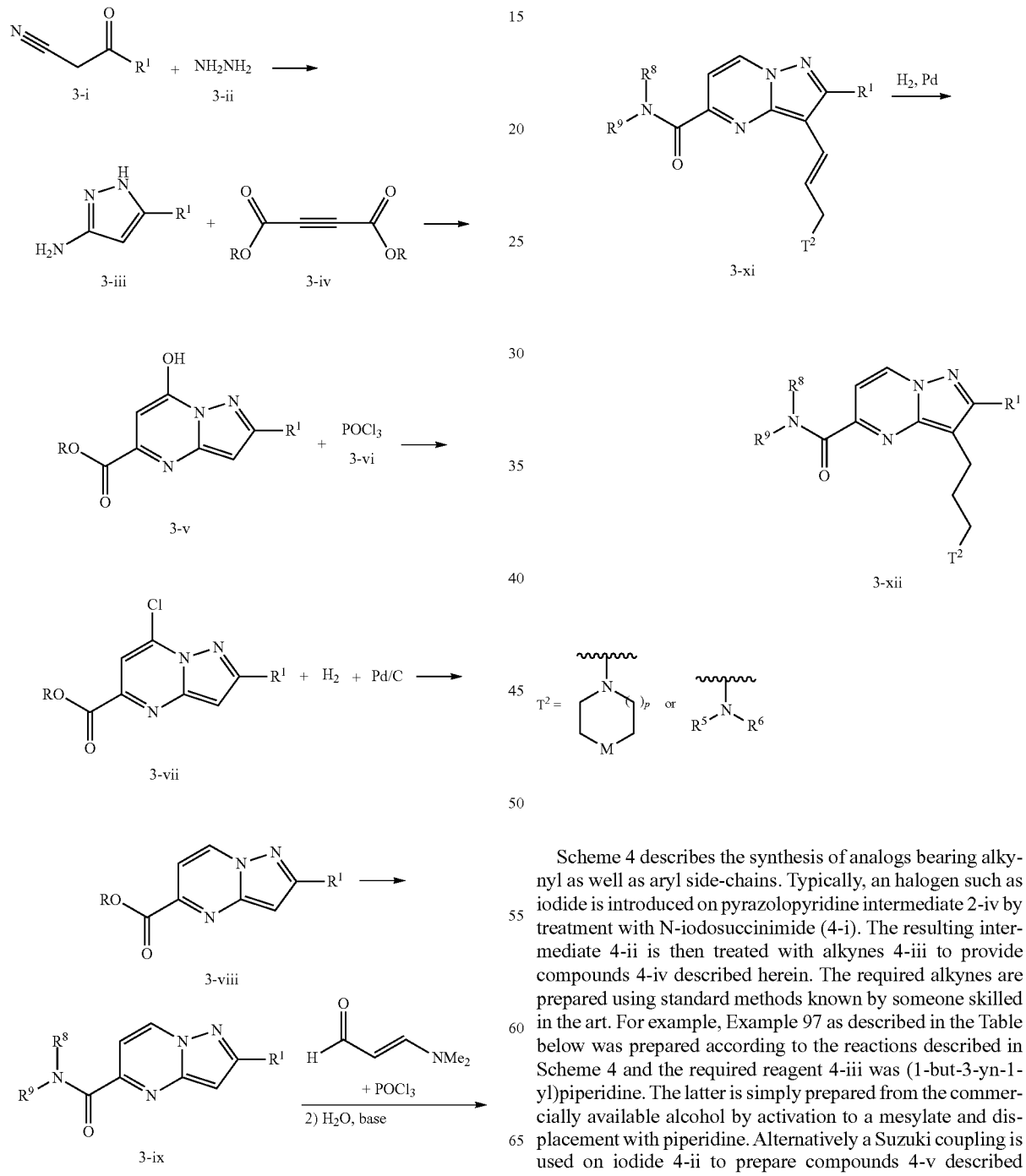

Scheme 4 describes the synthesis of analogs bearing alkynyl as well as aryl side-chains. Typically, an halogen such as iodide is introduced on pyrazolopyridine intermediate 2-iv by treatment with N-iodosuccinimide (4-i). The resulting intermediate 4-ii is then treated with alkynes 4-iii to provide compounds 4-iv described herein. The required alkynes are prepared using standard methods known by someone skilled in the art. For example, Example 97 as described in the Table below was prepared according to the reactions described in Scheme 4 and the required reagent 4-iii was (1-but-3-yn-1-yl)piperidine. The latter is simply prepared from the commercially available alcohol by activation to a mesylate and displacement with piperidine. Alternatively a Suzuki coupling is used on iodide 4-ii to prepare compounds 4-v described herein.

Scheme 4

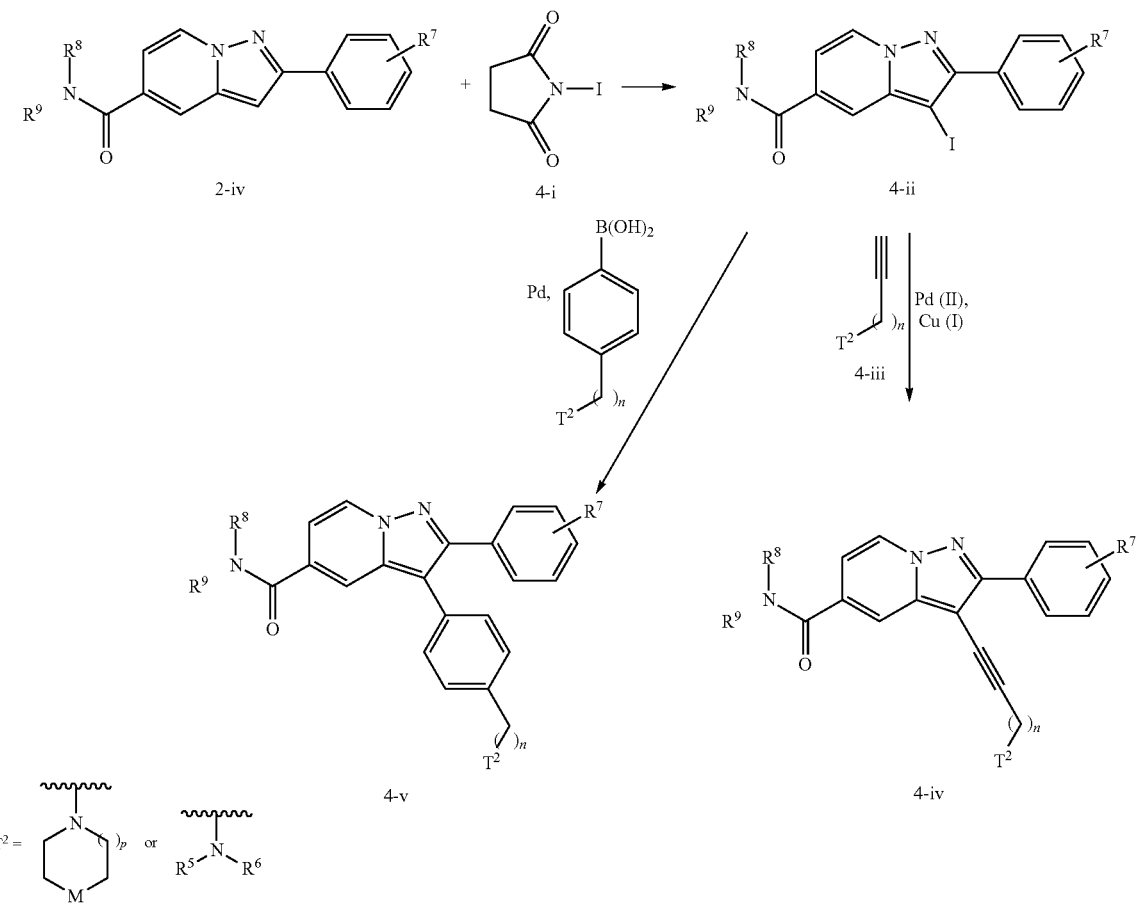

Schemes 5-7 describe the synthesis of analogs of the compounds as described herein that do not bear a substituted aryl attached to the pyrazolopyridine ring. The first step in Scheme 5 involves a reaction described in the literature (e.g J. Med. Chem. 2001, 44, 2691) where the N-aminopyridinium intermediates 5-i is reacted with alkyne dicarboxylates 5-ii to provide the diester intermediates 5-iii. Upon treatment in hot aqueous acid, the decarboxylated analogs 5-iv are obtained. Methods known by those skilled in the art are used to functionalize the carboxylic acid such as, for example, the formation of amide 5-v on which the side chain is introduced using the same methods described for Schemes 1-3 to provide the compounds 5-vi as described herein.

Scheme 5

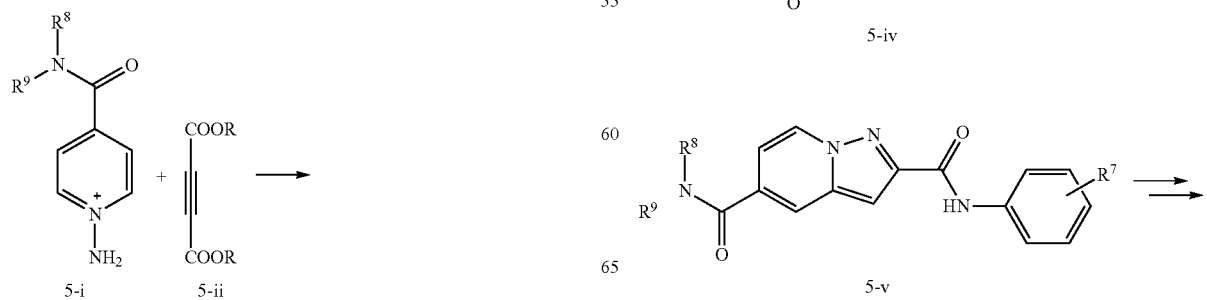

-continued

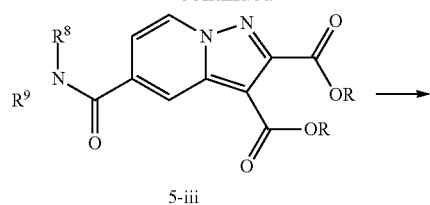

5-iii

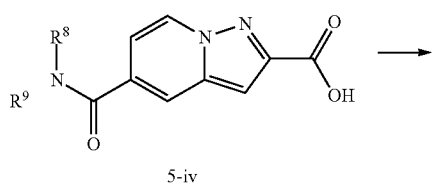

5-iv

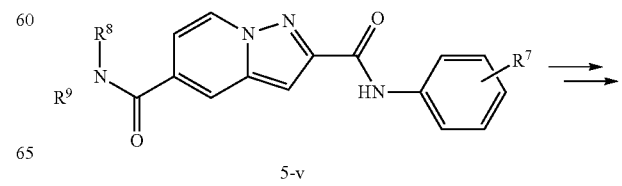

5-v

-continued

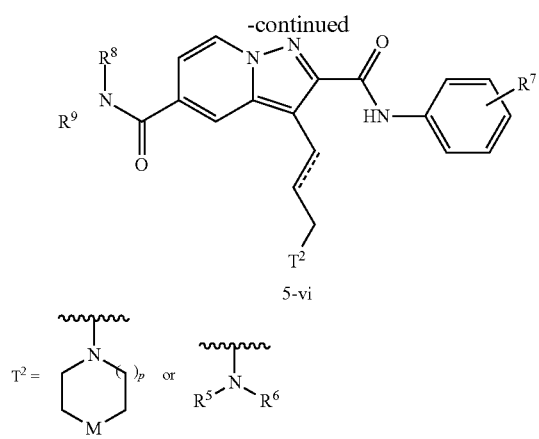

5-vi

Scheme 6 describes the synthesis of the bromo intermediates 6-iv. The N-aminopyridinium intermediate 5-i is treated with an alkyl bromopropiolate 6-i to afford bromide intermediates 6-ii in low yield. The alkyl ester 6-ii is then hydrolyzed to the carboxylic acid 6-iii with an alkoxide such as lithium alkoxide. Upon heating, intermediates 6-iii are decarboxylated to intermediates 6-iv. The side chain can be introduced as above to provide the olefinic compounds as described herein 6-v. Alternatively, the bromo intermediates 6-iv can be aminated with anilines 6-vi using methods known by those skilled in the art such as, but not limited to, the Buchwald reaction conditions. Side-chain introduction proceeds as above to provide compounds 6-viii as described herein. The common intermediates 6-iv can also be involved in a Suzuki-type coupling with Pd catalyst to produce intermediates 6-ix which are derived as above to the compounds 6-x as described herein.

Scheme 6

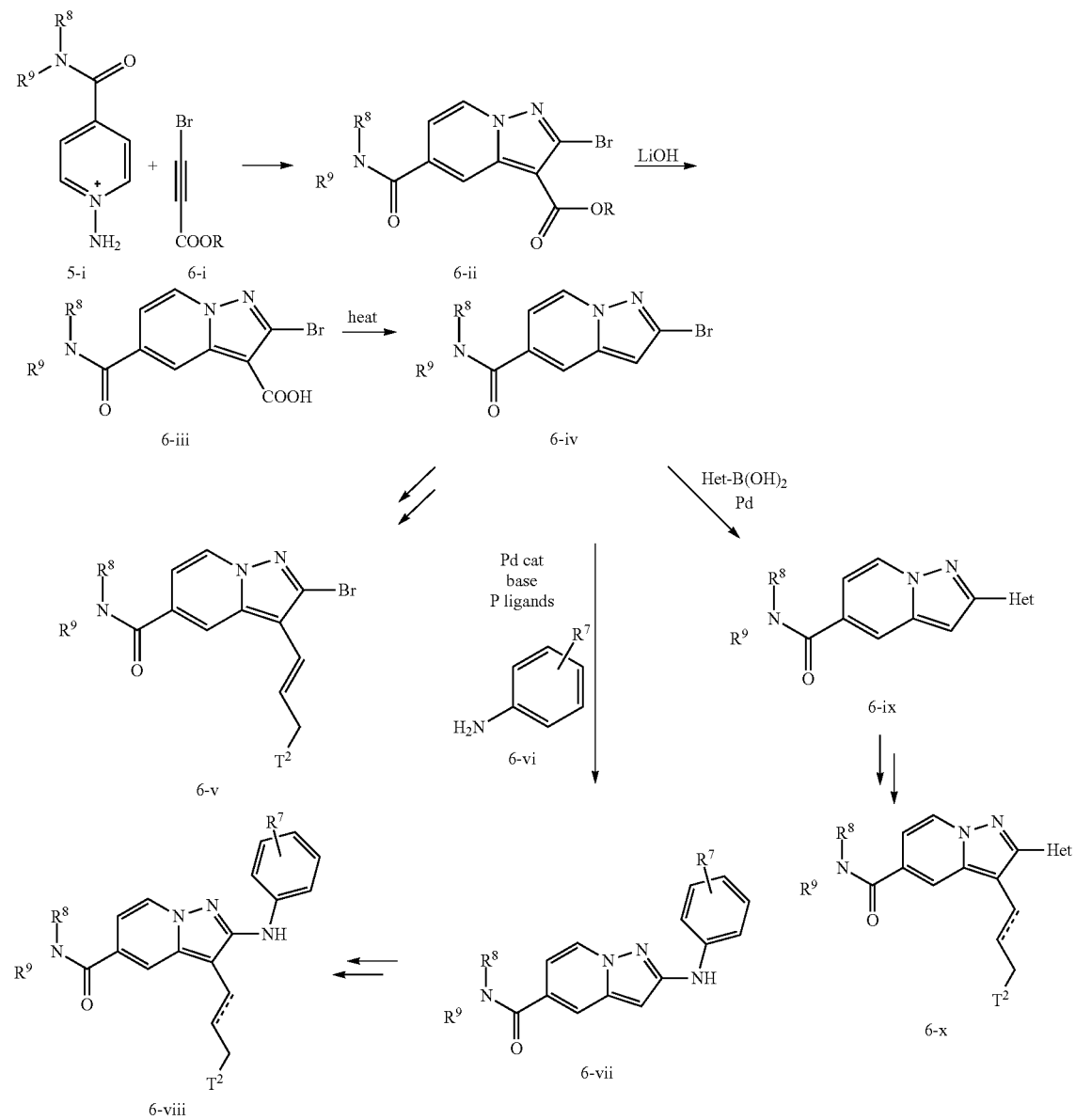

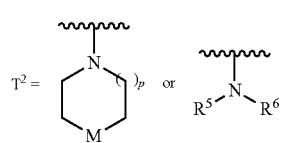

In Scheme 7, a Pd-catalyzed amination is carried out with intermediates 6-ii and 6-vi. The resulting products 7-i are then hydrolyzed to intermediates 7-ii which are transformed to the compounds 7-iii as described herein by using a standard peptide-type coupling procedure known by those skilled in the art.

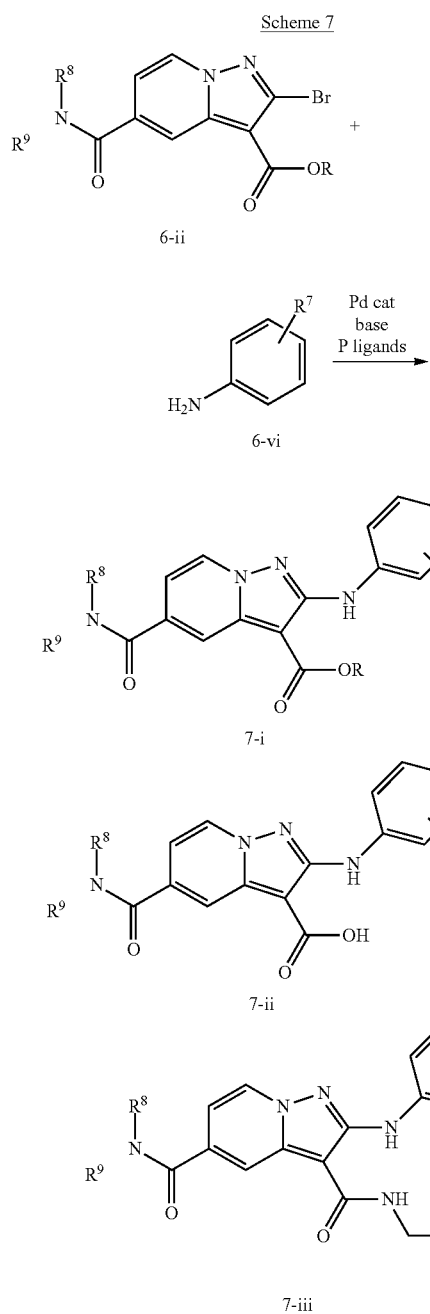

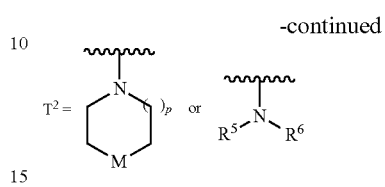

Scheme 8 describes the synthesis of compounds as described herein with other variations at the $R^3$ group (in structure IA). Thus, as an alternative to the carbonylation procedure described in Scheme 1, the intermediate 1-viii is subjected to an amination procedure to yield 8-i which can be reduced to compounds 8-ii as described above. Alternatively, compounds 8-iii are prepared by first treating intermediates 1-x with a reagent such as oxalyl chloride followed by the addition of nucleophiles such as, but not limited to, ammonia, methylamine and the sodium salt of hydrogen sulfide. Intermediates 1-x, after activation with oxalyl chloride, can be treated with an hydride source to provide the benzylic amines 8-iv of the present invention.

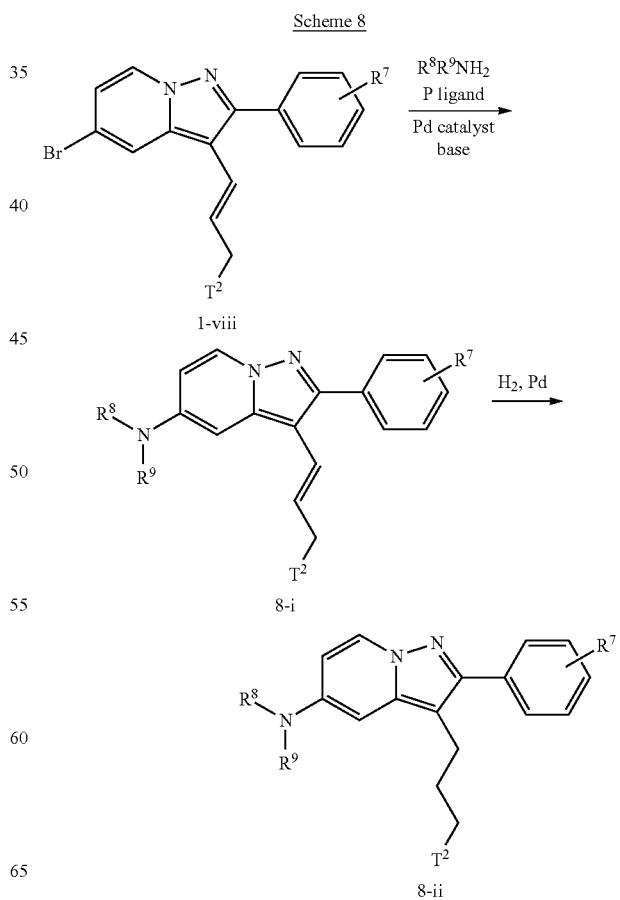

57
-continued

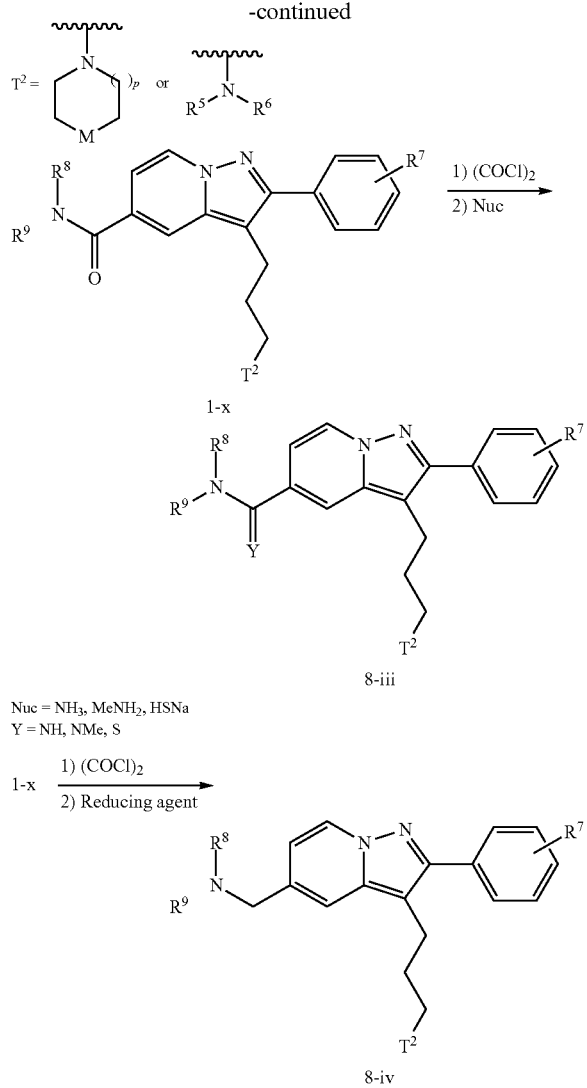

Nuc = NH₃, MeNH₂, HSNa
Y = NH, NMe, S

EXAMPLES

General

Analytical Reverse-Phase-HPLC Method:
  Solvent A: MeOH:H₂O:TFA (5:95:0.05)
  Solvent B: MeOH:H₂O:TFA (95:5:0.05)
  Flow: 3.0 mL/min.
  Gradient 0 to 100% B in 2.0 min.
  Column: ZorbaxC18, 3.5 microns, 4.6×30 mm
  Wavelength 220 nm
LC-MS Method:
  Solvent A: AcCN:H₂O:HCOOH (5:95:0.05)
  Solvent B: AcCN:H₂O:HCOOH (95:5:0.05)
  Gradient 0 to 100% B in 2.0 min.
  Flow: 0.3 mL/min
  Column: ZorbaxC18, 3.5 microns, 2.1×30 mm
  Wavelength 220 nm

58

EXPERIMENTAL PROCEDURES

Example 1

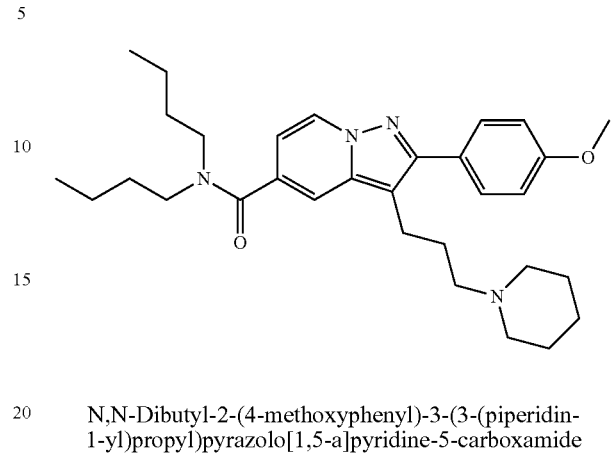

N,N-Dibutyl-2-(4-methoxyphenyl)-3-(3-(piperidin-1-yl)propyl)pyrazolo[1,5-a]pyridine-5-carboxamide Intermediate 1A

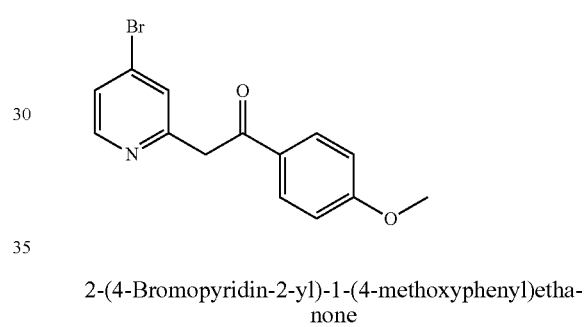

2-(4-Bromopyridin-2-yl)-1-(4-methoxyphenyl)ethanone

To a stirred solution of 4-bromo-2-methylpyridine (2.9 g, 16.8 mmol) and methyl 4-methoxybenzoate (2.8 g, 16.8 mmol) in tetrahydrofuran (42 mL) at 0° C. was added dropwise a 1M solution of lithium bis(trimethylsilyl)amide (33.6 mL, 33.6 mmol). The mixture was allowed to warm to room temperature and stirred for 3 days. A saturated solution of ammonium chloride (40 mL) was added and the mixture was diluted with ethyl acetate (50 mL). The separated aqueous layer was then extracted with ethyl acetate (3×25 mL). The combined organic layers were washed with brine, dried over anhydrous MgSO₄, filtered and concentrated under reduced pressure to afford a residue which was purified by automated flash-chromatography (ethyl acetate/hexanes; 15/85). The title compound was obtained as a bright yellow solid (3.8 g, 75%). LCMS m/z 306.0; 308.0 (M+H)⁺, ret. time=2.48 min.

Intermediate 1B

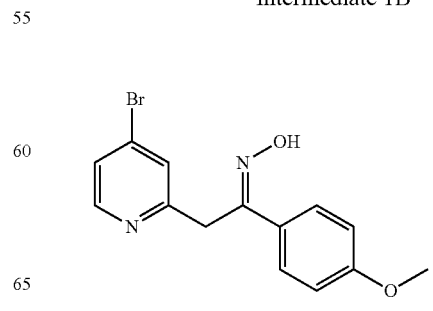

(Z)-2-(4-Bromopyridin-2-yl)-1-(4-methoxyphenyl) ethanone oxime

To a stirred solution of 2-(4-bromopyridin-2-yl)-1-(4-methoxyphenyl)ethanone (3.8 g, 12.4 mmol) and N,N-diisopropylethylamine (5.4 mL, 31 mmol) in methanol (60 mL) at room temperature was added hydroxylamine hydrochloride (1.7 g, 24.8 mmol). The mixture was stirred at 60° C. for 2 days. After cooling to room temperature, the precipitate formed was filtered and dried under vacuum to afford white needles (2.7 g, 68%). The material was used as is in the next step. LCMS m/z 321.0; 323.0 (M+H)+, ret. time=2.37 min.

Intermediate 1C

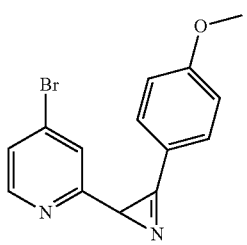 [SMILES: COc1ccc(C2=NC2c2cc(Br)ccn2)cc1]

4-Bromo-2-(3-(4-methoxyphenyl)-2H-azirin-2-yl) pyridine

To a stirred solution of (Z)-2-(4-bromopyridin-2-yl)-1-(4-methoxyphenyl)ethanone oxime (2.7 g, 8.4 mmol) and triethylamine (4.7 mL, 33.6 mmol) in dichloromethane at 0° C., was added trifluoroacetic anhydride (1.3 mL, 9.2 mmol). The mixture was stirred at 0° C. for 20 minutes then at room temperature for 5 hours. A saturated solution of ammonium chloride (20 mL) was added and the mixture was diluted with dichloromethane (20 mL). The separated aqueous layer was extracted with dichloromethane (3×25 mL). The combined organic layers were washed with brine, dried over anhydrous MgSO4, filtered and concentrated under reduced pressure to afford a residue which was purified by automated flash-chromatography (ethyl acetate/hexanes; 5/95). The title compound was obtained as a colorless solid (2.1 g, 83%); LCMS m/z 303.0, 305.0 (M+H)+, ret. time 2.57 min.

Intermediate 1D

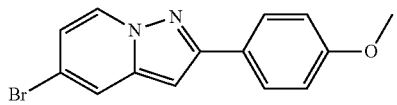 [SMILES: COc1ccc(-c2cc3cc(Br)ccn3n2)cc1]

5-Bromo-2-(4-methoxyphenyl)pyrazolo[1,5-a]pyridine

In a 20 mL microwave reactor was placed a solution of 4-bromo-2-(3-(4-methoxyphenyl)-2H-azirin-2-yl)pyridine (1.3 g, 4.3 mmol) and N,N-diisopropylethylamine (375 µL, 2.2 mmol) in 1,2-dichloroethane (10 mL). The mixture was heated to 175° C. for 1 hour. The cooled mixture afforded a precipitate which was filtered and dried under reduced pressure to afford the title compound as a white solid (910 mg, 70%). LCMS m/z 303.0, 305.0 (M+H)+, ret. time=2.88 min.

Intermediate 1E

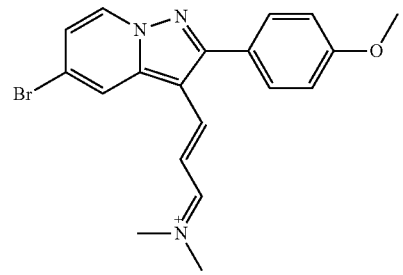

(E)-N-(3-(5-Bromo-2-(4-methoxyphenyl)pyrazolo[1,5-a]pyridin-3-yl)allylidene)-N-methylmethanaminium At 0° C., phosphoryl chloride (390 µL, 4.2 mmol) was added to a solution of (E)-3-(dimethylamino)acrylaldehyde (420 µL, 4.2 mmol) in 1,2-dichloroethane (5 mL) under a stream on nitrogen gas. After 5 minutes at 0° C., a solution of 5-bromo-2-(4-methoxyphenyl)pyrazolo[1,5-a]pyridine (640 mg, 2.1 mmol) in 1,2-dichloroethane (5 mL) was added and the ice bath was removed. The mixture was heated to 65° C. for 2.5 h at which time monitoring the reaction by LC indicated all starting material had converted to the title compound. Upon cooling to room temperature, addition of water resulted in the formation of a precipitate which was filtered and dried under reduced pressure to afford the title compound as a solid (470 mg, 57%). LCMS m/z 384.1, 386.1 M+, ret. time=2.17 min.

Intermediate 1F

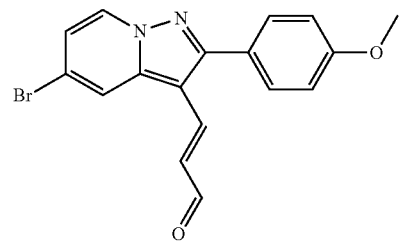 [SMILES: COc1ccc(-c2nn3ccc(Br)cc3c2/C=C/C=O)cc1]

(E)-3-(5-Bromo-2-(4-methoxyphenyl)pyrazolo[1,5-a]pyridin-3-yl)acrylaldehyde

To a stirred solution of (E)-N-(3-(5-bromo-2-(4-methoxyphenyl)pyrazolo[1,5-a]pyridin-3-yl)allylidene)-N-methylmethanaminium (470 mg, 1.22 mmol) in methanol (5 mL) was added a 15% solution of potassium bicarbonate (5 mL) and the mixture was stirred at room temperature for 1 h. Water was added and methanol was evaporated under reduced pressure. Filtration of the precipitate afforded 322 mg of the title compound. LCMS m/z 357.0, 359.0 (M+H)+, ret. time=2.70 min.

Intermediate 1G

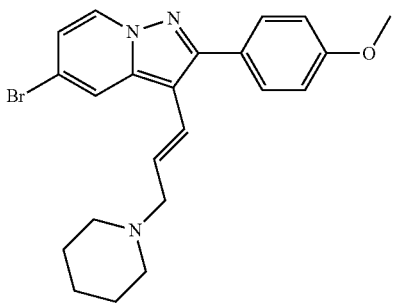 [SMILES: COc1ccc(-c2nn3ccc(Br)cc3c2/C=C/CN2CCCCC2)cc1]

(E)-5-Bromo-2-(4-methoxyphenyl)-3-(3-(piperidin-1-yl)prop-1-enyl)pyrazolo[1,5-a]pyridine To a mixture of (E)-3-(5-bromo-2-(4-methoxyphenyl) pyrazolo[1,5-a]pyridin-3-yl)acrylaldehyde (385 mg, 1.1 mmol) and piperidine (160 µL, 1.6 mmol) in 1,2-dichloroethane (5 mL) was added sodium triacetoxyborohydride (340 mg, 1.6 mmol). The mixture and stirred at r.t for 2.5 h and a saturated solution of ammonium chloride (10 mL) was added. The separated aqueous layer was then extracted with dichloromethane (3×25 mL). The combined organic layers were washed with brine, dried over anhydrous $MgSO_4$, filtered and concentrated under reduced pressure to afford a residue which was purified by automated flash-chromatography (methanol/dichloromethane; 15/85). The title compound was obtained as a bright yellow solid (354 mg, 77%). LCMS m/z 426.1; 428.1 (weak) $(M+H)^+$341.0; 343.0 (strong), ret time=2.15 min.

Intermediate 1H

Example 12

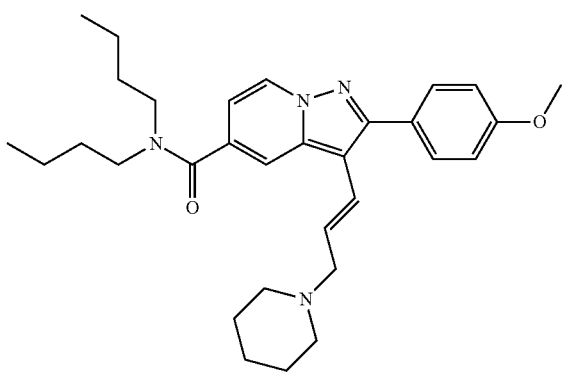 [SMILES: CCCCN(CCCC)C(=O)c1ccn2nc(-c3ccc(OC)cc3)c(/C=C/CN3CCCCC3)c2c1]

(E)-N,N-Dibutyl-2-(4-methoxyphenyl)-3-(3-(piperidin-1-yl)prop-1-enyl)pyrazolo[1,5-a]pyridine-5-carboxamide At room temperature in a 15-mL resealable vial, carbon monoxide was bubbled for 5 min. through a solution of (E)-5-bromo-2-(4-methoxyphenyl)-3-(3-(piperidin-1-yl)prop-1-enyl)pyrazolo[1,5-a]pyridine (137 mg, 0.32 mmol), N,N-di-n-butylamine (215 µL, 1.3 mmol) and triethylamine (0.5 mL) in toluene (2.5 mL). Palladium bis(triphenylphosphine) dichloride (2 mg) was then added and carbon monoxide was bubbled for an additional 5 min. at which time the vial was sealed and heated to 100° C. The mixture was heated to 100° C. for 12 h., cooled to room temperature and evaporated under reduced pressure. The residue was dissolved in DMF, filtered and purified by RP-HPLC with 30% Solvent B (0-3 min) then a gradient 30% to 100% Solvent B over 11 minutes (Solvent A: $MeOH:H_2O:TFA$ (5:95:0.05); Solvent B: $MeOH:H_2O$:TFA (95:5:0.05)) to afford, after freeze-drying overnight, 85 mg (50%) of the title compound as the TFA salt. LCMS m/z 503.3 (weak) $(M+H)^+$, and 418.3 (strong). ret time=2.30 min.

Example 1

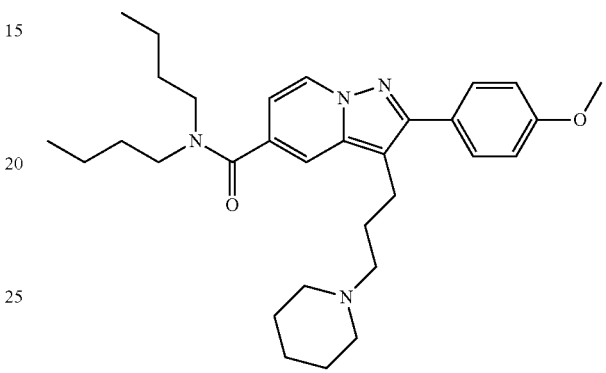

N,N-Dibutyl-2-(4-methoxyphenyl)-3-(3-(piperidin-1-yl)propyl)pyrazolo[1,5-a]pyridine-5-carboxamide A mixture of (E)-N,N-dibutyl-2-(4-methoxyphenyl)-3-(3-(piperidin-1-yl)prop-1-enyl)pyrazolo[1,5-a]pyridine-5-carboxamide (75 mg, 0.15 mmol) and 10% palladium on charcoal (7 mg) in a 1:1 mixture of methanol:ethyl acetate was vigorously stirred under an atmosphere of hydrogen for 12 h. The mixture was filtered through Celite and evaporated under reduced pressure. The residue was dissolved in N,N-dimethylformamide, filtered and purified by RP-HPLC with 30% Solvent B (0-3 min) then a gradient 30% to 100% Solvent B over 11 minutes (Solvent A: $MeOH:H_2O:TFA$ (5:95:0.05); Solvent B: $MeOH:H_2O:TFA$ (95:5:0.05)) to afford, after freeze-drying overnight, 57 mg (75%) of the title compound as the TFA salt LCMS m/z 505.4 $(M+H)^+$, ret. time=2.35 min.

Note: The above reduction protocol was used to prepare all saturated compounds in the Table except for Examples 11, 37, 38, 45, 83. Compound 11 was prepared as described below whereas compounds 37, 38, 45 and 83 were prepared using the procedure described below for Example 83.

Example 11

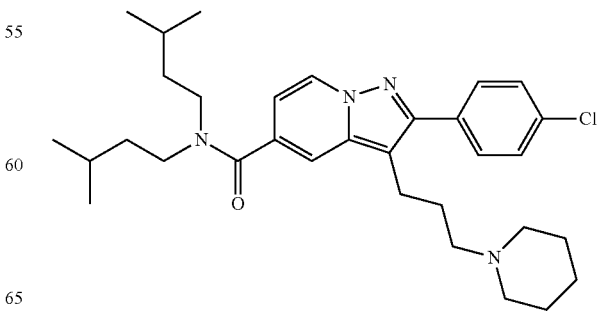

2-(4-Chlorophenyl)-N,N-diisopentyl-3-(3-(piperidin-1-yl)propyl)pyrazolo[1,5-a]pyridine-5-carboxamide A mixture of Example 10 (see Table 1) i.e. (E)-2-(4-chlorophenyl)-N,N-diisopentyl-3-(3-(piperidin-1-yl)prop-1-en-1-yl)pyrazolo[1,5-a]pyridine-5-carboxamide (60 mg, 0.09 mmol) and benzene sulphonylhydrazide (57 mg, 0.33 mmol) in N,N-dimethylformamide (1 mL) was heated to 100° C. for 12 h, cooled down to room temperature and diluted with saturated ammonium chloride (2 mL). The mixture was extracted with dichloromethane and the separated aqueous layer was backextracted with dichloromethane (3×10 mL). The combined organic layers were washed with brine, dried over anhydrous MgSO$_4$, filtered and concentrated under reduced pressure to afford a residue which was purified by RP-HPLC with 30% Solvent B (0-3 min) then a gradient 30% to 100% Solvent B over 11 minutes (Solvent A: MeOH:H$_2$O: TFA (5:95:0.05); Solvent B: MeOH:H$_2$O:TFA (95:5:0.05)) to afford, after freeze-drying overnight, 9.9 mg of the title compound as the TFA salt. LCMS m/z 537.3 (M+H)$^+$, ret. time 2.60 min.

The following example was prepared using chemistry described in Scheme 2:

Example 41

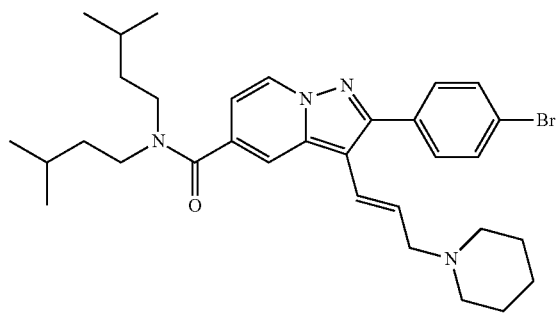

(E)-2-(4-Bromophenyl)-N,N-diisopentyl-3-(3-(piperidin-1-yl)prop-1-en-1-yl)pyrazolo[1,5-a]pyridine-5-carboxamide

Intermediate 41A

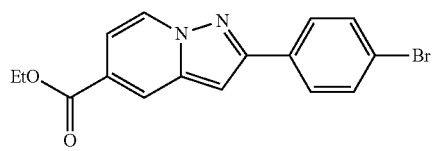 [SMILES: O=C(O)c1ccn2nc(-c3ccc(Br)cc3)cc2c1]

Ethyl 2-(4-bromophenyl)pyrazolo[1,5-a]pyridine-5-carboxylate

Related procedures are described in Org. Lett. 2010, 12, 516): 4-Ethoxycarbonyl-N-benzoyliminopyridinium ylid (JOC 2003, 68, 7119) (3.50 g, 13.0 mmol), para-tris-methoxyphenylphosphine (686 mg, 1.95 mmol), Palladium (II) bromide (173 mg, 0.65 mmol), silver triflate (8.93 g, 39.0 mmol) and (E)-1-Bromo-4-(2-iodovinyl)benzene (Org. Lett. 2008, 10, 5485) (4.02 g, 13.0 mmol) were placed in a 250 mL round bottom flask equipped a with magnetic stirrer. Dioxane (52 mL) was added. The mixture was degassed by bubbling nitrogen for 10 minutes with vigorous stirring and heated to 125-130° C. for 15-20 h. The mixture was then cooled to room temperature, diluted with CH$_2$Cl$_2$, filtered over Celite. The organic layer was then washed with saturated aqueous sodium bicarbonate and the organic phase was concentrated under reduced pressure. The crude product was triturated with methanol to afford 2.40 g (54%) of the title compound. LCMS m/z 345.0, 347.0 (M+H)$^+$, ret. time=3.05 min.

Intermediate 41B

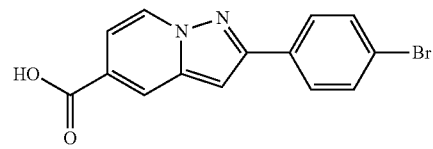

2-(4-Bromophenyl)pyrazolo[1,5-a]pyridine-5-carboxylic acid

Ethyl 2-(4-bromophenyl)pyrazolo[1,5-a]pyridine-5-carboxylate (2.40 g, 7.0 mmol) was dissolved in THF (50 mL) and water was added (12 mL) followed by LiOH—H$_2$O (877 mg, 20.9 mmol). The mixture was stirred overnight at room temperature and 1M HCl (ca 28 mL) was added. The mixture was extracted with EtOAc (2×25 mL) and the combined organic layers were washed with brine, dried over anhydrous MgSO$_4$, filtered and concentrated under reduced pressure to afford a crude white solid that was directly used into the next step. LCMS m/z 317.0, 319.0 (M+H)$^+$, ret. time 2.62 min.

Intermediate 41C

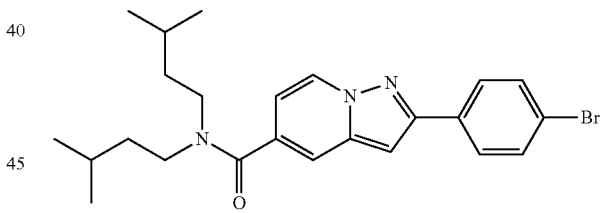

2-(p-Bromophenyl)pyrazolo[1,5-a]pyridine-5-carboxylic diisopentylamide 2-(4-bromophenyl)pyrazolo[1,5-a]pyridine-5-carboxylic acid (2.20 g, 7.0 mmol), diisopentylamine (2.13 mL, 1.64 g, 10.4 mmol) and hydroxybenzotriazole hydrate (1.59 g, 10.4 mmol) were dissolved in DMF (50 mL) and CH$_2$Cl$_2$ (25 mL) and 1-ethyl-3-(3-dimethylaminopropyl)carbodiimide hydrochloride (2.0 g, 10.4 mmol) was added and the mixture was stirred at room temperature overnight. A saturated solution of ammonium chloride (20 mL) was added and the mixture was diluted with dichloromethane (20 mL). The separated aqueous layer was then extracted with dichloromethane (3×25 mL). The combined organic layers were washed with brine, dried over anhydrous MgSO$_4$, filtered and concentrated under reduced pressure to afford a residue which was purified by column chromatography using 20% to 30% EtOAc in hexanes as eluant to provide 2.89 g of the title compound. LCMS m/z 456.2, 4582 (M+H)$^+$, ret. time=3.33 min.

Intermediate 41D

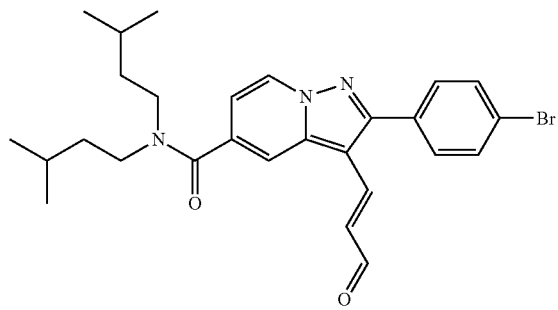 [SMILES: CC(C)CCN(CCC(C)C)C(=O)c1ccn2nc(-c3ccc(Br)cc3)c(/C=C/C=O)c2c1]

(E)-2-(4-Bromophenyl)-N,N-diisopentyl-3-(3-oxo-prop-1-en-1-yl)pyrazolo[1,5-a]pyridine-5-carboxamide Intermediate 41D was prepared from intermediate 41C using the procedures for the synthesis of Intermediates 1E and 1F above. LCMS m/z 510.2, 512.2 (M+H)$^+$, ret. time=3.19 min.

Example 41

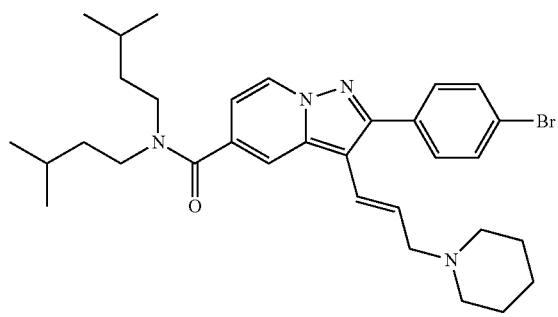 [SMILES: CC(C)CCN(CCC(C)C)C(=O)c1ccn2nc(-c3ccc(Br)cc3)c(/C=C/CN3CCCCC3)c2c1]

(E)-2-(4-Bromophenyl)-N,N-diisopentyl-3-(3-(piperidin-1-yl)prop-1-en-1-yl)pyrazolo[1,5-a]pyridine-5-carboxamide Example 41 was prepared from intermediate 41D using the procedure described for the preparation of intermediate 1G. LCMS m/z 579.2; 581.2 (weak) (M+H)$^+$, 496.2 (strong) ret. time 2.54 min.

Example 42

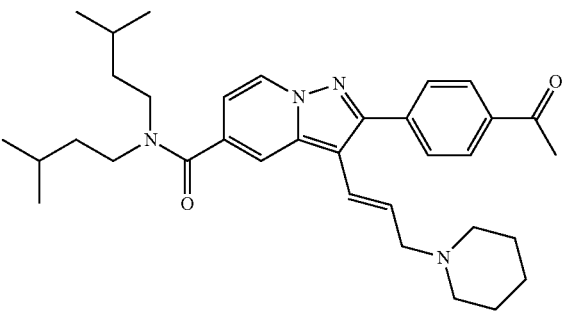 [SMILES: CC(=O)c1ccc(-c2nn3ccc(C(=O)N(CCC(C)C)CCC(C)C)cc3c2/C=C/CN2CCCCC2)cc1]

(E)-2-(4-Acetylphenyl)-N,N-diisopentyl-3-(3-(piperidin-1-yl)prop-1-en-1-yl)pyrazolo[1,5-a]pyridine-5-carboxamide To a mixture of Example 41 i.e. (E)-2-(4-bromophenyl)-N,N-diisopentyl-3-(3-(piperidin-1-yl)prop-1-en-1-yl)pyrazolo[1,5-a]pyridine-5-carboxamide (553 mg, 0.954 mmol) in toluene (14 mL) was added tributyl(1-ethoxy-vinyl)tin (1.03 g, 2.86 mmol) and tetrakis(triphenylphosphine) palladium (O) (55 mg, 0.05 mmol). The mixture was degassed by bubbling nitrogen into it for 10 minutes and was then heated to 120° C. for 4 h. The mixture was allowed to cool to room temperature and concentrated to a residue and dissolved in THF (12 mL). 1N HCl (3 mL) was added and the mixture was stirred at room temperature for 1 h. Sodium bicarbonate was slowly added until pH was reached 8-9 and the mixture was extracted with ethyl acetate (2×30 mL). The combined organics were washed with brine, filtered and concentrated under reduced pressure.

The residue was then purified by column chromatography using CH$_2$Cl$_2$, then 5% to 10% MeOH in CH$_2$Cl$_2$+2% Et$_3$N. The compound was further purified by preparative HPLC on a reverse-phase Zorbax SB-C18 column 21.2×100 mm eluted with MeOH-water-0.1% TFA. Isocratic 30% for 3 minutes then Gradient 30% to 100% MeOH over 14 minutes. LCMS m/z 543.4 (weak) (M+H)$^+$; 458.3 (strong). ret time=2.44 min.

Example 43

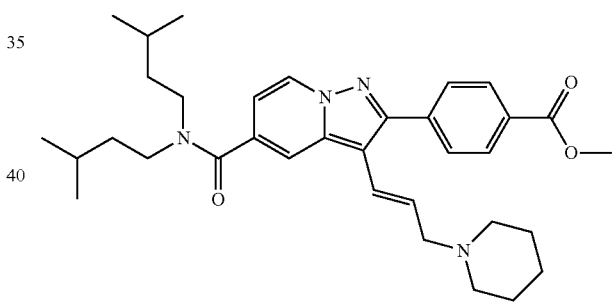

(E)-Methyl 4-(5-(diisopentylcarbamoyl)-3-(3-(piperidin-1-yl)prop-1-en-1-yl)pyrazolo[1,5-a]pyridin-2-yl)benzoate To a solution of Example 41 i.e. (E)-2-(4-bromophenyl)-N,N-diisopentyl-3-(3-(piperidin-1-yl)prop-1-en-1-yl)pyrazolo[1,5-a]pyridine-5-carboxamide (275 mg, 0.474 mmol) in toluene (3 mL), MeOH (4 mL) and Et$_3$N (0.5 mL) was added tetrakis(triphenylphosphine) palladium (O) (27 mg, 0.024 mmol) and the mixture was degassed by bubbling carbon monoxide. The flask was sealed and heated to 75-80° C. for 48 h. The mixture was then concentrated and purified by column chromatography using CH$_2$Cl$_2$, then 5% MeOH in CH$_2$Cl$_2$+2% Et$_3$N. The compound was further purified by passing through a sulfonic acid silica gel column with 5% MeOH in CH$_2$Cl$_2$ and then the compound was obtained using 1% NH$_4$OH in 10% MeOH in CH$_2$Cl$_2$ to afford 247 mg (93%) of ca 95% pure methylester. A fraction of this purified product was then further purified by Prep HPLC as described above to afford the title compound. LCMS m/z 559.8 (weak) (M+H)⁺, 474.3 (strong). ret. time=2.45 min.

Example 46

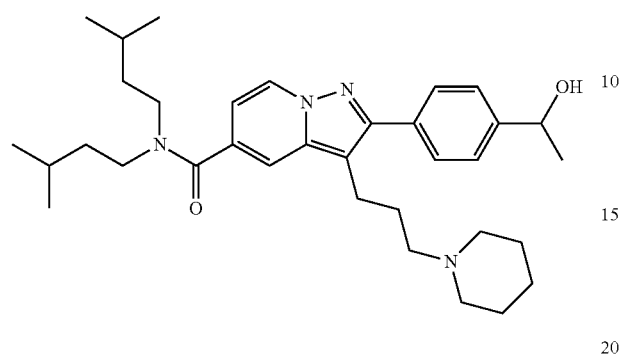

2-(4-(1-Hydroxyethyl)phenyl)-N,N-diisopentyl-3-(3-(piperidin-1-yl)propyl)pyrazolo[1,5-a]pyridine-5-carboxamide (E)-2-(4-acetylphenyl)-N,N-diisopentyl-3-(3-(piperidin-1-yl)prop-1-en-1-yl)pyrazolo[1,5-a]pyridine-5-carboxamide (80 mg, 0.15 mmol) was dissolved in MeOH (3 mL) and triethylamine (1 mL) and 10% Pd/C (40 mg) was added. The vessel was flushed with 3 cycles of vacuum then hydrogen from a balloon, and the reaction mixture was stirred for 4 h at room temperature, filtered through Celite and evaporated. The residue was purified by preparative HPLC on a reverse-phase Zorbax SB-C18 column 21.2×100 mm eluted with MeOH-water-0.1% TFA. Isocratic 30% for 3 minutes then Gradient 30% to 100% MeOH over 14 minutes. LCMS m/z 547.4 (weak) (M+H)⁺, 458.3 (strong). ret. time=2.35 min.

Example 47

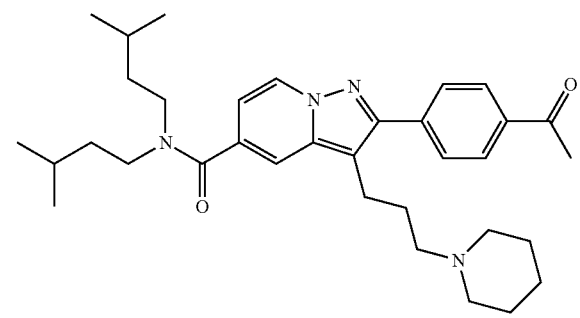 [SMILES: CC(=O)c1ccc(-c2nn3ccc(C(=O)N(CCC(C)C)CCC(C)C)cc3c2CCCN2CCCCC2)cc1]

2-(4-Acetylphenyl)-N,N-diisopentyl-3-(3-(piperidin-1-yl)propyl)pyrazolo[1,5-a]pyridine-5-carboxamide To a solution of 2-(4-(1-hydroxyethyl)phenyl)-N,N-diisopentyl-3-(3-(piperidin-1-yl)propyl)pyrazolo[1,5-a]pyridine-5-carboxamide (35 mg, 0.053 mmol) in chloroform (1 mL) was added activated manganese dioxide (92 mg, 1.06 mmol,) and the mixture was heated to 50° C. for 24 h. The reaction mixture was then diluted with dichloromethane and filtered through a 0.45 um filter, concentrated and then purified by preparative HPLC on a reverse-phase Zorbax SB-C18 col-umn 21.2×100 mm eluted with MeOH-water-0.1% TFA. Isocratic 30% for 3 minutes then Gradient: 30% to 100% MeOH over 14 minutes. LCMS m/z 545.4 (M+H)⁺, ret. time=2.45 min.

Example 83

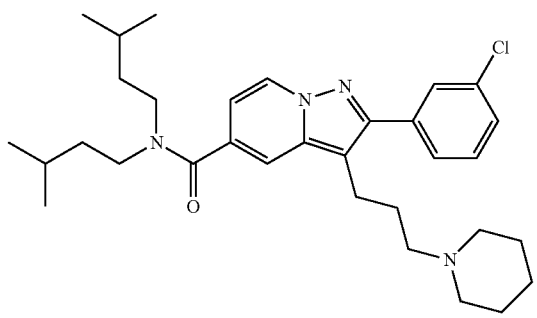 [SMILES: CC(C)CCN(CCC(C)C)C(=O)c1ccn2nc(-c3cccc(Cl)c3)c(CCCN3CCCCC3)c2c1]

2-(3-Chlorophenyl)-N,N-diisopentyl-3-(3-(piperidin-1-yl)propyl)pyrazolo[1,5-a]pyridine-5-carboxamide In a 15 mL sealed tube were added compound of Example 72 i.e. (E)-2-(3-chlorophenyl)-N,N-diisopentyl-3-(3-(piperidin-1-yl)prop-1-en-1-yl)pyrazolo[1,5-a]pyridine-5-carboxamide (160 mg, 0.299 mmol), trifluoroacetic acid (0.069 ml, 0.896 mmol), and triethylsilane (0.143 ml, 0.896 mmol) in chloroform (5 ml) and the mixture was heated to 80-100° C. overnight, cooled down to room temperature and assayed for conversion by HPLC/LCMS. LC indicated homogenous peak but LCMS indicated the presence of both olefin and saturated compounds. Then 140 μL of TFA and 280 μL of triethylsilane were added and the mixture was heated to 100° C. for 5 days and cool down to room temperature. Saturated sodium bicarbonate was slowly added and the separated organic layer was washed with brine and dried over sodium sulfate, filtered and evaporated under reduced pressure. The crude material was dissolved in DMF and purified on a reverse-phase Zorbax SB-C18 column 21.2×100 mm and was eluted with MeOH-water-0.1% TFA. Isocratic 30% for 3 minutes then Gradient: 30% to 100% MeOH over 14 minutes. LCMS m/z 537.3 (M+H)⁺, ret. time=2.55 min.

Example 88

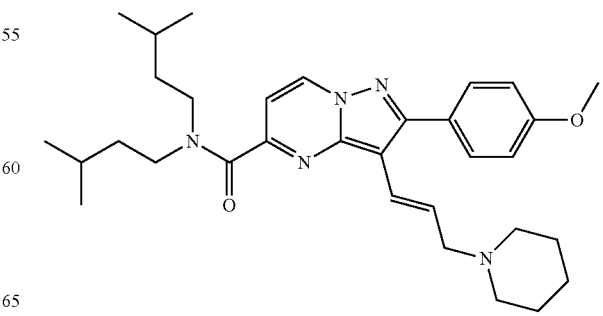

(E)-N,N-Diisopentyl-2-(4-methoxyphenyl)-3-(3-(piperidin-1-yl)prop-1-en-1-yl)pyrazolo[1,5-a]pyrimidine-5-carboxamide Intermediate 88A

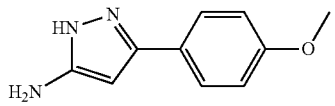

3-(4-Methoxyphenyl)-1H-pyrazol-5-amine

To a solution of 3-(4-methoxyphenyl)-3-oxopropanenitrile (5.0 g, 28.5 mmol) in ethanol (100 mL) was added hydrazine hydrate (2.8 mL, 57.1 mmol) at room temperature. The mixture was heated to reflux for 8 h, allowed to cool and concentrated under reduced pressure to about ¼ volume (25 mL). The resulting precipitate was allowed to stir overnight at room temperature, filtered and rinsed with ethanol (2 mL). The title product was dried under vacuum. Yield 4.15 g (77%); LCMS m/z 190.1 (M+H)$^+$, ret. time=1.56 min.

Intermediate 88B

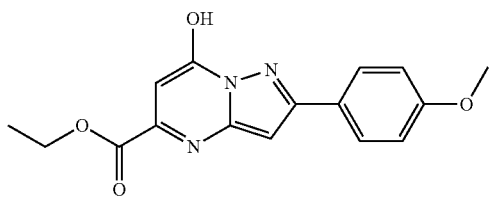 [SMILES: CCOC(=O)c1cc(O)n2nc(-c3ccc(OC)cc3)cc2n1]

Ethyl 7-hydroxy-2-(4-methoxyphenyl)pyrazolo[1,5-a]pyrimidine-5-carboxylate

Diethyl acetylenedicarboxylate (883 µL, 5.6 mmol) was added to a solution of 3-(4-methoxyphenyl)-1H-pyrazol-5-amine (1.1 g, 5.6 mmol) in acetic acid (5 mL). The very thick mixture was allowed to stand at room temperature with occasional stirring for 3 h. Ethyl acetate (5 mL) and hexanes (15 mL) were added and the precipitate was filtered, and dried under high vacuum. Yield: 1.26 g (76%); LCMS m/z 314.1 (M+H)$^+$, ret. time=2.25 min.

Intermediate 88C

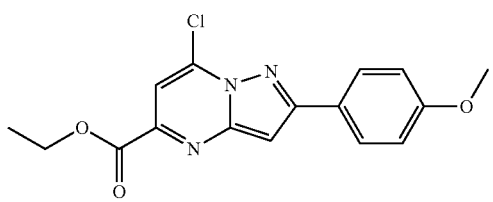

Ethyl 7-chloro-2-(4-methoxyphenyl)pyrazolo[1,5-a]pyrimidine-5-carboxylate

Ethyl 7-hydroxy-2-(4-methoxyphenyl)pyrazolo[1,5-a]pyrimidine-5-carboxylate (1.26 g; 4.03 mmol) was suspended in phosphoryl chloride (8 mL; 88 mmol) and the mixture was heated to 115° C. for 1 h. The reaction mixture was allowed to cool to room temperature and then carefully quenched into a cold mixture of methylene chloride and saturated sodium bicarbonate. The basic aqueous layer was back extracted once with methylene chloride and the combined organic phases were washed with brine. Concentration afforded a crude solid which was triturated in methanol (15 mL) at 60° C. for 5 min. and then at room temperature for an hour. Filtration afforded 808 mg (60%) of the title compound. LCMS m/z 332.1 (M+H)$^+$, ret. time=2.77 min.

Intermediate 88D

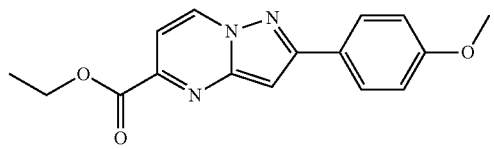 [SMILES: CCOC(=O)c1ccn2nc(-c3ccc(OC)cc3)cc2n1]

Ethyl 2-(4-methoxyphenyl)pyrazolo[1,5-a]pyrimidine-5-carboxylate

To a solution of ethyl 7-chloro-2-(4-methoxyphenyl)pyrazolo[1,5-a]pyrimidine-5-carboxylate (767 mg; 2.31 mmol) in methylene chloride (10 mL), methanol (10 mL) and triethylamine (2 mL) was added 10% Pd on carbon (77 mg) and the mixture was cooled to 0° C. The reaction flask was put under vacuum and then hydrogen was introduced using a balloon. A second cycle of vacuum and hydrogen purge was performed and the mixture was stirred at 0° C. for 1.5 h. The mixture was flushed with two cycles of vacuum and nitrogen, diluted with methylene chloride and then filtered through a 0.45 micron filter to remove the catalyst. Concentration afforded the crude product which was triturated in methanol (25 mL) and filtered to afford 485 mg (71%) of the title compound. LCMS m/z 298.1 (M+H)$^+$, ret. time=2.53 min.

Intermediate 88E

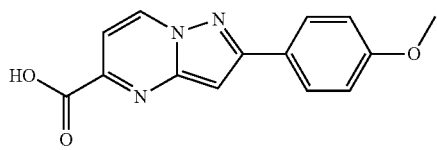 [SMILES: COc1ccc(-c2cc3nc(C(=O)O)ccn3n2)cc1]

2-(4-Methoxyphenyl)pyrazolo[1,5-a]pyrimidine-5-carboxylic acid

To a solution of ethyl 2-(4-methoxyphenyl)pyrazolo[1,5-a]pyrimidine-5-carboxylate (485 mg; 1.63 mmol) in THF (10 mL) and water (3 mL) was added lithium hydroxide hydrate (206 mg; 4.9 mmol) and the mixture was stirred at room temperature for 3 hours. Concentrated hydrochloric acid was then slowly added (ca. 0.5 mL) until pH reached 1 and the mixture was concentrated under reduced pressure. The resulting solid was dissolved in methylene chloride, filtered, concentrated and dried under high vacuum. The crude product was used directly in the next step. LCMS m/z 270.1 (M+H)$^+$, ret. time=2.20 min.

Intermediate 88F

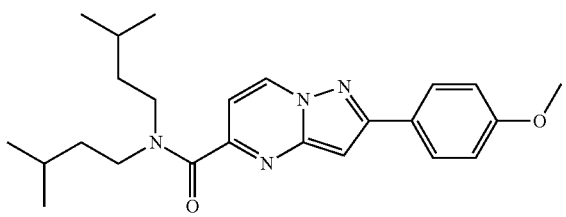 [SMILES: COc1ccc(-c2cc3nc(C(=O)N(CCC(C)C)CCC(C)C)ccn3n2)cc1]

N,N-Diisopentyl-2-(4-methoxyphenyl)pyrazolo[1,5-a]pyrimidine-5-carboxamide

To a solution of 2-(4-methoxyphenyl)pyrazolo[1,5-a]pyrimidine-5-carboxylic acid in DMF (10 mL) and methylene chloride (5 mL) was added diisopentylamine (0.67 mL; 512 mg; 3.3 mmol) and hydroxybenzotriazole monohydrate (499 mg; 3.3 mmol). The mixture was stirred for 10 min. at room temperature and 1-ethyl-3-(3-dimethylaminopropyl) carbodiimide hydrochloride (626 mg; 3.3 mmol) was added. The mixture was stirred overnight at room temperature. An additional amount of 1-ethyl-3-(3-dimethylaminopropyl) carbodiimide hydrochloride was then added (626 mg; 3.3 mmol) and the reaction mixture was heated to 50° C. for 30 min. The mixture was then cooled to room temperature, diluted with methylene chloride and saturated ammonium chloride was added. The aqueous layer was back extracted with methylene chloride and the combined organics were washed with water (3×10 mL) and brine. Concentration afforded a crude oil that was purified by flash-chromatography using first 100% methylene chloride then 5% methanol in methylene chloride to afford an oil that solidified under vacuum. This solid was taken into hot methanol (7 mL) and, upon cooling, a solid formed. Water (3 mL) was then added slowly and filtration afforded 590 mg (89%) of the title compound. LCMS m/z 409.3 (M+H)$^+$, ret. time=3.08 min.

Intermediate 88G

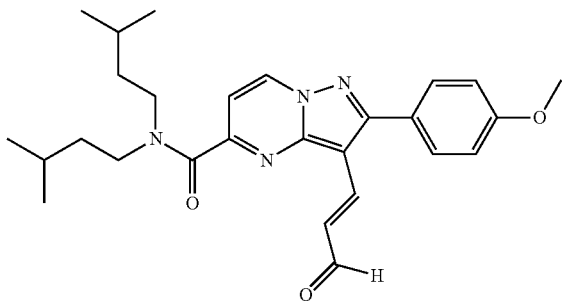 [SMILES: COc1ccc(-c2nn3ccc(C(=O)N(CCC(C)C)CCC(C)C)nc3c2/C=C/C=O)cc1]

(E)-N,N-Diisopentyl-2-(4-methoxyphenyl)-3-(3-oxoprop-1-en-1-yl)pyrazolo[1,5-a]pyrimidine-5-carboxamide To a solution of 3-(dimethylamino)acrolein (0.22 mL; 218 mg; 2.2 mmol) in N,N-dimethylformamide (3 mL) was added phosphoryl chloride (0.16 mL; 269 mg; 1.76 mmol) and the mixture was stirred at room temperature for 10 min. Then N,N-diisopentyl-2-(4-methoxyphenyl)pyrazolo[1,5-a]pyrimidine-5-carboxamide (180 mg; 0.44 mmol) in N,N-dimethylformamide (2 mL) was added and the mixture was heated to 65° C. for 4 h. Then triethylamine (2 mL) and water (2 mL) were slowly added at 60° C. and the mixture was stirred for 30 min. The mixture was cooled to room temperature and diluted with methylene chloride and water. The aqueous layer was back extracted with methylene chloride and the combined organic layers were washed with water (3×10 mL), brine and concentrated. The residue was purified by flash-chromatography using 5% methanol in methylene chloride as eluant. LCMS m/z 463.3 (M+H)$^+$, ret. time=2.98 min.

Example 88

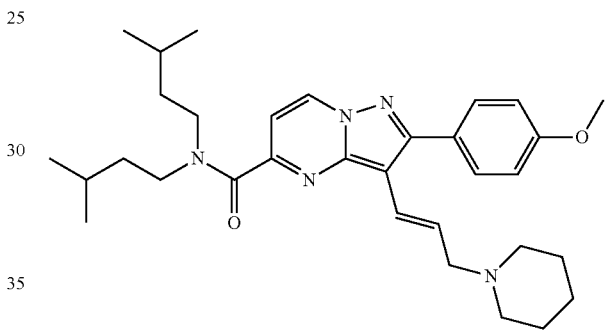

(E)-N,N-Diisopentyl-2-(4-methoxyphenyl)-3-(3-(piperidin-1-yl)prop-1-en-1-yl)pyrazolo[1,5-a]pyrimidine-5-carboxamide The title compound was synthesized from (E)-N,N-diisopentyl-2-(4-methoxyphenyl)-3-(3-oxoprop-1-en-1-yl)pyrazolo[1,5-a]pyrimidine-5-carboxamide using a procedure similar to the one described above for synthesis of intermediate 1G. LCMS m/z 532.4 (weak); 447.3 (strong) (M+H)$^+$, ret. time=2.45 min.

Example 89

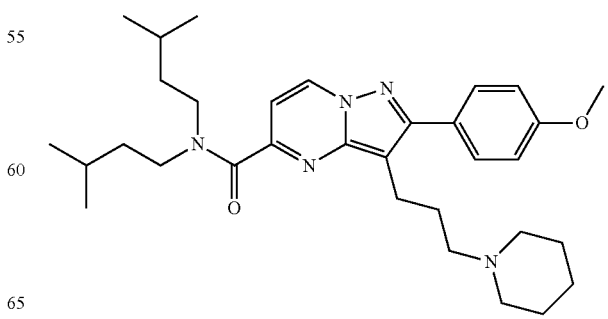

N,N-Diisopentyl-2-(4-methoxyphenyl)-3-(3-(piperidin-1-yl)propyl)pyrazolo[1,5-a]pyrimidine-5-carboxamide The title compound was prepared from (E)-N,N-diisopentyl-2-(4-methoxyphenyl)-3-(3-(piperidin-1-yl)prop-1-en-1-yl)pyrazolo[1,5-a]pyrimidine-5-carboxamide using a procedure similar to the one described above for the synthesis of intermediate 88D. LCMS m/z 534.4 (M+H)⁺, ret. time=2.44 min.

Example 141

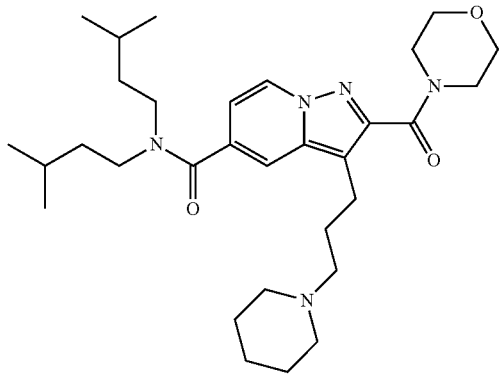 [SMILES: CC(C)CCN(CCC(C)C)C(=O)c1ccn2nc(C(=O)N3CCOCC3)c(CCCN3CCCCC3)c2c1]

N,N-diisopentyl-2-(morpholine-4-carbonyl)-3-(3-(piperidin-1-yl)propyl)pyrazolo[1,5-a]pyridine-5-carboxamide Intermediate 141A

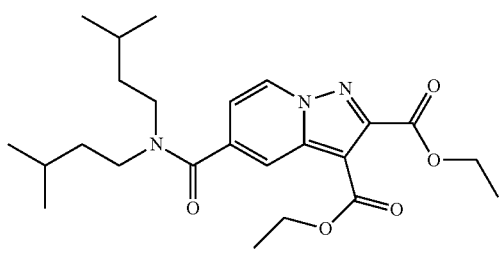 [SMILES: CCOC(=O)c1nn2ccc(C(=O)N(CCC(C)C)CCC(C)C)cc2c1C(=O)OCC]

diethyl 5-(diisopentylcarbamoyl)pyrazolo[1,5-a]pyridine-2,3-dicarboxylate

To a suspension of 1-amino-4-(diisopentylcarbamoyl)pyridin-1-ium-2,4-(dinitro)phenolate (Intermediate 142B) (1 g, 2.167 mmol) and potassium carbonate (0.599 g, 4.33 mmol) in THF (5 ml) at 0° C. was added diethyl but-2-ynedioate (0.249 ml, 2.383 mmol). The mixture was stirred at 0° C. for 1 h then at 22° C. for 12 hours. The mixture was diluted with water and extracted with ethyl acetate (3×25 ml). The combined organics were washed with brine, dried over Na₂SO₄, filtered and concentrated. The residue was purified by flash chromatography: ISCO gold 40 g eluting with 10% to 100% ethyl acetate in hexanes over 12 min. Pooled and concentrated desired fractions to afford, 0.48 g (50%) of the title compound as a tan coloured oil. LCMS m/z 445.7 (M+H)⁺. ret. time 2.49 min.

Intermediate 141B

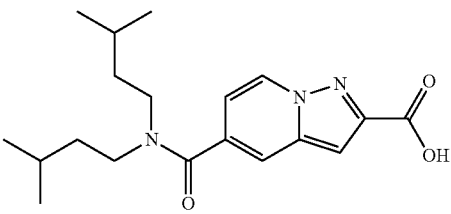 [SMILES: CC(C)CCN(CCC(C)C)C(=O)c1ccn2nc(C(=O)O)cc2c1]

5-(diisopentylcarbamoyl)pyrazolo[1,5-a]pyridine-2-carboxylic acid

Diethyl 5-(diisopentylcarbamoyl)pyrazolo[1,5-a]pyridine-2,3-dicarboxylate (0.35 g, 0.786 mmol) was added to 40% aqueous sulphuric acid (5 ml) and stirred at reflux for 3 h. The resulting suspension was cooled in an ice bath then extracted with ethyl acetate (3×25 ml). The combined organic layers were washed with brine and concentrated to afford, 0.29 g (98%) of the title compound as a white solid. LCMS m/z 346.2 (M+H)⁺. ret. time=2.57 min.

Intermediate 141C

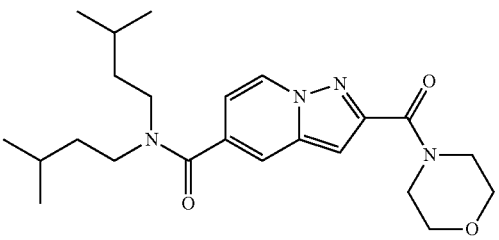 [SMILES: CC(C)CCN(CCC(C)C)C(=O)c1ccn2nc(C(=O)N3CCOCC3)cc2c1]

N,N-diisopentyl-2-(morpholine-4-carbonyl)pyrazolo[1,5-a]pyridine-5-carboxamide 5-(diisopentylcarbamoyl)pyrazolo[1,5-a]pyridine-2-carboxylic acid (0.29 g, 0.840 mmol), EDC (0.274 g, 1.427 mmol) and HOBT (0.219 g, 1.427 mmol) were combined in DMF (2.0 ml). Added triethylamine (0.351 ml, 2.52 mmol) and morpholine (0.073 ml, 0.840 mmol) and stirred at 22° C. for 12 h. The mixture was diluted with ethyl acetate (25 ml) and washed with water, saturated sodium bicarbonate solution and brine, dried over Na₂SO₄, filtered and concentrated. The residue was purified by flash chromatography: ISCO Gold 24 g using 0% to 100% ethyl acetate in hexanes over 11 min. Pooled and concentrated desired fractions to afford, 0.26 g (74%) of the title compound as a clear oil. LCMS m/z 415.3 (M+H)⁺. ret. time=2.27 min.

Intermediate 141D

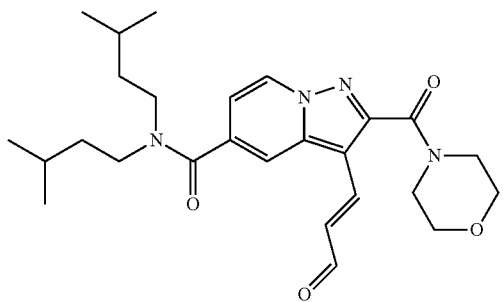 [SMILES: CC(C)CCN(CCC(C)C)C(=O)c1ccn2nc(C(=O)N3CCOCC3)c(/C=C/C=O)c2c1]

(E)-N,N-diisopentyl-2-(morpholine-4-carbonyl)-3-(3-oxoprop-1-en-1-yl)pyrazolo[1,5-a]pyridine-5-carboxamide To a stirred solution of dimethylacroleine (0.250 ml, 2.52 mmol) and POCl₃ (0.235 ml, 2.52 mmol) in dichloroethane (2 ml) at 0° C. for 15 min was added N,N-diisopentyl-2-(piperidine-1-carbonyl)pyrazolo[1,5-a]pyridine-5-carboxamide (0.26 g, 0.630 mmol). The mixture was heated to 65° C. for 6 h. Mixed more reagents for 15 min then added to solution above and stirred at 65° C. for 12 h. Water (20 ml) was added to the cooled mixture and extracted with DCM (3×25 ml). The combined organics (liquids and solids) were concentrated to afford a red semisolid. The residue was treated with saturated sodium bicarbonate (20 ml) and MeOH (20 ml) overnight. The suspension was neutralized with a saturated NH₄Cl solution and extracted with DCM (3×100 ml). The combined organics were dried over Na₂SO₄, filtered and concentrated. The residue was purified by flash chromatography: ISCO 24 g eluting with 0% to 100% ethyl acetate in hexanes over 12 min. Pooled and concentrated desired fractions to afford, 0.23 g (78%) of the title compound as a yellow oil. LCMS m/z 469.3 (M+H)⁺. ret. time=2.29 min Example 141E

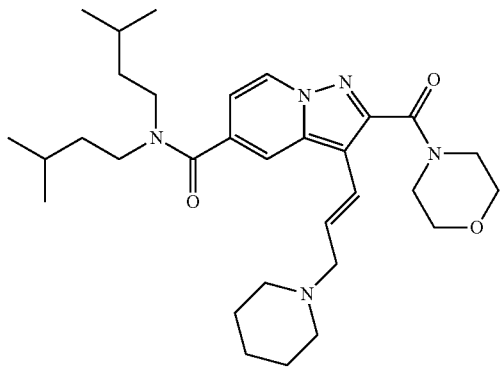 [SMILES: CC(C)CCN(CCC(C)C)C(=O)c1ccn2nc(C(=O)N3CCOCC3)c(/C=C/CN3CCCCC3)c2c1]

(E)-N,N-diisopentyl-2-(morpholine-4-carbonyl)-3-(3-(piperidin-1-yl)prop-1-en-1-yl)pyrazolo[1,5-a]pyridine-5-carboxamide To a stirred suspension of (E)-N,N-diisopentyl-2-(morpholine-4-carbonyl)-3-(3-oxoprop-1-en-1-yl)pyrazolo[1,5-a]pyridine-5-carboxamide (115 mg, 0.245 mmol) and piperidine (0.049 ml, 0.491 mmol) in dichloroethane (5 ml) was added sodium triacetoxyborohydride (104 mg, 0.491 mmol). After 12 h, 1M aqueous NaOH (25 mL) was added and the mixture was extracted with DCM (3×25 mL). The organic layers were dried over Na₂SO₄, filtered and concentrated. The residue was purified by prep HPLC with 20% Solvent B (0-3 min) then a gradient 20% to 100% Solvent B over 13 minutes (Solvent A: MeOH:H₂O:TFA (5:95:0.05); Solvent B: MeOH:H₂O:TFA (95:5:0.05)) to afford, after concentration of desired fractions, 115 mg (71%) of the title compound as the TFA salt. LCMS m/z 538.4 (M+H)⁺ (weak) and 453.2 (strong) ret. time=2.11 min.

Example 141

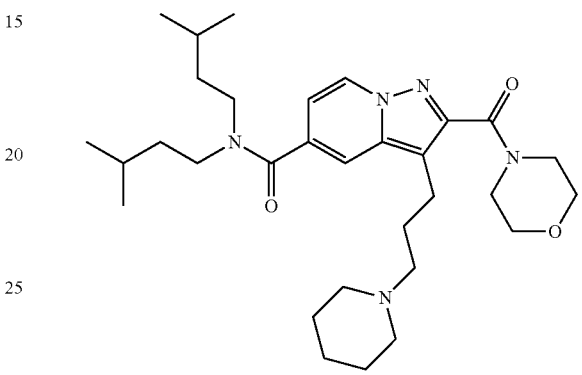

N,N-diisopentyl-2-(morpholine-4-carbonyl)-3-(3-(piperidin-1-yl)propyl)pyrazolo[1,5-a]pyridine-5-carboxamide A stirred suspension of ((E)-N,N-diisopentyl-2-(morpholine-4-carbonyl)-3-(3-(piperidin-1-yl)prop-1-en-1-yl)pyrazolo[1,5-a]pyridine-5-carboxamide (100 mg, 0.186 mmol) and 10% Pd/C (10 mg, 9.40 µmol) in MeOH (5 ml) was purged and stirred under a hydrogen atmosphere. After 12 h the mixture was filtered, concentrated and purified by prep HPLC with 20% Solvent B (0-3 min) then a gradient 20% to 100% Solvent B over 13 minutes (Solvent A: MeOH:H₂O:TFA (5:95:0.05); Solvent B: MeOH:H₂O:TFA (95:5:0.05)) to afford, after concentration of desired fractions, 66 mg (52%) of the title compound as the TFA salt. LCMS m/z 540.4 (M+H)⁺ ret. time=2.11 min.

Example 142

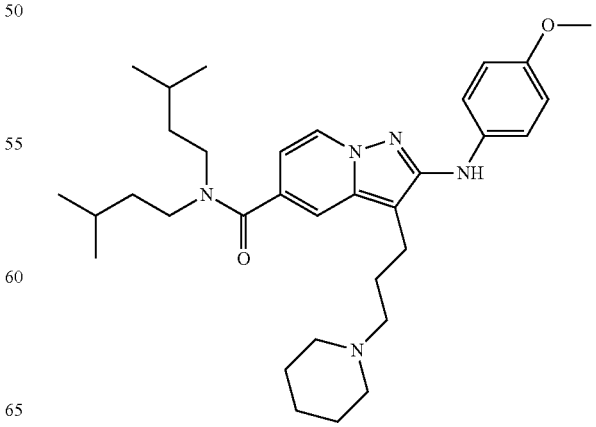

N,N-diisopentyl-2-((4-methoxyphenyl)amino)-3-(3-(piperidin-1-yl)propyl)pyrazolo[1,5-a]pyridine-5-carboxamide Intermediate 142A

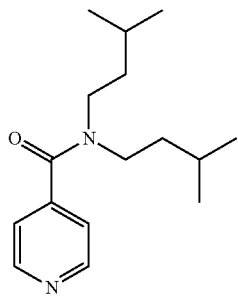 [SMILES: CC(C)CCN(CCC(C)C)C(=O)c1ccncc1]

N,N-diisopentylisonicotinamide

To a stirred solution of diisopentylamine (5.0 ML, 24.7 mmol) and triethylamine (9.4 mL, 67.4 mmol) in dichloromethane (23 mL) at 0° C. was added slowly isonicotinoyl chloride hydrochloride (4 g, 22.5 mmol). The mixture was allowed to warm to room temperature and stirred at room temperature for 2 hours. The mixture was diluted with saturated sodium bicarbonate and the separated aqueous layer was extracted with methylene chloride (3×25 mL). The combined organics were washed with water (10 mL), brine, dried (anh. sodium sulfate), filtered and evaporated. The residue solidified upon standing to afford 4.7 g of an orange solid. LCMS m/z 263.2 (M+H)$^+$.

Intermediate 142B

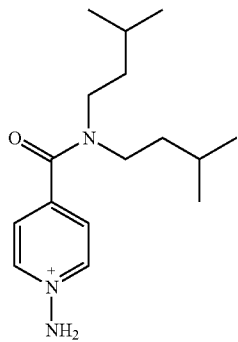

1-amino-4-(diisopentylcarbamoyl)pyridin-1-ium

The reaction conditions reported by Charette in J. Org. Chem. 2003, 68, 7119 were used: A solution of N,N-diisopentylisonicotinamide (1.0 g, 3.8 mmol) and O-(2,4-dinitrophenyl)hydroxylamine (1.043 g, 4.19 mmol) in acetonitrile was stirred at 40° C. for 12 hours. The mixture was allowed to cool, concentrated and the residue was triturated in ether overnight. The resulting solid was filtered and dried to afford N-aminopyridinium 2,4-(dinitro)phenolate (1.4 g, 3.03 mmol, 80% yield) as a yellow solid. LCMS m/z 278.2 (M+H)$^+$.

Intermediate 142C

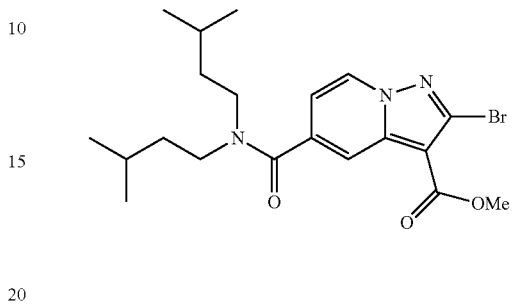

methyl 2-bromo-5-(diisopentylcarbamoyl)pyrazolo[1,5-a]pyridine-3-carboxylate

A suspension of N-aminopyridinium 2,4-(dinitro)phenolate (10 g, 21.67 mmol), methyl 3-bromopropiolate (3.12 ml, 26.0 mmol) and potassium carbonate (5.99 g, 43.3 mmol) in degassed DMF (75 ml) was stirred at 0° C. for 5 minutes and at 22° C. for 18 h. The mixture was diluted with ethyl acetate (100 mL) and washed with water (3×25 mL), brine, dried over anhydrous sodium sulfate, filtered and concentrated. The residue was purified by flash chromatography on silica gel (120 g, 0% to 100% ethyl acetate/hexanes over 19 min). to provide methyl 2-bromo-5-(diisopentylcarbamoyl)pyrazolo[1,5-a]pyridine-3-carboxylate (0.52 g, 1.186 mmol, 5.47% yield). LCMS m/z 438.4, 440.1 (M+H)$^+$.

Intermediate 142D

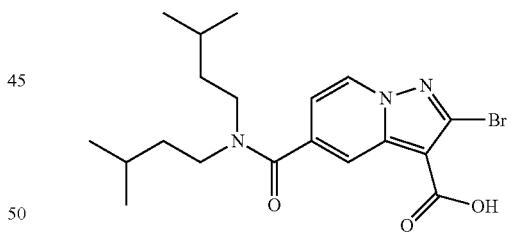

2-bromo-5-(diisopentylcarbamoyl)pyrazolo[1,5-a]pyridine-3-carboxylic acid

To a stirred solution of methyl 2-bromo-5-(diisopentylcarbamoyl)pyrazolo[1,5-a]pyridine-3-carboxylate (0.47 g, 1.072 mmol) in THF (15 ml) and MeOH (15 ml) was added 2M aqueous LiOH solution (10.00 ml, 20 mmol). The mixture was stirred at 30° C. for 4 h then concentrated partially, acidified with 1N HCl and extracted with ethyl acetate (3×40 ml). The combined organics were dried over anhydrous sodium sulphate, filtered and concentrated. The orange solid was triturated with methyl tert-butyl ether (10 ml) to afford 2-bromo-5-(diisopentylcarbamoyl)pyrazolo[1,5-a]pyridine- 3-carboxylic acid (0.291 g, 0.679 mmol, 63.3% yield) LCMS m/z 424.1, 426.1 (M+H)⁺, ret. time=2.21 min.

Intermediate 142E

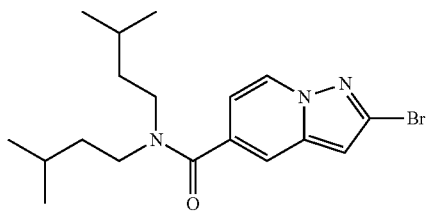 [SMILES: CC(C)CCN(CCC(C)C)C(=O)c1ccn2nc(Br)cc2c1]

2-bromo-N,N-diisopentylpyrazolo[1,5-a]pyridine-5-carboxamide

A solution of 2-bromo-5-(diisopentylcarbamoyl)pyrazolo[1,5-a]pyridine-3-carboxylic acid (0.285 g, 0.672 mmol) in diphenyl ether (6 ml) was heated to 210° C. for 9 hours. The mixture was allowed to cool, loaded on a silica gel pad, rinsed with diethyl ether (10 mL) and dried thoroughly under vacuum. The dried silica gel pad was then connected to a 24 g silica gel ISCO Gold cartridge and eluted with hexanes for 3 min then 0% to 100% ethyl acetate over 11 min. Concentration of the desired fractions afforded 2-bromo-N,N-diisopentylpyrazolo[1,5-a]pyridine-5-carboxamide (0.19 g, 0.475 mmol, 70.7% yield) as a yellow oil. LCMS m/z 380.1, 382.1 (M+H)⁺

Intermediate 142F

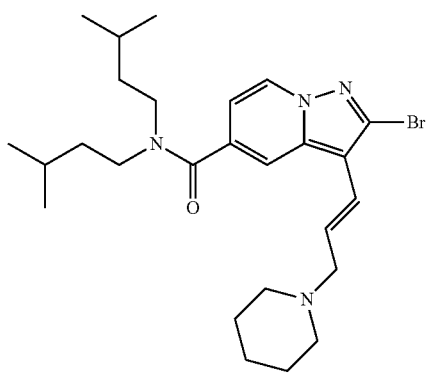 [SMILES: CC(C)CCN(CCC(C)C)C(=O)c1ccn2nc(Br)c(/C=C/CN3CCCCC3)c2c1]

(E)-2-bromo-N,N-diisopentyl-3-(3-(piperidin-1-yl)prop-1-en-1-yl)pyrazolo[1,5-a]pyridine-5-carboxamide Starting from intermediate 142E, The intermediate 142F was obtained following procedures 1E, 1F and 1G described above. LCMS m/z 503.2, 505.2 (M+H)⁺

Intermediate 142G

Example 138

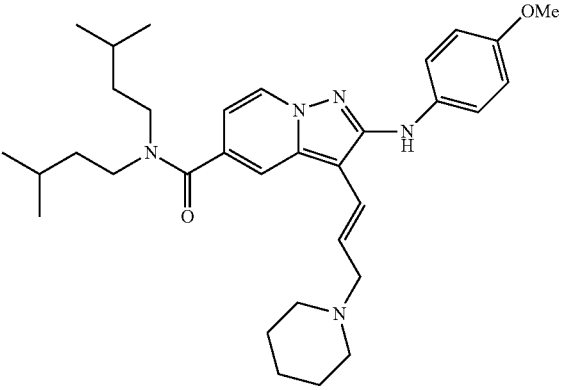 [SMILES: COc1ccc(Nc2nn3ccc(C(=O)N(CCC(C)C)CCC(C)C)cc3c2/C=C/CN2CCCCC2)cc1]

(E)-N,N-diisopentyl-2-((4-methoxphenyl)amino)-3-(3-(piperidin-1-yl)prop-1-en-1-yl)pyrazolo[1,5-a]pyridine-5-carboxamide In a sealed tube 4-methoxyaniline (18.34 mg, 0.149 mmol), tris(dibenzylideneacetone)dipalladium (4.55 mg, 4.97 μmol) and (9,9-dimethyl-9H-xanthene-4,5-diyl)bis(diphenylphosphine) (5.75 mg, 9.93 μmol) were added to a suspension of (E)-2-bromo-N,N-diisopentyl-3-(3-(piperidin-1-yl)prop-1-en-1-yl)pyrazolo[1,5-a]pyridine-5-carboxamide (50 mg, 0.099 mmol) and potassium phosphate, dibasic (57.1 mg, 0.328 mmol) in toluene (5 ml). The mixture was heated at 110° C. overnight. The reaction mixture was cooled to room temperature, diluted with water and extracted with ethyl acetate (3×25 mL). The combined organics were washed with brine, dried over anh. sodium sulfate, filtered and concentrated. The residue was purified by SCX (silica-gel supported sulfonic acid) then by preparative HPLC (20% to 100% MeOH in water (0.05% TFA) in 7 minutes) to afford N,N-diisopentyl-2-((4-methoxyphenyl)amino)-3-(3-(piperidin-1-yl)prop-1-en-1-yl)pyrazolo[1,5-a]pyridine-5-carboxamide. LCMS m/z 546.4 (M+H)⁺ weak, 461.3 (strong); ret. time=2.19 min.

Example 142

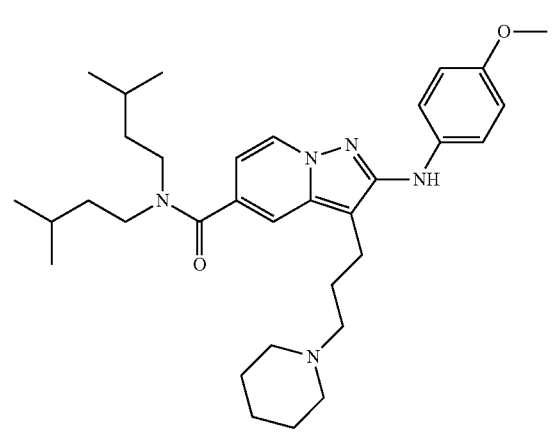 [SMILES: COc1ccc(Nc2nn3ccc(C(=O)N(CCC(C)C)CCC(C)C)cc3c2CCCN2CCCCC2)cc1]

N,N-diisopentyl-2-((4-methoxyphenyl)amino)-3-(3-(piperidin-1-yl)propyl)pyrazolo[1,5-a]pyridine-5-carboxamide The hydrogenation procedure described for Example 1 was followed using (E)-N,N-diisopentyl-2-((4-methoxyphenyl)amino)-3-(3-(piperidin-1-yl)prop-1-en-1-yl)pyrazolo[1,5-a]pyridine-5-carboxamide. LCMS m/z 548.4 (M+H)⁺; ret. time=2.19 min.

Example 149

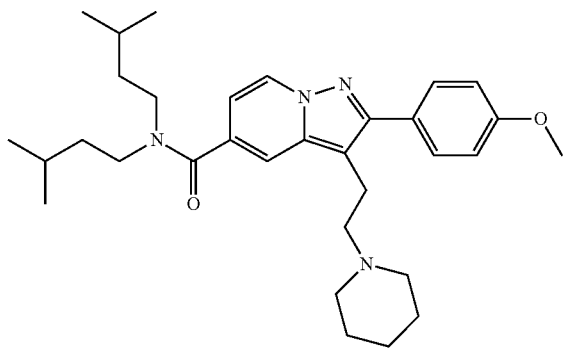 [SMILES: COc1ccc(-c2nn3ccc(C(=O)N(CCC(C)C)CCC(C)C)cc3c2CCN2CCCCC2)cc1]

N,N-diisopentyl-2-(4-methoxyphenyl)-3-(2-(piperidin-1-yl)ethyl)pyrazolo[1,5-a]pyridine-5-carboxamide Intermediate 149A

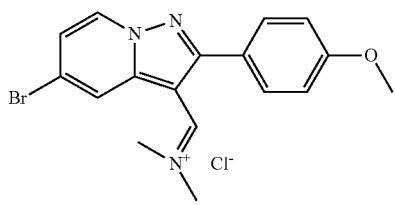 [SMILES: COc1ccc(-c2nn3ccc(Br)cc3c2C=[N+](C)C)cc1 ; [Cl-]]

N-((5-bromo-2-(4-methoxyphenyl)pyrazolo[1,5-a]pyridin-3-yl)methylene)-N-methylmethanaminium chloride To a stirred suspension of 5-bromo-2-(4-methoxyphenyl)pyrazolo[1,5-a]pyridine (200 mg, 0.66 mmol) in 1,2-dichloroethane (6 mL) was added N-(Chloromethylene)-N-methylmethanaminium chloride (195 mg, 1.5 mmol). The mixture was stirred at 20° C. for 20 h then heated to 50° C. for 1 h at which time monitoring the reaction by LC indicated all starting material had converted to the title compound. The solids were collected by filtration and dried under reduced pressure to afford the title compound as a solid (260 mg, 100%). LCMS m/z 331.0, 333.0 (M-(CH₃)₂NH+H₂O)⁺, ret. time=2.13 min.

Intermediate 149B

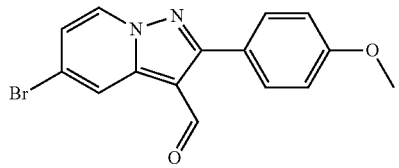 [SMILES: COc1ccc(-c2nn3ccc(Br)cc3c2C=O)cc1]

5-bromo-2-(4-methoxyphenyl)pyrazolo[1,5-a]pyridine-3-carbaldehyde

To a stirred solution of N-((5-bromo-2-(4-methoxyphenyl)pyrazolo[1,5-a]pyridin-3-yl)methylene)-N-methylmethanaminium chloride (260 mg, 0.66 mmol) in methanol (3 mL) was added a 3% solution of potassium bicarbonate (3.1 mL) and the mixture was stirred at room temperature for 2 h. The solids were collected by filtration and dried under reduced pressure to afford the title compound as a solid (201 mg, 92%). LCMS m/z 331.0, 333.0 (M+H)⁺, ret. time=2.13 min.

Intermediate 149C

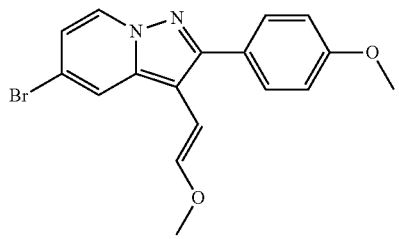 [SMILES: CO/C=C/c1c(-c2ccc(OC)cc2)nn2ccc(Br)cc12]

5-bromo-2-(4-methoxyphenyl)-3-(2-methoxyvinyl)pyrazolo[1,5-a]pyridine

To a solution of methoxymethyltriphenylphosphonium chloride (298 mg, 0.87 mmol) in methanol (3 ml) was added a solution of sodium methoxide 25% wt. in methanol (0.20 ml, 0.87 mmol). The resulting white suspension was stirred at 20° C. for 30 minutes. The mixture was concentrated to dryness and azeotroped with toluene (6 ml) twice. The resulting solid was suspended in toluene (2 ml). A suspension of 5-bromo-2-(4-methoxyphenyl)pyrazolo[1,5-a]pyridine-3-carbaldehyde (180 mg, 0.54 mmol) in toluene (4 ml) was added to the ylide suspension. Heated the resulting mixture to 85-90° C. and stirred for 1.25 h. Cooled to 20° C. and stirred 17.5 h. In a separate flask, to a solution of methoxymethyltriphenylphosphonium chloride (298 mg, 0.87 mmol) in methanol (3 ml) was added a solution of sodium methoxide 25% wt. in methanol (0.20 ml, 0.87 mmol). The resulting white suspension was stirred for 30 minutes, concentrated and azeotroped with toluene (6 ml) twice. The resulting solid was suspended in toluene (2 ml) and added to the reaction mixture which was heated to 90° C. for 2 h at which time monitoring the reaction by LC indicated all starting material had converted to the title compound. to the mixture was cooled to 20° C., filtered through a 0.45 μm filter and rinsed with toluene (2 mL). The filtrate was concentrated under reduced pressure to afford a residue that was purified by automated ISCO chromatography (ethyl acetate/hexane; 25/75). The title compound was obtained as a bright yellow solid (168 mg, 86%). LCMS m/z 359.0 (M+H)+, ret. time=2.31 (cis isomer) and 2.34 min (trans isomer).

Intermediate 149D

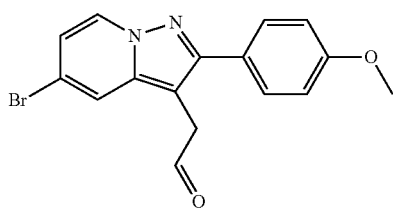 [SMILES: COc1ccc(-c2nn3ccc(Br)cc3c2CC=O)cc1]

2-(5-bromo-2-(4-methoxyphenyl)pyrazolo[1,5-a]pyridin-3-yl)acetaldehyde

To a stirred solution of 5-bromo-2-(4-methoxyphenyl)-3-(2-methoxyvinyl)pyrazolo[1,5-a]pyridine (160 mg, 0.45 mmol) in THF (7.3 ml) was added a 4N HCl solution in water (2.45 ml, 9.8 mmol). Heated to 50° C. and stirred for 4 h at which time monitoring the reaction by LC indicated all starting material had converted to the title compound. The solution was cooled to 20° C. and a saturated solution of sodium bicarbonate (10 mL) and ethyl acetate (15 mL) were added The organic layer was dried over anhydrous MgSO4, filtered and concentrated to dryness to afford a residue that was purified by automated ISCO chromatography (ethyl acetate/dichloromethane; 7/93). The title compound was obtained as a tan solid (43 mg, 28%). LCMS m/z 345.0, 347.0 (M+H)+, ret. time=2.02, 2.12 min. Peak at 2.01 is hydrate of the aldehyde LCMS m/z 363.1, 365.1 (M+H)+ and peak at 2.12 is methyl hemiacetal of the aldehyde LCMS m/z 377.1, 379.1 (M+H)+ both formed under LCMS conditions.

Intermediate 149E

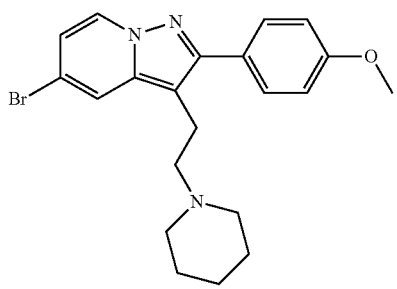 [SMILES: COc1ccc(-c2nn3ccc(Br)cc3c2CCN2CCCCC2)cc1]

5-bromo-2-(4-methoxyphenyl)-3-(2-(piperidin-1-yl)ethyl)pyrazolo[1,5-a]pyridine

To a solution of 2-(5-bromo-2-(4-methoxyphenyl)pyrazolo[1,5-a]pyridin-3-yl)acetaldehyde (40 mg, 0.12 mmol) and piperidine (23 μl, 0.23 mmol) in 1,2-dichloroethane (3.5 ml) was added sodium triacetoxyborohydride (49 m, 0.23 mmol). The reaction mixture was stirred at 20° C. for 17 h. The reaction mixture was diluted with dichloromethane (10 mL) and washed with a 5% sodium bicarbonate solution (6 mL). The organic layer was dried over anhydrous MgSO4, filtered and concentrated under reduced pressure to give a residue that was purified by automated ISCO chromatography (methanol/dichloromethane; 5/95). The title compound was obtained as a white solid (28 mg, 58%). LCMS m/z 414.1, 416.1 (M+H)+, ret. time=1.76 min.

Example 149

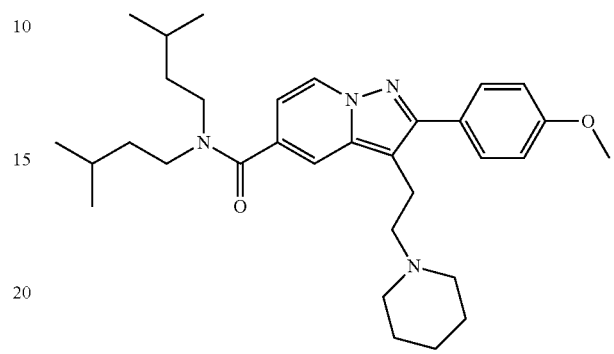

N,N-diisopentyl-2-(4-methoxyphenyl)-3-(2-(piperidin-1-yl)ethyl)pyrazolo[1,5-a]pyridine-5-carboxamide At room temperature in a 15-mL resealable vial, carbon monoxide was bubbled for 5 min. through a solution of 5-bromo-2-(4-methoxyphenyl)-3-(2-(piperidin-1-yl)ethyl)pyrazolo[1,5-a]pyridine (28 mg, 0.068 mmol), diisopentylamine (42 μL, 0.20 mmol) and triethylamine (188 μL, 1.35 mmol) in toluene (3.5 mL). Palladium bis(triphenylphosphine) dichloride (4.7 mg, 6.8 μmol) was then added and carbon monoxide was bubbled for an additional 5 min. at which time the vial was sealed and heated to 100° C. for 66 h., cooled down to room temperature and evaporated under reduced pressure. The residue was dissolved in DMF, filtered and purified by RP-HPLC with 30% Solvent B (0-3 min) then a gradient 30% to 100% Solvent B over 12 minutes (Solvent A: MeOH:H2O:TFA (5:95:0.05); Solvent B: MeOH:H2O:TFA (95:5:0.05)) to afford, after freeze-drying overnight, 34 mg (80%) of the title compound as the TFA salt. LCMS m/z 519.4 (M+H)+, ret. time=2.12 min.

Example 164

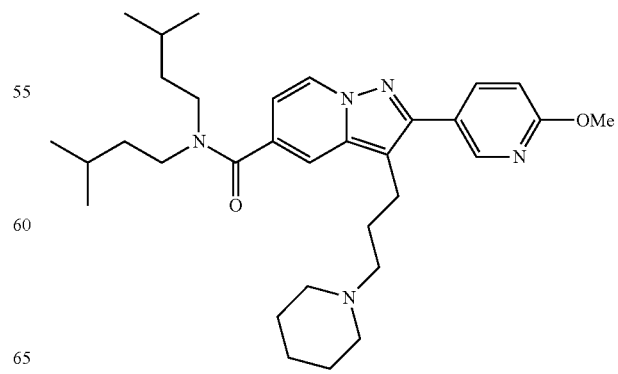

85

N,N-diisopentyl-2-(6-methoxypyridin-3-yl)-3-(3-(piperidin-1-yl)propyl)pyrazolo[1,5-a]pyridine-5-carboxamide Intermediate 164A

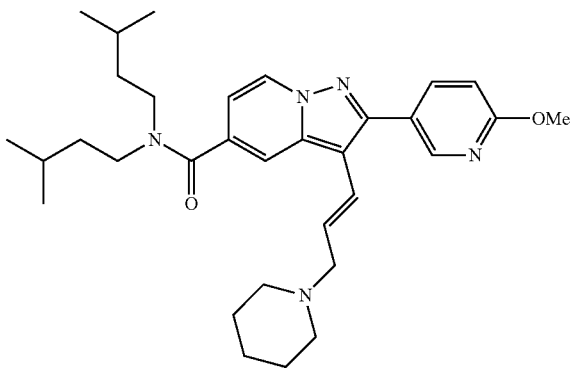 [SMILES: COc1ccc(-c2nn3ccc(C(=O)N(CCC(C)C)CCC(C)C)cc3c2/C=C/CN2CCCCC2)cn1]

(E)-N,N-diisopentyl-2-(6-methoxypyridin-3-yl)-3-(3-(piperidin-1-yl)prop-1-en-1-yl)pyrazolo[1,5-a]pyridine-5-carboxamide To a solution of (E)-2-bromo-N,N-diisopentyl-3-(3-(piperidin-1-yl)prop-1-en-1-yl)pyrazolo[1,5-a]pyridine-5-carboxamide (Intermediate 142F) (30 mg, 0.060 mmol) and (6-methoxypyridin-3-yl)boronic acid (10.94 mg, 0.071 mmol) in dimethoxyethane (2 ml) was added a 2M sodium carbonate solution (0.089 ml, 0.179 mmol) and palladium tetrakis triphenylphosphine (6.88 mg, 5.96 µmol). The mixture was heated to 80° C. for 12 h. More palladium cat (6.88 mg, 5.96 µmol) was added and the mixture was heated an extra 12 h. The cooled mixture was extracted with ethyl acetate (3×25 ml), dried over anhydrous $Na_2SO_4$, filtered and concentrated. The residue was purified by RP-HPLC with 20% Solvent B (0-3 min) then a gradient 20% to 100% Solvent B over 13 minutes (Solvent A: $MeOH:H_2O:TFA$ (5:95:0.05); Solvent B: $MeOH:H_2O:TFA$ (95:5:0.05)) to afford, after concentration of desired fractions, 9 mg (20%) of the title compound as the TFA salt. LCMS m/z 532.4 (weak) $(M+H)^+$, and 447.3 (strong). ret. time=2.06 min.

Example 164

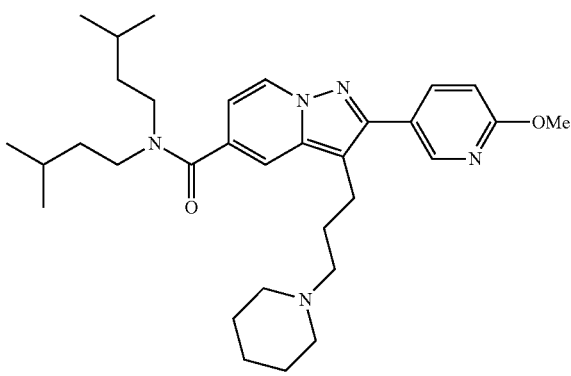 [SMILES: COc1ccc(-c2nn3ccc(C(=O)N(CCC(C)C)CCC(C)C)cc3c2CCCN2CCCCC2)cn1]

86

N,N-diisopentyl-2-(6-methoxypyridin-3-yl)-3-(3-(piperidin-1-yl)propyl)pyrazolo[1,5-a]pyridine-5-carboxamide The hydrogenation procedure described for Example 1 was followed using (E)-N,N-diisopentyl-2-(6-methoxypyridin-3-yl)-3-(3-(piperidin-1-yl)prop-1-en-1-yl)pyrazolo[1,5-a]pyridine-5-carboxamide. LCMS m/z 534.5 $(M+H)^+$; ret. time=2.16 min.

Example 165

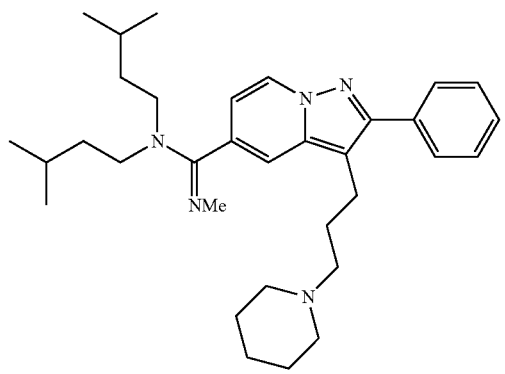

N,N-diisopentyl-N'-methyl-2-phenyl-3-(3-(piperidin-1-yl)propyl)pyrazolo[1,5-a]pyridine-5-carboximidamide At room temperature, oxalyl chloride (0.26 mL, 3.0 mmol) was added to N,N-diisopentyl-2-phenyl-3-(3-(piperidin-1-yl)propyl)pyrazolo[1,5-a]pyridine-5-carboxamide (75 mg, 0.15 mmol) in dichloromethane (1 mL) and the mixture was heated to 50° C. for 20 minutes and was then poured into 1.5 mL of 2N methylamine in methanol. The mixture was evaporated under reduced pressure and the residue was dissolved in DMF, filtered and purified by RP-HPLC with 30% Solvent B (0-3 min) then a gradient 30% to 100% Solvent B over 12 minutes (Solvent A: $MeOH:H_2O:TFA$ (5:95:0.05); Solvent B: $MeOH:H_2O:TFA$ (95:5:0.05)) to afford, after freeze-drying overnight, 65 mg (59%) of the title compound as the TFA salt. LCMS m/z 516.4 $(M+H)^+$, ret. time=1.82 min.

TABLE 1

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 1 | 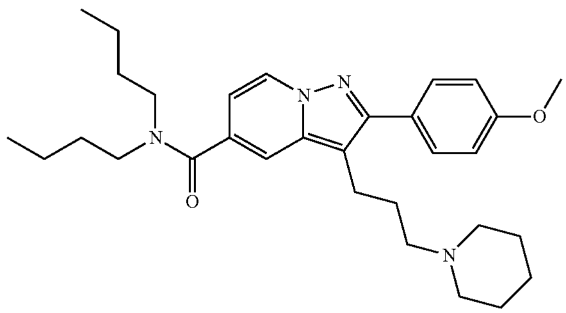 [SMILES: CCCCN(CCCC)C(=O)c1ccn2nc(-c3ccc(OC)cc3)c(CCCN3CCCCC3)c2c1] | 2.03 | 505.4 | C |
| 2 | 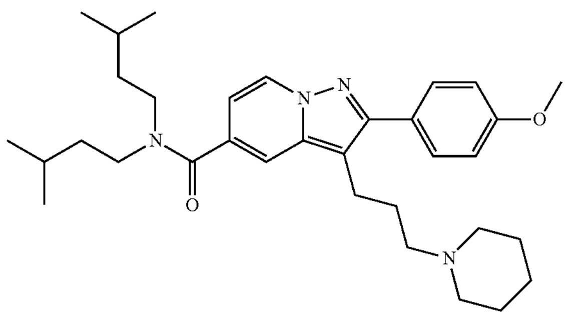 [SMILES: COc1ccc(-c2nn3ccc(C(=O)N(CCC(C)C)CCC(C)C)cc3c2CCCN2CCCCC2)cc1] | 2.15 | 533.4 | C |
| 3 | 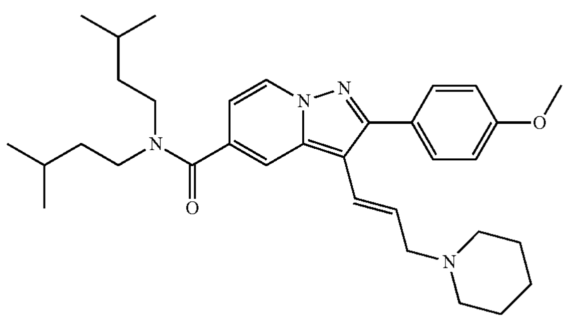 [SMILES: COc1ccc(-c2nn3ccc(C(=O)N(CCC(C)C)CCC(C)C)cc3c2/C=C/CN2CCCCC2)cc1] | 2.14 | 531.3 (weak) and 446.3 (strong)* | B |
| 4 | 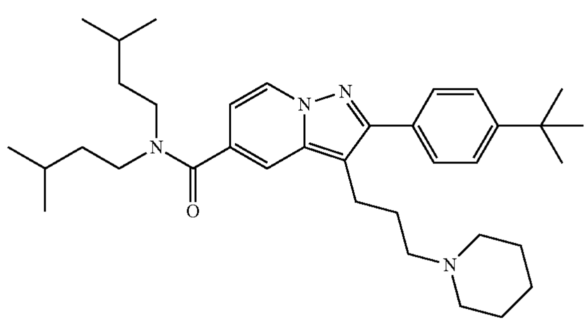 [SMILES: CC(C)CCN(CCC(C)C)C(=O)c1ccn2nc(-c3ccc(C(C)(C)C)cc3)c(CCCN3CCCCC3)c2c1] | 2.30 | 559.4 | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 5 | 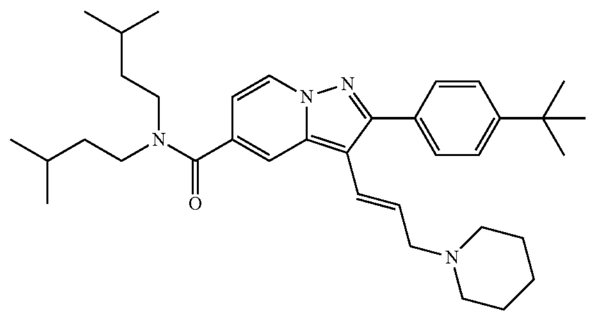 [SMILES: CC(C)CCN(CCC(C)C)C(=O)c1ccn2nc(-c3ccc(C(C)(C)C)cc3)c(/C=C/CN3CCCCC3)c2c1] | 2.30 | 557.4 (weak) and 472.3 (strong)* | C |
| 6 | 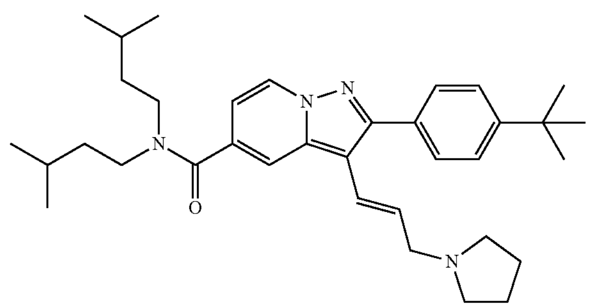 [SMILES: CC(C)CCN(CCC(C)C)C(=O)c1ccn2nc(-c3ccc(C(C)(C)C)cc3)c(/C=C/CN3CCCC3)c2c1] | 2.29 | 543.4 (weak) and 472.3 (strong)* | C |
| 7 | 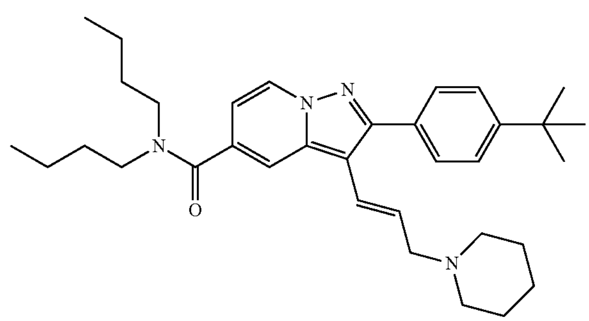 [SMILES: CCCCN(CCCC)C(=O)c1ccn2nc(-c3ccc(C(C)(C)C)cc3)c(/C=C/CN3CCCCC3)c2c1] | 2.22 | 444.3 (weak) and 472.3 (strong)* | D |
| 8 | 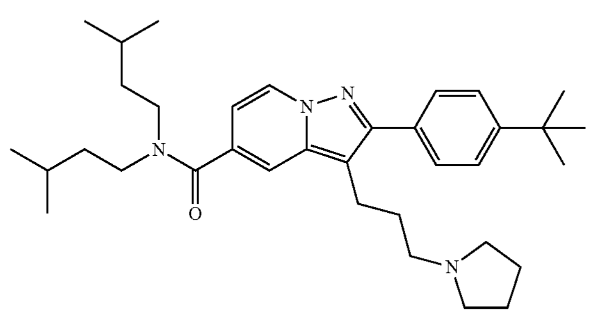 [SMILES: CC(C)CCN(CCC(C)C)C(=O)c1ccn2nc(-c3ccc(C(C)(C)C)cc3)c(CCCN3CCCC3)c2c1] | 2.26 | 545.4 | C |

TABLE 1-continued
Analytical HPLC retention time, LCMS data and $IC_{50}$ data (Activity range for $IC_{50}$ values: A < 500 nM; 500 nM < B < 1000 nM; 1000 nM < C < 5000 nM; 5000 < D < 15000 nM)
| Cpd No | Structure | HPLC RT (min) analytical | MS: $(M + H)^+$ see footnote* | $IC_{50}$ |
|---|---|---|---|---|
| 9 | 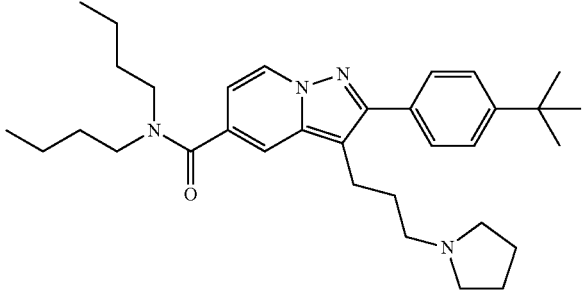 [SMILES: CCCCN(CCCC)C(=O)c1ccn2nc(-c3ccc(C(C)(C)C)cc3)c(CCCN3CCCC3)c2c1] | 2.20 | 517.4 | D |
| 10 | 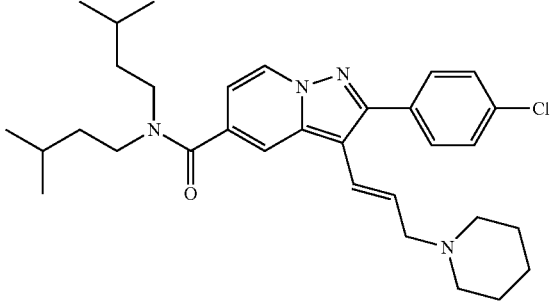 [SMILES: CC(C)CCN(CCC(C)C)C(=O)c1ccn2nc(-c3ccc(Cl)cc3)c(/C=C/CN3CCCCC3)c2c1] | 2.19 | 535.3 (weak) and 450.2 (strong)* | B |
| 11 | 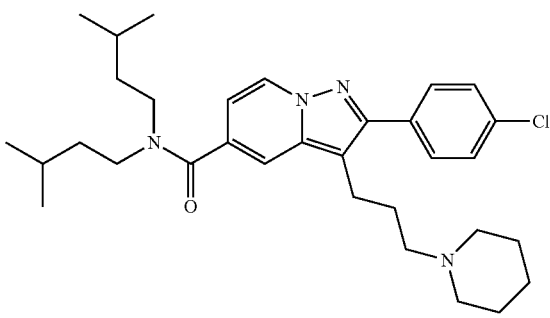 [SMILES: CC(C)CCN(CCC(C)C)C(=O)c1ccn2nc(-c3ccc(Cl)cc3)c(CCCN3CCCCC3)c2c1] | 2.20 | 537.3 | C |
| 12 | 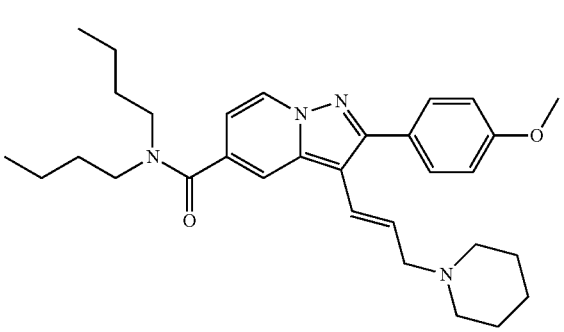 [SMILES: CCCCN(CCCC)C(=O)c1ccn2nc(-c3ccc(OC)cc3)c(/C=C/CN3CCCCC3)c2c1] | 2.04 | 503.3 (weak) and 418.3 (strong)* | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 13 | 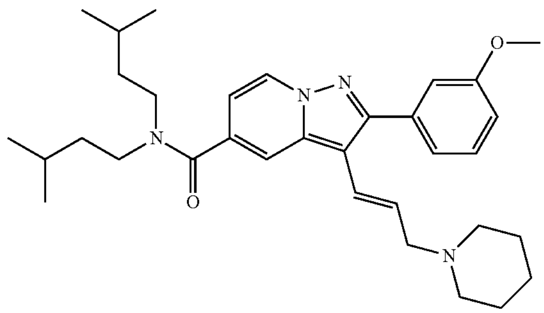 [SMILES: COc1cccc(-c2nn3ccc(C(=O)N(CCC(C)C)CCC(C)C)cc3c2/C=C/CN2CCCCC2)c1] | 2.14 | 531.4 (weak) and 446.3 (strong)* | B |
| 14 | 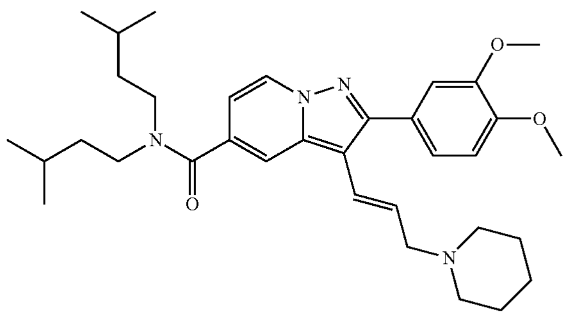 [SMILES: COc1ccc(-c2nn3ccc(C(=O)N(CCC(C)C)CCC(C)C)cc3c2/C=C/CN2CCCCC2)cc1OC] | 2.09 | 561.4 (weak) and 476.3 (strong)* | A |
| 15 | 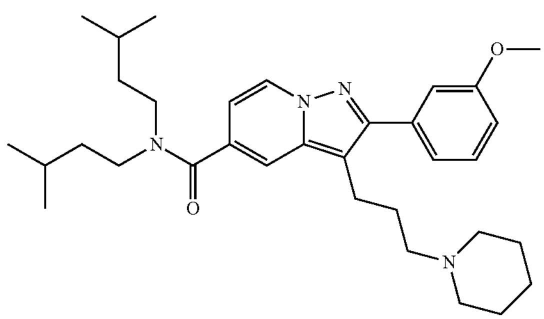 [SMILES: COc1cccc(-c2nn3ccc(C(=O)N(CCC(C)C)CCC(C)C)cc3c2CCCN2CCCCC2)c1] | 2.14 | 533.4 | A |
| 16 | 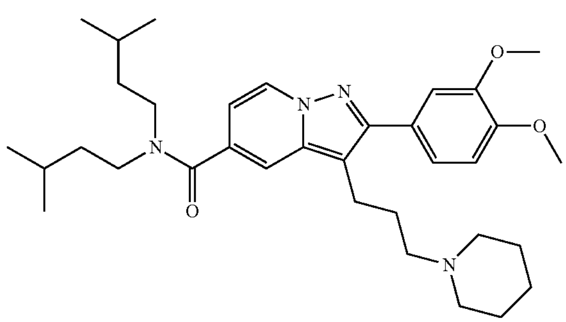 [SMILES: COc1ccc(-c2nn3ccc(C(=O)N(CCC(C)C)CCC(C)C)cc3c2CCCN2CCCCC2)cc1OC] | 2.11 | 563.4 | A |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 17 | 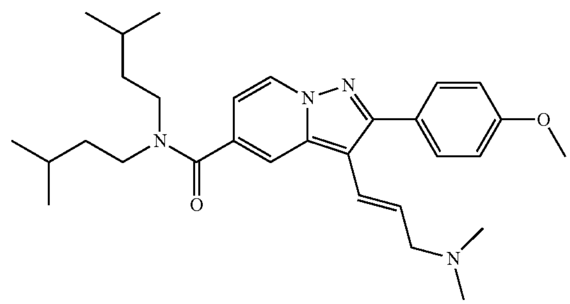 [SMILES: COc1ccc(-c2nn3ccc(C(=O)N(CCC(C)C)CCC(C)C)cc3c2/C=C/CN(C)C)cc1] | 2.12 | 491.3 (weak) and 446.3 (strong)* | D |
| 18 | 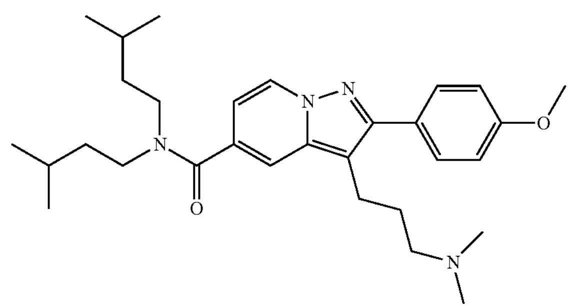 [SMILES: COc1ccc(-c2nn3ccc(C(=O)N(CCC(C)C)CCC(C)C)cc3c2CCCN(C)C)cc1] | 2.14 | 493.4 | D |
| 19 | 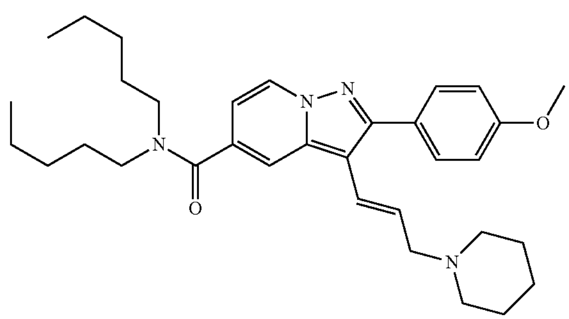 [SMILES: CCCCCN(CCCCC)C(=O)c1ccn2nc(-c3ccc(OC)cc3)c(/C=C/CN3CCCCC3)c2c1] | 2.17 | 531.4 (weak) and 446.3 (strong)* | C |
| 20 | 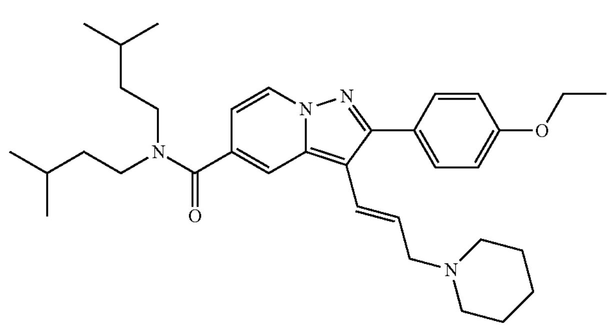 [SMILES: CCOc1ccc(-c2nn3ccc(C(=O)N(CCC(C)C)CCC(C)C)cc3c2/C=C/CN2CCCCC2)cc1] | 2.14 | 545.4 (weak) and 460.3 (strong)* | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 21 | 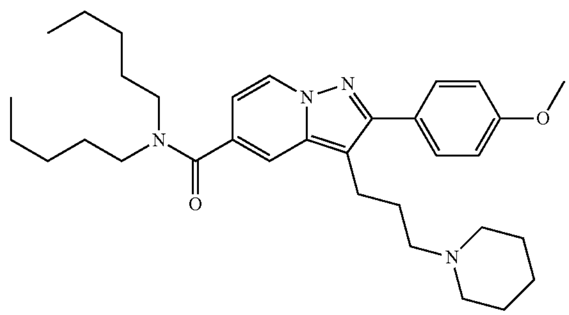 [SMILES: CCCCCN(CCCCC)C(=O)c1ccn2nc(-c3ccc(OC)cc3)c(CCCN3CCCCC3)c2c1] | 2.17 | 533.4 | C |
| 22 | 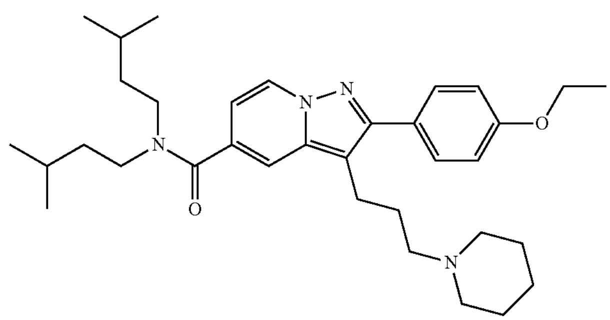 [SMILES: CCOc1ccc(-c2nn3ccc(C(=O)N(CCC(C)C)CCC(C)C)cc3c2CCCN2CCCCC2)cc1] | 2.15 | 547.4 | B |
| 23 | 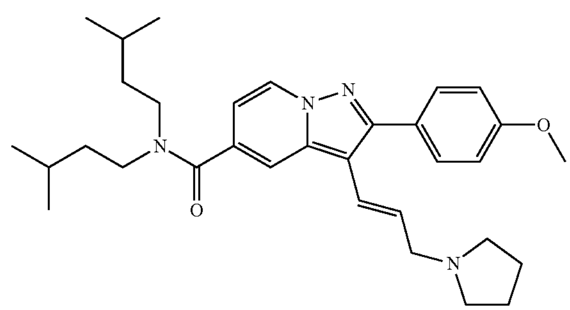 [SMILES: COc1ccc(-c2nn3ccc(C(=O)N(CCC(C)C)CCC(C)C)cc3c2/C=C/CN2CCCC2)cc1] | 2.17 | 517.3 (weak); 446.3 (strong)* | C |
| 24 | 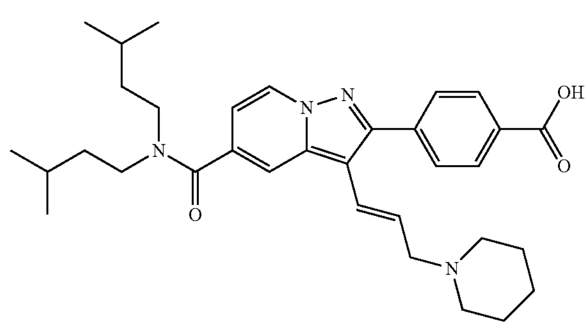 [SMILES: CC(C)CCN(CCC(C)C)C(=O)c1ccn2nc(-c3ccc(C(=O)O)cc3)c(/C=C/CN3CCCCC3)c2c1] | 2.11 | 545.7 (weak); 460.3 (strong)* | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 25 | 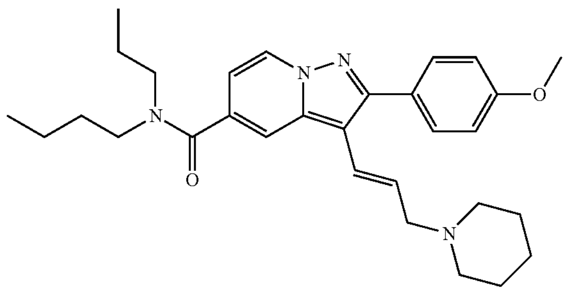 [SMILES: CCCCN(CCC)C(=O)c1ccn2nc(-c3ccc(OC)cc3)c(/C=C/CN3CCCCC3)c2c1] | 1.97 | 489.3 (weak) and 404.2 (strong)* | C |
| 26 | 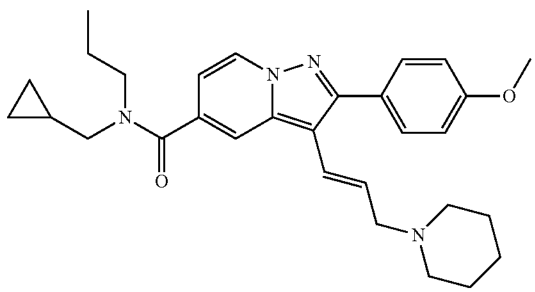 [SMILES: CCCN(CC1CC1)C(=O)c1ccn2nc(-c3ccc(OC)cc3)c(/C=C/CN3CCCCC3)c2c1] | 1.91 | 487.3 (weak) and 402.2 (strong)* | D |
| 27 | 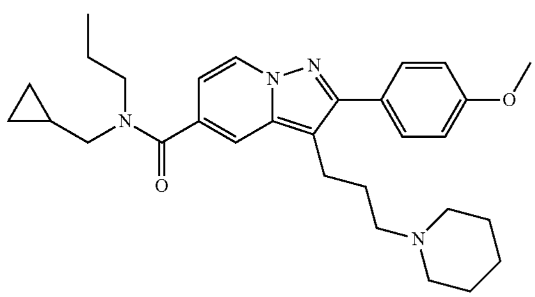 | 1.90 | 489.3 | D |
| 28 | 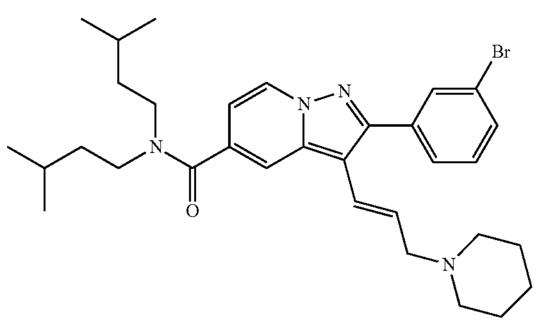 [SMILES: CC(C)CCN(CCC(C)C)C(=O)c1ccn2nc(-c3cccc(Br)c3)c(/C=C/CN3CCCCC3)c2c1] | 2.22 | 579.2; 581.2 (weak) and 494.2; 496.2 (strong)* | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 29 | 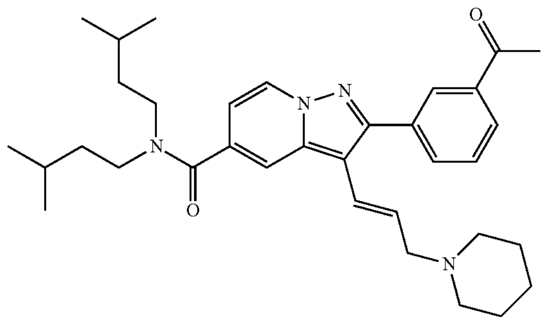 [SMILES: CC(=O)c1cccc(-c2nn3ccc(C(=O)N(CCC(C)C)CCC(C)C)cc3c2/C=C/CN2CCCCC2)c1] | 2.12 | 543.4* | B |
| 30 | 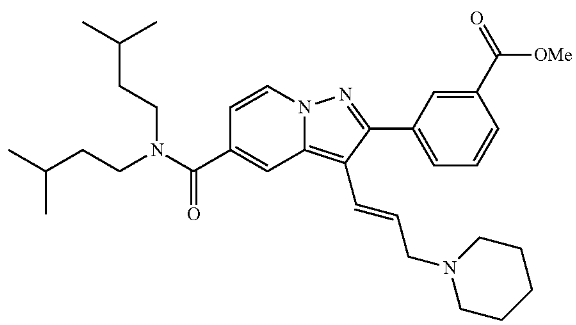 [SMILES: COC(=O)c1cccc(-c2nn3ccc(C(=O)N(CCC(C)C)CCC(C)C)cc3c2/C=C/CN2CCCCC2)c1] | 2.16 | 559.7* | A |
| 31 | 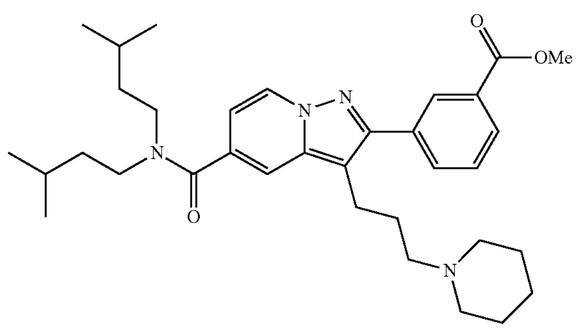 [SMILES: COC(=O)c1cccc(-c2nn3ccc(C(=O)N(CCC(C)C)CCC(C)C)cc3c2CCCN2CCCCC2)c1] | 2.16 | 561.7 | A |
| 32 | 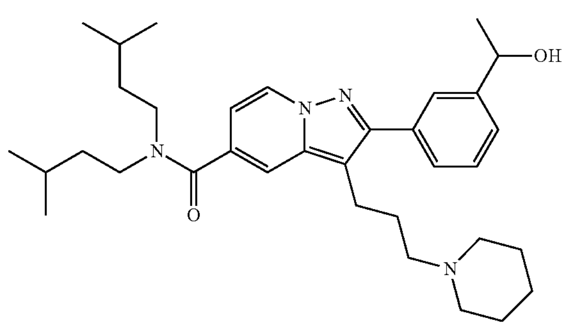 [SMILES: CC(C)CCN(CCC(C)C)C(=O)c1ccn2nc(-c3cccc(C(C)O)c3)c(CCCN3CCCCC3)c2c1] | 2.11 | 547.8 | B |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 33 | 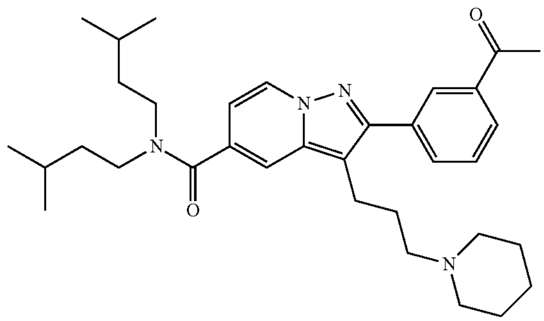 [SMILES: CC(=O)c1cccc(-c2nn3ccc(C(=O)N(CCC(C)C)CCC(C)C)cc3c2CCCN2CCCCC2)c1] | 2.14 | 545.4 | A |
| 34 | 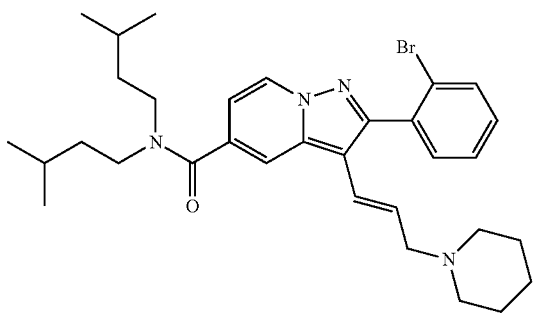 [SMILES: CC(C)CCN(CCC(C)C)C(=O)c1ccn2nc(-c3ccccc3Br)c(/C=C/CN3CCCCC3)c2c1] | 2.13 | 579.2; 581.2 (weak) and 494.2; 496.2 (strong)* | C |
| 35 | 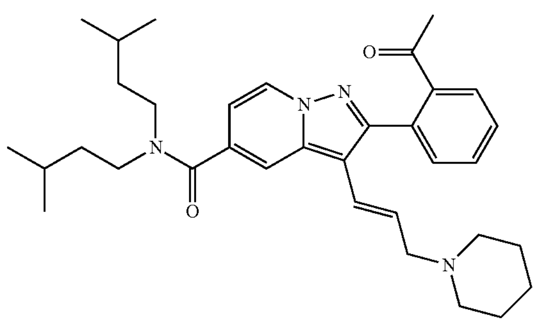 [SMILES: CC(=O)c1ccccc1-c1nn2ccc(C(=O)N(CCC(C)C)CCC(C)C)cc2c1/C=C/CN1CCCCC1] | 2.13 | 543.4* | C |
| 36 | 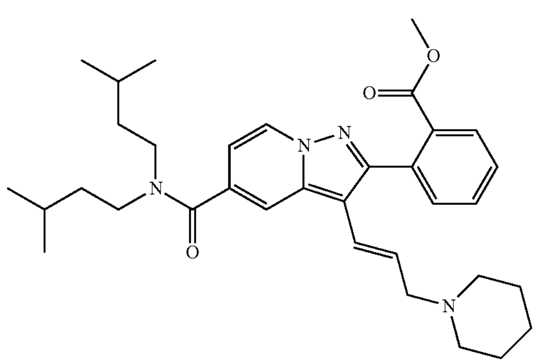 [SMILES: COC(=O)c1ccccc1-c1nn2ccc(C(=O)N(CCC(C)C)CCC(C)C)cc2c1/C=C/CN1CCCCC1] | 2.07 | 559.4* | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 37 | 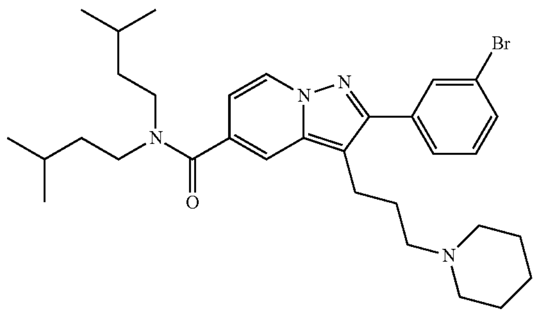 [SMILES: CC(C)CCN(CCC(C)C)C(=O)c1ccn2nc(-c3cccc(Br)c3)c(CCCN3CCCCC3)c2c1] | 2.24 | 581.2; 583.2 | A |
| 38 | 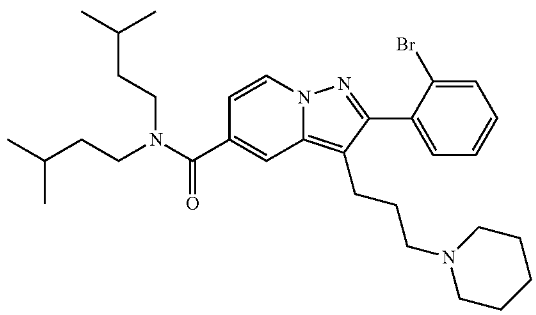 [SMILES: CC(C)CCN(CCC(C)C)C(=O)c1ccn2nc(-c3ccccc3Br)c(CCCN3CCCCC3)c2c1] | 2.14 | 581.2; 583.2 | C |
| 39 | 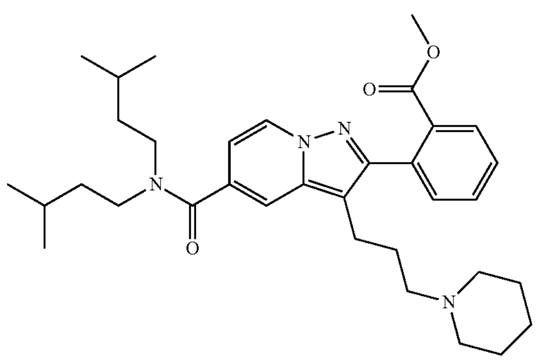 [SMILES: COC(=O)c1ccccc1-c1nn2ccc(C(=O)N(CCC(C)C)CCC(C)C)cc2c1CCCN1CCCCC1] | 2.09 | 561.3 | C |
| 40 | 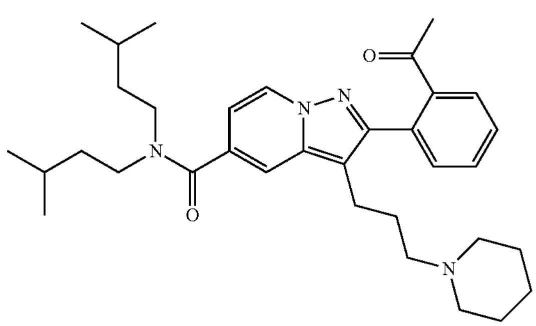 [SMILES: CC(=O)c1ccccc1-c1nn2ccc(C(=O)N(CCC(C)C)CCC(C)C)cc2c1CCCN1CCCCC1] | 2.10 | 545.3 | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)+ see footnote* | IC$_{50}$ |
|---|---|---|---|---|
| 41 | 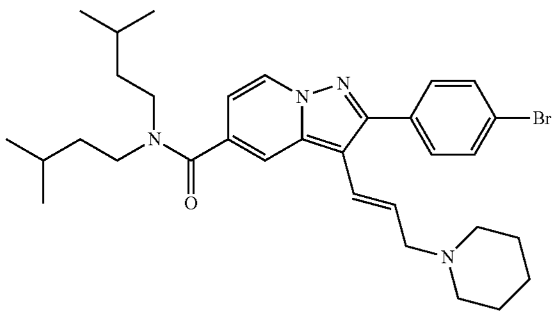 [SMILES: CC(C)CCN(CCC(C)C)C(=O)c1ccn2nc(-c3ccc(Br)cc3)c(/C=C/CN3CCCCC3)c2c1] | 2.22 | 579.2; 581.2 (weak) and 494.2; 496.2 (strong)* | C |
| 42 | 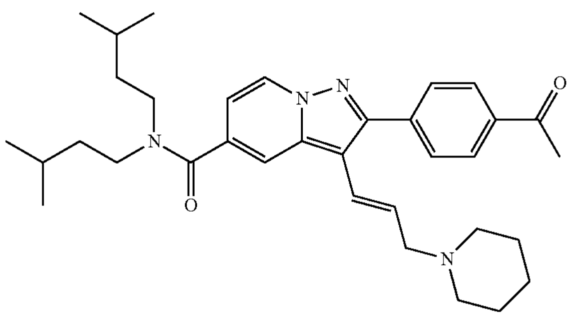 [SMILES: CC(=O)c1ccc(-c2nn3ccc(C(=O)N(CCC(C)C)CCC(C)C)cc3c2/C=C/CN2CCCCC2)cc1] | 2.12 | 543.4 (weak) and 458.3* | B |
| 43 | 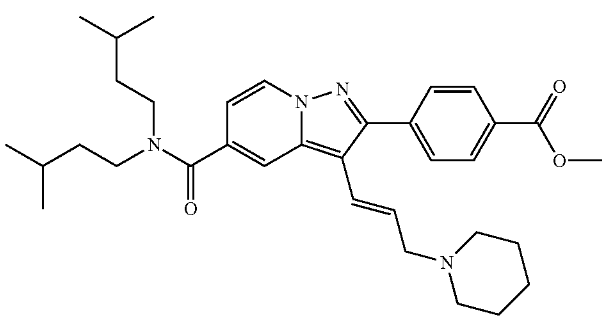 [SMILES: COC(=O)c1ccc(-c2nn3ccc(C(=O)N(CCC(C)C)CCC(C)C)cc3c2/C=C/CN2CCCCC2)cc1] | 2.18 | 559.4 (weak) and 474.3* | B |
| 44 | 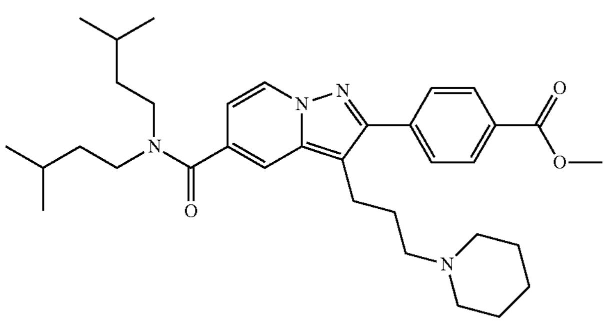 [SMILES: COC(=O)c1ccc(-c2nn3ccc(C(=O)N(CCC(C)C)CCC(C)C)cc3c2CCCN2CCCCC2)cc1] | 2.19 | 561.3 | B |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)+ see footnote* | IC$_{50}$ |
|---|---|---|---|---|
| 45 | 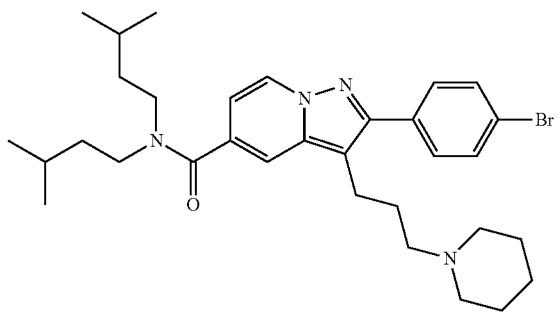 | 2.26 | 581.2 and 583.2 | A |
| 46 | 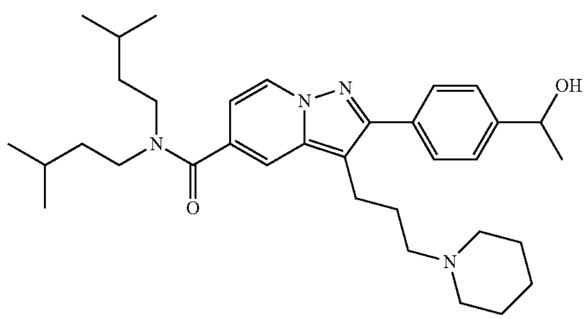 | 2.14 | 547.4 | A |
| 47 | 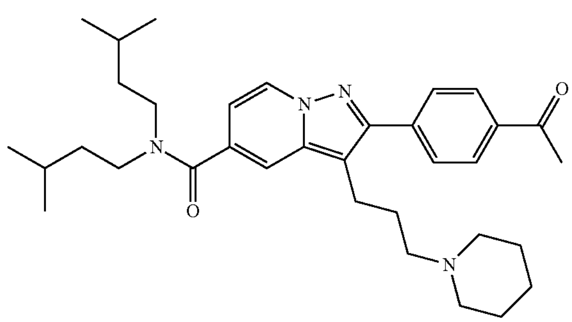 | 2.14 | 545.3 | B |
| 48 | 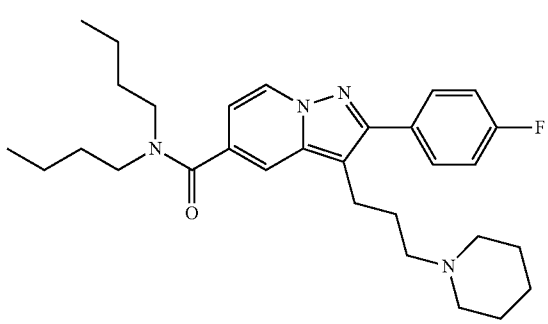 [SMILES: CCCCN(CCCC)C(=O)c1ccn2nc(-c3ccc(F)cc3)c(CCCN3CCCCC3)c2c1] | 2.03 | 493.3 | B |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)+ see footnote* | IC$_{50}$ |
|---|---|---|---|---|
| 49 | 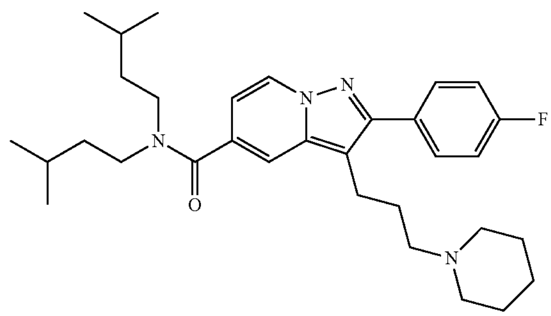 [SMILES: CC(C)CCN(CCC(C)C)C(=O)c1ccn2nc(-c3ccc(F)cc3)c(CCCN3CCCCC3)c2c1] | 2.14 | 521.4 | A |
| 50 | 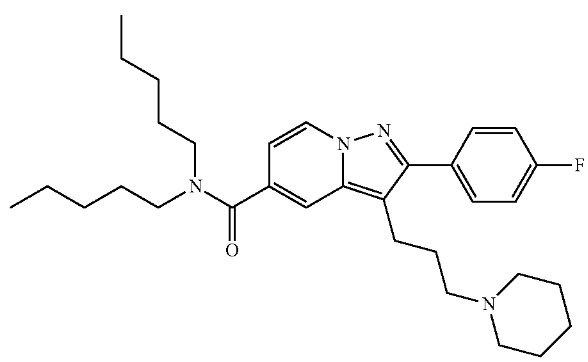 [SMILES: CCCCCN(CCCCC)C(=O)c1ccn2nc(-c3ccc(F)cc3)c(CCCN3CCCCC3)c2c1] | 2.16 | 521.4 | C |
| 51 | 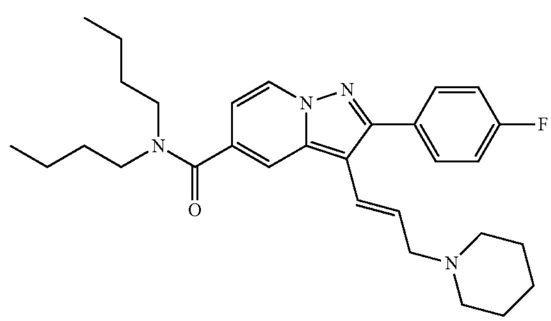 [SMILES: CCCCN(CCCC)C(=O)c1ccn2nc(-c3ccc(F)cc3)c(/C=C/CN3CCCCC3)c2c1] | 2.06 | 491.3 (weak); 406.2 (strong)* | C |
| 52 | 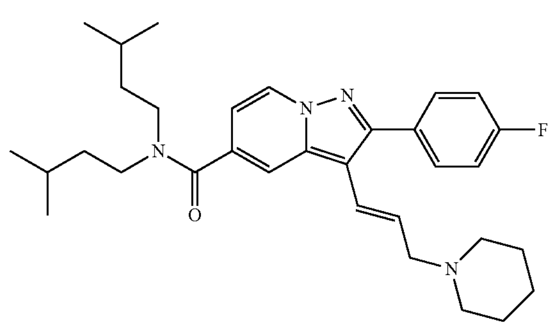 [SMILES: CC(C)CCN(CCC(C)C)C(=O)c1ccn2nc(-c3ccc(F)cc3)c(/C=C/CN3CCCCC3)c2c1] | 2.16 | 519.4 (weak); 434.3 (strong)* | B |

TABLE 1-continued
Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)
| Cpd No | Structure | HPLC RT (min) analytical | MS: (M + H)$^+$ see footnote* | IC$_{50}$ |
|---|---|---|---|---|
| 53 | 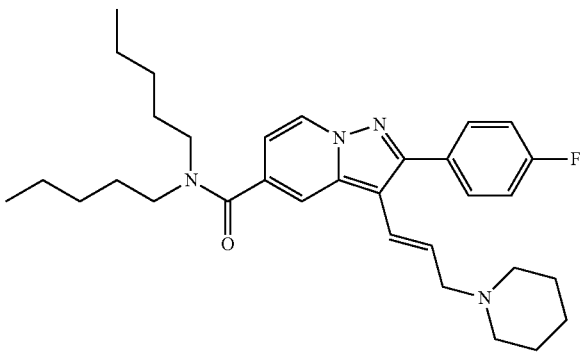 [SMILES: CCCCCN(CCCCC)C(=O)c1ccn2nc(-c3ccc(F)cc3)c(/C=C/CN3CCCCC3)c2c1] | 2.18 | 519.4 (weak); 434.3 (strong)* | C |
| 54 | 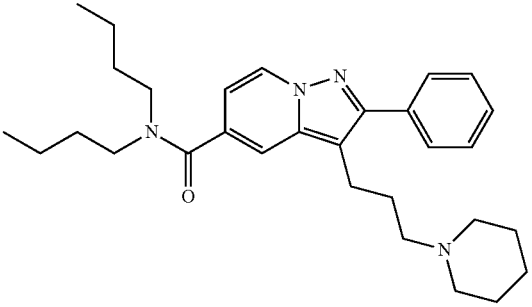 [SMILES: CCCCN(CCCC)C(=O)c1ccn2nc(-c3ccccc3)c(CCCN3CCCCC3)c2c1] | 2.00 | 475.3 | B |
| 55 | 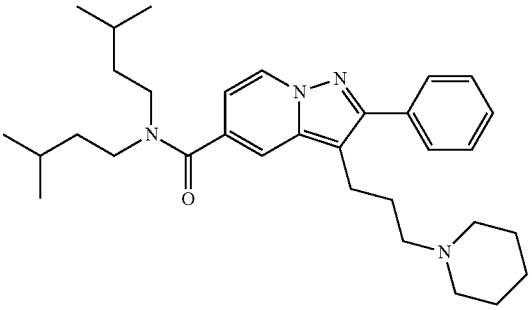 | 2.13 | 503.4 | C |
| 56 | 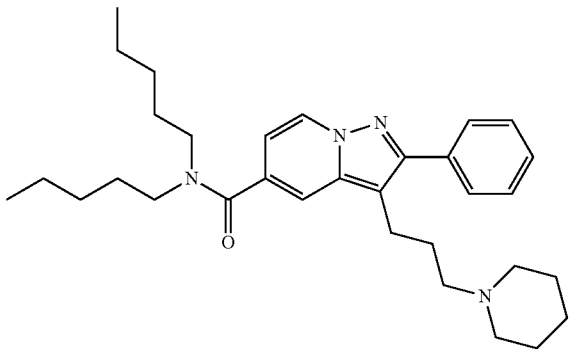 [SMILES: CCCCCN(CCCCC)C(=O)c1ccn2nc(-c3ccccc3)c(CCCN3CCCCC3)c2c1] | 2.16 | 503.4 | B |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 57 | 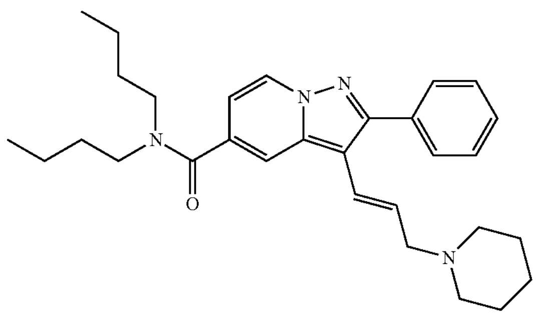 [SMILES: CCCCN(CCCC)C(=O)c1ccn2nc(-c3ccccc3)c(/C=C/CN3CCCCC3)c2c1] | 2.02 | 473.3 (weak); 388.2 (strong)* | C |
| 58 | 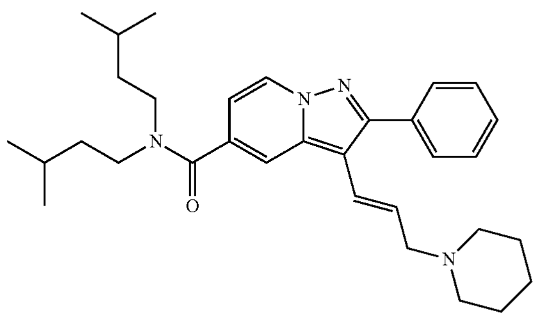 [SMILES: CC(C)CCN(CCC(C)C)C(=O)c1ccn2nc(-c3ccccc3)c(/C=C/CN3CCCCC3)c2c1] | 2.11 | 501.4 (weak); 416.3 (strong)* | B |
| 59 | 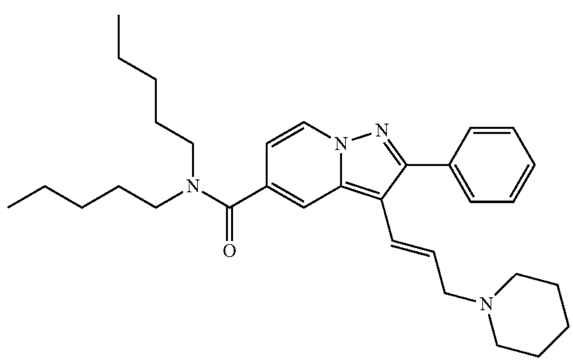 [SMILES: CCCCCN(CCCCC)C(=O)c1ccn2nc(-c3ccccc3)c(/C=C/CN3CCCCC3)c2c1] | 2.12 | 501.4 (weak); 416.3 (strong)* | C |
| 60 | 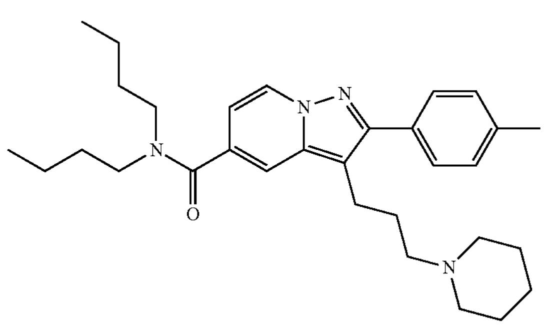 [SMILES: CCCCN(CCCC)C(=O)c1ccn2nc(-c3ccc(C)cc3)c(CCCN3CCCCC3)c2c1] | 2.08 | 489.4 | B |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 61 | 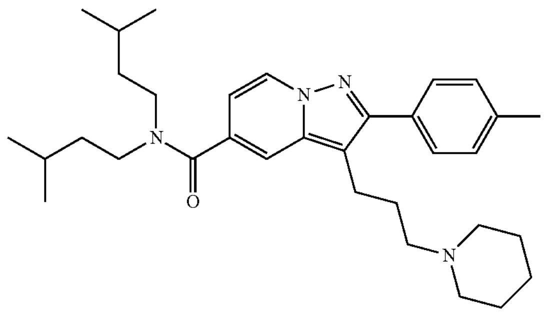 [SMILES: Cc1ccc(-c2nn3ccc(C(=O)N(CCC(C)C)CCC(C)C)cc3c2CCCN2CCCCC2)cc1] | 2.19 | 517.4 | A |
| 62 | 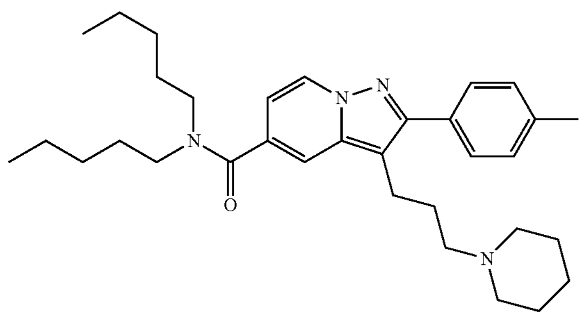 [SMILES: CCCCCN(CCCCC)C(=O)c1ccn2nc(-c3ccc(C)cc3)c(CCCN3CCCCC3)c2c1] | 2.22 | 517.4 | C |
| 63 | 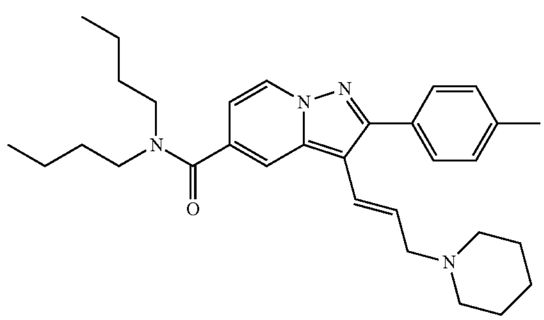 [SMILES: CCCCN(CCCC)C(=O)c1ccn2nc(-c3ccc(C)cc3)c(/C=C/CN3CCCCC3)c2c1] | 2.09 | 587.4 (weak); 402.3 (strong)* | B |
| 64 | 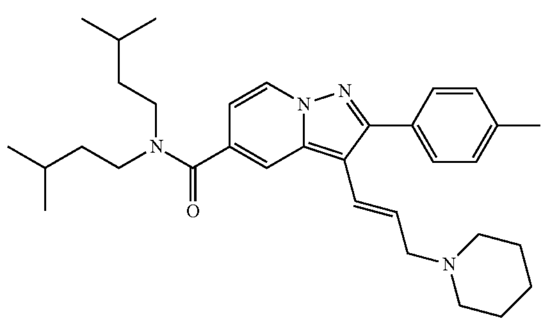 [SMILES: Cc1ccc(-c2nn3ccc(C(=O)N(CCC(C)C)CCC(C)C)cc3c2/C=C/CN2CCCCC2)cc1] | 2.18 | 515.4 (weak); 430.3 (strong)* | A |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)+ see footnote* | IC$_{50}$ |
|---|---|---|---|---|
| 65 | 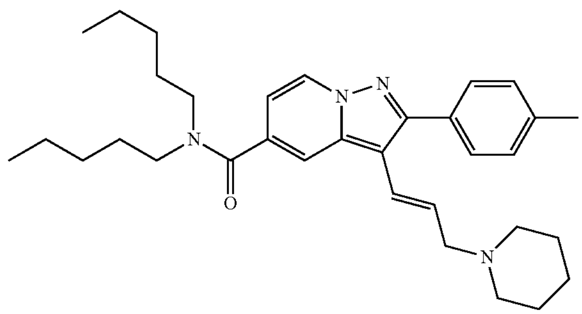 [SMILES: CCCCCN(CCCCC)C(=O)c1ccn2nc(-c3ccc(C)cc3)c(/C=C/CN3CCCCC3)c2c1] | 2.20 | 515.4 (weak); 430.3 (strong)* | C |
| 66 | 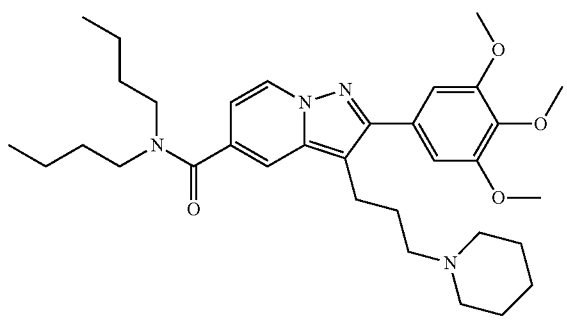 [SMILES: CCCCN(CCCC)C(=O)c1ccn2nc(-c3cc(OC)c(OC)c(OC)c3)c(CCCN3CCCCC3)c2c1] | 1.99 | 565.4 | B |
| 67 | 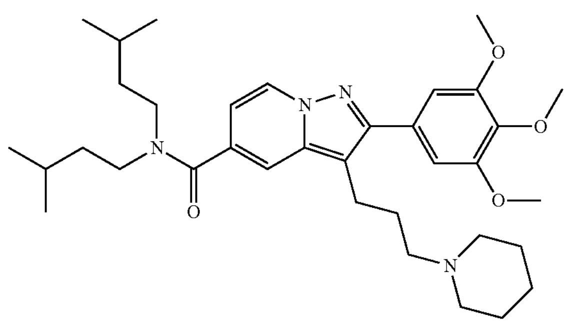 | 2.11 | 593.4 | A |
| 68 | 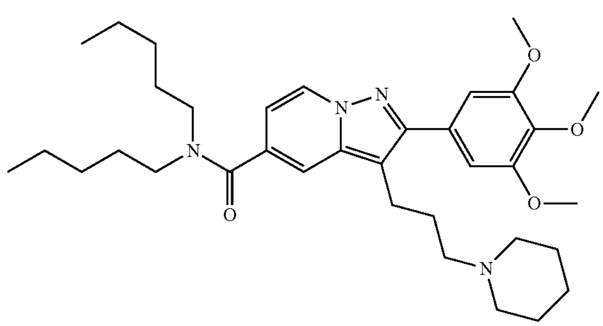 [SMILES: CCCCCN(CCCCC)C(=O)c1ccn2nc(-c3cc(OC)c(OC)c(OC)c3)c(CCCN3CCCCC3)c2c1] | 2.16 | 593.4 | B |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 69 | 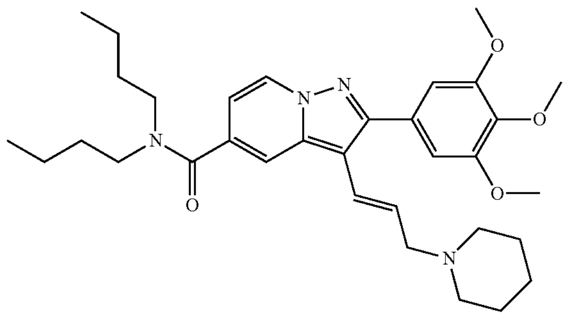 [SMILES: CCCCN(CCCC)C(=O)c1ccn2nc(-c3cc(OC)c(OC)c(OC)c3)c(/C=C/CN3CCCCC3)c2c1] | 2.00 | 563.4 (weak); 473.3 (strong)* | B |
| 70 | 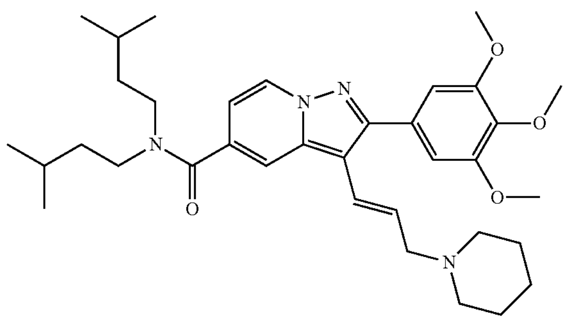 [SMILES: COc1cc(-c2nn3ccc(C(=O)N(CCC(C)C)CCC(C)C)cc3c2/C=C/CN2CCCCC2)cc(OC)c1OC] | 2.26 | 591.4 (weak); 506.3 (strong)* | A |
| 71 | 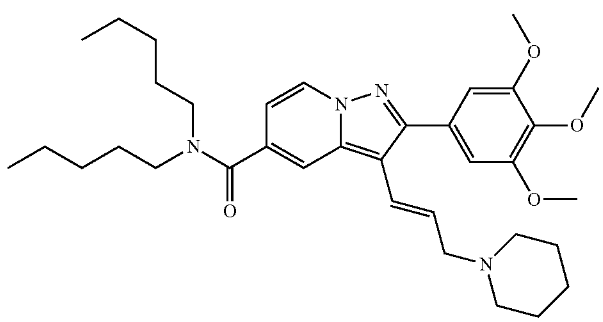 [SMILES: CCCCCN(CCCCC)C(=O)c1ccn2nc(-c3cc(OC)c(OC)c(OC)c3)c(/C=C/CN3CCCCC3)c2c1] | 2.26 | 591.4 (weak); 506.3 (strong)* | C |
| 72 | 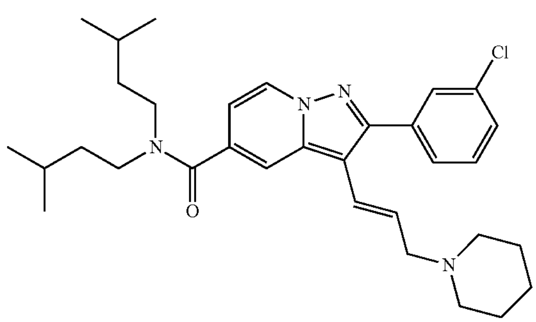 [SMILES: CC(C)CCN(CCC(C)C)C(=O)c1ccn2nc(-c3cccc(Cl)c3)c(/C=C/CN3CCCCC3)c2c1] | 2.19 | 535.3 (weak); 450.2 (strong)* | B |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 73 | 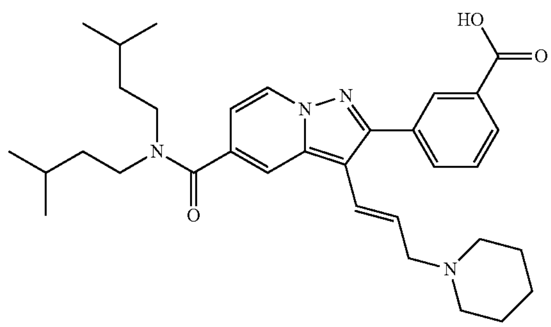 [SMILES: CC(C)CCN(CCC(C)C)C(=O)c1ccn2nc(-c3cccc(C(=O)O)c3)c(/C=C/CN3CCCCC3)c2c1] | 2.14 | 545.3 (weak); 460.3 (strong)* | C |
| 74 | 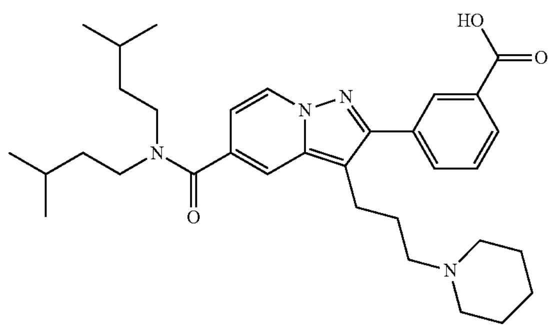 [SMILES: CC(C)CCN(CCC(C)C)C(=O)c1ccn2nc(-c3cccc(C(=O)O)c3)c(CCCN3CCCCC3)c2c1] | 2.14 | 547.3 | C |
| 75 | 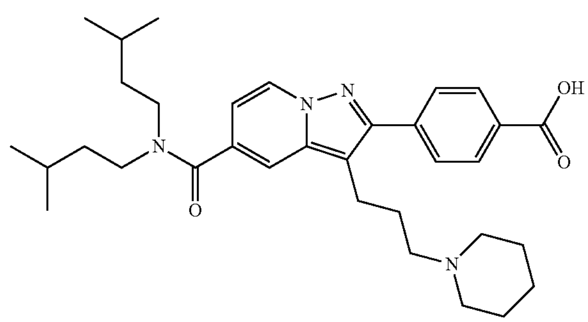 [SMILES: CC(C)CCN(CCC(C)C)C(=O)c1ccn2nc(-c3ccc(C(=O)O)cc3)c(CCCN3CCCCC3)c2c1] | 2.13 | 547.4 | C |
| 76 | 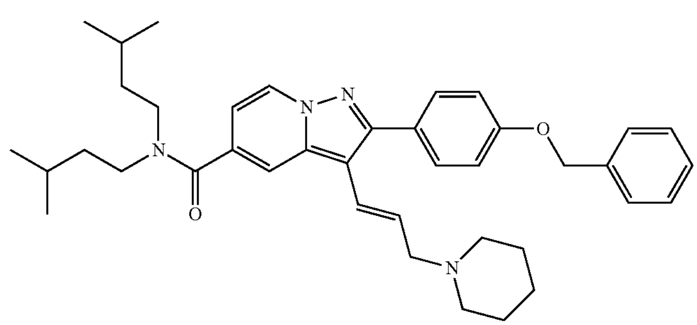 [SMILES: CC(C)CCN(CCC(C)C)C(=O)c1ccn2nc(-c3ccc(OCc4ccccc4)cc3)c(/C=C/CN3CCCCC3)c2c1] | 2.26 | 607.3 (weak); 522.3 (strong)* | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 77 | 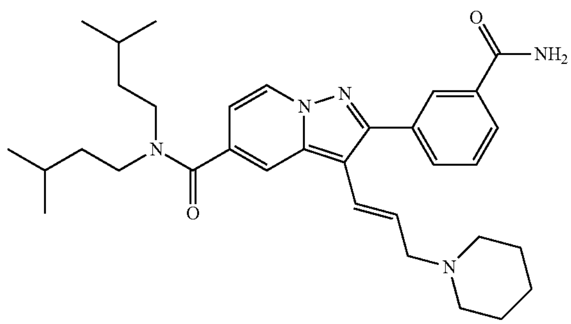 [SMILES: CC(C)CCN(CCC(C)C)C(=O)c1ccn2nc(-c3cccc(C(N)=O)c3)c(/C=C/CN3CCCCC3)c2c1] | 2.05 | 544.4 (weak); 459.3 (strong)* | A |
| 78 | 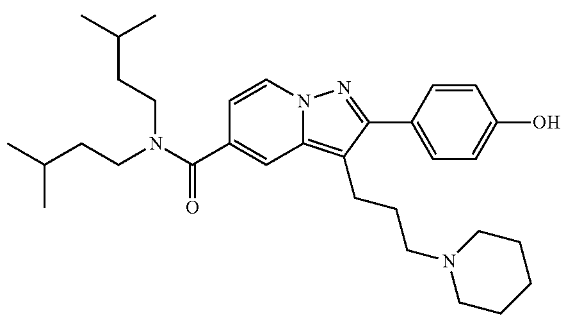 | 2.07 | 519.4 | A |
| 79 | 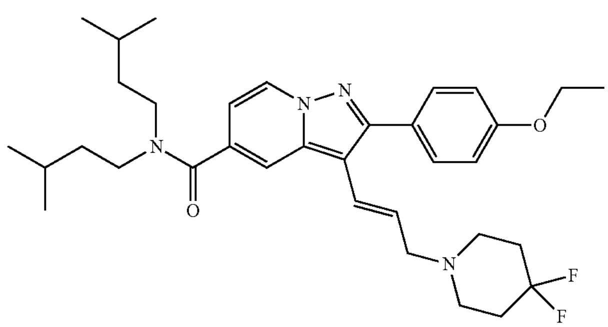 [SMILES: CCOc1ccc(-c2nn3ccc(C(=O)N(CCC(C)C)CCC(C)C)cc3c2/C=C/CN2CCC(F)(F)CC2)cc1] | 2.19 | 581.7 (weak); 460.3 (strong)* | D |
| 80 | 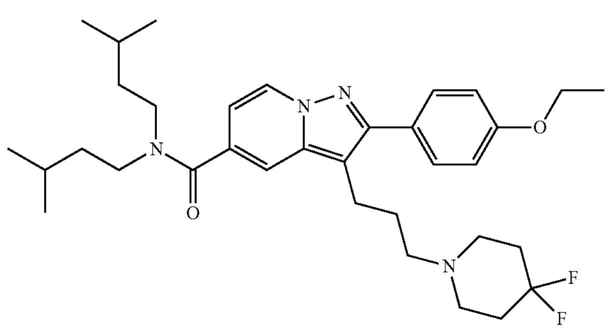 [SMILES: CCOc1ccc(-c2nn3ccc(C(=O)N(CCC(C)C)CCC(C)C)cc3c2CCCN2CCC(F)(F)CC2)cc1] | 2.20 | 583.4 | D |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 81 | 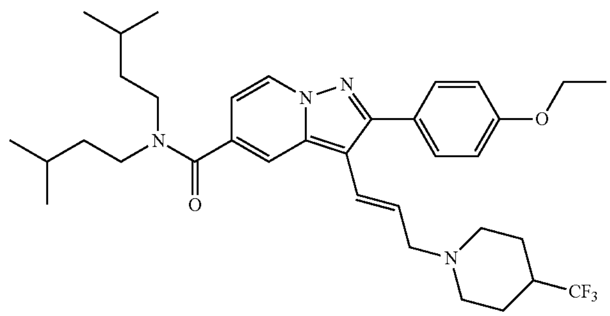 [SMILES: CCOc1ccc(-c2nn3ccc(C(=O)N(CCC(C)C)CCC(C)C)cc3c2/C=C/CN2CCC(C(F)(F)F)CC2)cc1] | 2.19 | 613.4 (weak); 460.3 (strong)* | D |
| 82 | 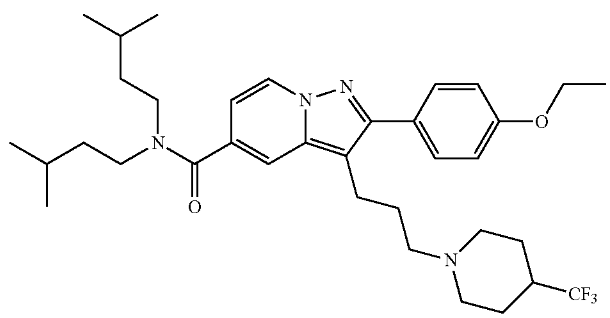 [SMILES: CCOc1ccc(-c2nn3ccc(C(=O)N(CCC(C)C)CCC(C)C)cc3c2CCCN2CCC(C(F)(F)F)CC2)cc1] | 2.19 | 615.4 | D |
| 83 | 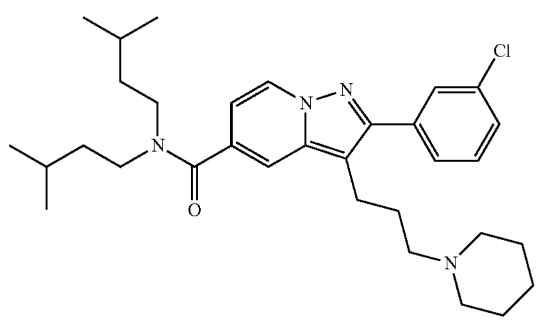 [SMILES: CC(C)CCN(CCC(C)C)C(=O)c1ccn2nc(-c3cccc(Cl)c3)c(CCCN3CCCCC3)c2c1] | 2.20 | 535.3 | A |
| 84 | 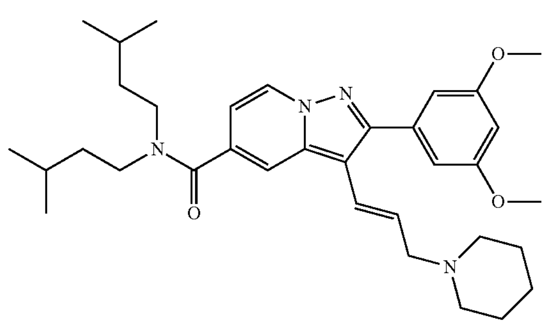 [SMILES: COc1cc(OC)cc(-c2nn3ccc(C(=O)N(CCC(C)C)CCC(C)C)cc3c2/C=C/CN2CCCCC2)c1] | 2.16 | 561.4 (weak); 476.3 (strong)* | A |

TABLE 1-continued

Analytical HPLC retention time, LCMS data and $IC_{50}$ data (Activity range for $IC_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)+ see footnote* | $IC_{50}$ |
|---|---|---|---|---|
| 85 | 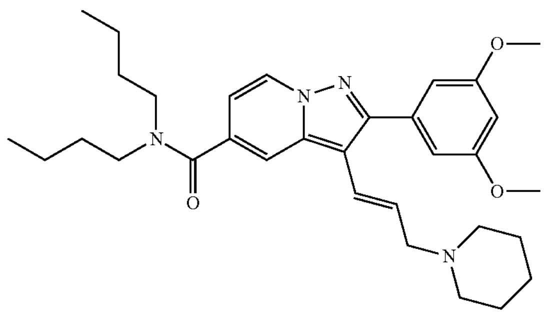 [SMILES: CCCCN(CCCC)C(=O)c1ccn2nc(-c3cc(OC)cc(OC)c3)c(/C=C/CN3CCCCC3)c2c1] | 2.06 | 533.4 (weak); 448.3 (strong)* | B |
| 86 | 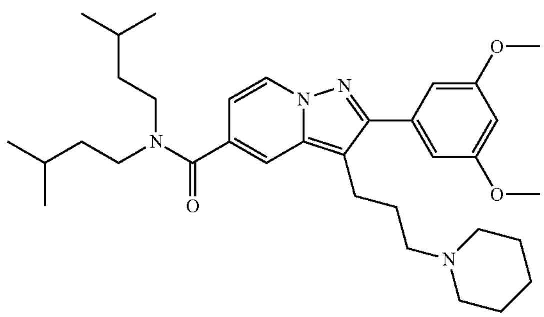 [SMILES: COc1cc(OC)cc(-c2nn3ccc(C(=O)N(CCC(C)C)CCC(C)C)cc3c2CCCN2CCCCC2)c1] | 2.16 | 563.4 | A |
| 87 | 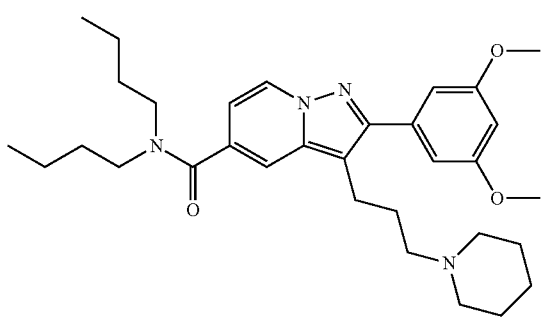 [SMILES: CCCCN(CCCC)C(=O)c1ccn2nc(-c3cc(OC)cc(OC)c3)c(CCCN3CCCCC3)c2c1] | 2.06 | 535.4 | C |
| 88 | 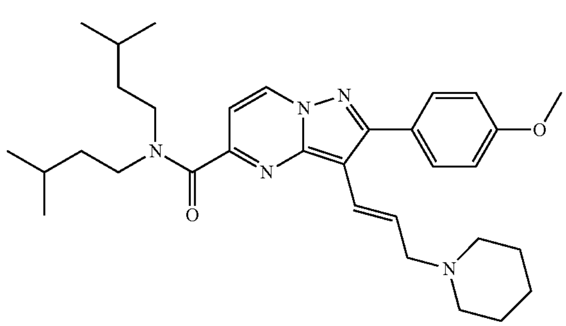 | 2.11 | 532.4 (weak); 447.3 (strong)* | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 89 | 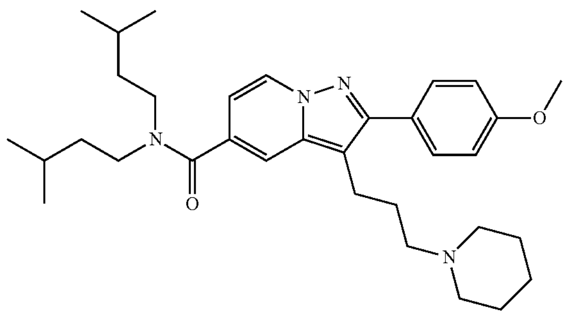 | 2.13 | 534.4 | C |
| 90 | 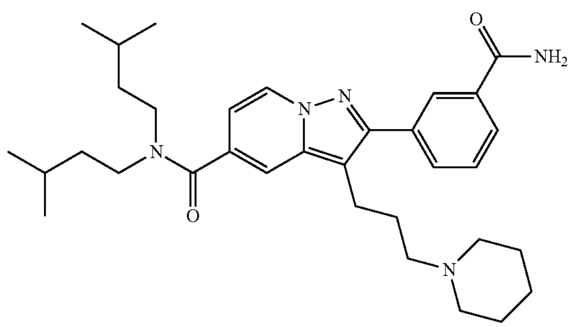 [SMILES: CC(C)CCN(CCC(C)C)C(=O)c1ccn2nc(-c3cccc(C(N)=O)c3)c(CCCN3CCCCC3)c2c1] | 2.05 | 546.4 | A |
| 91 | 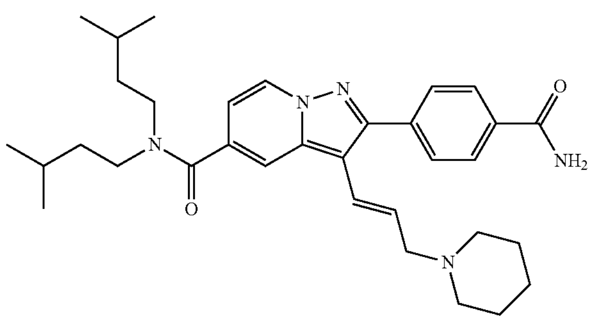 [SMILES: CC(C)CCN(CCC(C)C)C(=O)c1ccn2nc(-c3ccc(C(N)=O)cc3)c(/C=C/CN3CCCCC3)c2c1] | 2.02 | 544.3 (weak); 459.3 (strong)* | B |
| 92 | 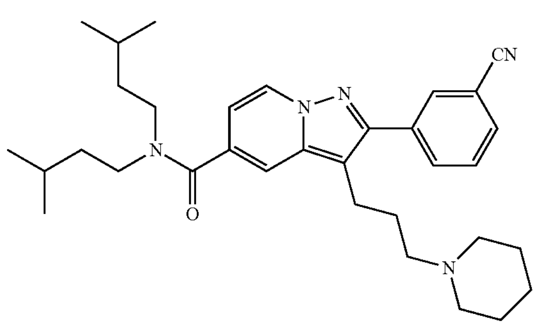 | 2.11 | 528.4 | A |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 93 | 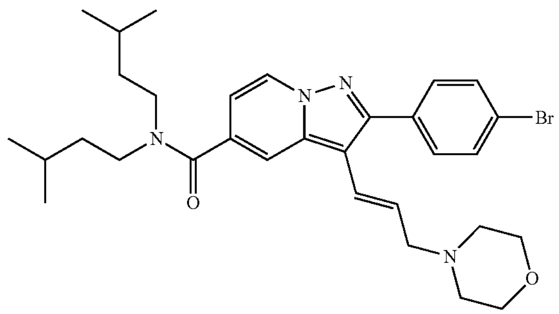 | 2.19 | 494.2; 496.2* | D |
| 94 | 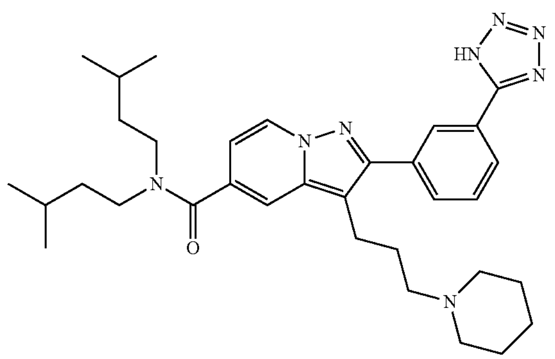 [SMILES: CC(C)CCN(CCC(C)C)C(=O)c1ccn2nc(-c3cccc(-c4nnn[nH]4)c3)c(CCCN3CCCCC3)c2c1] | 2.11 | 571.4 | B |
| 95 | 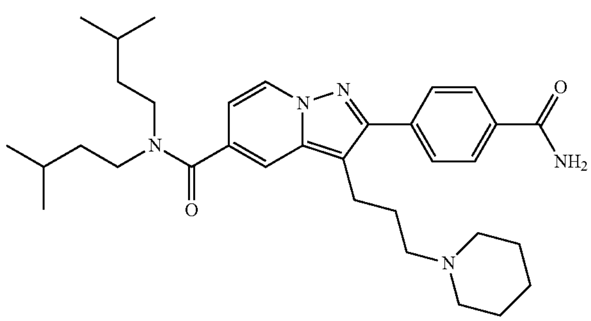 [SMILES: CC(C)CCN(CCC(C)C)C(=O)c1ccn2nc(-c3ccc(C(N)=O)cc3)c(CCCN3CCCCC3)c2c1] | 2.03 | 546.4 | A |
| 96 | 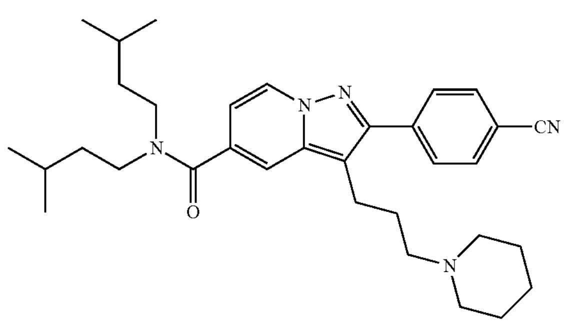 | 2.12 | 528.4 | A |

TABLE 1-continued
Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)
| Cpd No | Structure | HPLC RT (min) analytical | MS: (M + H)$^+$ see footnote* | IC$_{50}$ |
|---|---|---|---|---|
| 97 | 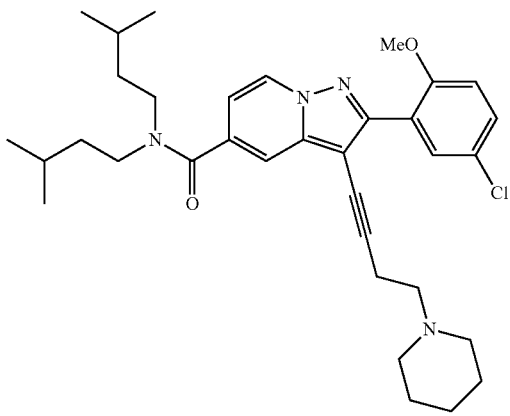 [SMILES: COc1ccc(Cl)cc1-c1nn2ccc(C(=O)N(CCC(C)C)CCC(C)C)cc2c1C#CCCN1CCCCC1] | 2.17 | 577.3 | C |
| 98 | 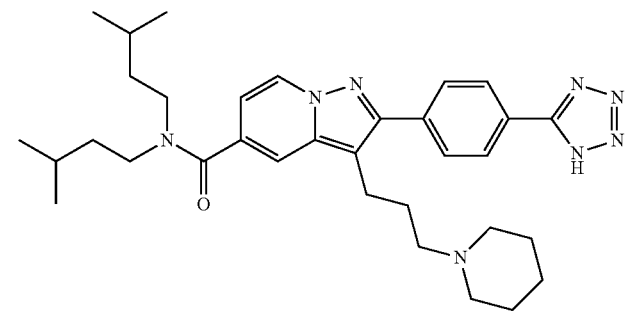 [SMILES: CC(C)CCN(CCC(C)C)C(=O)c1ccn2nc(-c3ccc(-c4nnn[nH]4)cc3)c(CCCN3CCCCC3)c2c1] | 2.10 | 571.4 | C |
| 99 | 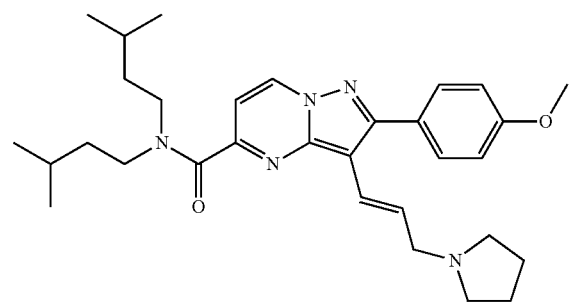 [SMILES: COc1ccc(-c2nn3ccc(C(=O)N(CCC(C)C)CCC(C)C)nc3c2/C=C/CN2CCCC2)cc1] | 2.08 | 518.3 (weak); 447.3 (strong)* | C |
| 100 | 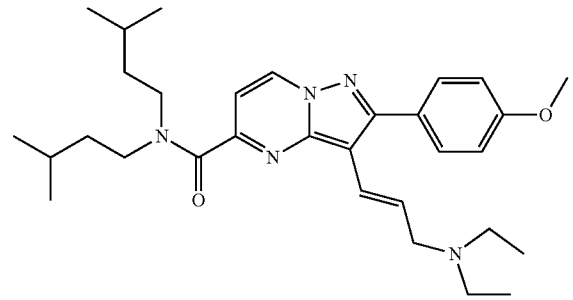 | 2.09 | 520.3 (weak); 447.3 (strong)* | D |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 101 | 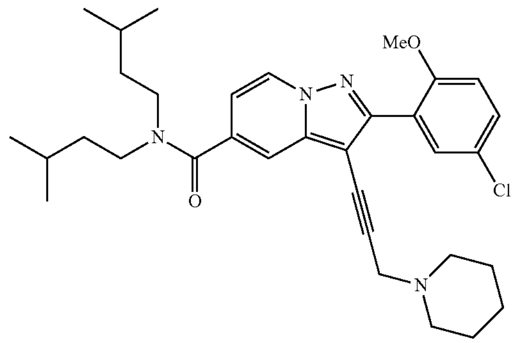 [SMILES: COc1ccc(Cl)cc1-c1nn2ccc(C(=O)N(CCC(C)C)CCC(C)C)cc2c1C#CCN1CCCCC1] | 2.14 | 563.3* | A |
| 102 | 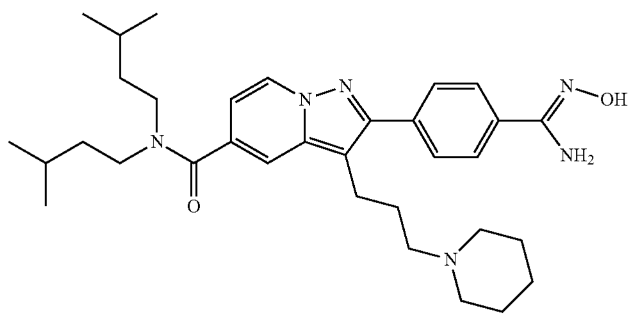 [SMILES: CC(C)CCN(CCC(C)C)C(=O)c1ccn2nc(-c3ccc(/C(N)=N/O)cc3)c(CCCN3CCCCC3)c2c1] | 1.91 | 561.4 | A |
| 103 | 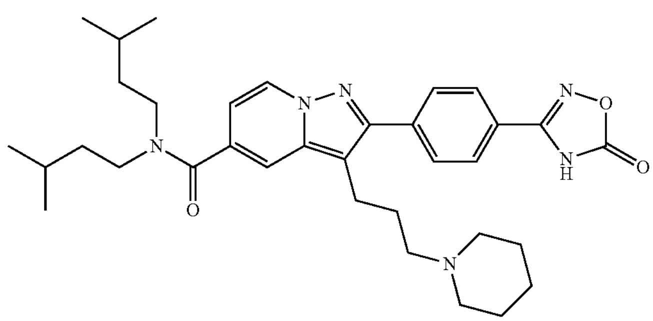 [SMILES: CC(C)CCN(CCC(C)C)C(=O)c1ccn2nc(-c3ccc(-c4noc(=O)[nH]4)cc3)c(CCCN3CCCCC3)c2c1] | 2.12 | 587.4 | B |
| 104 | 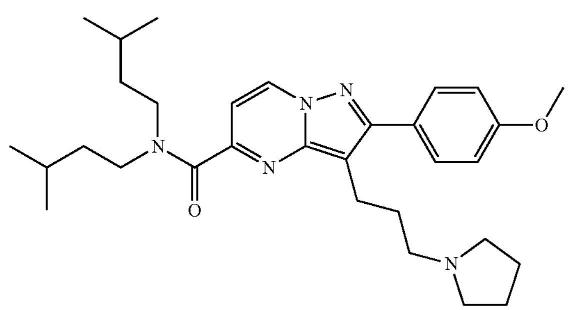 [SMILES: COc1ccc(-c2nn3ccc(C(=O)N(CCC(C)C)CCC(C)C)nc3c2CCCN2CCCC2)cc1] | 2.11 | 520.4 | D |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 105 | 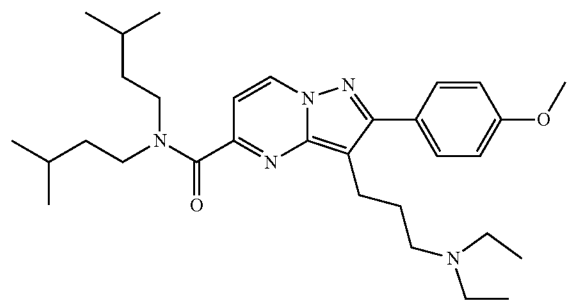 [SMILES: CCN(CC)CCCc1c(-c2ccc(OC)cc2)nn2ccc(C(=O)N(CCC(C)C)CCC(C)C)nc12] | 2.13 | 522.4 | D |
| 106 | 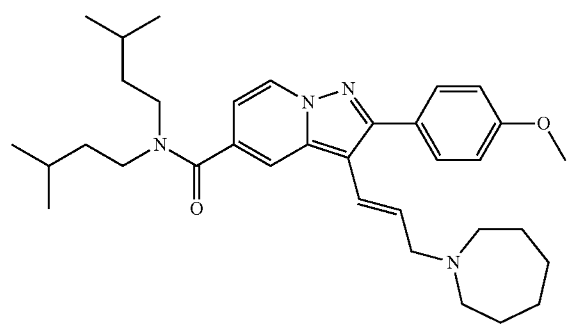 [SMILES: COc1ccc(-c2nn3ccc(C(=O)N(CCC(C)C)CCC(C)C)cc3c2/C=C/CN2CCCCCC2)cc1] | 2.16 | 545.4 (weak); 446.3 (strong)* | C |
| 107 | 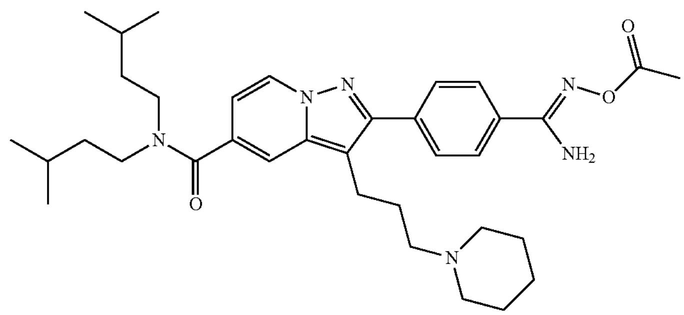 [SMILES: CC(=O)O/N=C(\N)c1ccc(-c2nn3ccc(C(=O)N(CCC(C)C)CCC(C)C)cc3c2CCCN2CCCCC2)cc1] | 2.06 | 603.4 | A |
| 108 | 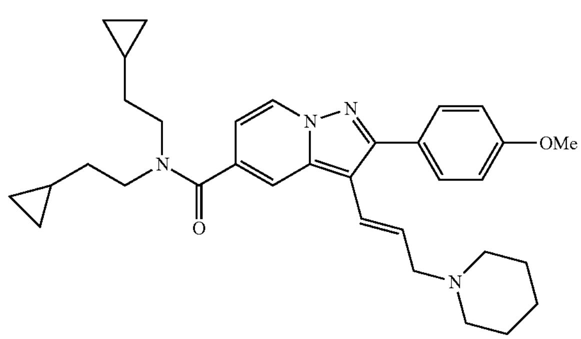 [SMILES: COc1ccc(-c2nn3ccc(C(=O)N(CCC4CC4)CCC4CC4)cc3c2/C=C/CN2CCCCC2)cc1] | 2.04 | 527.3 (weak); 442.3 (strong)* | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 109 | 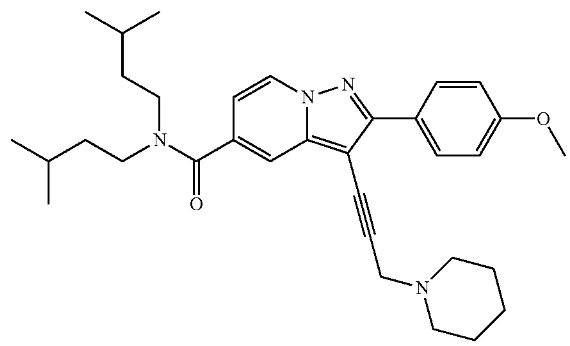 [SMILES: COc1ccc(-c2nn3ccc(C(=O)N(CCC(C)C)CCC(C)C)cc3c2C#CCN2CCCCC2)cc1] | 2.16 | 529.4 (weak); 444.3 (strong)* | C |
| 110 | 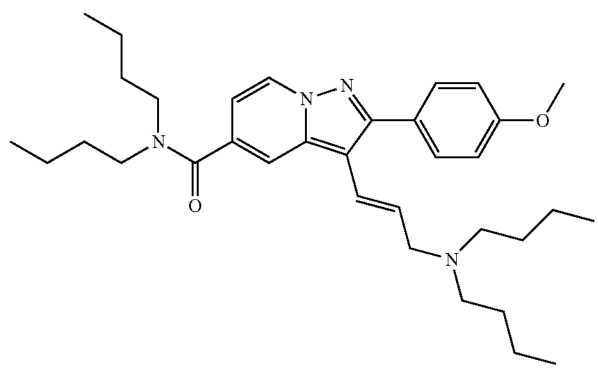 [SMILES: CCCCN(C/C=C/c1c(-c2ccc(OC)cc2)nn2ccc(C(=O)N(CCCC)CCCC)cc12)CCCC] | 2.16 | 547.4 | D |
| 111 | 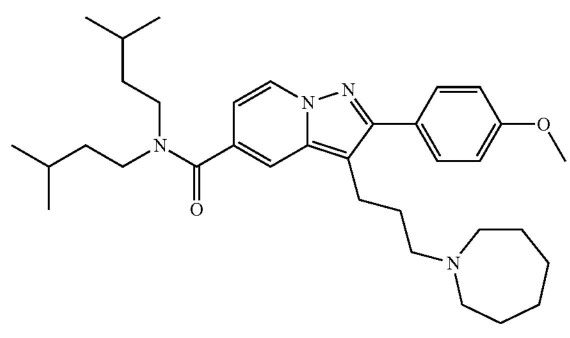 [SMILES: COc1ccc(-c2nn3ccc(C(=O)N(CCC(C)C)CCC(C)C)cc3c2CCCN2CCCCCC2)cc1] | 2.15 | 547.4 | C |
| 112 | 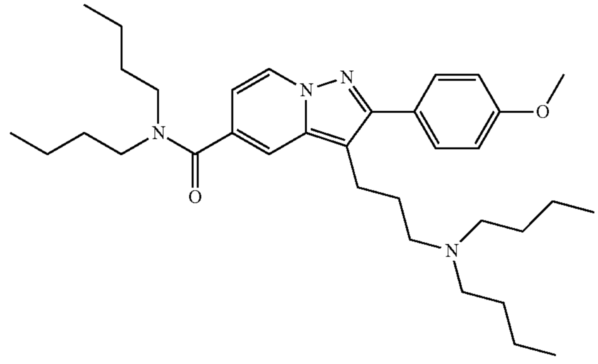 [SMILES: CCCCN(CCCC)CCCc1c(-c2ccc(OC)cc2)nn2ccc(C(=O)N(CCCC)CCCC)cc12] | 2.14 | 549.4 | C |

TABLE 1-continued
Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)
| Cpd No | Structure | HPLC RT (min) analytical | MS: (M + H)+ see footnote* | IC$_{50}$ |
|---|---|---|---|---|
| 113 | 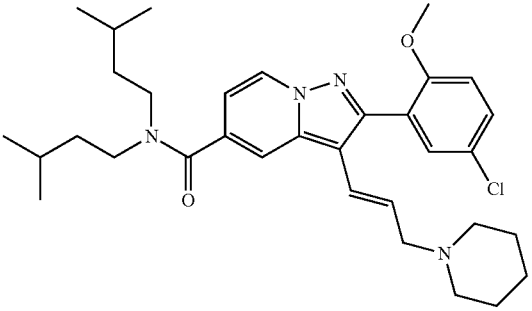 [SMILES: COc1ccc(Cl)cc1-c1nn2ccc(C(=O)N(CCC(C)C)CCC(C)C)cc2c1/C=C/CN1CCCCC1] | 2.16 | 565.3 (weak) 480.2 (strong) | C |
| 114 | 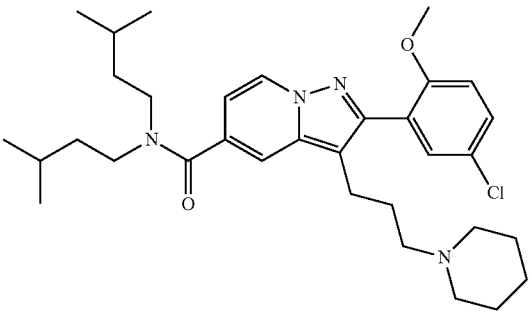 [SMILES: COc1ccc(Cl)cc1-c1nn2ccc(C(=O)N(CCC(C)C)CCC(C)C)cc2c1CCCN1CCCCC1] | 2.16 | 567.4 | C |
| 115 | 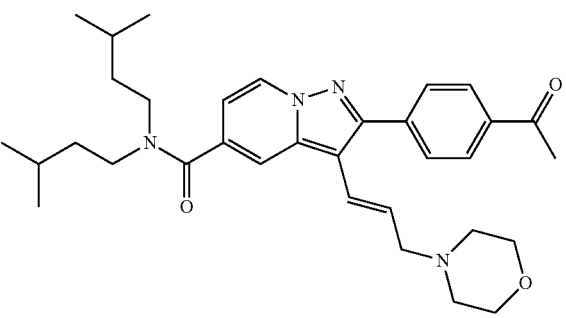 [SMILES: CC(=O)c1ccc(-c2nn3ccc(C(=O)N(CCC(C)C)CCC(C)C)cc3c2/C=C/CN2CCOCC2)cc1] | 2.10 | 458.2* | C |
| 116 | 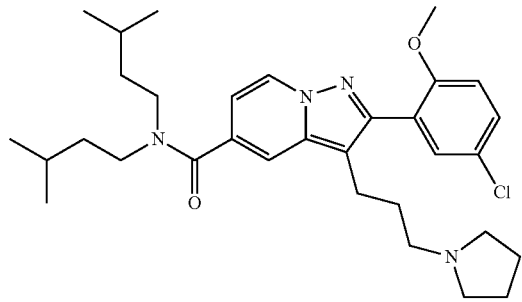 [SMILES: COc1ccc(Cl)cc1-c1nn2ccc(C(=O)N(CCC(C)C)CCC(C)C)cc2c1CCCN1CCCC1] | 2.18 | 553.3 | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 117 | 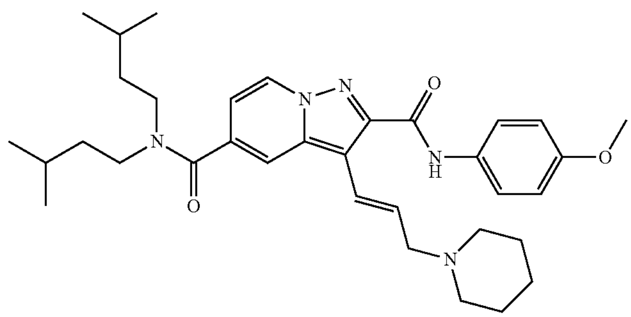 [SMILES: COc1ccc(NC(=O)c2nn3ccc(C(=O)N(CCC(C)C)CCC(C)C)cc3c2/C=C/CN2CCCCC2)cc1] | 2.15 | 574.4 | C |
| 118 | 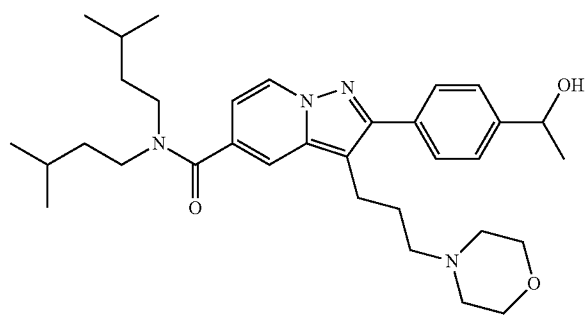 | 2.08 | 549.4 | C |
| 119 | 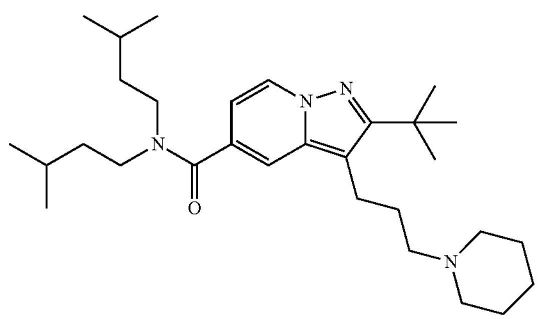 [SMILES: CC(C)CCN(CCC(C)C)C(=O)c1ccn2nc(C(C)(C)C)c(CCCN3CCCCC3)c2c1] | 2.18 | 483.4 | A |
| 120 | 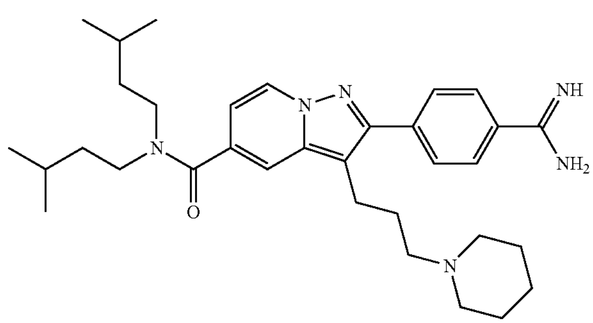 [SMILES: CC(C)CCN(CCC(C)C)C(=O)c1ccn2nc(-c3ccc(C(=N)N)cc3)c(CCCN3CCCCC3)c2c1] | 1.90 | 545.4 | A |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)+ see footnote* | IC$_{50}$ |
|---|---|---|---|---|
| 121 | 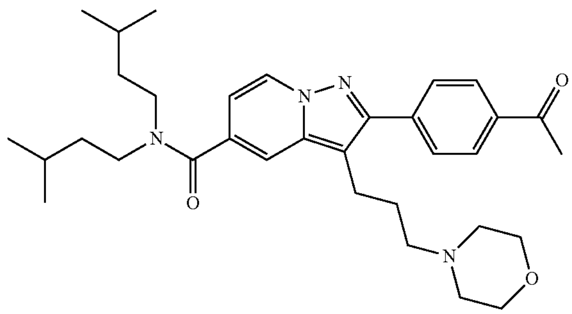 | 2.11 | 547.4 | C |
| 122 | 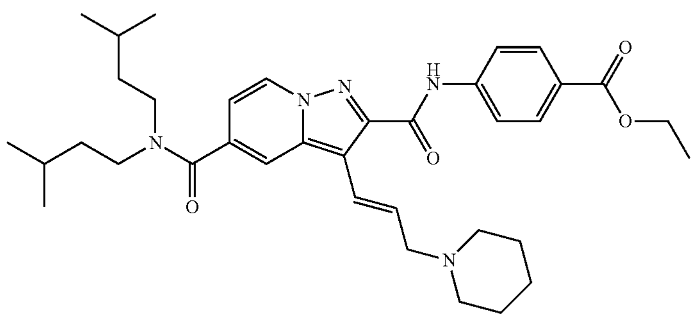 [SMILES: CCOC(=O)c1ccc(NC(=O)c2nn3ccc(C(=O)N(CCC(C)C)CCC(C)C)cc3c2/C=C/CN2CCCCC2)cc1] | 2.22 | 616.4 | C |
| 123 | 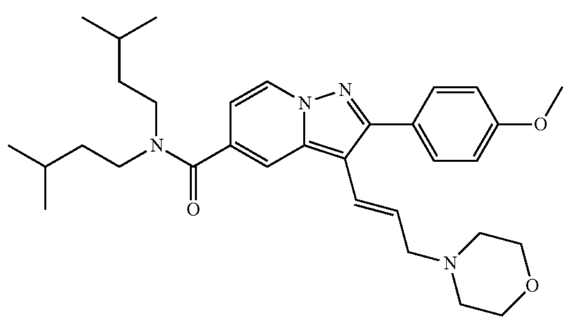 | 2.09 | 533.3 (weak); 446.3 (strong)* | C |
| 124 | 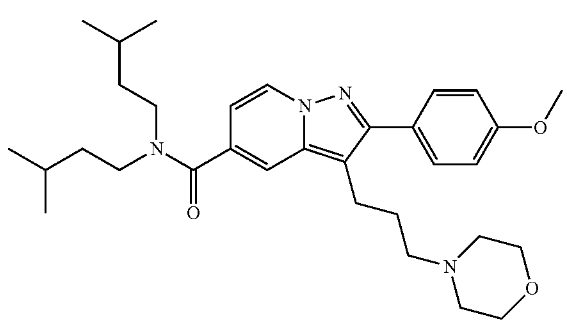 [SMILES: COc1ccc(-c2nn3ccc(C(=O)N(CCC(C)C)CCC(C)C)cc3c2CCCN2CCOCC2)cc1] | 2.15 | 535.4 | A |

TABLE 1-continued
Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)
| Cpd No | Structure | HPLC RT (min) analytical | MS: (M + H)$^+$ see footnote* | IC$_{50}$ |
|---|---|---|---|---|
| 125 | 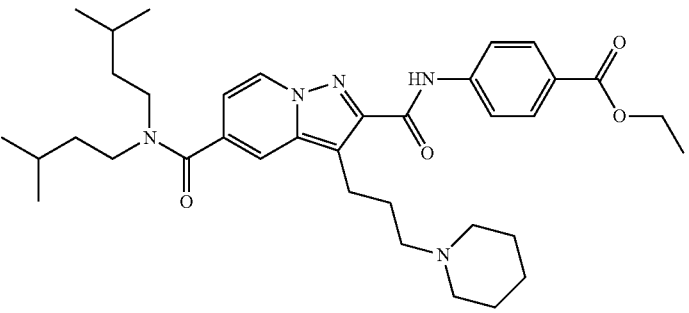 [SMILES: CCOC(=O)c1ccc(NC(=O)c2nn3ccc(C(=O)N(CCC(C)C)CCC(C)C)cc3c2CCCN2CCCCC2)cc1] | 2.24 | 618.4 | C |
| 126 | 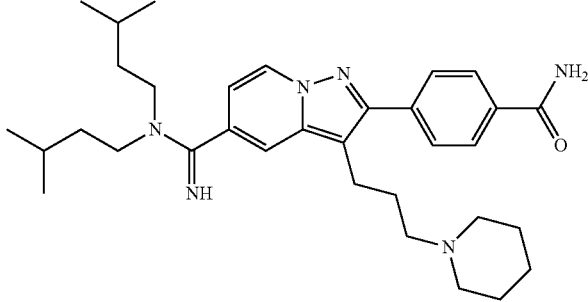 [SMILES: CC(C)CCN(CCC(C)C)C(=N)c1ccn2nc(-c3ccc(C(N)=O)cc3)c(CCCN3CCCCC3)c2c1] | 1.70 | 545.4 | A |
| 127 | 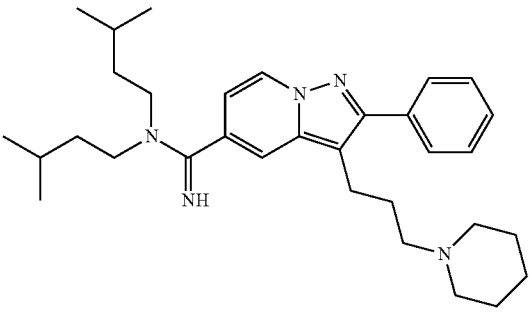 [SMILES: CC(C)CCN(CCC(C)C)C(=N)c1ccn2nc(-c3ccccc3)c(CCCN3CCCCC3)c2c1] | 1.85 | 502.4 | B |
| 128 | 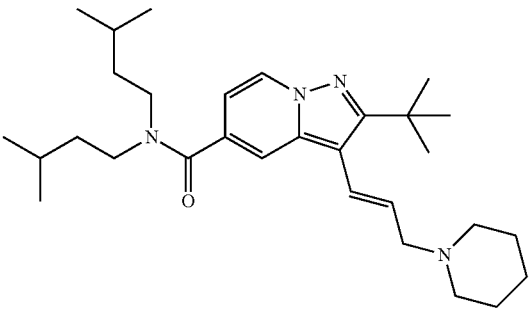 [SMILES: CC(C)CCN(CCC(C)C)C(=O)c1ccn2nc(C(C)(C)C)c(/C=C/CN3CCCCC3)c2c1] | 2.18 | 482.4 (weak); 396.3 (strong)* | C |

TABLE 1-continued
Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)
| Cpd No | Structure | HPLC RT (min) analytical | MS: (M + H)$^+$ see footnote* | IC$_{50}$ |
|---|---|---|---|---|
| 129 | 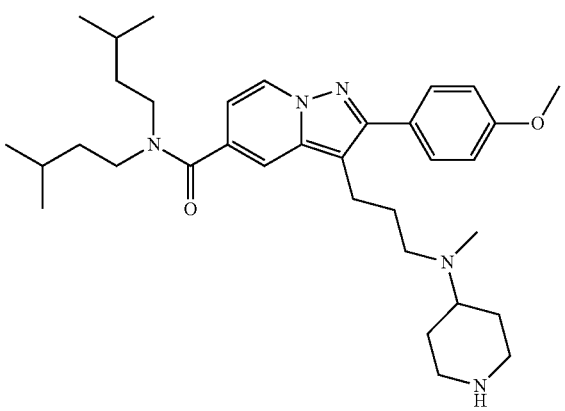 [SMILES: COc1ccc(-c2nn3ccc(C(=O)N(CCC(C)C)CCC(C)C)cc3c2CCCN(C)C2CCNCC2)cc1] | 2.03 | 562.4 | B |
| 130 | 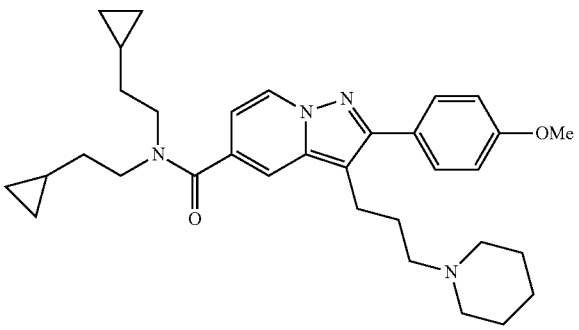 [SMILES: COc1ccc(-c2nn3ccc(C(=O)N(CCC4CC4)CCC4CC4)cc3c2CCCN2CCCCC2)cc1] | 2.07 | 529.4 | B |
| 131 | 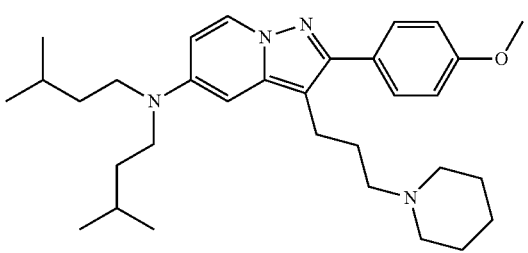 [SMILES: COc1ccc(-c2nn3ccc(N(CCC(C)C)CCC(C)C)cc3c2CCCN2CCCCC2)cc1] | 2.22 | 505.4 | D |
| 132 | 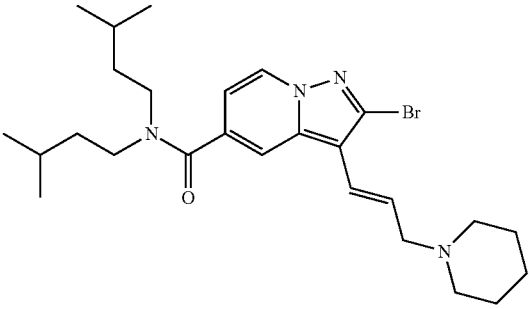 [SMILES: CC(C)CCN(CCC(C)C)C(=O)c1ccn2nc(Br)c(/C=C/CN3CCCCC3)c2c1] | 2.41 | 505.2 (weak) 420.2 (strong)* | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)+ see footnote* | IC$_{50}$ |
|---|---|---|---|---|
| 133 | 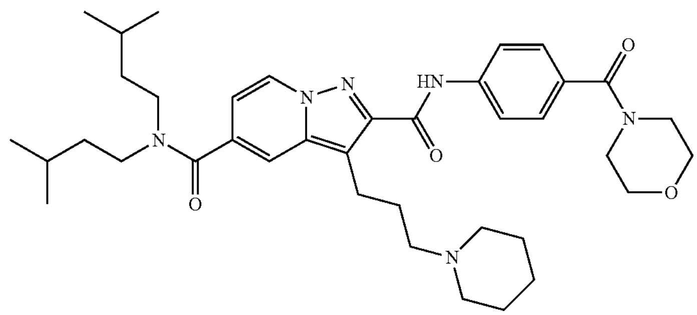 [SMILES: CC(C)CCN(CCC(C)C)C(=O)c1ccn2nc(C(=O)Nc3ccc(C(=O)N4CCOCC4)cc3)c(CCCN3CCCCC3)c2c1] | 2.10 | 659.4 | D |
| 134 | 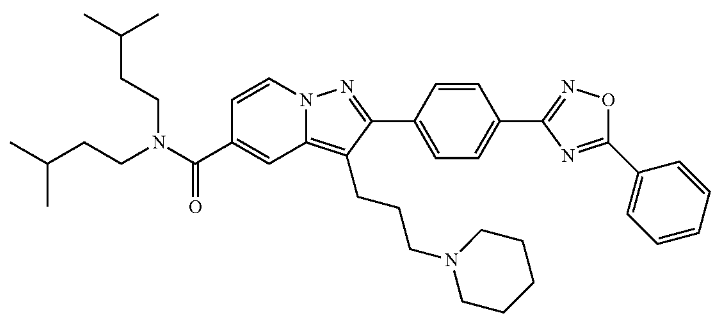 | 2.37 | 647.4 | C |
| 135 | 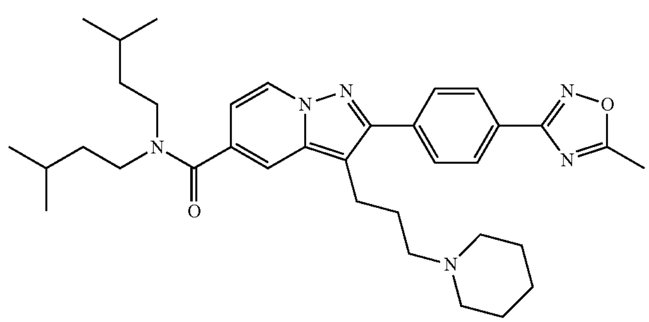 [SMILES: Cc1nc(-c2ccc(-c3nn4ccc(C(=O)N(CCC(C)C)CCC(C)C)cc4c3CCCN3CCCCC3)cc2)no1] | 2.22 | 585.4 | A |
| 136 | 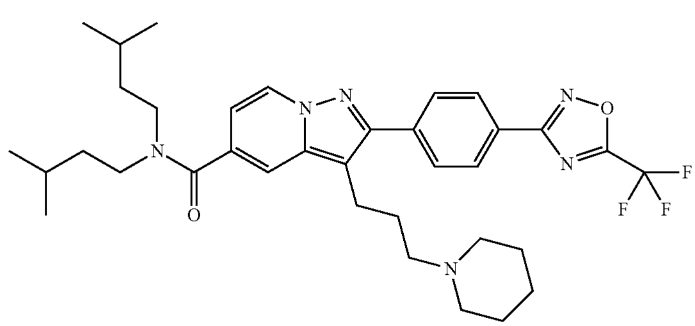 [SMILES: CC(C)CCN(CCC(C)C)C(=O)c1ccn2nc(-c3ccc(-c4noc(C(F)(F)F)n4)cc3)c(CCCN3CCCCC3)c2c1] | 2.32 | 639.4 | C |

TABLE 1-continued
Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)
| Cpd No | Structure | HPLC RT (min) analytical | MS: (M + H)$^+$ see footnote* | IC$_{50}$ |
|---|---|---|---|---|
| 137 | 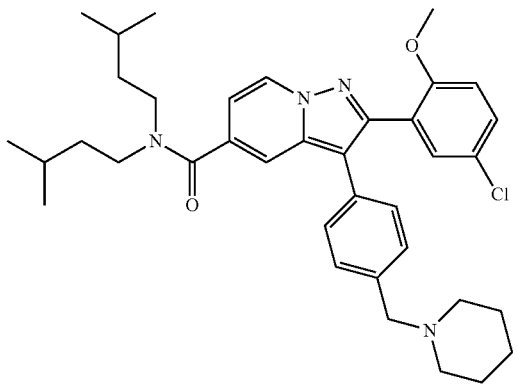 [SMILES: COc1ccc(Cl)cc1-c1nn2ccc(C(=O)N(CCC(C)C)CCC(C)C)cc2c1-c1ccc(CN2CCCCC2)cc1] | 2.22 | 615.3 | C |
| 138 | 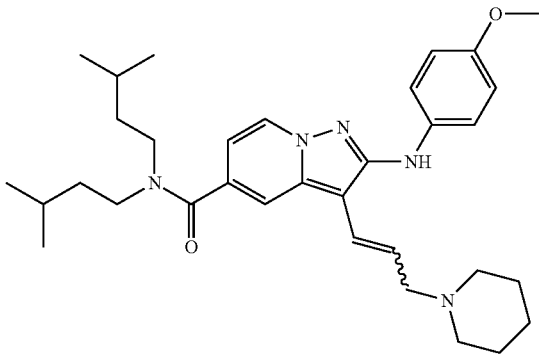 [SMILES: COc1ccc(Nc2nn3ccc(C(=O)N(CCC(C)C)CCC(C)C)cc3c2C=CCN2CCCCC2)cc1] | 2.19 | 546.4 (weak) 461.3 (strong) | A |
| 139 | 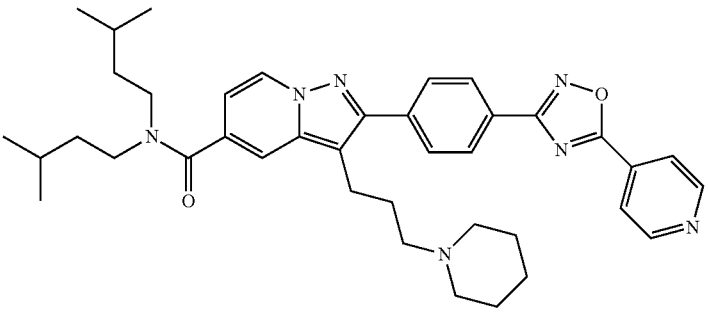 | 2.27 | 648.4 | A |
| 140 | 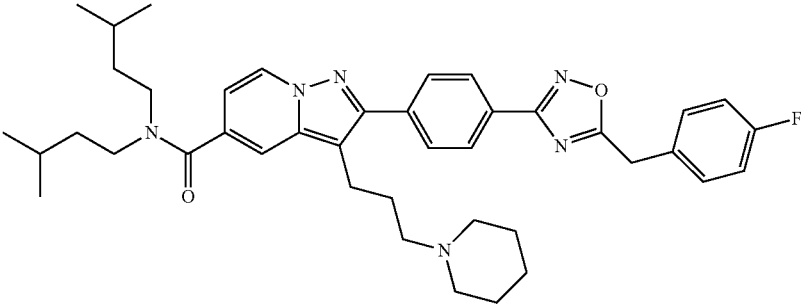 [SMILES: CC(C)CCN(CCC(C)C)C(=O)c1ccn2nc(-c3ccc(-c4noc(Cc5ccc(F)cc5)n4)cc3)c(CCCN3CCCCC3)c2c1] | 2.32 | 679.4 | D |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 141 | 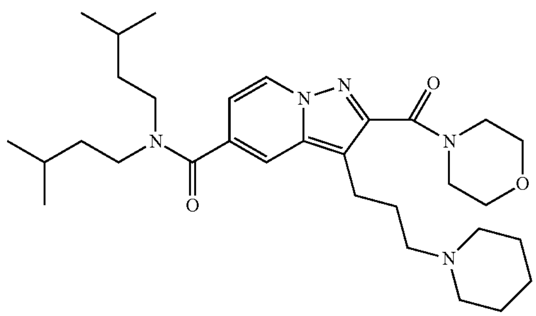 [SMILES: CC(C)CCN(CCC(C)C)C(=O)c1ccn2nc(C(=O)N3CCOCC3)c(CCCN3CCCCC3)c2c1] | 2.02 | 540.4 | D |
| 142 | 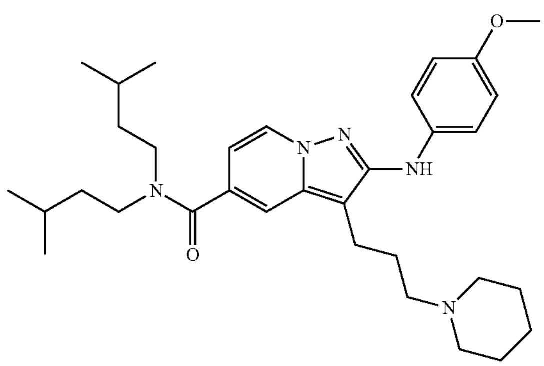 [SMILES: COc1ccc(Nc2nn3ccc(C(=O)N(CCC(C)C)CCC(C)C)cc3c2CCCN2CCCCC2)cc1] | 2.19 | 548.4 | A |
| 143 | 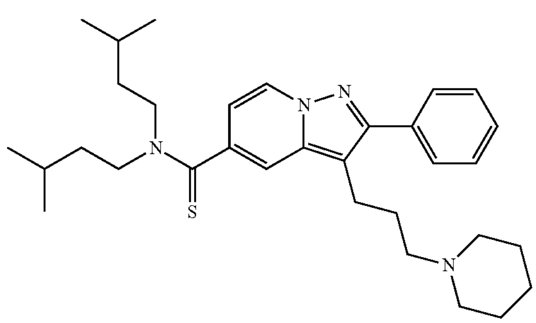 [SMILES: CC(C)CCN(CCC(C)C)C(=S)c1ccn2nc(-c3ccccc3)c(CCCN3CCCCC3)c2c1] | 2.17 | 519.3 | C |
| 144 | 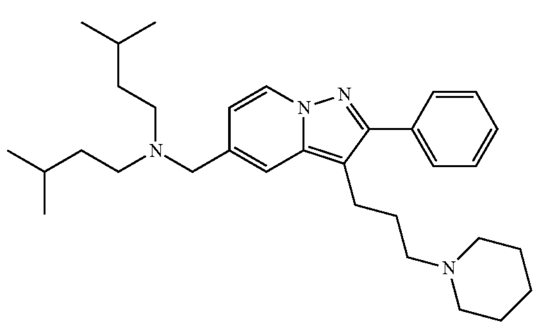 [SMILES: CC(C)CCN(CCC(C)C)Cc1ccn2nc(-c3ccccc3)c(CCCN3CCCCC3)c2c1] | 1.73 | 489.4 | D |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 145 | 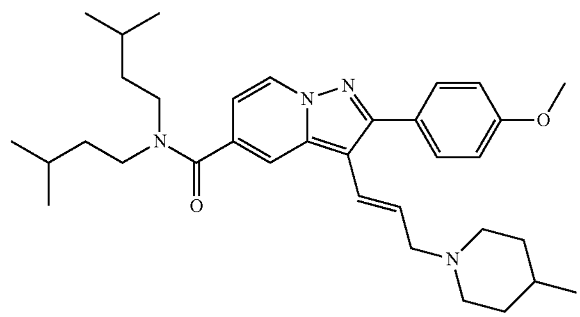 [SMILES: COc1ccc(-c2nn3ccc(C(=O)N(CCC(C)C)CCC(C)C)cc3c2/C=C/CN2CCC(C)CC2)cc1] | 2.18 | 545.4 (weak); 446.3 (strong)* | A |
| 146 | 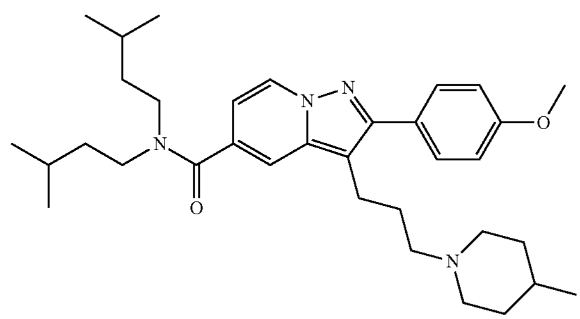 [SMILES: COc1ccc(-c2nn3ccc(C(=O)N(CCC(C)C)CCC(C)C)cc3c2CCCN2CCC(C)CC2)cc1] | 2.20 | 547.4 | C |
| 147 | 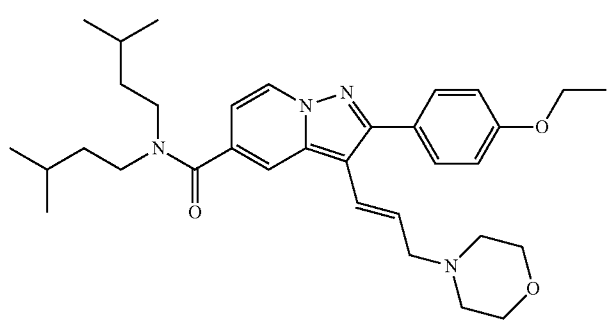 | 2.17 | 547.4 (weak); 460.3 (strong)* | D |
| 148 | 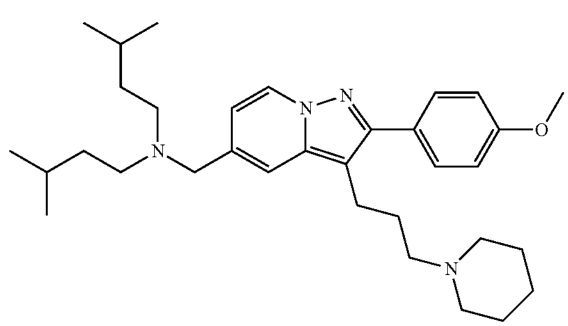 [SMILES: COc1ccc(-c2nn3ccc(CN(CCC(C)C)CCC(C)C)cc3c2CCCN2CCCCC2)cc1] | 1.62 | 491.4 | D |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 149 | 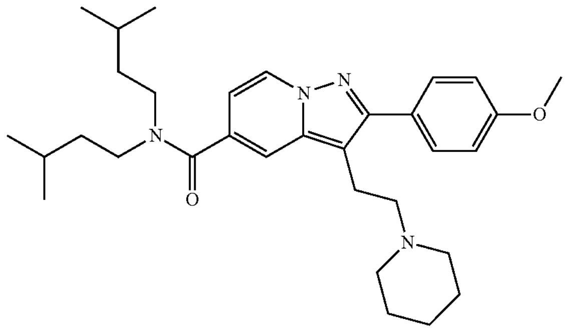 [SMILES: COc1ccc(-c2nn3ccc(C(=O)N(CCC(C)C)CCC(C)C)cc3c2CCN2CCCCC2)cc1] | 2.12 | 519.4 | D |
| 150 | 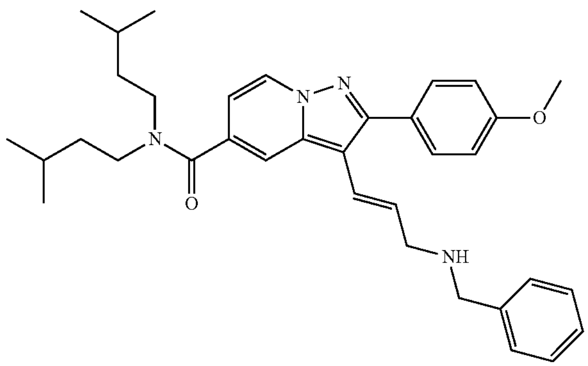 [SMILES: COc1ccc(-c2nn3ccc(C(=O)N(CCC(C)C)CCC(C)C)cc3c2/C=C/CNCc2ccccc2)cc1] | 2.22 | 553.4 (weak); 446.3 (strong)* | D |
| 151 | 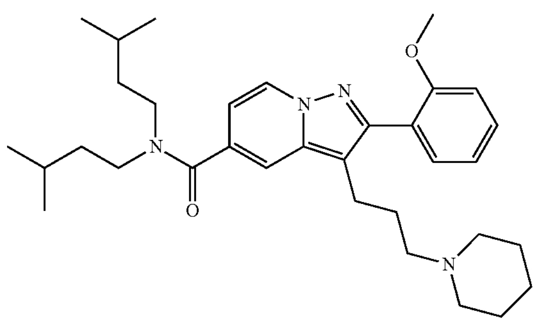 [SMILES: COc1ccccc1-c1nn2ccc(C(=O)N(CCC(C)C)CCC(C)C)cc2c1CCCN1CCCCC1] | 2.01 | 533.4 | C |
| 152 | 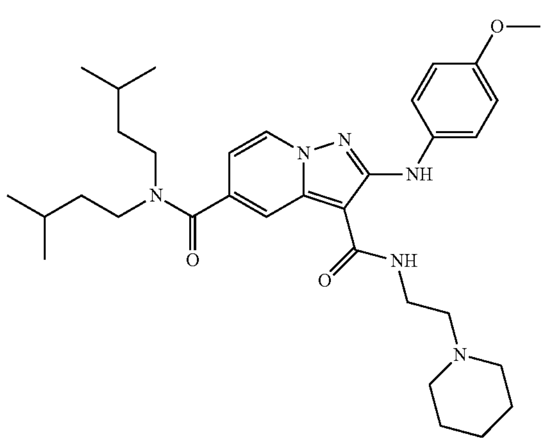 [SMILES: COc1ccc(Nc2nn3ccc(C(=O)N(CCC(C)C)CCC(C)C)cc3c2C(=O)NCCN2CCCCC2)cc1] | 2.19 | 576.8 | B |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 153 | 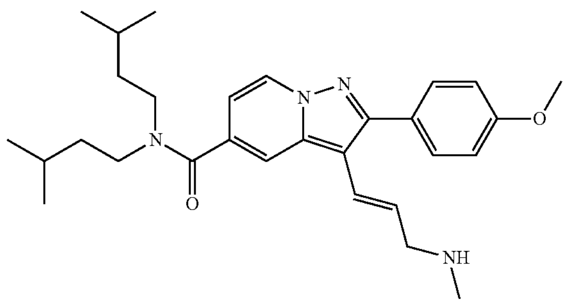 [SMILES: CNC/C=C/c1c(-c2ccc(OC)cc2)nn2ccc(C(=O)N(CCC(C)C)CCC(C)C)cc12] | 2.13 | 477.3 (weak); 446.3 (strong)* | D |
| 154 | 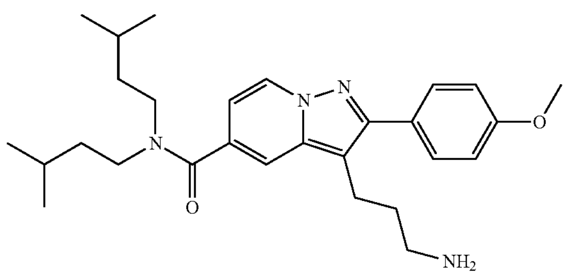 [SMILES: COc1ccc(-c2nn3ccc(C(=O)N(CCC(C)C)CCC(C)C)cc3c2CCCN)cc1] | 2.17 | 465.3 | D |
| 155 | 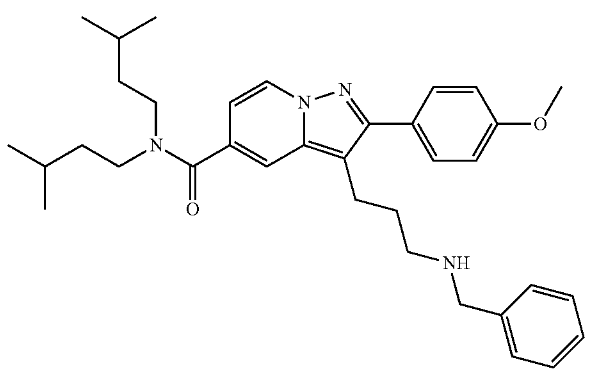 [SMILES: COc1ccc(-c2nn3ccc(C(=O)N(CCC(C)C)CCC(C)C)cc3c2CCCNCc2ccccc2)cc1] | 2.23 | 555.4 | C |
| 156 | 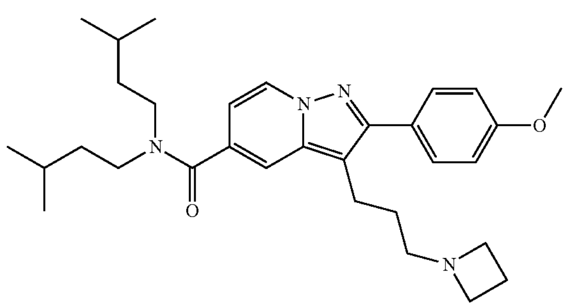 [SMILES: COc1ccc(-c2nn3ccc(C(=O)N(CCC(C)C)CCC(C)C)cc3c2CCCN2CCC2)cc1] | 2.13 | 505.4 | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 157 | 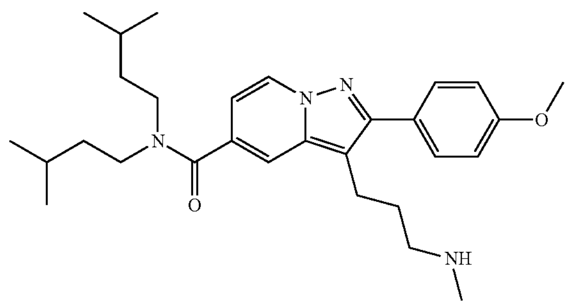 [SMILES: CNCCCc1c(-c2ccc(OC)cc2)nn2ccc(C(=O)N(CCC(C)C)CCC(C)C)cc12] | 2.13 | 479.3 | D |
| 158 | 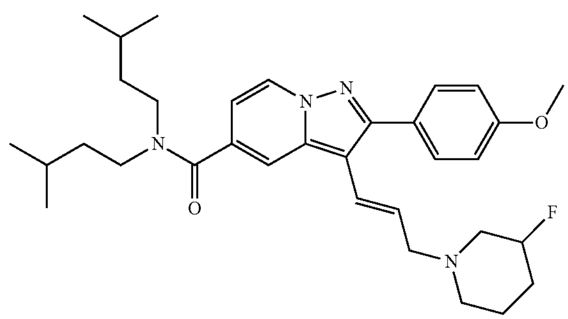 [SMILES: COc1ccc(-c2nn3ccc(C(=O)N(CCC(C)C)CCC(C)C)cc3c2/C=C/CN2CCCC(F)C2)cc1] | 2.14 | 549.4 (weak); 446.3 (strong)* | C |
| 159 | 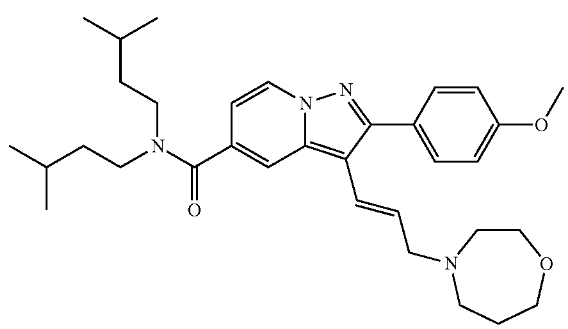 [SMILES: COc1ccc(-c2nn3ccc(C(=O)N(CCC(C)C)CCC(C)C)cc3c2/C=C/CN2CCCOCC2)cc1] | 2.13 | 547.4 (weak); 446.3 (strong)* | B |
| 160 | 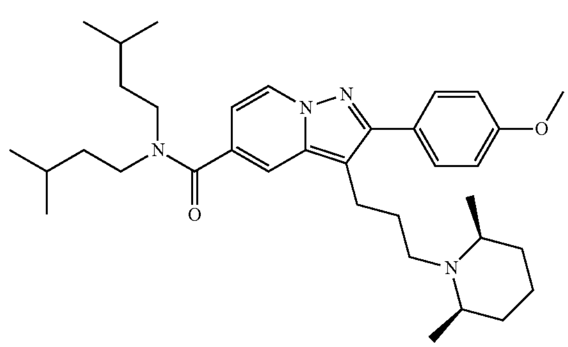 [SMILES: COc1ccc(-c2nn3ccc(C(=O)N(CCC(C)C)CCC(C)C)cc3c2CCCN2[C@H](C)CCC[C@@H]2C)cc1] | 2.17 | 561.4 | C |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 161 | 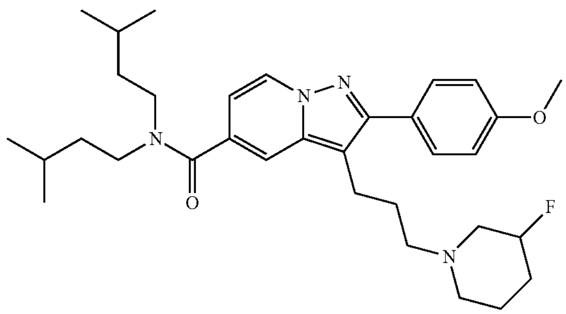 [SMILES: COc1ccc(-c2nn3ccc(C(=O)N(CCC(C)C)CCC(C)C)cc3c2CCCN2CCCC(F)C2)cc1] | 2.17 | 551.4 | C |
| 162 | 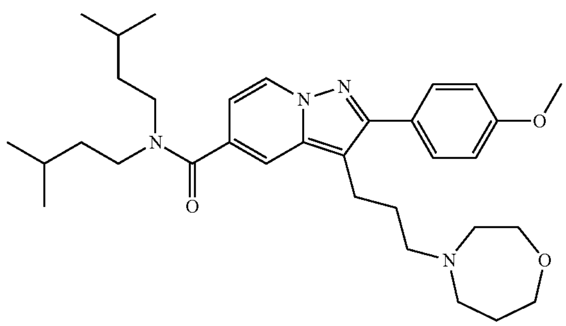 [SMILES: COc1ccc(-c2nn3ccc(C(=O)N(CCC(C)C)CCC(C)C)cc3c2CCCN2CCCOCC2)cc1] | 2.15 | 549.4 | B |
| 163 | 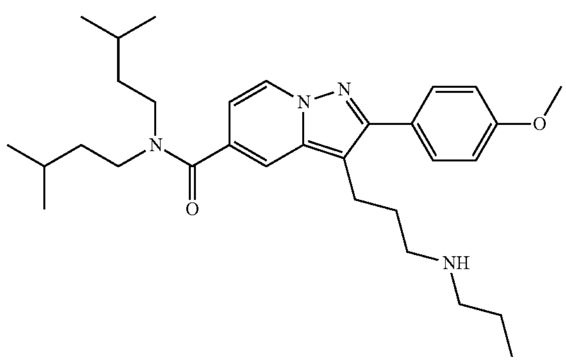 [SMILES: CCCNCCCc1c(-c2ccc(OC)cc2)nn2ccc(C(=O)N(CCC(C)C)CCC(C)C)cc12] | 2.18 | 507.4 | C |
| 164 | 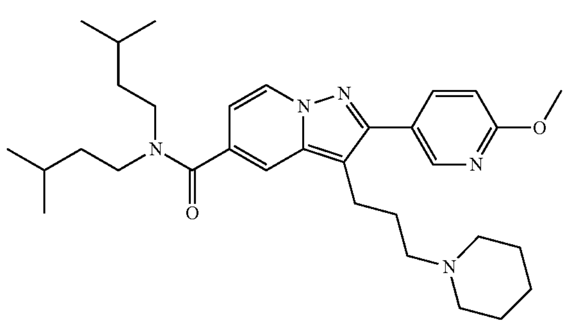 | 2.16 | 534.5 | A |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 165 | 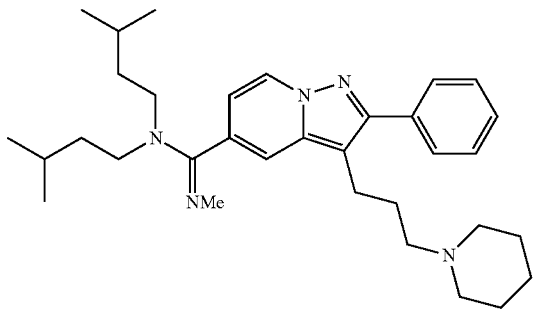 | 1.82 | 516.4 | A |
| 166 | 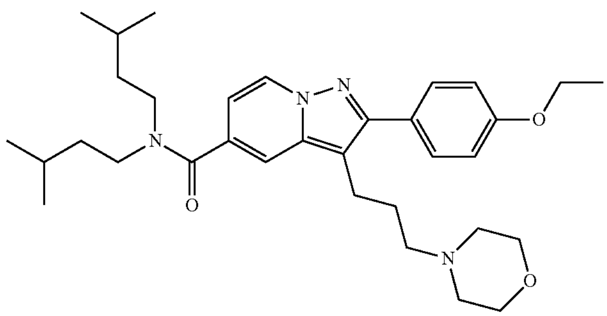 [SMILES: CCOc1ccc(-c2nn3ccc(C(=O)N(CCC(C)C)CCC(C)C)cc3c2CCCN2CCOCC2)cc1] | 2.19 | 549.4 | C |
| 167 | 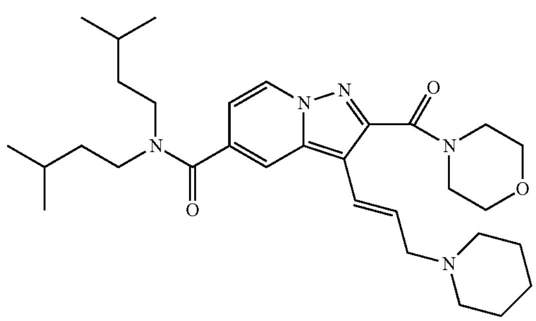 [SMILES: CC(C)CCN(CCC(C)C)C(=O)c1ccn2nc(C(=O)N3CCOCC3)c(/C=C/CN3CCCCC3)c2c1] | 1.98 | 538.4 (weak); 453.2 (strong)* | D |
| 168 | 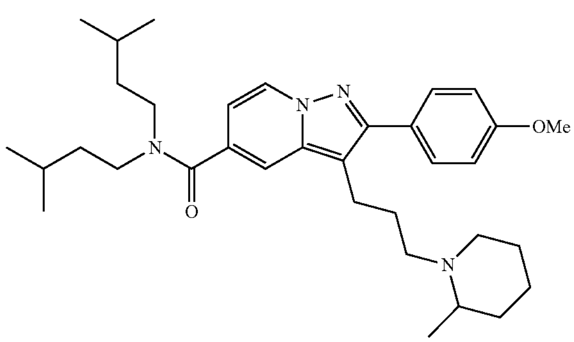 [SMILES: COc1ccc(-c2nn3ccc(C(=O)N(CCC(C)C)CCC(C)C)cc3c2CCCN2CCCCC2C)cc1] | 2.12 | 547.4 | B |

TABLE 1-continued

Analytical HPLC retention time, LCMS data and IC$_{50}$ data (Activity range for IC$_{50}$ values: A < 500 nM; 500 nM < B < 1000 nM; 1000 nM < C < 5000 nM; 5000 < D < 15000 nM)

| Cpd No | Structure | HPLC RT (min) analytical | MS: (M + H)$^+$ see footnote* | IC$_{50}$ |
|---|---|---|---|---|
| 169 | 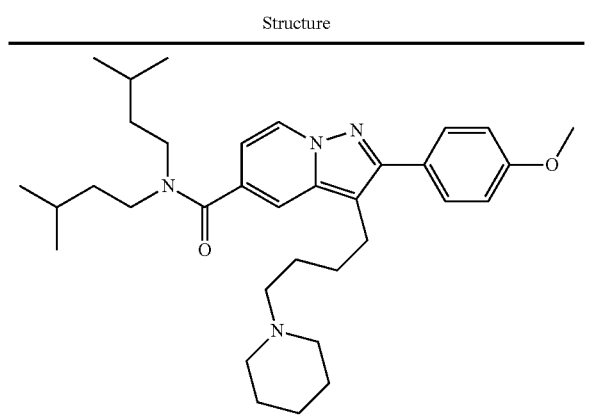 | 2.17 | 545.4 (weak); 446.3 (strong)* | B |

*Typically, the allylic and proargylic amines in the Table showed weak or no protonated molecular ion in the mass spectra. Instead a strong peak corresponding to a fragment was observed (e.g. M$^+$—amine moiety)

IC$_{50}$ data (Activity range for IC50 values: A < 500 nM; 500 nM < B < 1000 nM; 1000 nM < C < 5000 nM); 5000 < D < 15000 nM)

TABLE 2

The following compounds are further contemplated

Structure

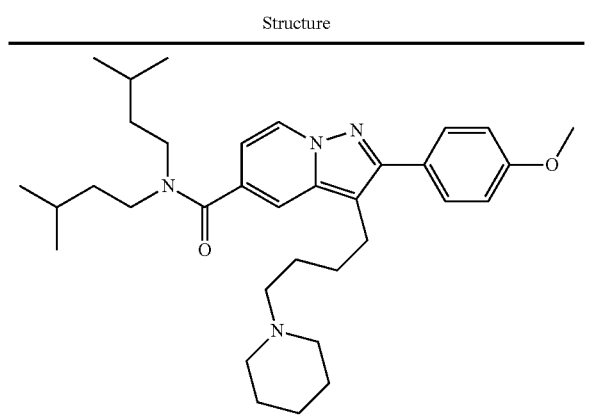

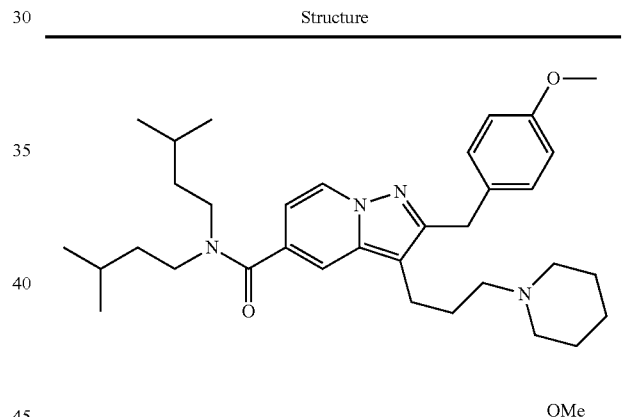

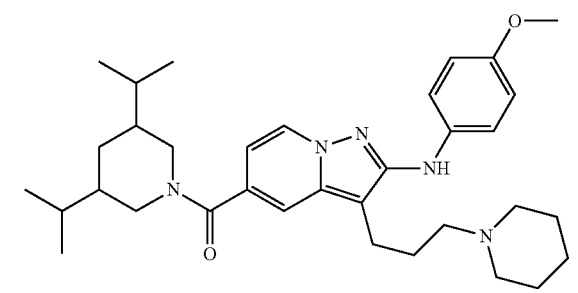 [SMILES: COc1ccc(Nc2nn3ccc(C(=O)N4CC(C(C)C)CC(C(C)C)C4)cc3c2CCCN2CCCCC2)cc1]

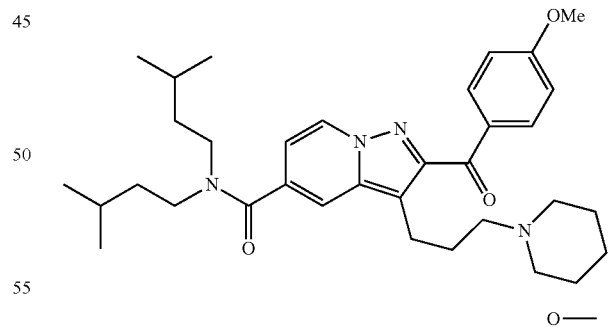

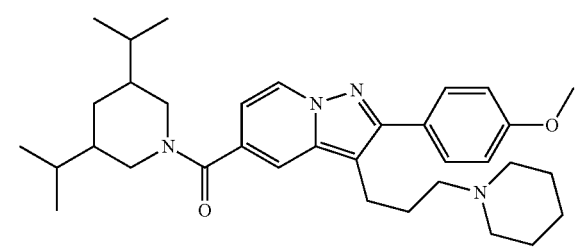 [SMILES: COc1ccc(-c2nn3ccc(C(=O)N4CC(C(C)C)CC(C(C)C)C4)cc3c2CCCN2CCCCC2)cc1]

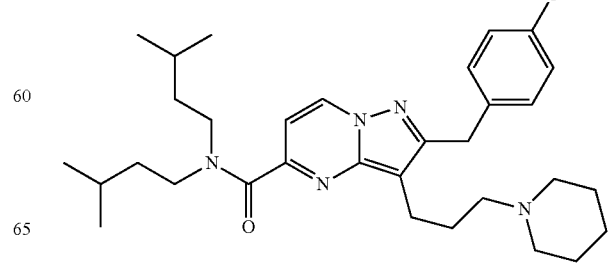

TABLE 2-continued

The following compounds are further contemplated

Structure

TABLE 2-continued

The following compounds are further contemplated

Structure

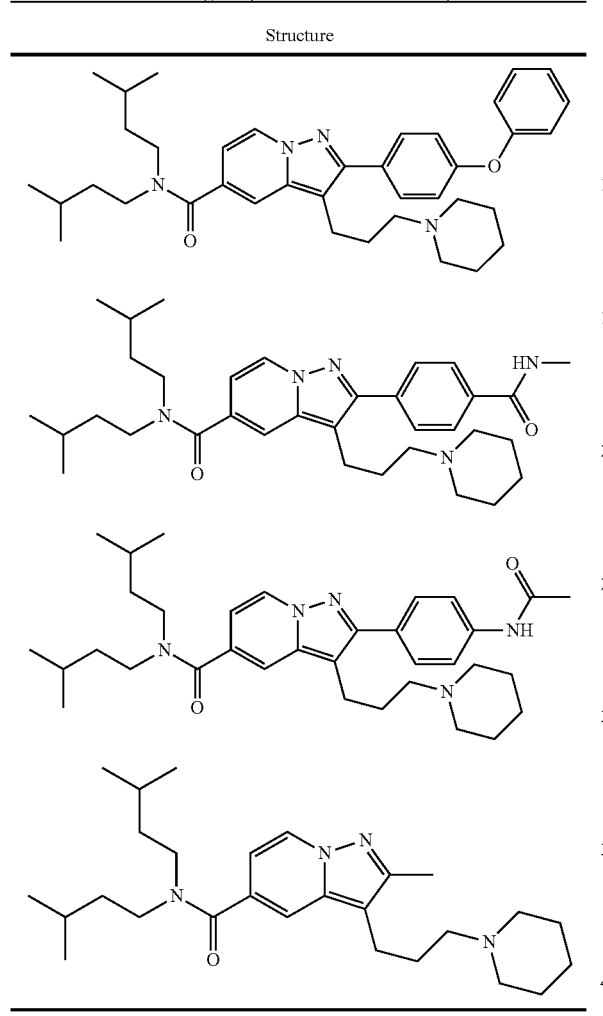

Assays

To test the ability of a compound to modulate the stability, activity, and/or cell surface localization of an MC4R polypeptide, a labeled or unlabeled test compound is brought in contact with the MC4R protein or a fragment thereof and the amount of the test compound bound to the MC4R protein or to the fragment thereof is measured. This can be achieved for example as follows:
(a) contacting a first cell with a test compound for a time period sufficient to allow the cell to respond to said contact with the test compound;
(b) determining/measuring the conformational stability, activity, and/or cell surface localization of a MC4R polypeptide (or a fragment thereof comprising a ligand binding domain) in the cell (or on the cell surface) contacted in step (a); and comparing the stability, activity, and/or cell surface localization of the MC4R polypeptide determined in step (b) to that of an MC4R polypeptide in a control cell that has not been contacted with the test compound; wherein a detectable change in the stability, activity, and/or cell surface localization of the MC4R polypeptide in the first cell in response to contact with the test compound compared to the stability level of the MC4R polypeptide in the control cell that has not been contacted with the test compound, indicates that the test compound modulates the stability of the MC4R polypeptide and is a candidate compound for the treatment of a disorder associated with reduced MC4R stability or activity. The cell can either be a host cell transformed with a non-endogenous wild-type or mutant MC4R, or an endogenously-MC4R-expressing cell, including mutant and wild-type MC4Rs. Such cells include the "obesity neurons" such as GTI-7 cells, described above, those described in MacKenzie et al., Current Medicinal Chemistry-Immunology, Endocrine & Metabolic Agents 2004; 4: 113-117, which endogenously express MC4R, or transformed cells expressing normal or mutated, tagged MC4R such as the HEK293 cells described in Blondet et al., J Biochem 2004; 135: 541-546.

Cyclic AMP Assay

Intracellular cyclic 3'-5' adenosine monophosphate (cAMP) accumulation was measured using a competitive immunoassay based on HTRF (Homogeneous Time-Resolved Fluorescence) technology (cAMP dynamic-2, Cis-Bio).

HEK293T stable cell line expressing double-tagged WT-hMC4R construct were collected and washed in cAMP buffer (1XD-PBS pH 7.4, 0.1% glucose). 40,000 cells/well were then dispensed in 96-well plates in cAMP buffer [1XD-PBS, 1% BSA, 0.1% Glucose, 0.75 mM 3-isobutyl-1methyl-xanthine (IBMX, Sigma)] and incubated either for antagonist competition assay: 1 hour at 37° C. with various concentrations of compound [0.01 nM-10 μM] followed by 30 min incubation at 37° C. with 4 nM of NDP-α-MSH (Sigma) or for agonist assay: 1 hour at 37° C. with various concentrations of compound [0.01 nM-10 μM]. 10,000 cells were transferred in 384-well plates, lysed and incubated with cAMP labeled with the dye d2 and anti-cAMP M-Antibody labeled with Cryptate following the manufacturer's protocol.

Reading of HTRF signal was performed on Artemis TR-FRET plate reader (Cosmo Bio).

Curve Fitting

All curve fitting was conducted using non-linear regression analyses from PRISM (version 4.0c, GraphPad Inc.) and the determination of Rmax and EC50 or IC50 parameters were obtained from sigmoidal dose-response phase (variable slope) equation.

Generation of WT-hMC4R Double Tagged Construct

A cDNA encoding a wild-type human MC4R with a 3 tandem copies of Hemaglutinine (HA) epitope sequence from UMR cDNA resource center was modified using known techniques in the art (e.g., PCR, cloning) to fused in frame at the C-terminal a venus-Yellow Fluorescent Protein (YFP) cDNA.

The resultant cDNA was then subcloned in eukaryotic expression vector, e.g. pcDNA 3.1(+) (Invitrogen).

Generation of Double Tagged WT-hMC4R Stable Cell Line and Cell Culture

The double tagged WT-hMC4R was transfected in HEK293T cells with lipofectamine (Invitrogen) following the manufacturer's instructions and permanently transfected clonal cell lines were selected by resistance to the neomycin analog G418.

HEK293T stable cell line expressing wild-type human melanocortin 4 receptor (WT-hMC4R) containing an N-terminal 3xHA epitope tag and an intracellular C-terminal venus-yellow fluorescent protein (v-YFP) were maintained at 37° C. in humidified air containing 5% CO2 in Dulbecoo's modified Eagle's medium (DMEM) supplemented with 10% fetal bovine serum (FBS), 100 U/ml penicillin/streptomycin (DMEM complete/10% FBS). Cells were generally at 70%-80% confluence on the day of assay.

Other Embodiments

From the foregoing description, it will be apparent to one of ordinary skill in the art that variations and modifications may be made to the discovery described herein to adapt it to various usages and conditions. Such embodiments are also within the scope of the discovery.

What is claimed is:

1. A compound of Formula IA:

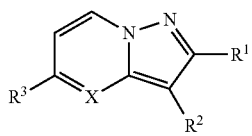

I wherein
$R^1$ is
1) halogen,
2) $C_1$-$C_6$ alkyl,
3) $C_3$-$C_7$ cycloalkyl,
4) aryl,
5) heteroaryl,
6) $NHR^4$,
7) $C(O)NHR^4$,
8) $C(O)$-aryl,
9) $C(O)$-heteroaryl, or
10) $C(O)$ heterocyclyl,
wherein the aryl and the heteroaryl are optionally substituted with one or more $R^7$ substituents;
$R^2$ is
1) $C_1$-$C_6$ alkyl-heterocyclyl,
2) $C_1$-$C_6$ alkyl-$NR^5R^6$,
3) $C_3$-$C_6$ alkenyl-heterocyclyl,
4) $C_3$-$C_6$ alkenyl-$NR^5R^6$,
5) $C_3$-$C_6$ alkynyl-heterocyclyl,
6) $C_3$-$C_6$ alkynyl-$NR^5R^6$,
7) aryl $C_1$-$C_3$ alkyl-heterocyclyl, or
8) $C(O)NH$ $C_2$-$C_6$ alkyl-heterocyclyl,
wherein the heterocyclyl is optionally substituted with one or more $C_1$-$C_6$ alkyl substituents, or one or more halo substituents, or one or more haloalkyl substituents;
$R^3$ is
1) $NR^8R^9$,
2) $C(O)NR^8R^9$,
3) $C(=NH)NR^8R^9$,
4) $C(=NC_1$-$C_6$ alkyl)$NR^8R^9$,
5) $C(S)NR^8R^9$,
6) $CH_2NR^8R^9$, or
7) $C(O)$heterocyclyl optionally substituted with a $C_1$-$C_6$ alkyl substituent;
$R^4$ is
1) aryl,
2) heteroaryl,
3) $C_1$-$C_6$ alkyl-aryl,
4) $C_1$-$C_6$ alkyl-heteroaryl,
5) $C_1$-$C_6$ alkyl-$NHC(O)$ $C_1$-$C_6$ alkyl,
6) $C_1$-$C_6$ alkyl-O—$C_1$-$C_6$ alkyl, or
7) $C_1$-$C_6$ alkyl-heterocyclyl,
wherein the aryl, the heteroaryl and the heterocyclyl are optionally substituted with one or more $R^7$ substituents;
$R^5$ and $R^6$ are both or each independently, 1) H,
2) $C_1$-$C_6$ alkyl,
3) $C_1$-$C_6$ alkyl-aryl, or
4) heterocyclyl;
$R^7$ is
1) CN,
2) halogen,
3) haloalkyl,
4) $C_1$-$C_6$ alkyl,
5) $OC_1$-$C_6$ alkyl,
6) O-aryl,
7) O—$C_1$-$C_6$alkyl-aryl,
8) $C(O)OC_1$-$C_6$ alkyl,
9) $C(O)$ $C_1$-$C_6$ alkyl,
10) $C(O)$ aryl,
11) $C(O)$ heteroaryl,
12) $C(O)NH$ $C_1$-$C_6$ alkyl,
13) $NHC(O)$ $C_1$-$C_6$ alkyl,
14) $C(O)OH$,
15) $C(O)NH_2$,
16) $NO_2$,
17) heterocyclyl,
18) $C_1$-$C_6$ alkyl heterocyclyl,
19) heteroaryl,
20) aryl,
21) $NH_2$,
22) OH,
23) $CH(OH)$ $C_1$-$C_6$ alkyl,
24) $C(OH)(C_1$-$C_6$ alkyl$)_2$,
25) $C(NH_2)$=NH,
26) $C(NH_2)$=N—OH, or
27) $C(NH_2)$=N—OC(O) $C_1$-$C_6$alkyl,
wherein the heteroaryl is optionally substituted with aryl, $C_1$-$C_6$ alkyl, haloalkyl, heteroaryl or $CH_2$-aryl-F; and
$R^8$ and $R^9$ are both or each independently
1) $C_3$-$C_7$-alkyl, or
2) $C_1$-$C_4$-alkyl-$C_3$-$C_6$-cycloalkyl,
or a pharmaceutically acceptable salt thereof to allow the drug to penetrate the cell membrane; or a prodrug, or the compound is labeled with a detectable label or an affinity tag thereof.

2. The compound according to claim 1 having the formulae:

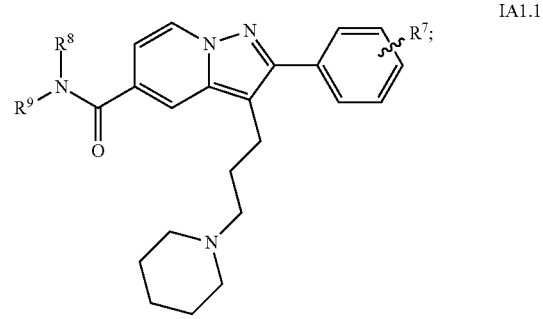

IA1.1

-continued
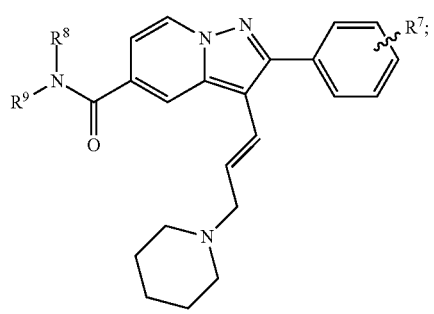
IA1.2
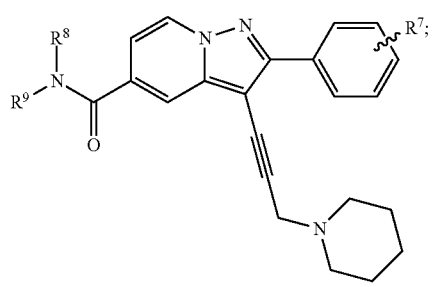
IA1.3
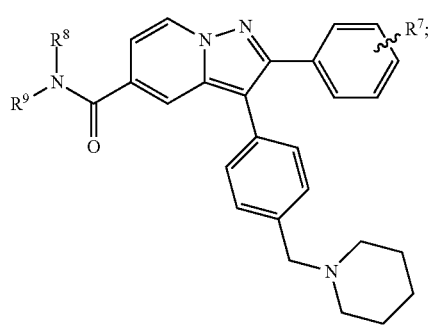
IA1.4
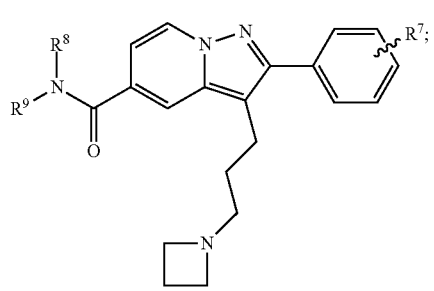
IA1.5
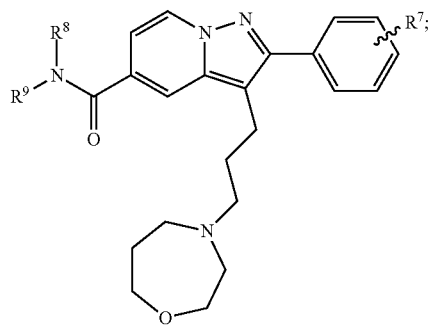
IA1.6
-continued
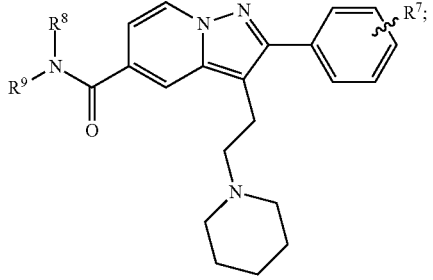
IA1.7
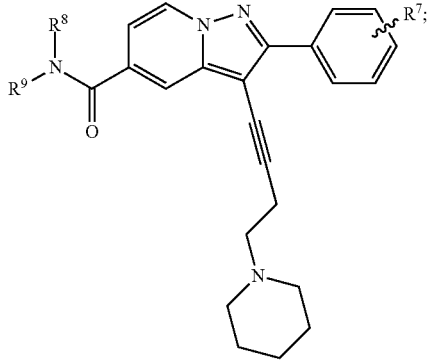
IA1.8
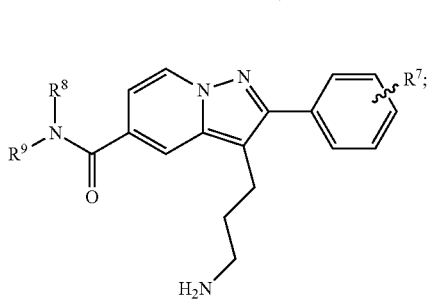
IA2.1
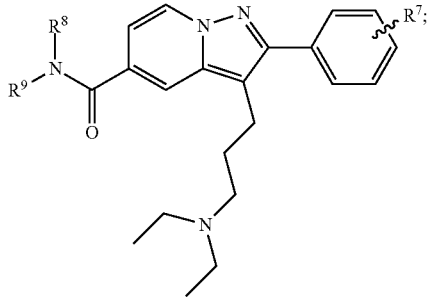
IA2.2
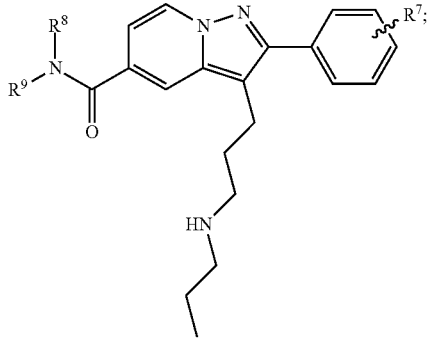
IA2.3

-continued
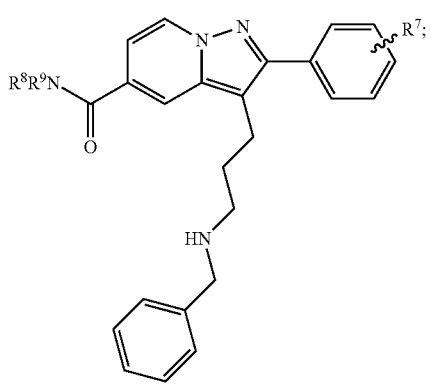
IA2.4
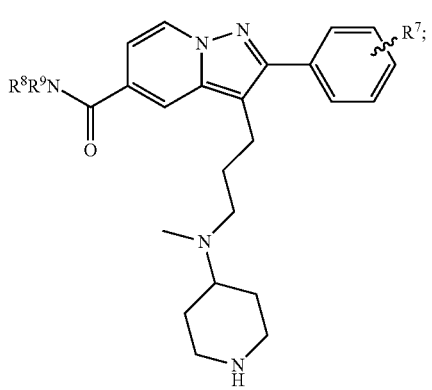
IA2.5
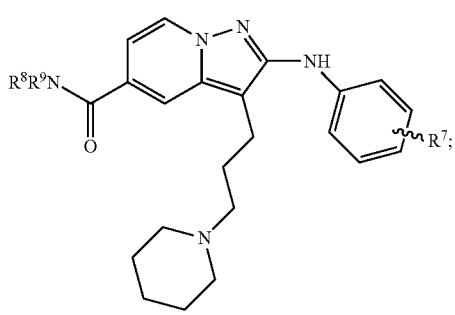
IA3.1
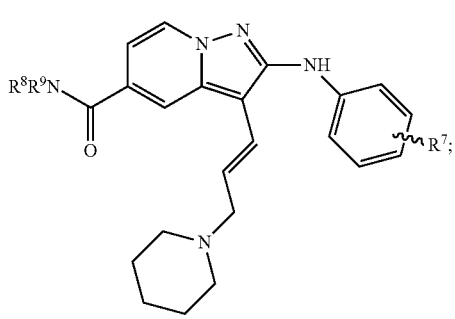
IA3.2
-continued
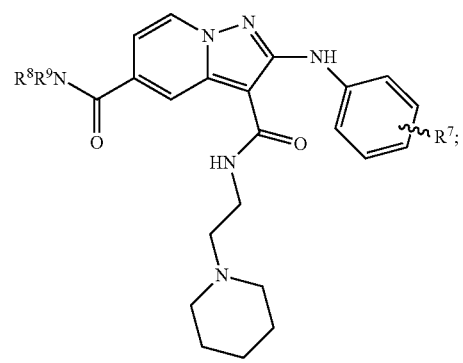
IA3.3
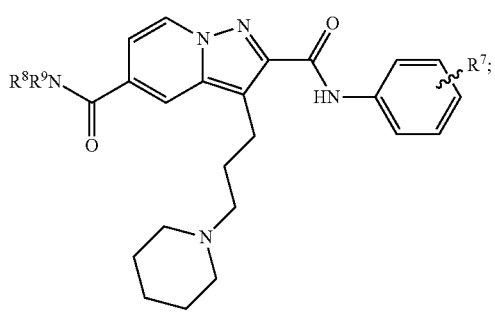
IA3.4
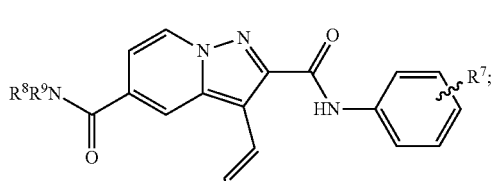
IA3.5
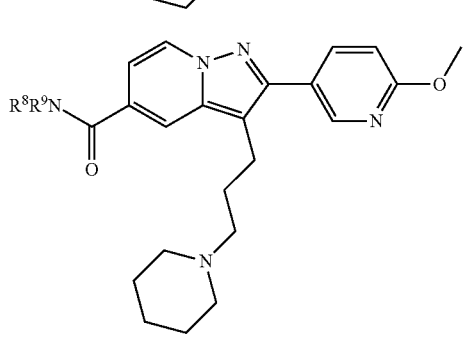
IA5.1
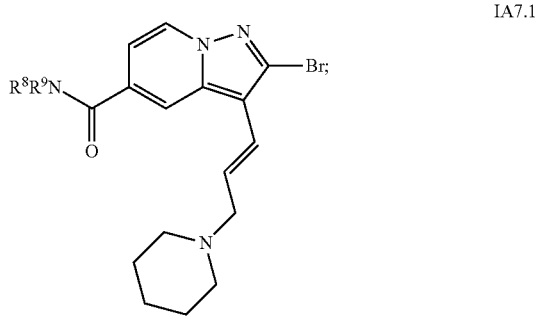
IA7.1

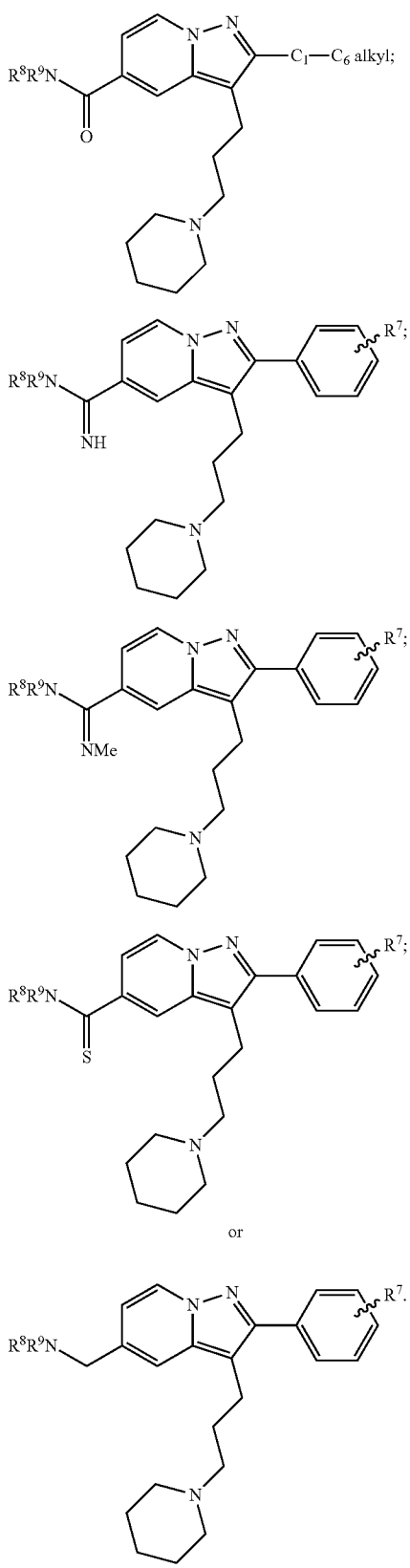

3. The compound according to claim 1, in which $R^1$ is selected from the group consisting of:

aryl optionally substituted with one or more $R^7$ substituents,
phenyl substituted with one $R^7$ substituent,
phenyl substituted with two $R^7$ substituents,
phenyl substituted with three $R^7$ substituents,
heteroaryl substituted with one $R^7$ substituent,
NH-aryl substituted with one $R^7$ substituent,
C(O)NH-aryl substituted with one $R^7$ substituent,
halogen, and
$C_1$-$C_6$-alkyl.

4. The compound according to claim 1, in which $R^2$ is selected from the group consisting of:

$C_1$-$C_6$ alkyl-heterocyclyl, wherein the heterocyclyl is optionally substituted with one or more $C_1$-$C_6$ alkyl substituents, or one or more halo substituents, or one or more haloalkyl substituents;

$C_3$-$C_6$ alkenyl-heterocyclyl, wherein the heterocyclyl is optionally substituted with one or more $C_1$-$C_6$ alkyl substituents, or one or more halo substituents, or one or more haloalkyl substituents;

$C_3$-$C_6$ alkynyl-heterocyclyl, wherein the heterocyclyl is optionally substituted with one or more $C_1$-$C_6$ alkyl substituents, or one or more halo substituents, or one or more haloalkyl substituents;

aryl alkyl-heterocyclyl, wherein the heterocyclyl is optionally substituted with one or more $C_1$-$C_6$ alkyl substituents, or one or more halo substituents, or one or more haloalkyl substituents; and C(O)NH $C_2$-$C_6$ alkynyl-heterocyclyl, wherein the heterocyclyl is optionally substituted with one or more $C_1$-$C_6$ alkyl substituents, or one or more halo substituents, or one or more haloalkyl substituents.

5. The compound according to claim 1, in which $R^3$ is selected from the group consisting of:

$C(O)NR^8R^9$,
$C(=NH)NR^8R^9$,
$C(=NMe)NR^8R^9$,
$C(S)NR^8R^9$, and
$CH_2NR^8R^9$.

6. The compound according to claim 1, in which $R^4$ is selected from the group consisting of:

aryl substituted with one $R^7$ substituent,
aryl substituted with one $OC_1$-$C_6$ alkyl substituent,
aryl substituted with one $C(O)OC_1$-$C_6$ alkyl substituent,
aryl substituted with one $C(O)NH_2$ substituent, and
aryl substituted with one carboxylic acid substituent.

7. The compound according to claim 1, in which $R^5$ and $R^6$ are as follows:

$R^5$ and $R^6$ are both hydrogen;
$R^5$ is hydrogen and $R^6$ is $C_1$-$C_6$ alkyl;
$R^5$ is hydrogen and $R^6$ is $C_1$-$C_6$ alkyl-aryl;
$R^5$ and $R^6$ are both $C_1$-$C_6$ alkyl; or
$R^5$ is heterocyclyl and $R^6$ is $C_1$-$C_6$ alkyl.

8. The compound according to claim 1, in which $R^7$ is

1) CN,
2) halogen,
3) $C_1$-$C_6$ alkyl,
4) $OC_1$-$C_6$ alkyl,
5) $C(O)OC_1$-$C_6$ alkyl,
6) $C(O)$ $C_1$-$C_6$ alkyl,
7) C(O) heteroaryl,
8) C(O)OH,
9) $C(O)NH_2$,
10) heterocyclyl,
11) heteroaryl,
12) C(OH) $C_1$-$C_6$ alkyl,
13) $C(NH_2)=NH$, 14) C(NH$_2$)=N—OH, or
15) C(NH$_2$)=N—OC(O) C$_1$-C$_6$alkyl.

9. The compound according to claim 1, in which R$^8$ and R$^9$ are as follows:
both R$^8$ and R$^9$ are both C$_1$-C$_6$ alkyl;
R$^8$ and R$^9$ are both C$_1$-C$_4$ alkyl-C$_3$-C$_6$ cycloakyl; or
R$^8$ is C$_3$-C$_6$ alkyl and R$^9$ is C$_1$-C$_4$ alkyl-C$_3$-C$_6$ cycloakyl.

10. A compound according to claim 1 or a pharmaceutically acceptable salt thereof, and selected from the group consisting of:

| Cpd No | Structure |
|---|---|
| 1 | 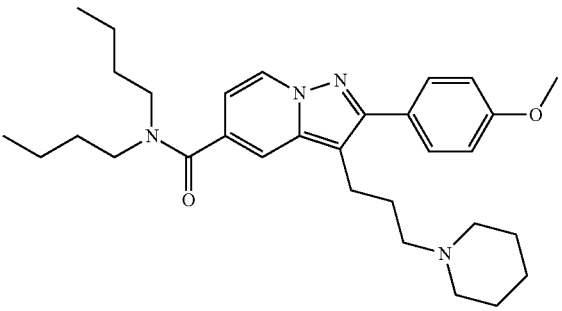 |
| 2 | 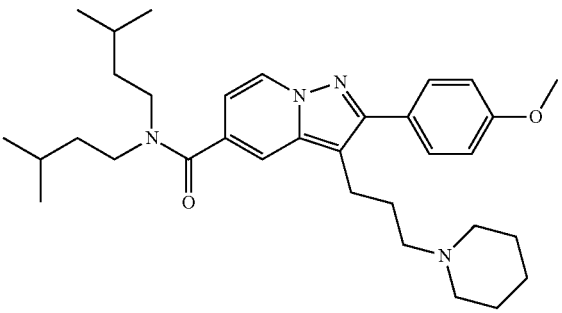 |
| 3 | 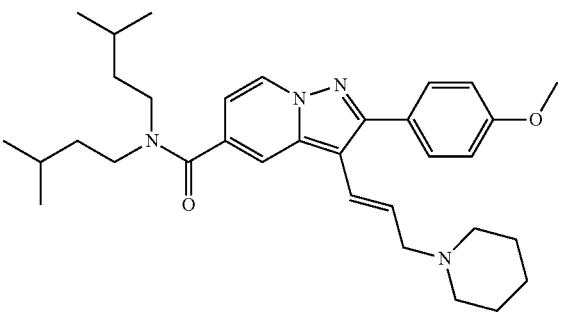 |
| 4 | 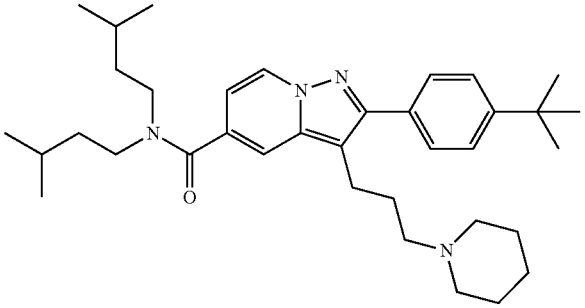 |

-continued
| Cpd No | Structure |
|---|---|
| 5 | 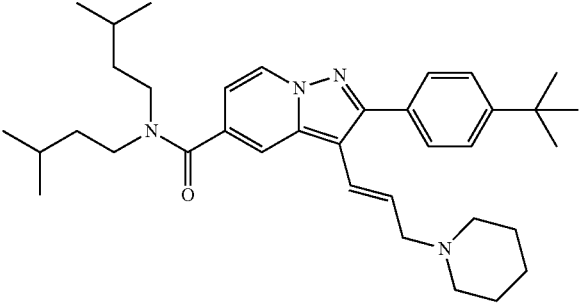 |
| 6 | 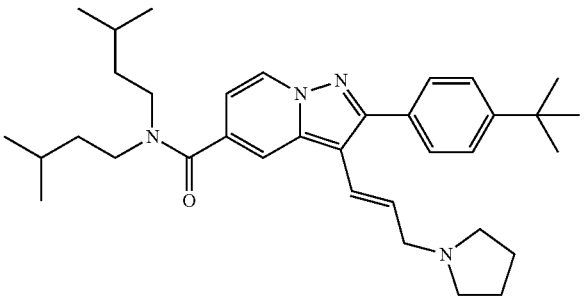 |
| 7 | 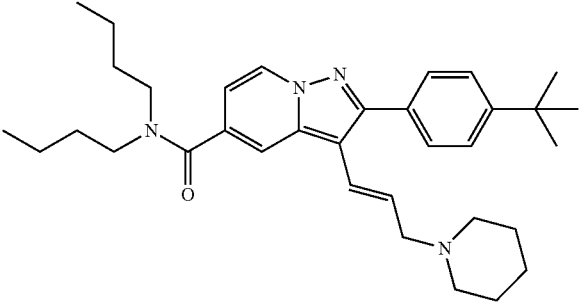 |
| 8 | 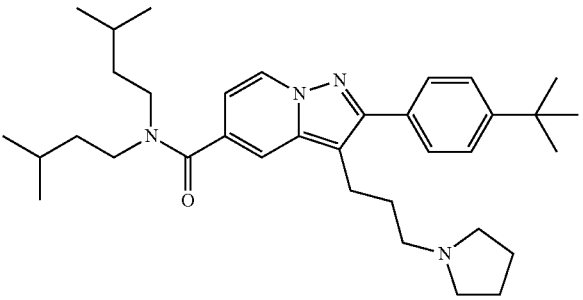 |
| 9 | 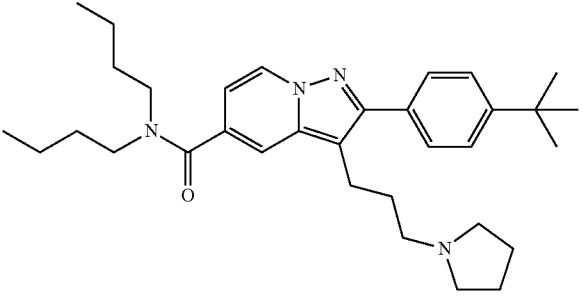 |

-continued
| Cpd No | Structure |
|---|---|
| 10 | 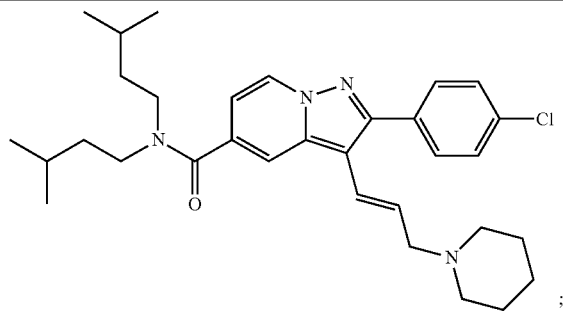 |
| 11 | 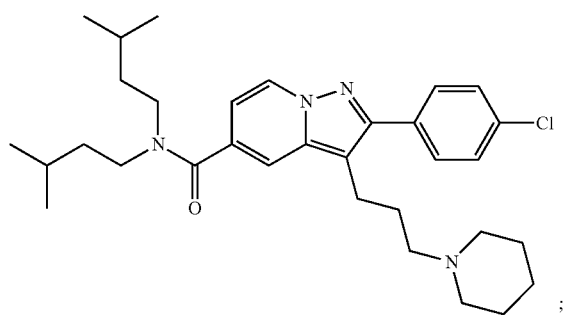 |
| 12 | 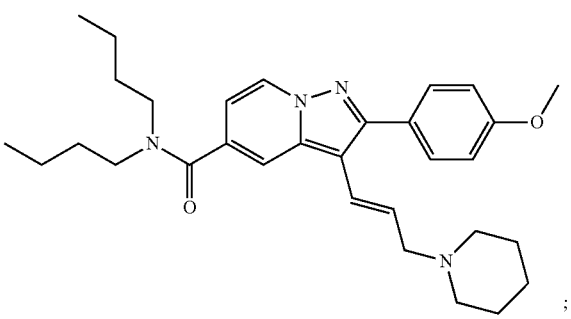 [SMILES: CCCCN(CCCC)C(=O)c1ccn2nc(-c3ccc(OC)cc3)c(/C=C/CN3CCCCC3)c2c1] |
| 13 | 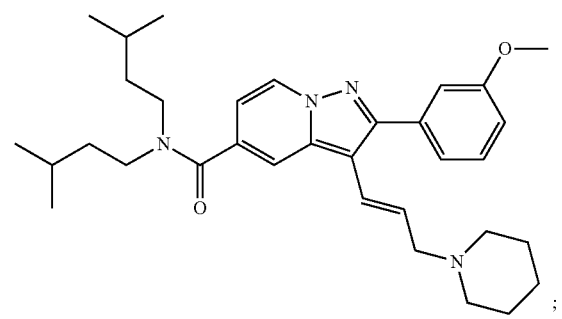 [SMILES: COc1cccc(-c2nn3ccc(C(=O)N(CCC(C)C)CCC(C)C)cc3c2/C=C/CN2CCCCC2)c1] |
| 14 | 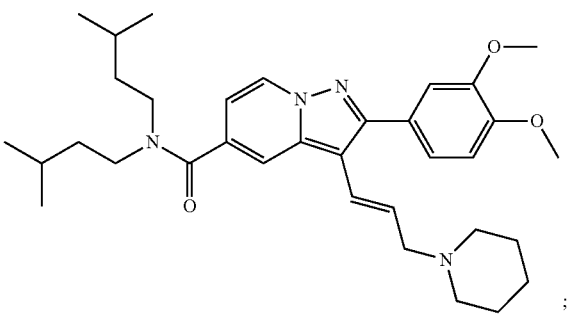 [SMILES: COc1ccc(-c2nn3ccc(C(=O)N(CCC(C)C)CCC(C)C)cc3c2/C=C/CN2CCCCC2)cc1OC] |

| Cpd No | Structure |
|---|---|
| 15 | 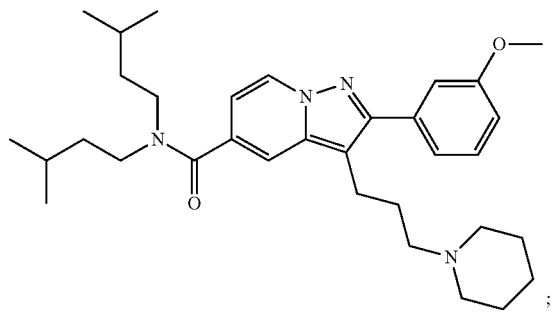 [SMILES: COc1cccc(-c2nn3ccc(C(=O)N(CCC(C)C)CCC(C)C)cc3c2CCCN2CCCCC2)c1] |
| 16 | 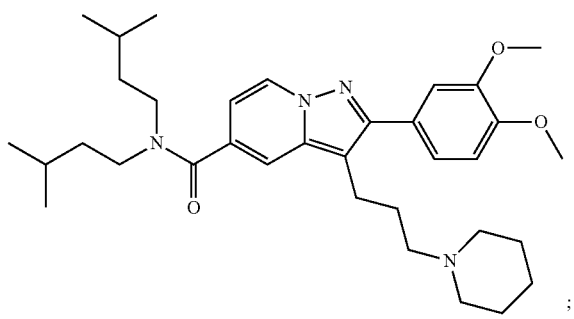 [SMILES: COc1ccc(-c2nn3ccc(C(=O)N(CCC(C)C)CCC(C)C)cc3c2CCCN2CCCCC2)cc1OC] |
| 17 | 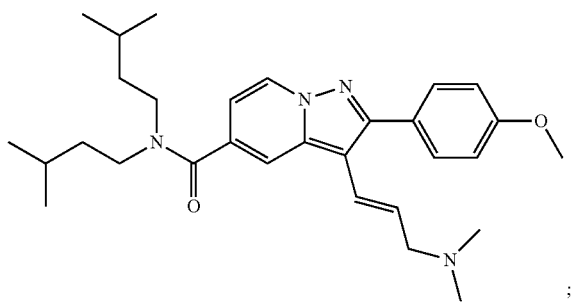 [SMILES: COc1ccc(-c2nn3ccc(C(=O)N(CCC(C)C)CCC(C)C)cc3c2/C=C/CN(C)C)cc1] |
| 18 | 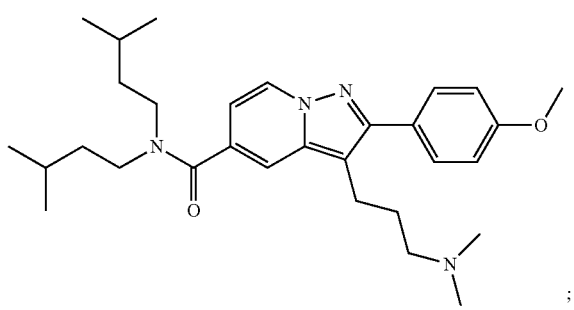 [SMILES: COc1ccc(-c2nn3ccc(C(=O)N(CCC(C)C)CCC(C)C)cc3c2CCCN(C)C)cc1] |
| 19 | 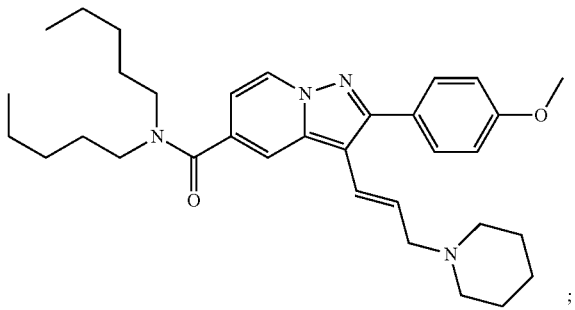 [SMILES: CCCCCN(CCCCC)C(=O)c1ccn2nc(-c3ccc(OC)cc3)c(/C=C/CN3CCCCC3)c2c1] |

-continued
| Cpd No | Structure |
|---|---|
| 20 | 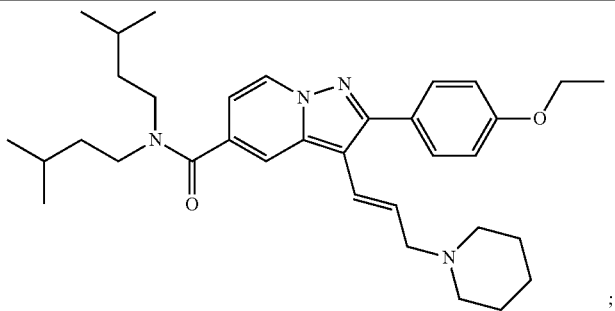 ; |
| 21 | 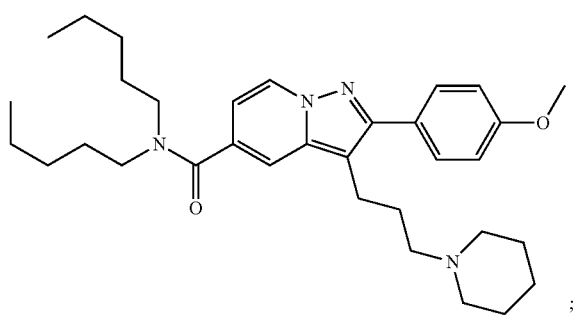 [SMILES: CCCCCN(CCCCC)C(=O)c1ccn2nc(-c3ccc(OC)cc3)c(CCCN3CCCCC3)c2c1] ; |
| 22 | 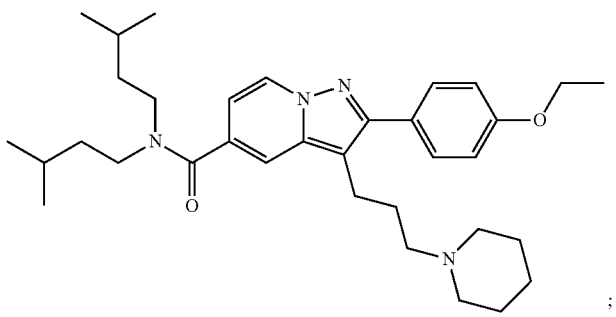 [SMILES: CCOc1ccc(-c2nn3ccc(C(=O)N(CCC(C)C)CCC(C)C)cc3c2CCCN2CCCCC2)cc1] ; |
| 23 | 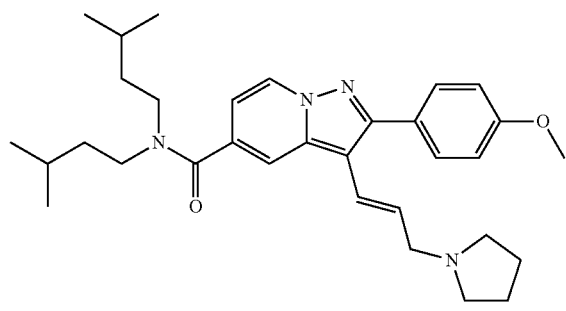 ; |
| 24 | 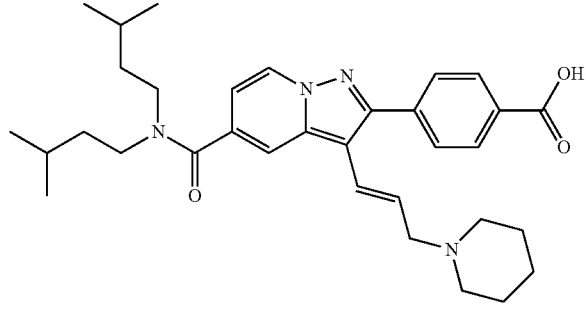 ; |

-continued
| Cpd No | Structure |
|---|---|
| 25 | 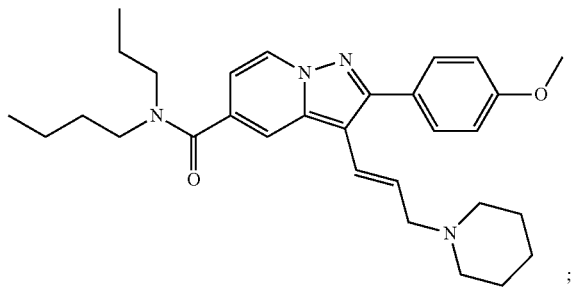 [SMILES: CCCCN(CCC)C(=O)c1ccn2nc(-c3ccc(OC)cc3)c(/C=C/CN3CCCCC3)c2c1] ; |
| 26 | 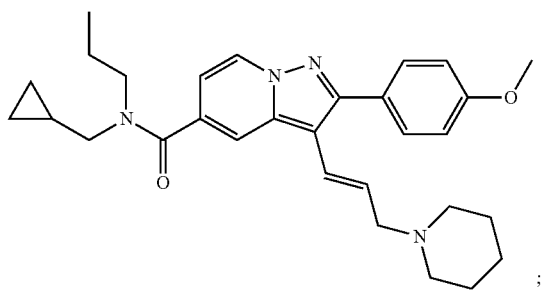 [SMILES: CCCN(CC1CC1)C(=O)c1ccn2nc(-c3ccc(OC)cc3)c(/C=C/CN3CCCCC3)c2c1] ; |
| 27 | 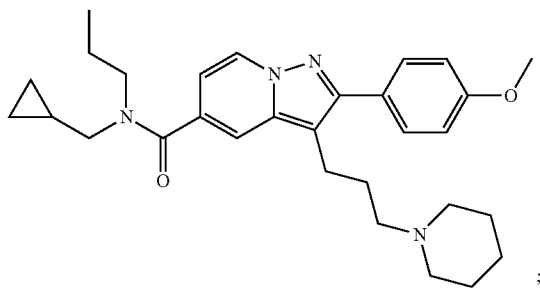 [SMILES: CCCN(CC1CC1)C(=O)c1ccn2nc(-c3ccc(OC)cc3)c(CCCN3CCCCC3)c2c1] ; |
| 28 | 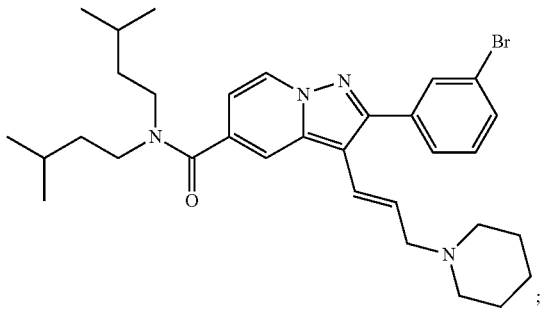 ; |
| 29 | 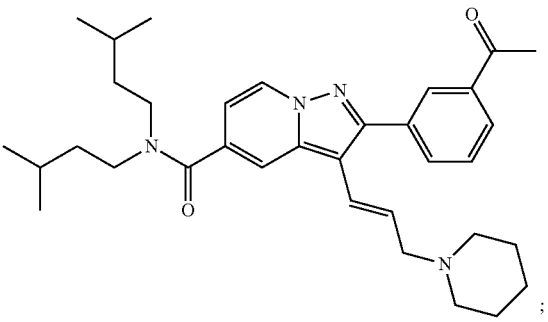 [SMILES: CC(=O)c1cccc(-c2nn3ccc(C(=O)N(CCC(C)C)CCC(C)C)cc3c2/C=C/CN2CCCCC2)c1] ; |

| Cpd No | Structure |
|---|---|
| 30 | 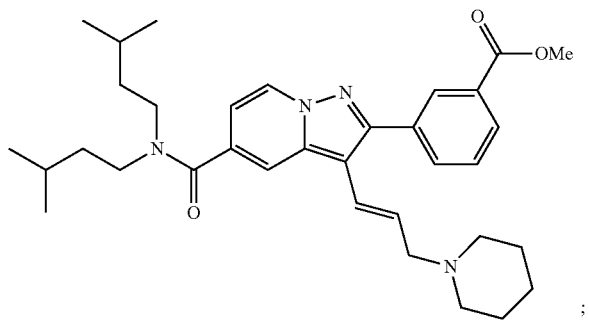 [SMILES: COC(=O)c1cccc(-c2nn3ccc(C(=O)N(CCC(C)C)CCC(C)C)cc3c2/C=C/CN2CCCCC2)c1] |
| 31 | 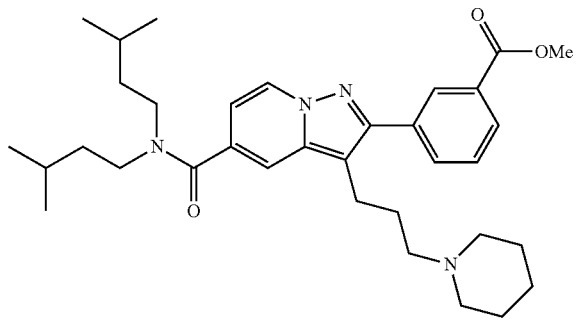 |
| 32 | 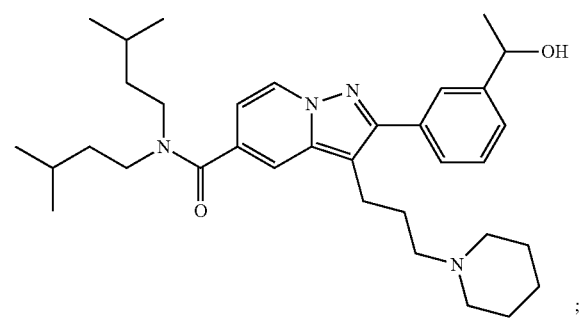 [SMILES: CC(C)CCN(CCC(C)C)C(=O)c1ccn2nc(-c3cccc(C(C)O)c3)c(CCCN3CCCCC3)c2c1] |
| 33 | 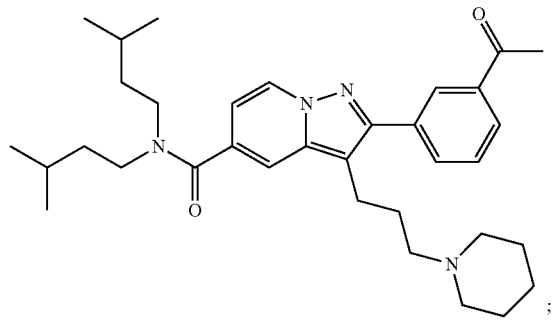 [SMILES: CC(=O)c1cccc(-c2nn3ccc(C(=O)N(CCC(C)C)CCC(C)C)cc3c2CCCN2CCCCC2)c1] |

| Cpd No | Structure |
|---|---|
| 34 | 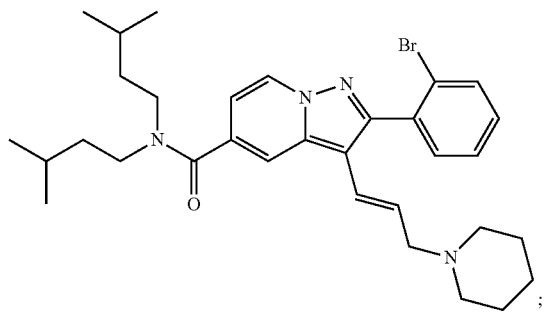 [SMILES: CC(C)CCN(CCC(C)C)C(=O)c1ccn2nc(-c3ccccc3Br)c(/C=C/CN3CCCCC3)c2c1] |
| 35 | 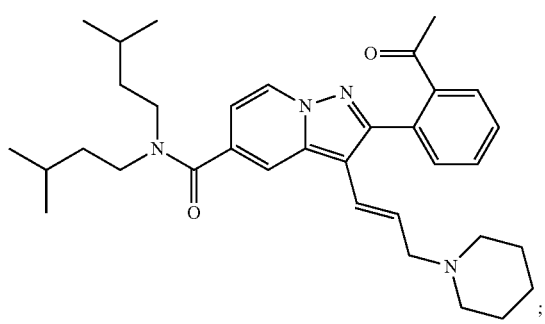 [SMILES: CC(=O)c1ccccc1-c1nn2ccc(C(=O)N(CCC(C)C)CCC(C)C)cc2c1/C=C/CN1CCCCC1] |
| 36 | 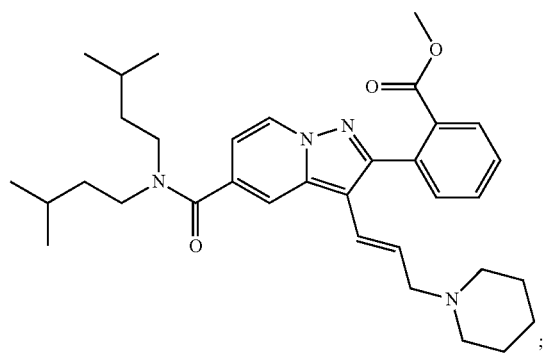 [SMILES: COC(=O)c1ccccc1-c1nn2ccc(C(=O)N(CCC(C)C)CCC(C)C)cc2c1/C=C/CN1CCCCC1] |
| 37 | 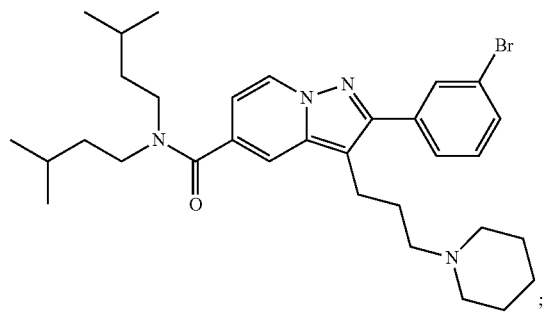 [SMILES: CC(C)CCN(CCC(C)C)C(=O)c1ccn2nc(-c3cccc(Br)c3)c(CCCN3CCCCC3)c2c1] |

| Cpd No | Structure |
|---|---|
| 38 | 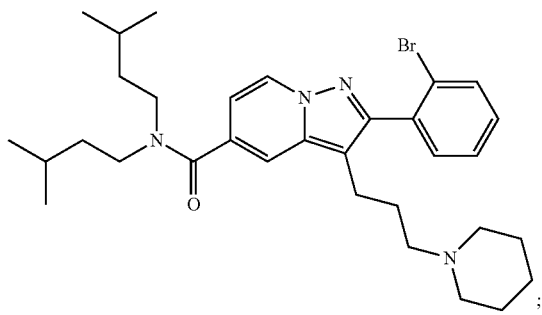 [SMILES: CC(C)CCN(CCC(C)C)C(=O)c1ccn2nc(-c3ccccc3Br)c(CCCN3CCCCC3)c2c1] |
| 39 | 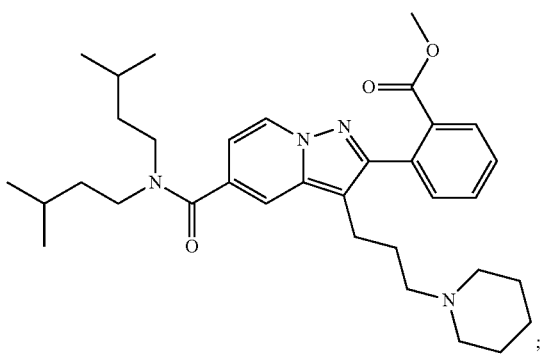 [SMILES: COC(=O)c1ccccc1-c1nn2ccc(C(=O)N(CCC(C)C)CCC(C)C)cc2c1CCCN1CCCCC1] |
| 40 | 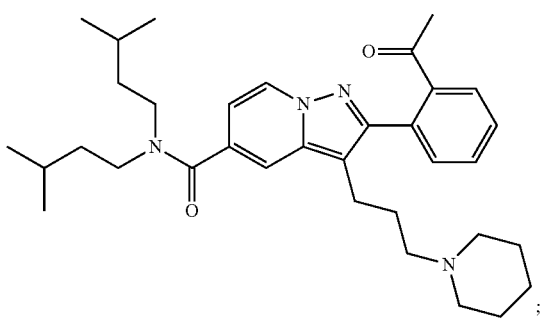 [SMILES: CC(=O)c1ccccc1-c1nn2ccc(C(=O)N(CCC(C)C)CCC(C)C)cc2c1CCCN1CCCCC1] |
| 41 | 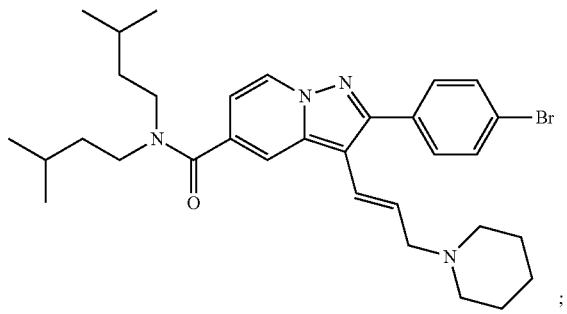 [SMILES: CC(C)CCN(CCC(C)C)C(=O)c1ccn2nc(-c3ccc(Br)cc3)c(/C=C/CN3CCCCC3)c2c1] |

-continued
| Cpd No | Structure |
|---|---|
| 42 | 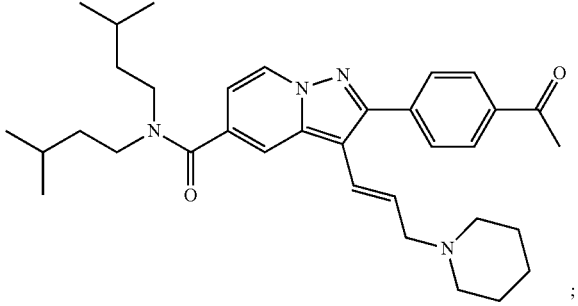 [SMILES: CC(=O)c1ccc(-c2nn3ccc(C(=O)N(CCC(C)C)CCC(C)C)cc3c2/C=C/CN2CCCCC2)cc1] |
| 43 | 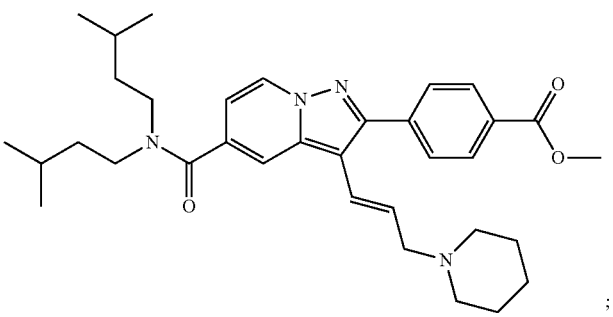 [SMILES: COC(=O)c1ccc(-c2nn3ccc(C(=O)N(CCC(C)C)CCC(C)C)cc3c2/C=C/CN2CCCCC2)cc1] |
| 44 | 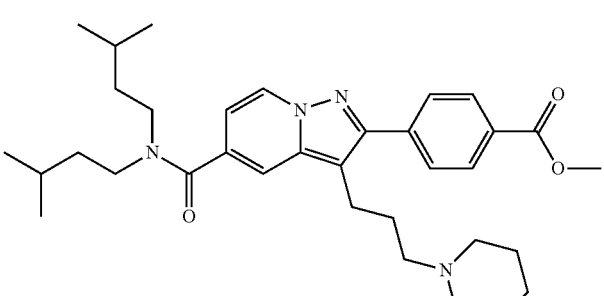 |
| 45 | 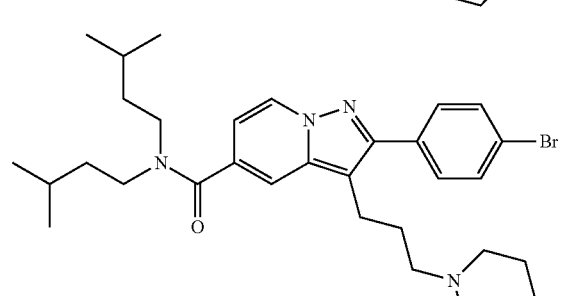 |
| 46 | 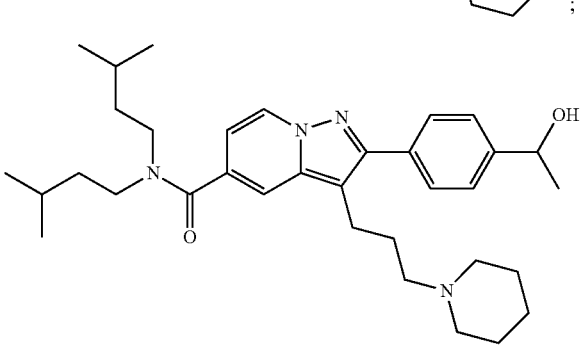 |

-continued
| Cpd No | Structure |
|---|---|
| 47 | 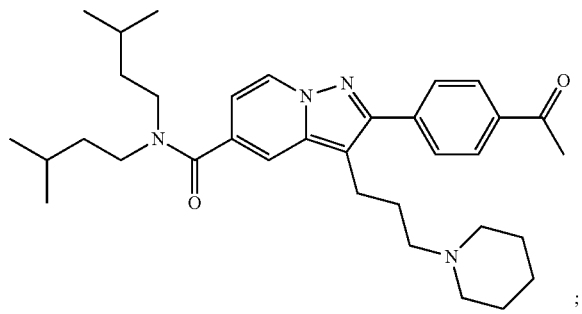 [SMILES: CC(=O)c1ccc(-c2nn3ccc(C(=O)N(CCC(C)C)CCC(C)C)cc3c2CCCN2CCCCC2)cc1] ; |
| 48 | 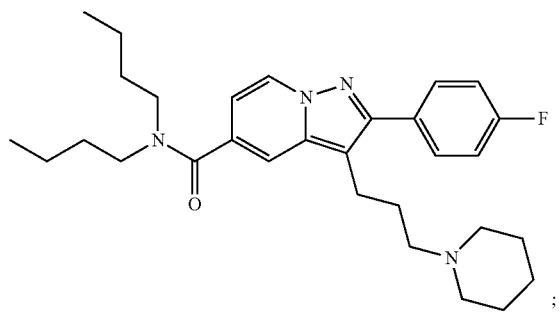 [SMILES: CCCCN(CCCC)C(=O)c1ccn2nc(-c3ccc(F)cc3)c(CCCN3CCCCC3)c2c1] ; |
| 49 | 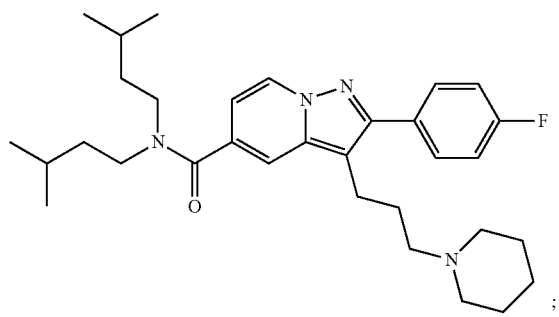 [SMILES: CC(C)CCN(CCC(C)C)C(=O)c1ccn2nc(-c3ccc(F)cc3)c(CCCN3CCCCC3)c2c1] ; |
| 50 | 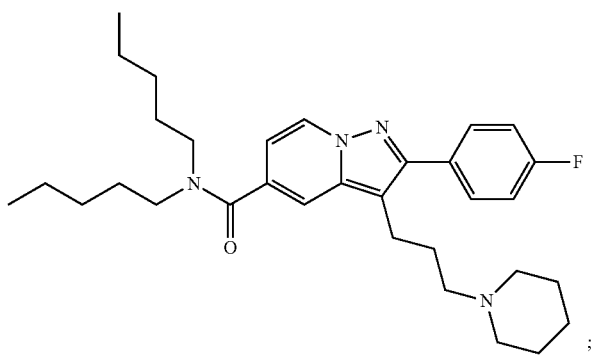 [SMILES: CCCCCN(CCCCC)C(=O)c1ccn2nc(-c3ccc(F)cc3)c(CCCN3CCCCC3)c2c1] ; |

| Cpd No | Structure |
|---|---|
| 51 | 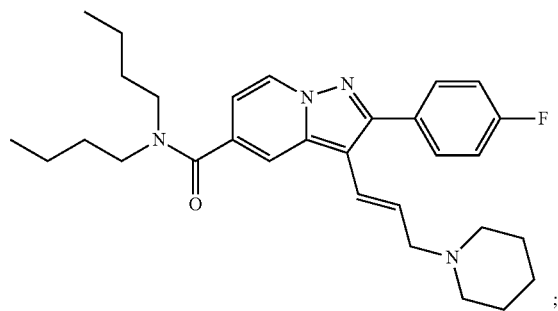 [SMILES: CCCCN(CCCC)C(=O)c1ccn2nc(-c3ccc(F)cc3)c(/C=C/CN3CCCCC3)c2c1] |
| 52 | 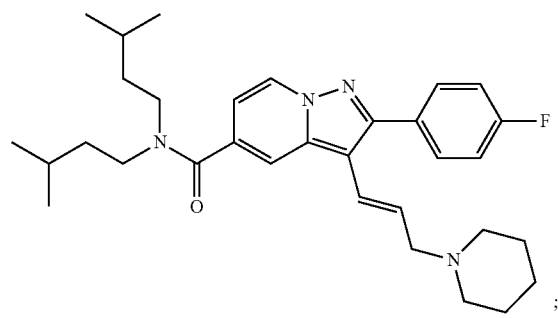 |
| 53 | 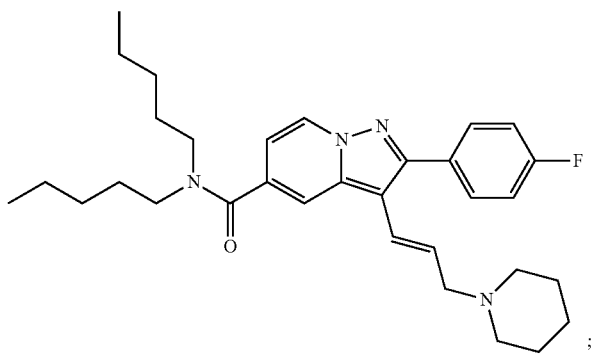 [SMILES: CCCCCN(CCCCC)C(=O)c1ccn2nc(-c3ccc(F)cc3)c(/C=C/CN3CCCCC3)c2c1] |
| 54 | 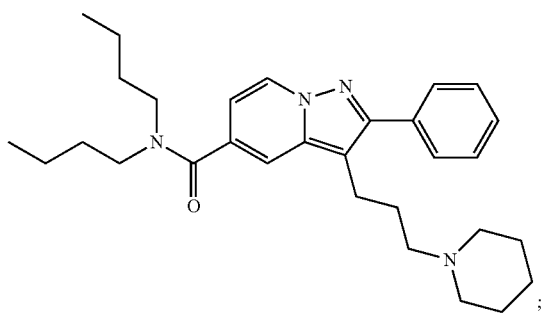 [SMILES: CCCCN(CCCC)C(=O)c1ccn2nc(-c3ccccc3)c(CCCN3CCCCC3)c2c1] |

-continued
| Cpd No | Structure |
|---|---|
| 55 | 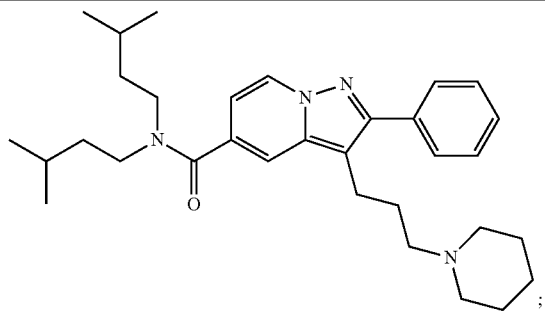 |
| 56 | 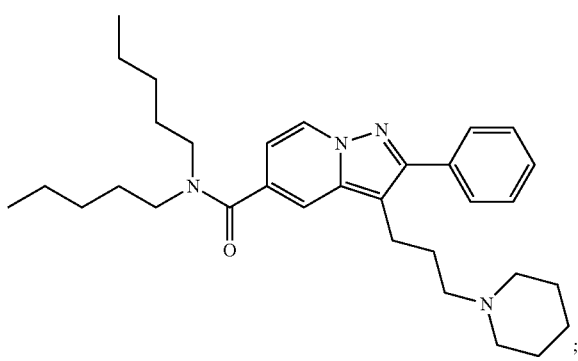 [SMILES: CCCCCN(CCCCC)C(=O)c1ccn2nc(-c3ccccc3)c(CCCN3CCCCC3)c2c1] |
| 57 | 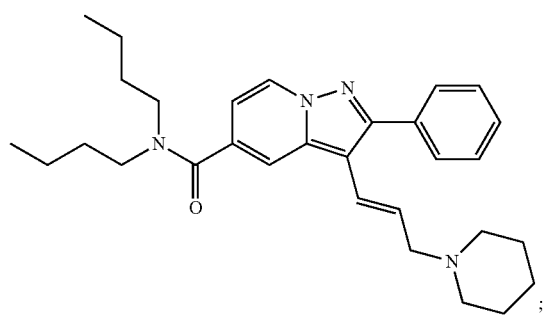 [SMILES: CCCCN(CCCC)C(=O)c1ccn2nc(-c3ccccc3)c(/C=C/CN3CCCCC3)c2c1] |
| 58 | 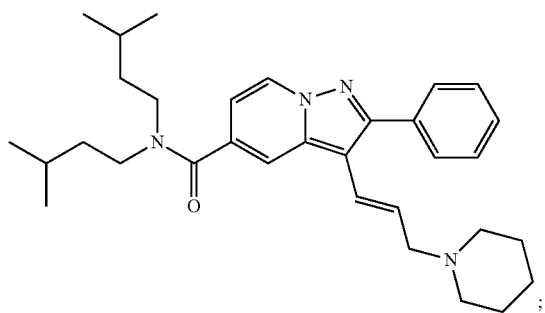 [SMILES: CC(C)CCN(CCC(C)C)C(=O)c1ccn2nc(-c3ccccc3)c(/C=C/CN3CCCCC3)c2c1] |

-continued

| Cpd No | Structure |
|---|---|
| 59 | 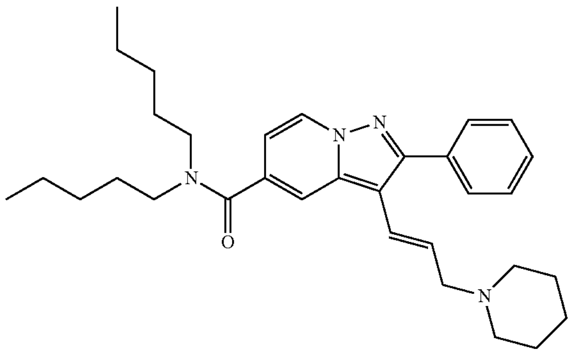 |
| 60 | 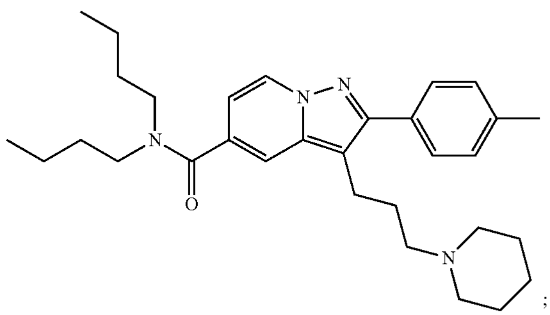 [SMILES: CCCCN(CCCC)C(=O)c1ccn2nc(-c3ccc(C)cc3)c(CCCN3CCCCC3)c2c1] |
| 61 | 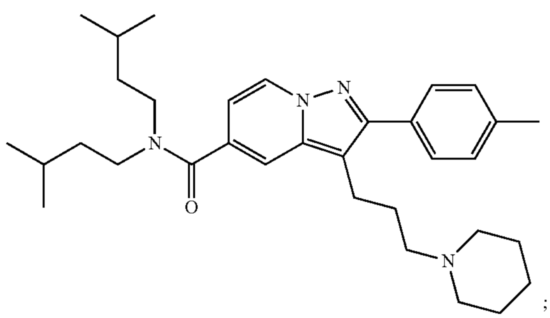 [SMILES: Cc1ccc(-c2nn3ccc(C(=O)N(CCC(C)C)CCC(C)C)cc3c2CCCN2CCCCC2)cc1] |
| 62 | 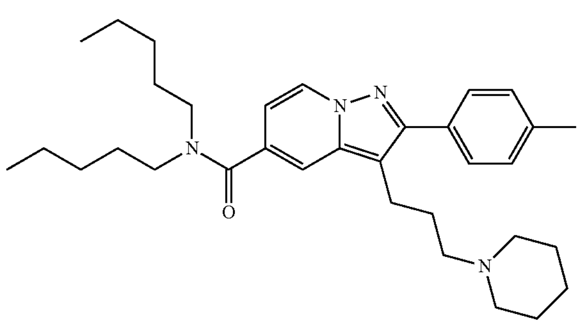 |

-continued

| Cpd No | Structure |
|---|---|
| 63 | 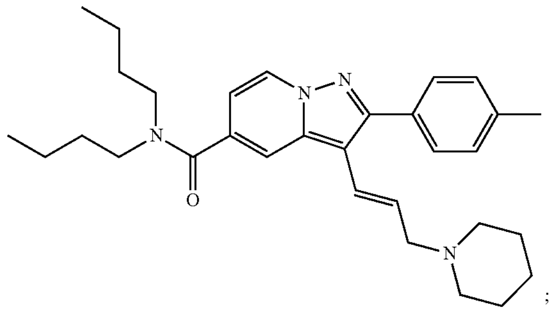 [SMILES: CCCCN(CCCC)C(=O)c1ccn2nc(-c3ccc(C)cc3)c(/C=C/CN3CCCCC3)c2c1] |
| 64 | 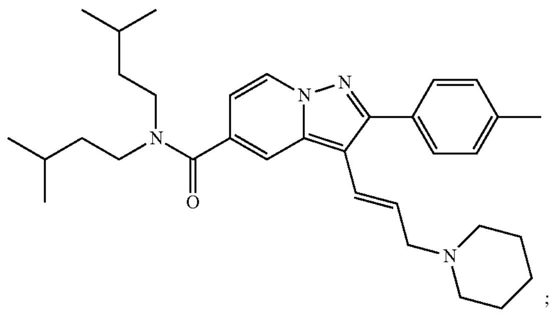 [SMILES: Cc1ccc(-c2nn3ccc(C(=O)N(CCC(C)C)CCC(C)C)cc3c2/C=C/CN2CCCCC2)cc1] |
| 65 | 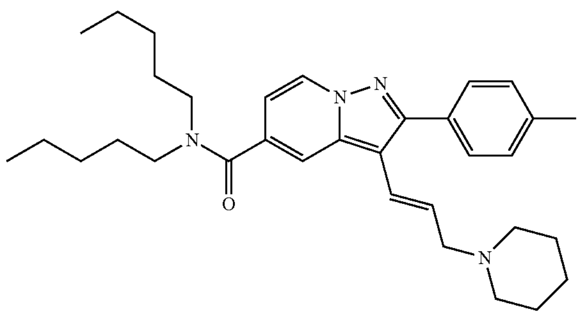 |
| 66 | 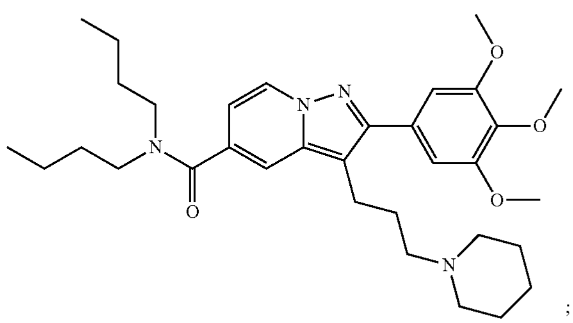 [SMILES: CCCCN(CCCC)C(=O)c1ccn2nc(-c3cc(OC)c(OC)c(OC)c3)c(CCCN3CCCCC3)c2c1] |
| 67 | 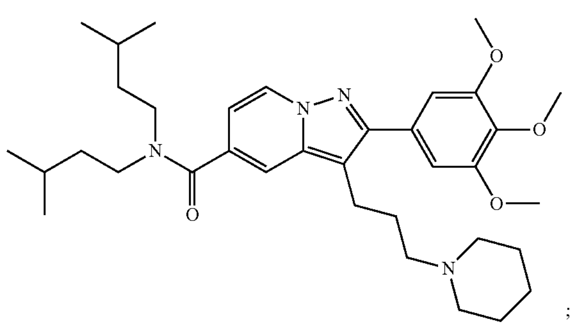 [SMILES: COc1cc(-c2nn3ccc(C(=O)N(CCC(C)C)CCC(C)C)cc3c2CCCN2CCCCC2)cc(OC)c1OC] |

| Cpd No | Structure |
|---|---|
| 68 | 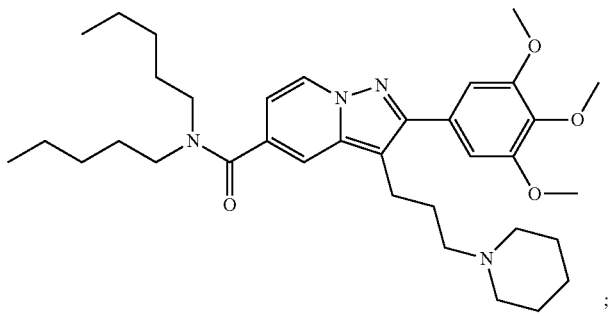 [SMILES: CCCCCN(CCCCC)C(=O)c1ccn2nc(-c3cc(OC)c(OC)c(OC)c3)c(CCCN3CCCCC3)c2c1] |
| 69 | 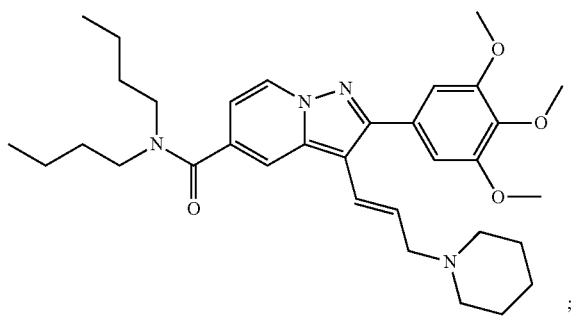 [SMILES: CCCCN(CCCC)C(=O)c1ccn2nc(-c3cc(OC)c(OC)c(OC)c3)c(/C=C/CN3CCCCC3)c2c1] |
| 70 | 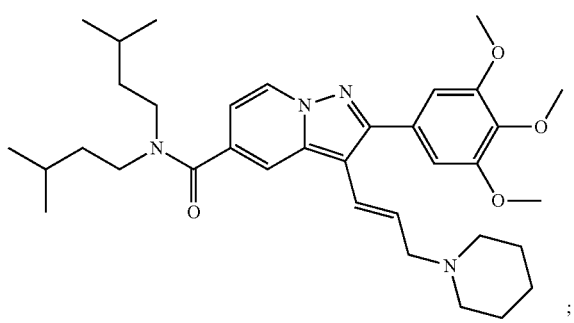 [SMILES: COc1cc(-c2nn3ccc(C(=O)N(CCC(C)C)CCC(C)C)cc3c2/C=C/CN2CCCCC2)cc(OC)c1OC] |
| 71 | 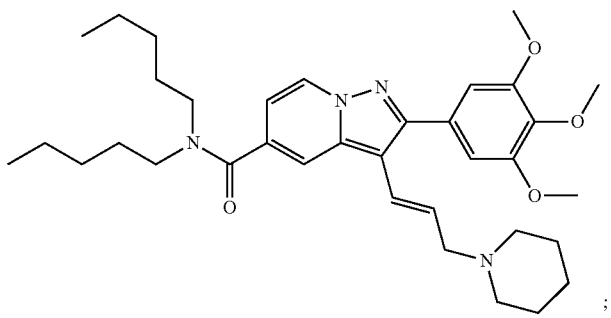 [SMILES: CCCCCN(CCCCC)C(=O)c1ccn2nc(-c3cc(OC)c(OC)c(OC)c3)c(/C=C/CN3CCCCC3)c2c1] |

-continued
| Cpd No | Structure |
|---|---|
| 72 | 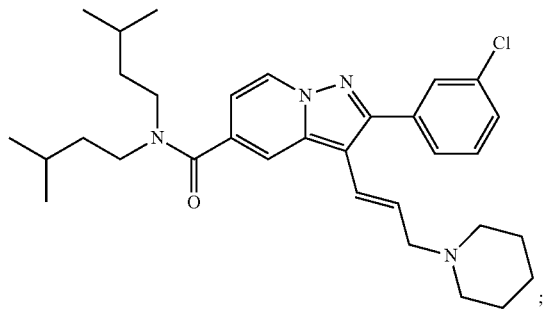 [SMILES: CC(C)CCN(CCC(C)C)C(=O)c1ccn2nc(-c3cccc(Cl)c3)c(/C=C/CN3CCCCC3)c2c1] ; |
| 73 | 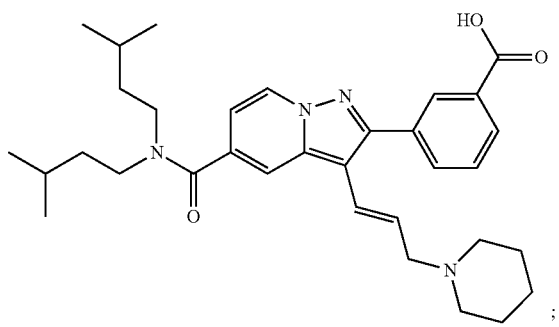 [SMILES: CC(C)CCN(CCC(C)C)C(=O)c1ccn2nc(-c3cccc(C(=O)O)c3)c(/C=C/CN3CCCCC3)c2c1] ; |
| 74 | 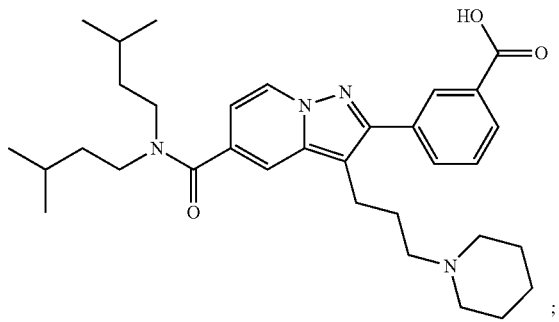 [SMILES: CC(C)CCN(CCC(C)C)C(=O)c1ccn2nc(-c3cccc(C(=O)O)c3)c(CCCN3CCCCC3)c2c1] ; |
| 75 | 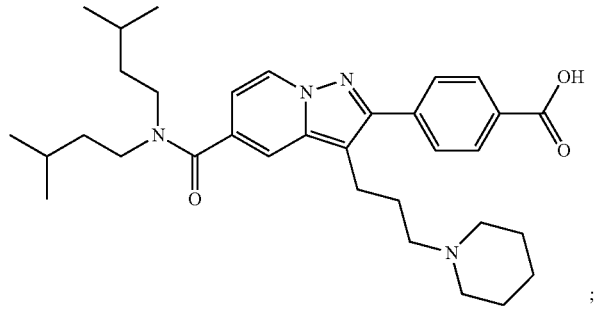 [SMILES: CC(C)CCN(CCC(C)C)C(=O)c1ccn2nc(-c3ccc(C(=O)O)cc3)c(CCCN3CCCCC3)c2c1] ; |
| 76 | 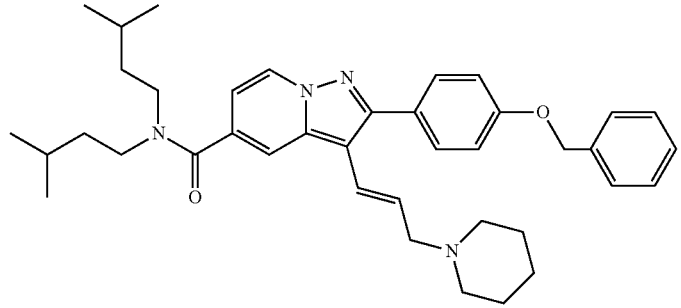 ; |

| Cpd No | Structure |
|---|---|
| 77 | 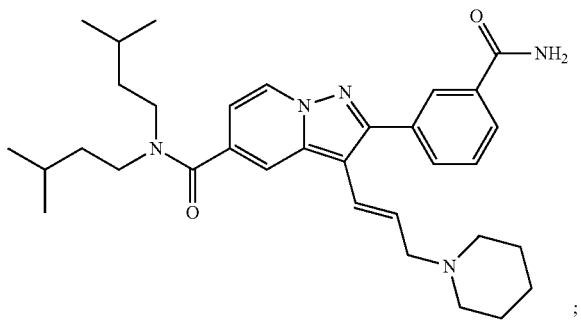 [SMILES: CC(C)CCN(CCC(C)C)C(=O)c1ccn2nc(-c3cccc(C(N)=O)c3)c(/C=C/CN3CCCCC3)c2c1] |
| 78 | 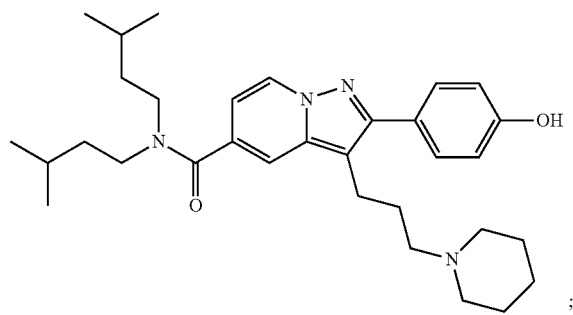 [SMILES: CC(C)CCN(CCC(C)C)C(=O)c1ccn2nc(-c3ccc(O)cc3)c(CCCN3CCCCC3)c2c1] |
| 79 | 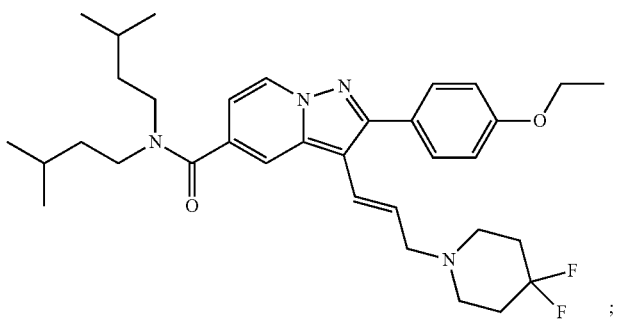 [SMILES: CCOc1ccc(-c2nn3ccc(C(=O)N(CCC(C)C)CCC(C)C)cc3c2/C=C/CN2CCC(F)(F)CC2)cc1] |
| 80 | 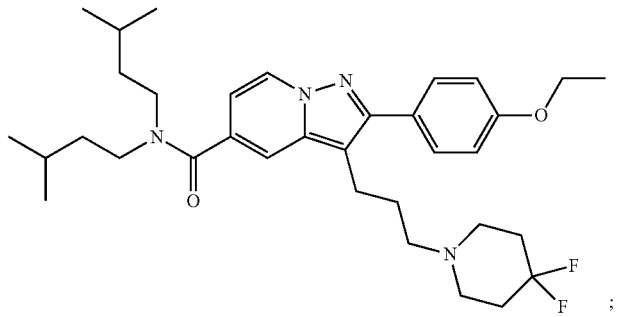 [SMILES: CCOc1ccc(-c2nn3ccc(C(=O)N(CCC(C)C)CCC(C)C)cc3c2CCCN2CCC(F)(F)CC2)cc1] |

| Cpd No | Structure |
|---|---|
| 81 | 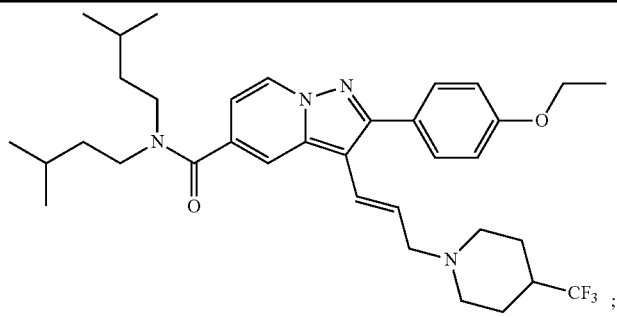 |
| 82 | 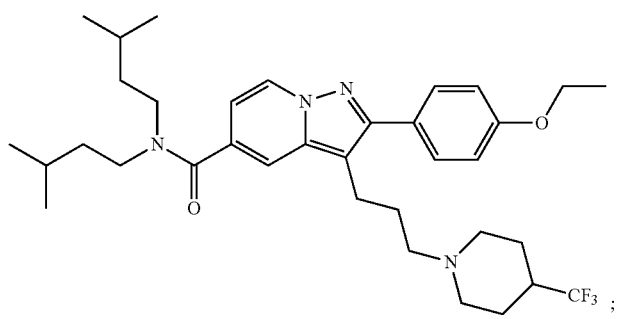 [SMILES: CCOc1ccc(-c2nn3ccc(C(=O)N(CCC(C)C)CCC(C)C)cc3c2CCCN2CCC(C(F)(F)F)CC2)cc1] |
| 83 | 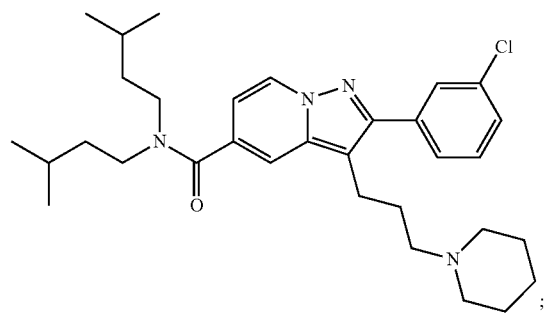 [SMILES: CC(C)CCN(CCC(C)C)C(=O)c1ccn2nc(-c3cccc(Cl)c3)c(CCCN3CCCCC3)c2c1] |
| 84 | 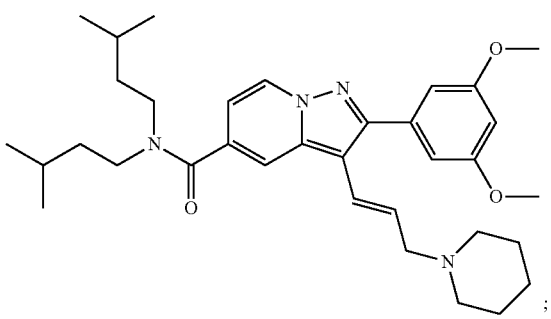 [SMILES: COc1cc(OC)cc(-c2nn3ccc(C(=O)N(CCC(C)C)CCC(C)C)cc3c2/C=C/CN2CCCCC2)c1] |
| 85 | 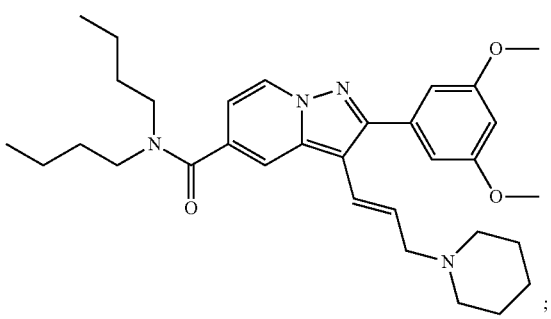 [SMILES: CCCCN(CCCC)C(=O)c1ccn2nc(-c3cc(OC)cc(OC)c3)c(/C=C/CN3CCCCC3)c2c1] |

US 9,018,395 B2
223                                                                                                     224
-continued
| Cpd No | Structure |
|---|---|
| 86 | 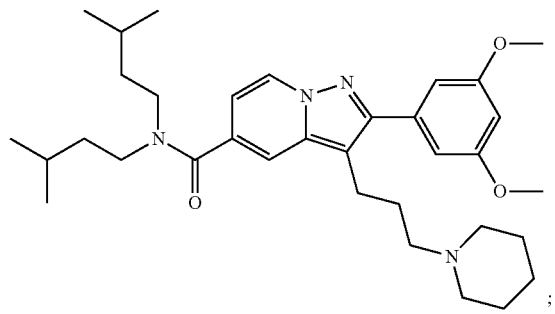 [SMILES: COc1cc(OC)cc(-c2nn3ccc(C(=O)N(CCC(C)C)CCC(C)C)cc3c2CCCN2CCCCC2)c1] |
| 87 | 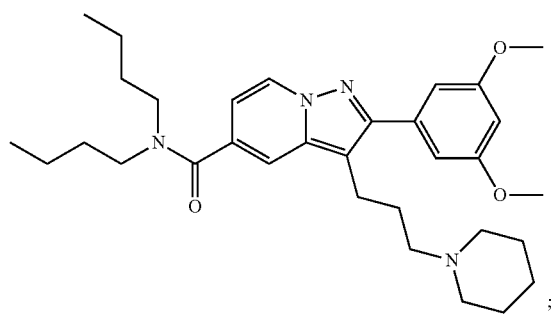 [SMILES: CCCCN(CCCC)C(=O)c1ccn2nc(-c3cc(OC)cc(OC)c3)c(CCCN3CCCCC3)c2c1] |
| 90 | 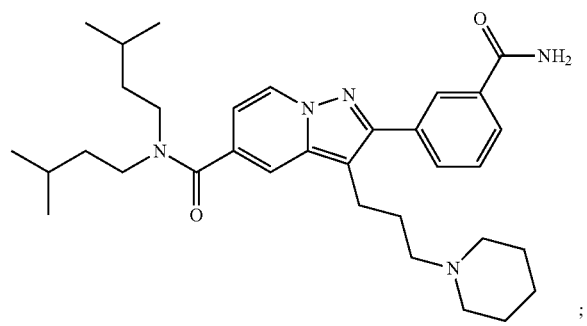 [SMILES: CC(C)CCN(CCC(C)C)C(=O)c1ccn2nc(-c3cccc(C(N)=O)c3)c(CCCN3CCCCC3)c2c1] |
| 91 | 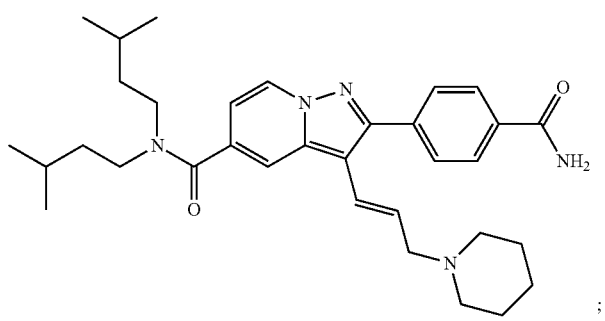 [SMILES: CC(C)CCN(CCC(C)C)C(=O)c1ccn2nc(-c3ccc(C(N)=O)cc3)c(/C=C/CN3CCCCC3)c2c1] |
| 92 | 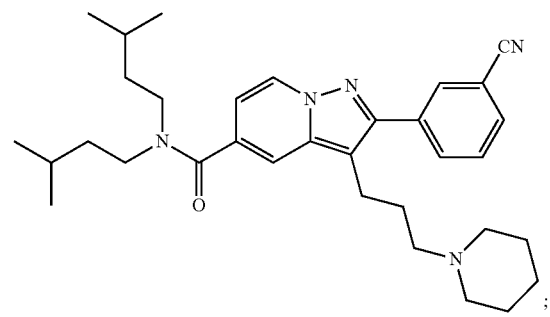 [SMILES: CC(C)CCN(CCC(C)C)C(=O)c1ccn2nc(-c3cccc(C#N)c3)c(CCCN3CCCCC3)c2c1] |

-continued
| Cpd No | Structure |
|---|---|
| 93 | 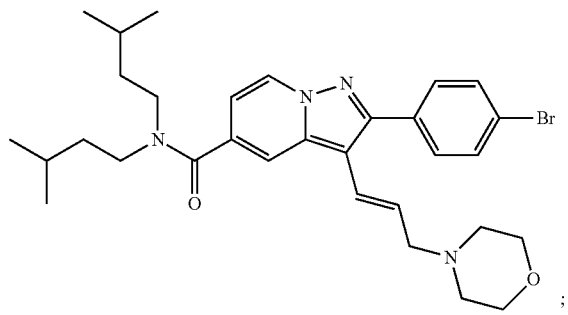 [SMILES: CC(C)CCN(CCC(C)C)C(=O)c1ccn2nc(-c3ccc(Br)cc3)c(/C=C/CN3CCOCC3)c2c1] |
| 94 | 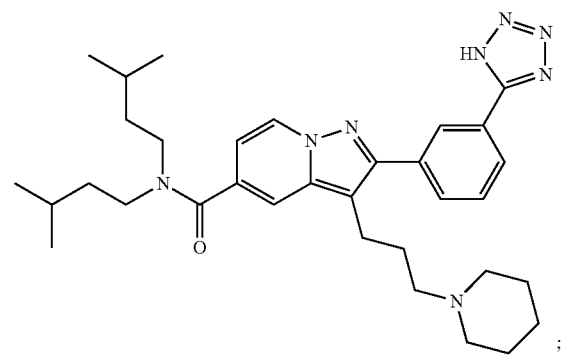 [SMILES: CC(C)CCN(CCC(C)C)C(=O)c1ccn2nc(-c3cccc(-c4nnn[nH]4)c3)c(CCCN3CCCCC3)c2c1] |
| 95 | 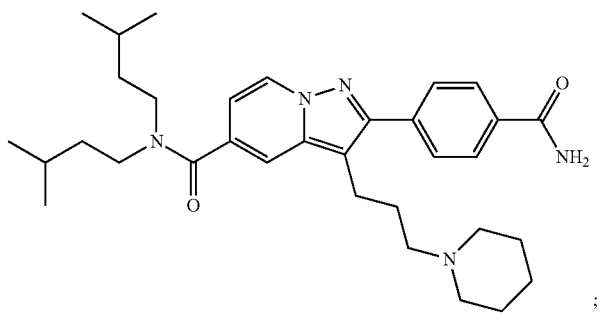 [SMILES: CC(C)CCN(CCC(C)C)C(=O)c1ccn2nc(-c3ccc(C(N)=O)cc3)c(CCCN3CCCCC3)c2c1] |
| 96 | 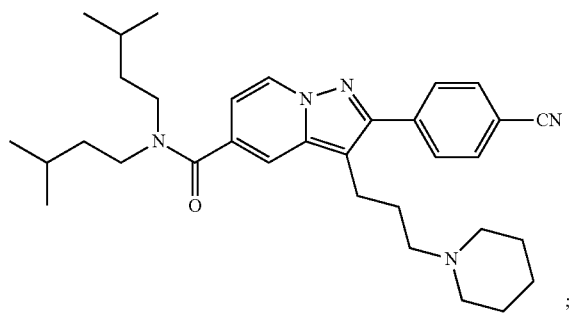 [SMILES: CC(C)CCN(CCC(C)C)C(=O)c1ccn2nc(-c3ccc(C#N)cc3)c(CCCN3CCCCC3)c2c1] |

-continued
| Cpd No | Structure |
|---|---|
| 97 | 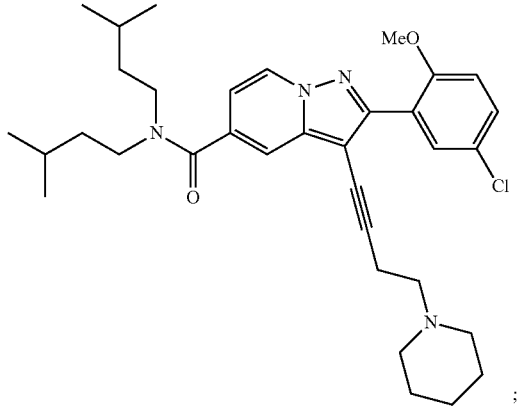 [SMILES: COc1ccc(Cl)cc1-c1nn2ccc(C(=O)N(CCC(C)C)CCC(C)C)cc2c1C#CCCN1CCCCC1] |
| 98 | 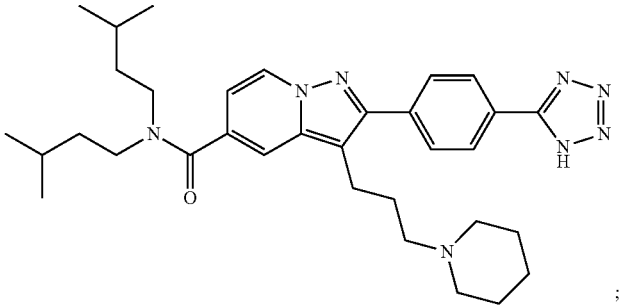 [SMILES: CC(C)CCN(CCC(C)C)C(=O)c1ccn2nc(-c3ccc(-c4nnn[nH]4)cc3)c(CCCN3CCCCC3)c2c1] |
| 101 | 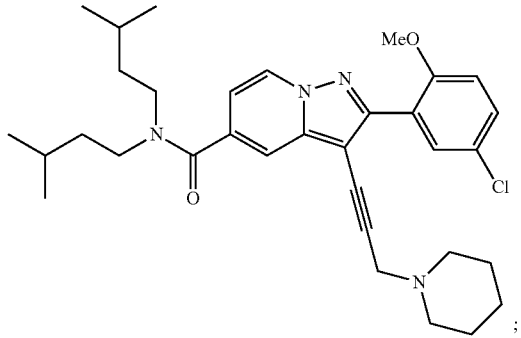 [SMILES: COc1ccc(Cl)cc1-c1nn2ccc(C(=O)N(CCC(C)C)CCC(C)C)cc2c1C#CCN1CCCCC1] |
| 102 | 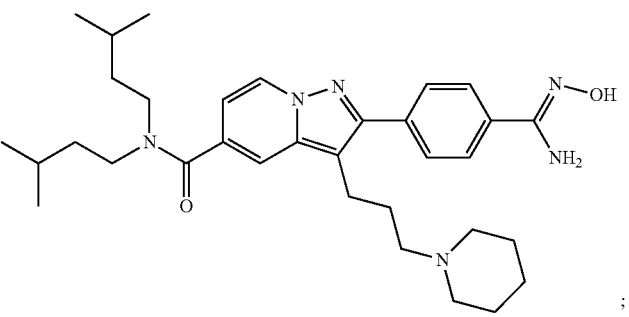 [SMILES: CC(C)CCN(CCC(C)C)C(=O)c1ccn2nc(-c3ccc(/C(N)=N/O)cc3)c(CCCN3CCCCC3)c2c1] |

-continued
| Cpd No | Structure |
|---|---|
| 103 | 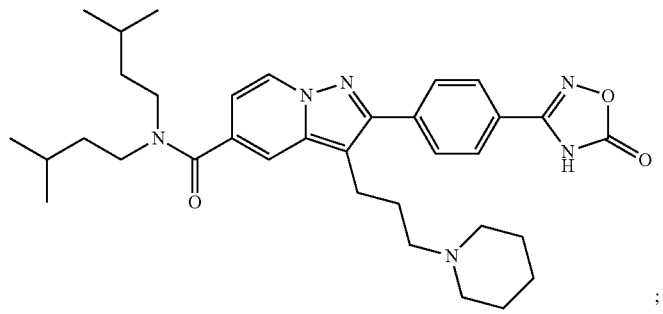 [SMILES: CC(C)CCN(CCC(C)C)C(=O)c1ccn2nc(-c3ccc(-c4noc(=O)[nH]4)cc3)c(CCCN3CCCCC3)c2c1] ; |
| 106 | 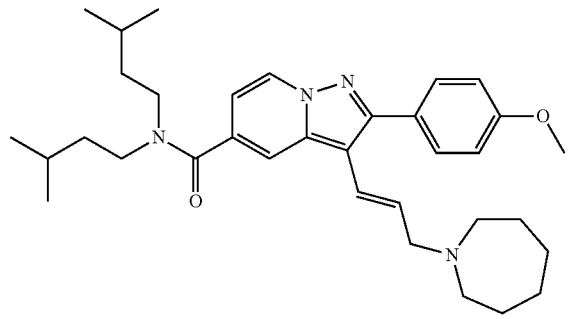 ; |
| 107 | 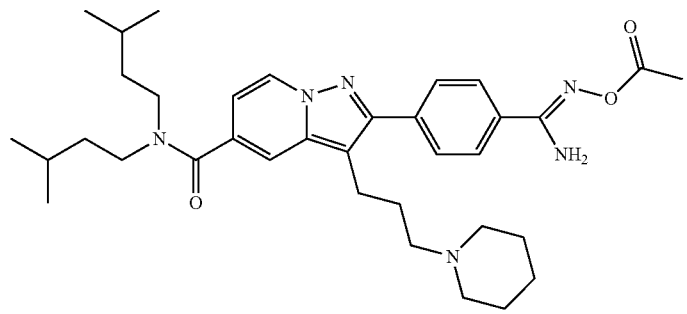 ; |
| 108 | 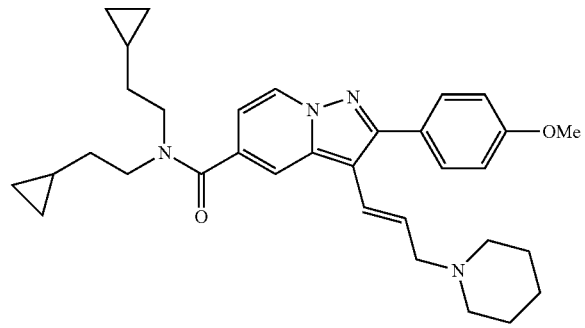 ; |

-continued
| Cpd No | Structure |
|---|---|
| 109 | 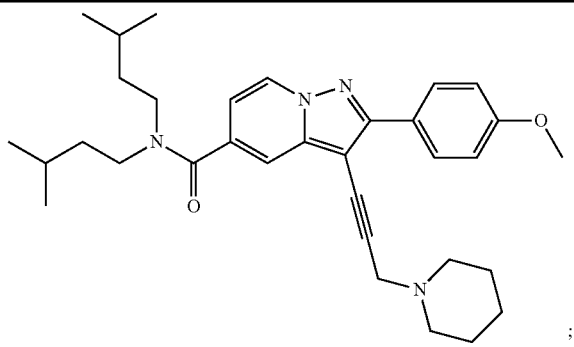 |
| 110 | 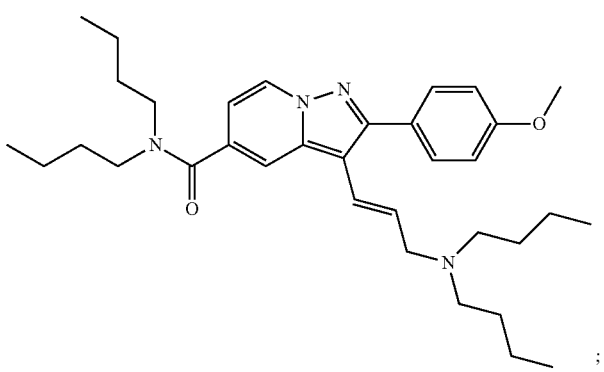 [SMILES: CCCCN(C/C=C/c1c(-c2ccc(OC)cc2)nn2ccc(C(=O)N(CCCC)CCCC)cc12)CCCC] |
| 111 | 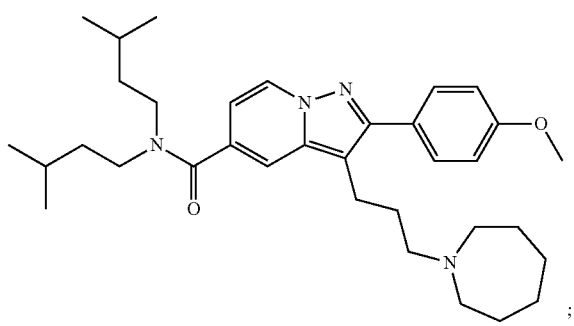 [SMILES: COc1ccc(-c2nn3ccc(C(=O)N(CCC(C)C)CCC(C)C)cc3c2CCCN2CCCCCC2)cc1] |
| 112 | 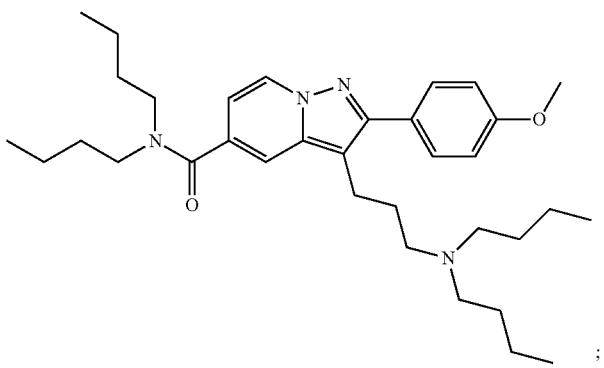 [SMILES: CCCCN(CCCC)CCCc1c(-c2ccc(OC)cc2)nn2ccc(C(=O)N(CCCC)CCCC)cc12] |

-continued
| Cpd No | Structure |
|---|---|
| 113 | 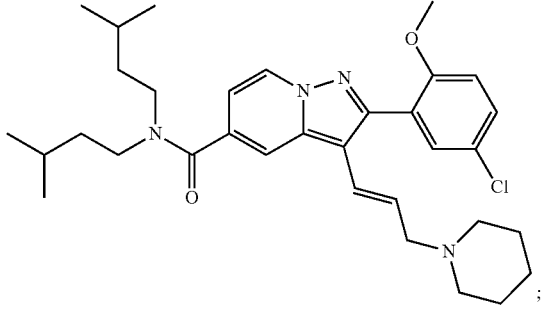 [SMILES: COc1ccc(Cl)cc1-c1nn2ccc(C(=O)N(CCC(C)C)CCC(C)C)cc2c1/C=C/CN1CCCCC1] ; |
| 114 | 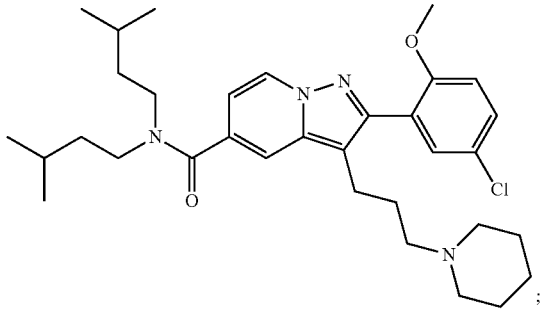 [SMILES: COc1ccc(Cl)cc1-c1nn2ccc(C(=O)N(CCC(C)C)CCC(C)C)cc2c1CCCN1CCCCC1] ; |
| 115 | 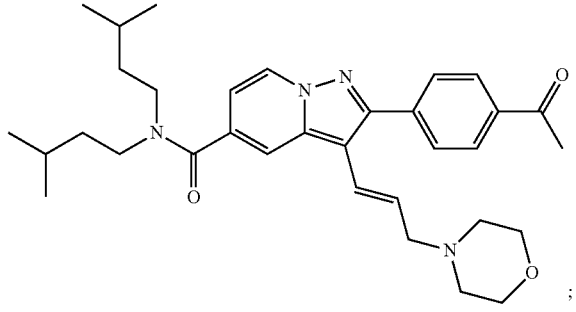 [SMILES: CC(=O)c1ccc(-c2nn3ccc(C(=O)N(CCC(C)C)CCC(C)C)cc3c2/C=C/CN2CCOCC2)cc1] ; |
| 116 | 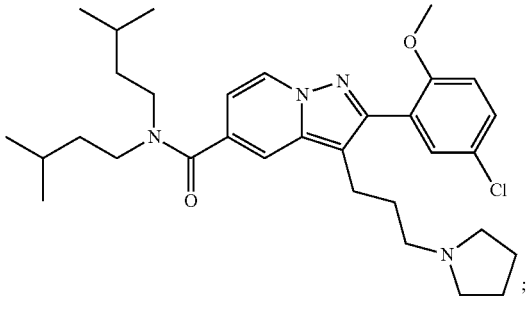 [SMILES: COc1ccc(Cl)cc1-c1nn2ccc(C(=O)N(CCC(C)C)CCC(C)C)cc2c1CCCN1CCCC1] ; |
| 117 | 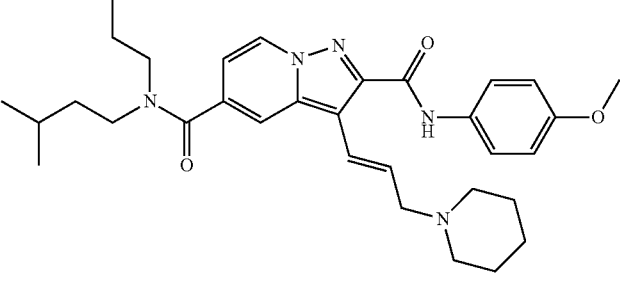 ; |

| Cpd No | Structure |
|---|---|
| 118 | 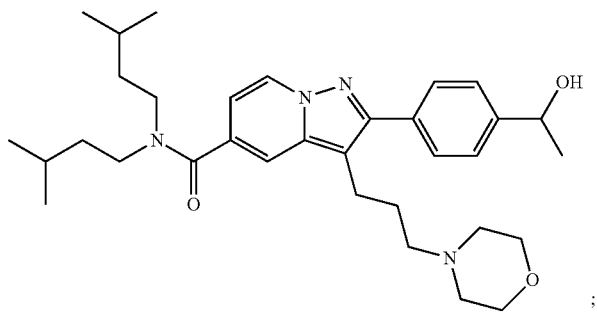 [SMILES: CC(C)CCN(CCC(C)C)C(=O)c1ccn2nc(-c3ccc(C(C)O)cc3)c(CCCN3CCOCC3)c2c1] ; |
| 119 | 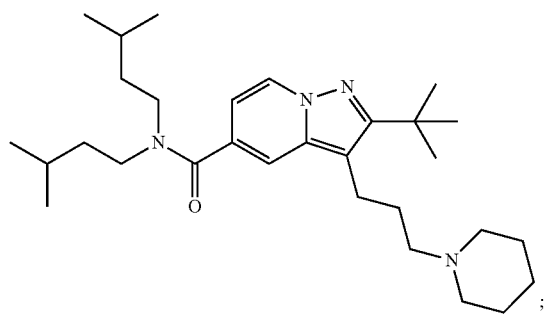 [SMILES: CC(C)CCN(CCC(C)C)C(=O)c1ccn2nc(C(C)(C)C)c(CCCN3CCCCC3)c2c1] ; |
| 120 | 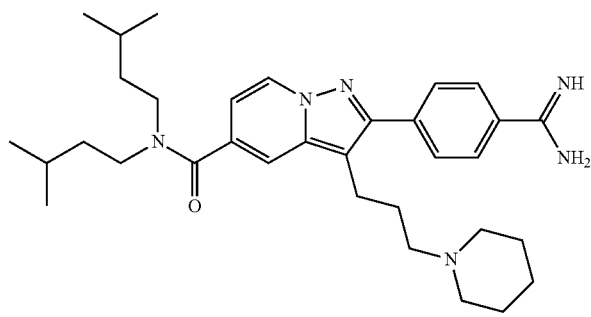 ; |
| 121 | 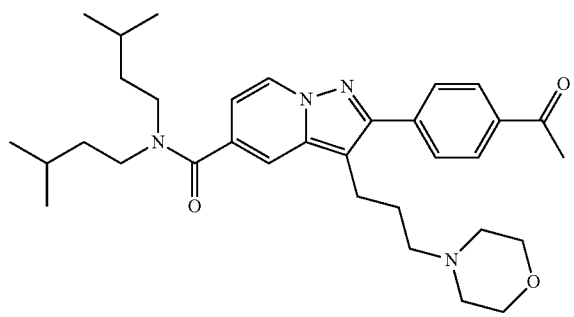 ; |
| 122 | 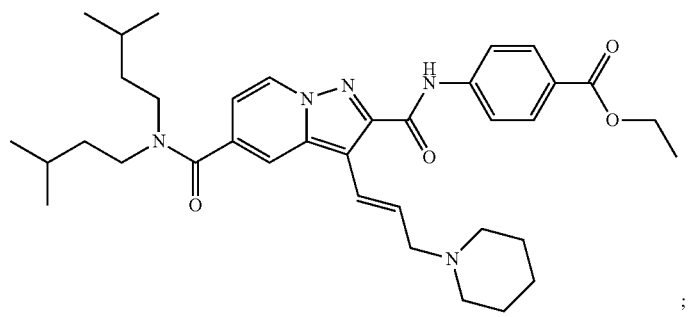 [SMILES: CCOC(=O)c1ccc(NC(=O)c2nn3ccc(C(=O)N(CCC(C)C)CCC(C)C)cc3c2/C=C/CN2CCCCC2)cc1] ; |

-continued
| Cpd No | Structure |
|---|---|
| 123 | 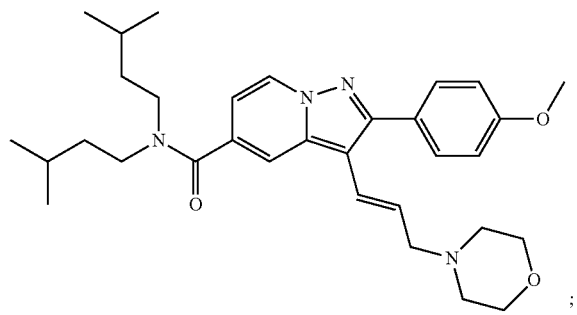 [SMILES: COc1ccc(-c2nn3ccc(C(=O)N(CCC(C)C)CCC(C)C)cc3c2/C=C/CN2CCOCC2)cc1] ; |
| 124 | 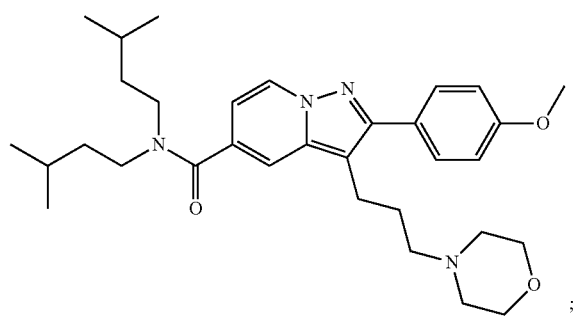 [SMILES: COc1ccc(-c2nn3ccc(C(=O)N(CCC(C)C)CCC(C)C)cc3c2CCCN2CCOCC2)cc1] ; |
| 125 | 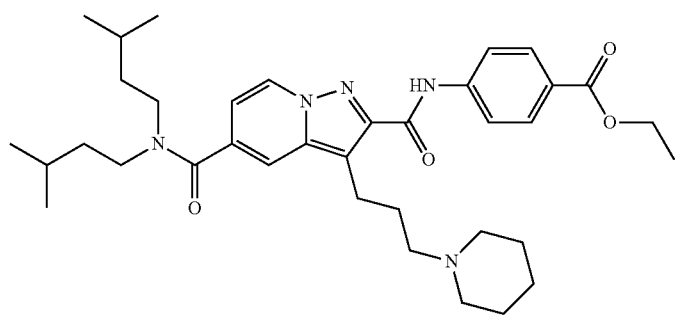 ; |
| 126 | 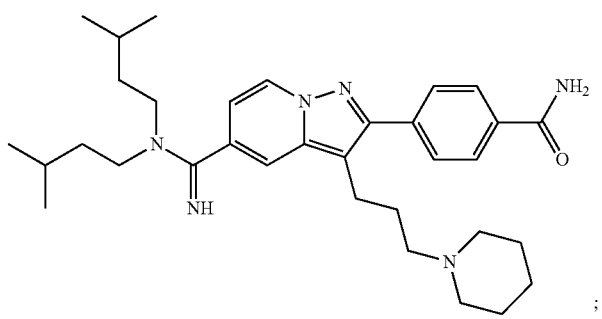 [SMILES: CC(C)CCN(CCC(C)C)C(=N)c1ccn2nc(-c3ccc(C(N)=O)cc3)c(CCCN3CCCCC3)c2c1] ; |
| 127 | 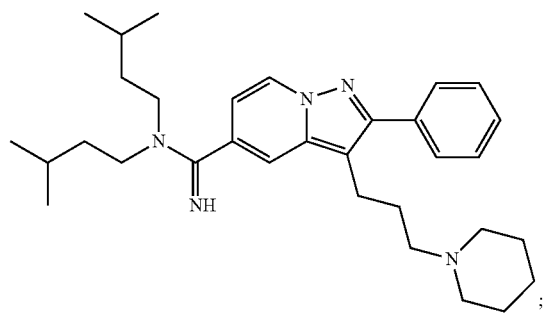 [SMILES: CC(C)CCN(CCC(C)C)C(=N)c1ccn2nc(-c3ccccc3)c(CCCN3CCCCC3)c2c1] ; |

| Cpd No | Structure |
|---|---|
| 128 | 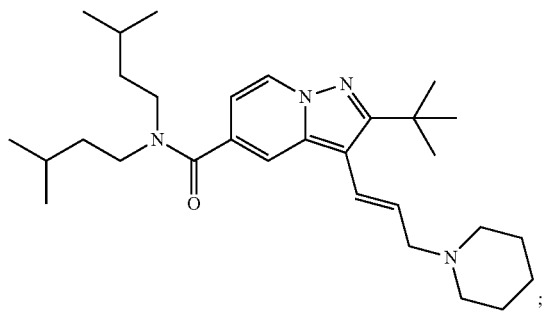 [SMILES: CC(C)CCN(CCC(C)C)C(=O)c1ccn2nc(C(C)(C)C)c(/C=C/CN3CCCCC3)c2c1] |
| 129 | 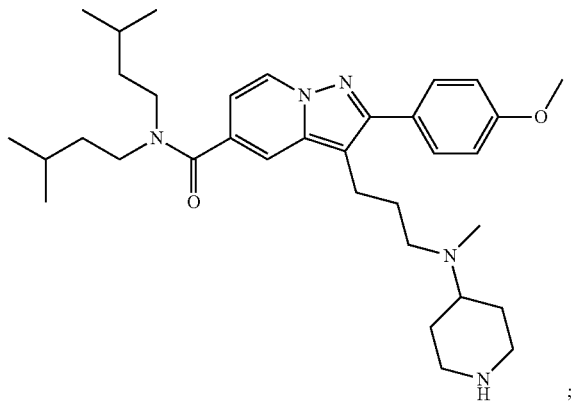 [SMILES: COc1ccc(-c2nn3ccc(C(=O)N(CCC(C)C)CCC(C)C)cc3c2CCCN(C)C2CCNCC2)cc1] |
| 130 | 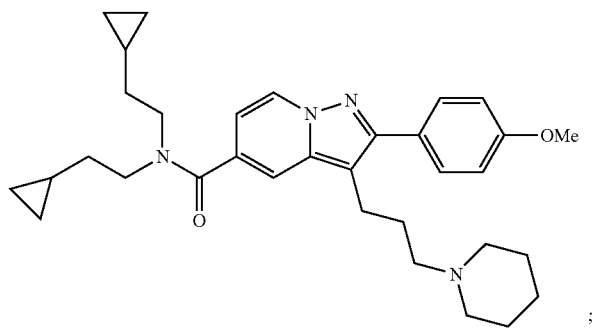 [SMILES: COc1ccc(-c2nn3ccc(C(=O)N(CCC4CC4)CCC4CC4)cc3c2CCCN2CCCCC2)cc1] |
| 131 | 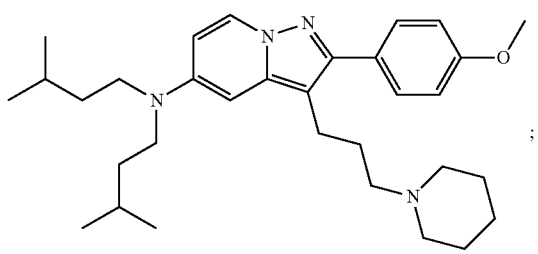 [SMILES: COc1ccc(-c2nn3ccc(N(CCC(C)C)CCC(C)C)cc3c2CCCN2CCCCC2)cc1] |

| Cpd No | Structure |
|---|---|
| 132 | 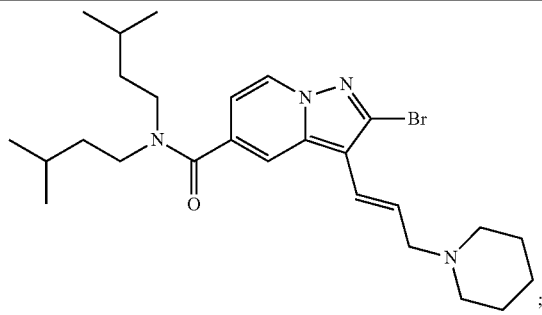 |
| 133 | 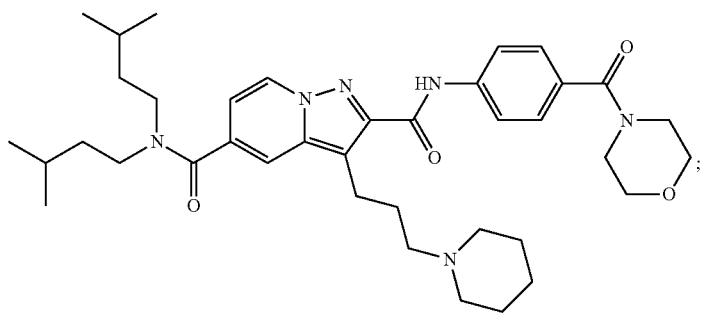 [SMILES: CC(C)CCN(CCC(C)C)C(=O)c1ccn2nc(C(=O)Nc3ccc(C(=O)N4CCOCC4)cc3)c(CCCN3CCCCC3)c2c1] |
| 134 | 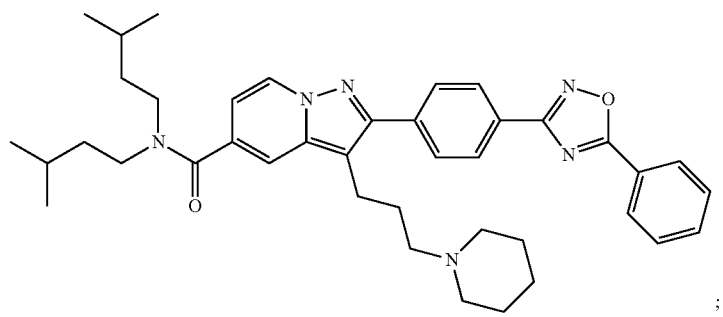 [SMILES: CC(C)CCN(CCC(C)C)C(=O)c1ccn2nc(-c3ccc(-c4noc(-c5ccccc5)n4)cc3)c(CCCN3CCCCC3)c2c1] |
| 135 | 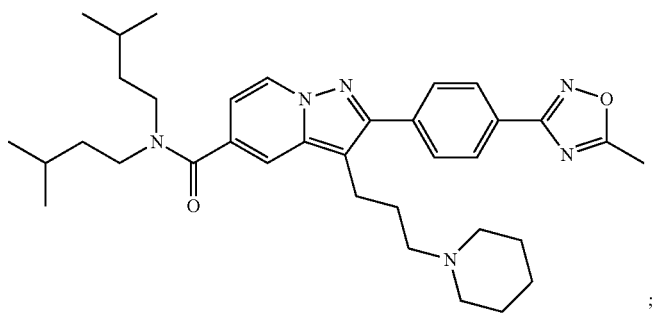 [SMILES: Cc1nc(-c2ccc(-c3nn4ccc(C(=O)N(CCC(C)C)CCC(C)C)cc4c3CCCN3CCCCC3)cc2)no1] |
| 136 | 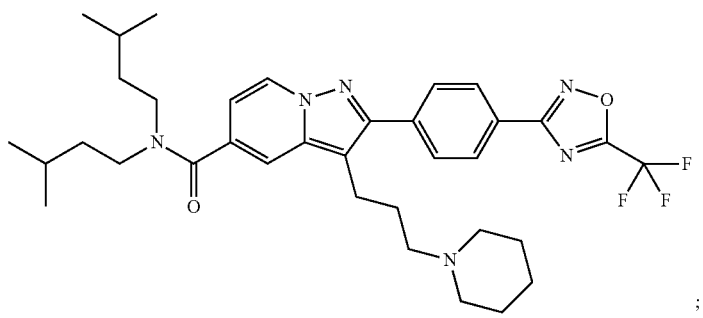 [SMILES: CC(C)CCN(CCC(C)C)C(=O)c1ccn2nc(-c3ccc(-c4noc(C(F)(F)F)n4)cc3)c(CCCN3CCCCC3)c2c1] |

US 9,018,395 B2
-continued
| Cpd No | Structure |
|---|---|
| 137 | 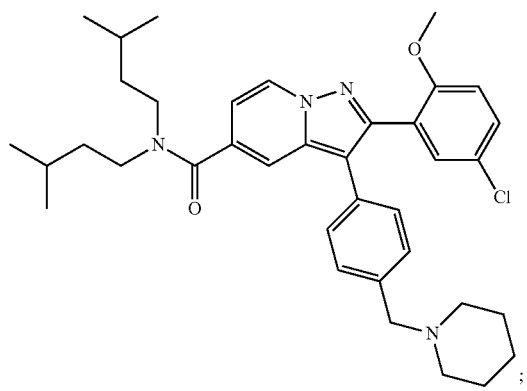 [SMILES: COc1ccc(Cl)cc1-c1nn2ccc(C(=O)N(CCC(C)C)CCC(C)C)cc2c1-c1ccc(CN2CCCCC2)cc1] |
| 138 | 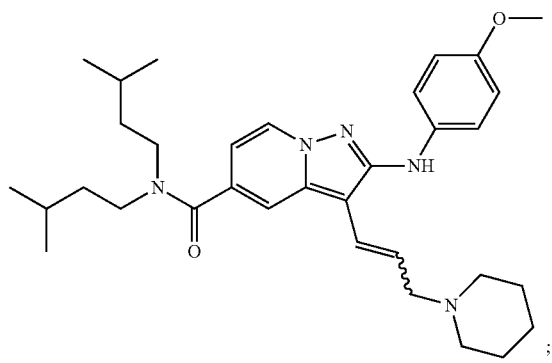 [SMILES: COc1ccc(Nc2nn3ccc(C(=O)N(CCC(C)C)CCC(C)C)cc3c2C=CCN2CCCCC2)cc1] |
| 139 | 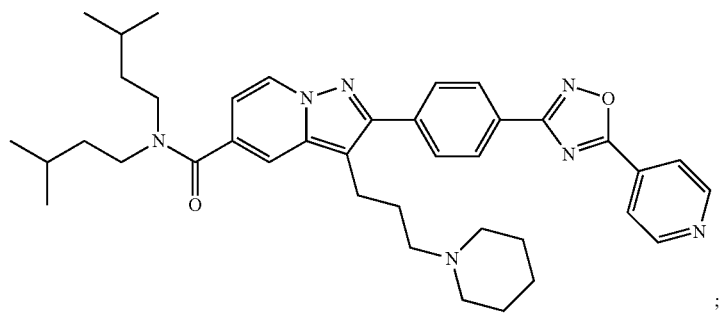 [SMILES: CC(C)CCN(CCC(C)C)C(=O)c1ccn2nc(-c3ccc(-c4noc(-c5ccncc5)n4)cc3)c(CCCN3CCCCC3)c2c1] |
| 140 | 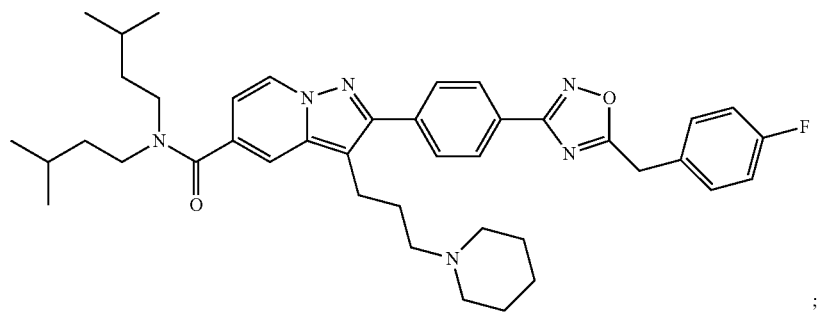 [SMILES: CC(C)CCN(CCC(C)C)C(=O)c1ccn2nc(-c3ccc(-c4noc(Cc5ccc(F)cc5)n4)cc3)c(CCCN3CCCCC3)c2c1] |

| Cpd No | Structure |
|---|---|
| 141 | 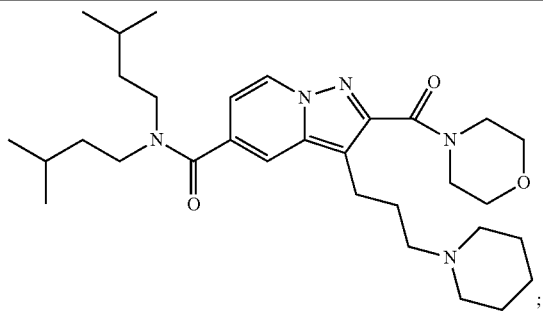 |
| 142 | 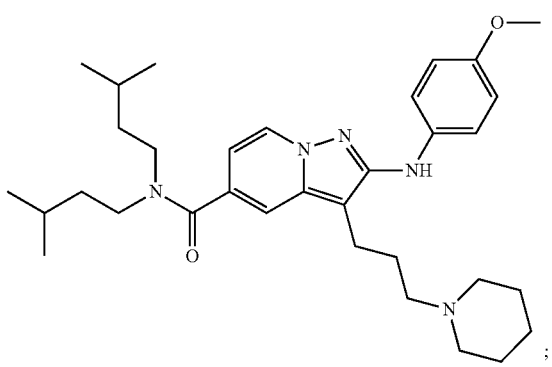 [SMILES: COc1ccc(Nc2nn3ccc(C(=O)N(CCC(C)C)CCC(C)C)cc3c2CCCN2CCCCC2)cc1] |
| 143 | 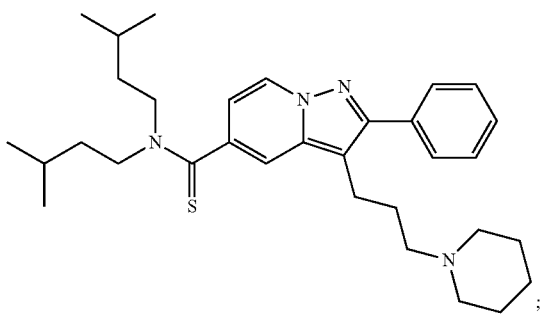 [SMILES: CC(C)CCN(CCC(C)C)C(=S)c1ccn2nc(-c3ccccc3)c(CCCN3CCCCC3)c2c1] |
| 144 | 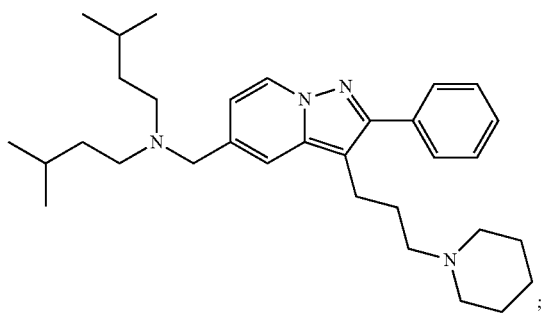 [SMILES: CC(C)CCN(CCC(C)C)Cc1ccn2nc(-c3ccccc3)c(CCCN3CCCCC3)c2c1] |

-continued
| Cpd No | Structure |
|---|---|
| 145 | 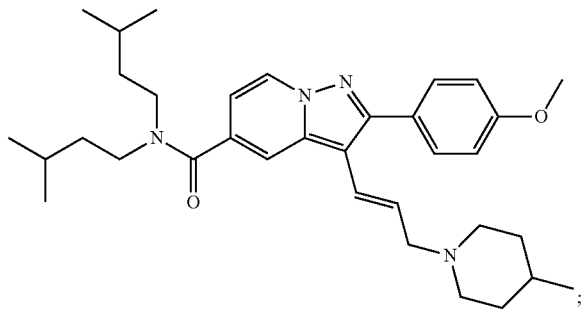 [SMILES: COc1ccc(-c2nn3ccc(C(=O)N(CCC(C)C)CCC(C)C)cc3c2/C=C/CN2CCC(C)CC2)cc1] |
| 146 | 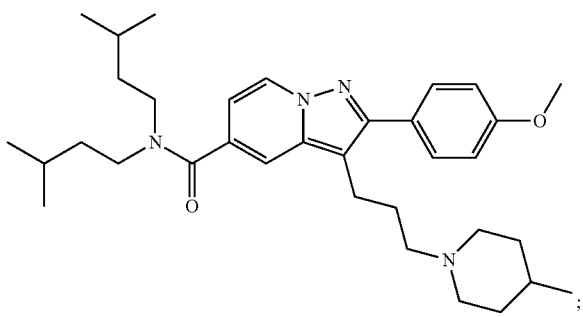 [SMILES: COc1ccc(-c2nn3ccc(C(=O)N(CCC(C)C)CCC(C)C)cc3c2CCCN2CCC(C)CC2)cc1] |
| 147 | 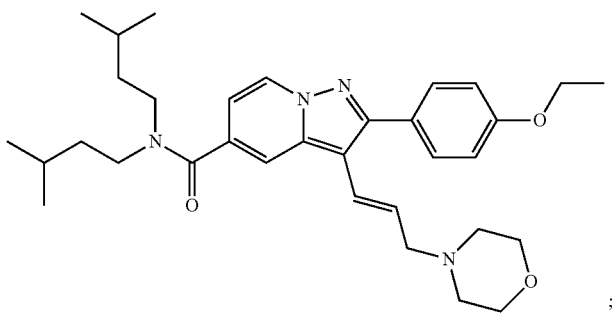 [SMILES: CCOc1ccc(-c2nn3ccc(C(=O)N(CCC(C)C)CCC(C)C)cc3c2/C=C/CN2CCOCC2)cc1] |
| 148 | 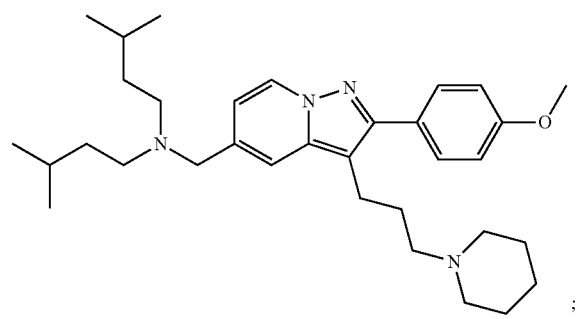 [SMILES: COc1ccc(-c2nn3ccc(CN(CCC(C)C)CCC(C)C)cc3c2CCCN2CCCCC2)cc1] |
| 149 | 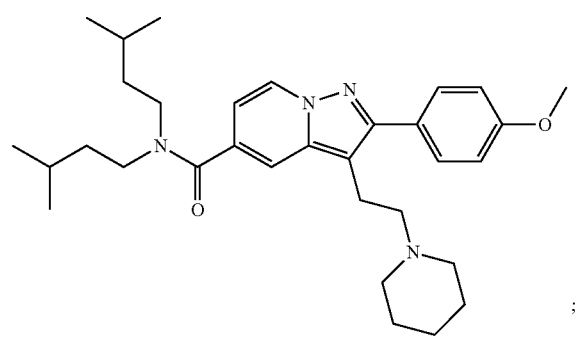 [SMILES: COc1ccc(-c2nn3ccc(C(=O)N(CCC(C)C)CCC(C)C)cc3c2CCN2CCCCC2)cc1] |

| Cpd No | Structure |
|---|---|
| 150 | 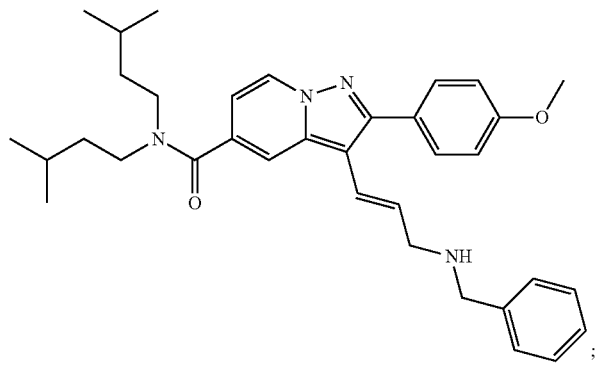 [SMILES: COc1ccc(-c2nn3ccc(C(=O)N(CCC(C)C)CCC(C)C)cc3c2/C=C/CNCc2ccccc2)cc1] |
| 151 | 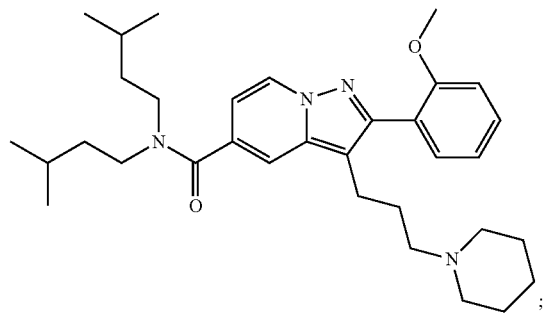 [SMILES: COc1ccccc1-c1nn2ccc(C(=O)N(CCC(C)C)CCC(C)C)cc2c1CCCN1CCCCC1] |
| 152 | 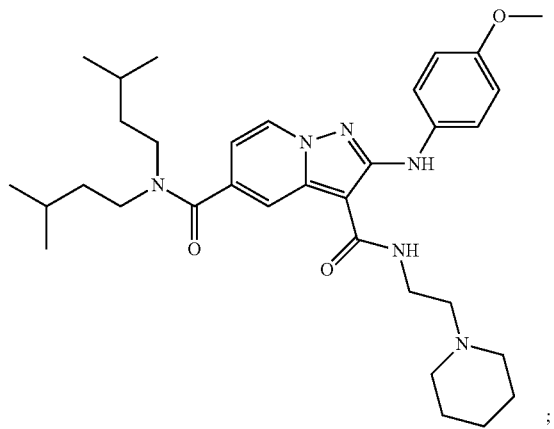 [SMILES: COc1ccc(Nc2nn3ccc(C(=O)N(CCC(C)C)CCC(C)C)cc3c2C(=O)NCCN2CCCCC2)cc1] |
| 153 | 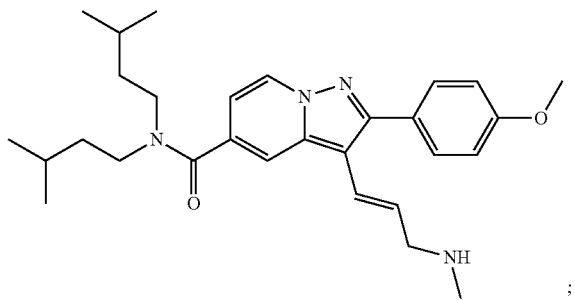 [SMILES: CNC/C=C/c1c(-c2ccc(OC)cc2)nn2ccc(C(=O)N(CCC(C)C)CCC(C)C)cc12] |

-continued
| Cpd No | Structure |
|---|---|
| 154 | 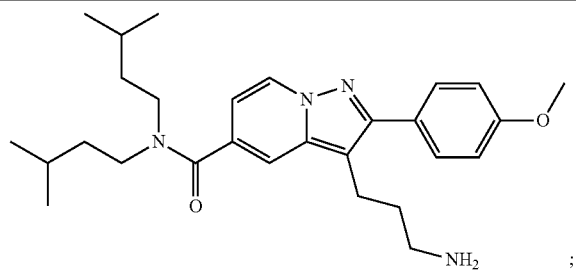 ; |
| 155 | 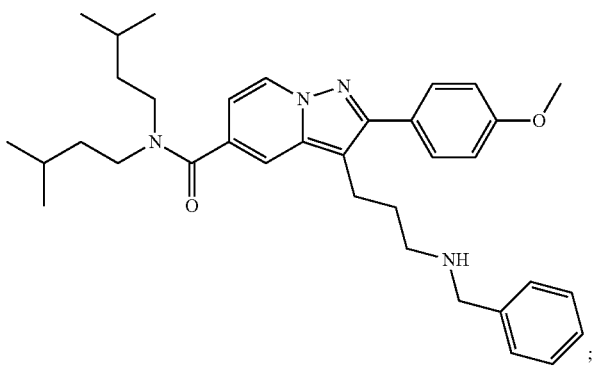 [SMILES: COc1ccc(-c2nn3ccc(C(=O)N(CCC(C)C)CCC(C)C)cc3c2CCCNCc2ccccc2)cc1] ; |
| 156 | 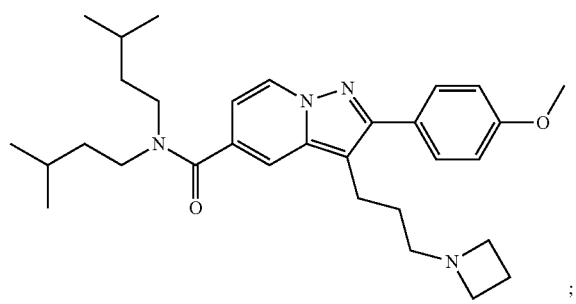 [SMILES: COc1ccc(-c2nn3ccc(C(=O)N(CCC(C)C)CCC(C)C)cc3c2CCCN2CCC2)cc1] ; |
| 157 | 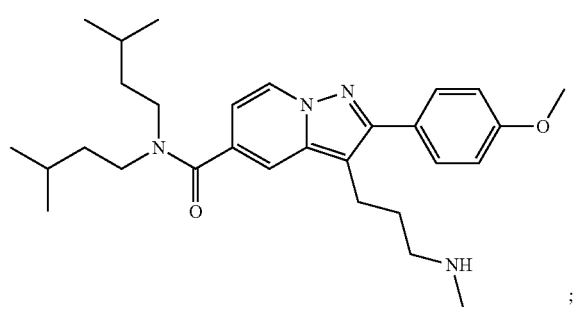 ; |
| 158 | 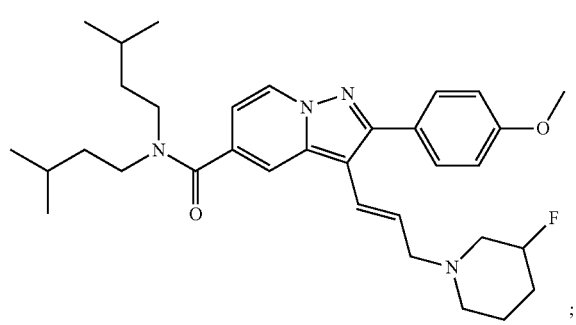 [SMILES: COc1ccc(-c2nn3ccc(C(=O)N(CCC(C)C)CCC(C)C)cc3c2/C=C/CN2CCCC(F)C2)cc1] ; |

-continued
| Cpd No | Structure |
|---|---|
| 159 | 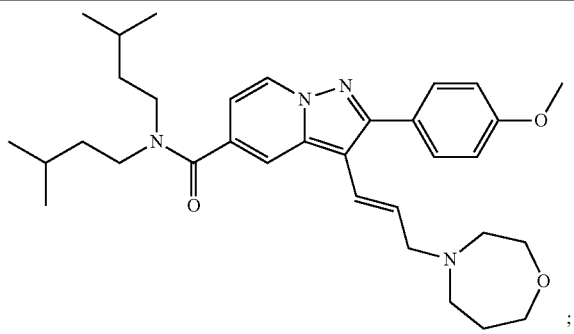 ; |
| 160 | 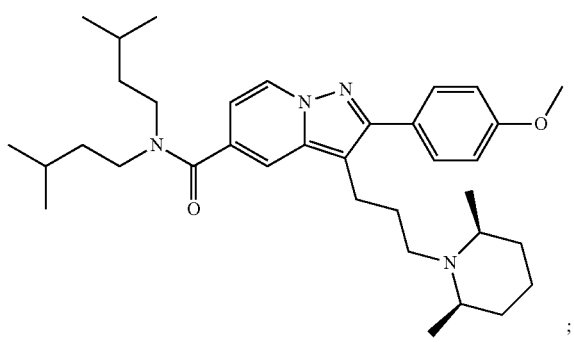 [SMILES: COc1ccc(-c2nn3ccc(C(=O)N(CCC(C)C)CCC(C)C)cc3c2CCCN2[C@H](C)CCC[C@@H]2C)cc1] ; |
| 161 | 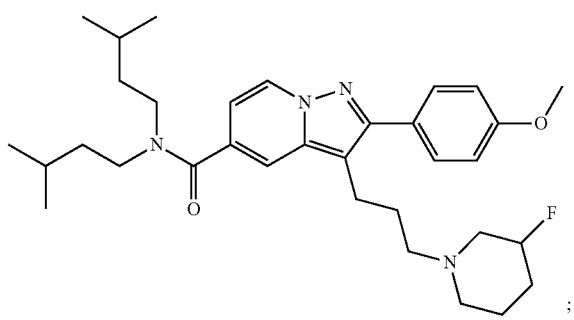 [SMILES: COc1ccc(-c2nn3ccc(C(=O)N(CCC(C)C)CCC(C)C)cc3c2CCCN2CCCC(F)C2)cc1] ; |
| 162 | 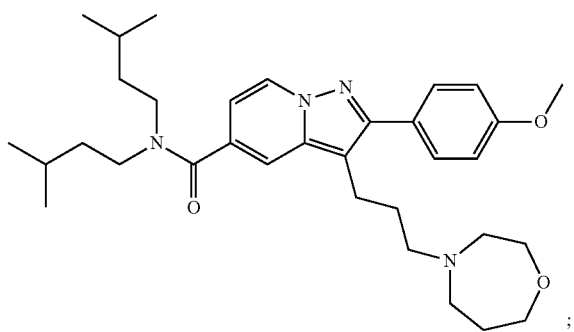 [SMILES: COc1ccc(-c2nn3ccc(C(=O)N(CCC(C)C)CCC(C)C)cc3c2CCCN2CCCOCC2)cc1] ; |

-continued
| Cpd No | Structure |
|---|---|
| 163 | 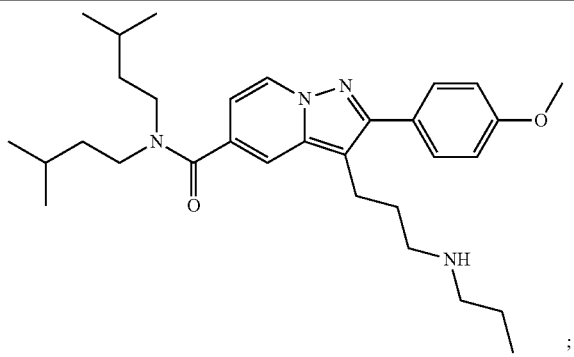 |
| 164 | 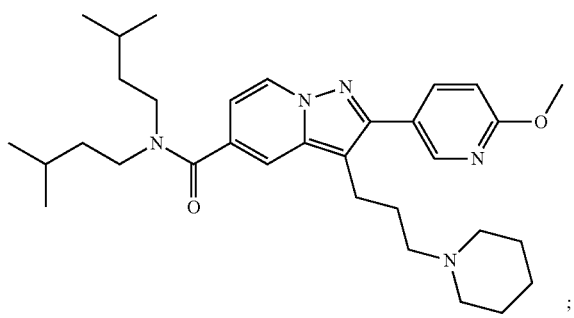 [SMILES: COc1ccc(-c2nn3ccc(C(=O)N(CCC(C)C)CCC(C)C)cc3c2CCCN2CCCCC2)cn1] |
| 165 | 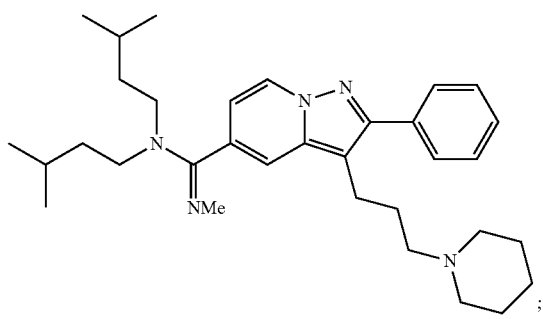 |
| 166 | 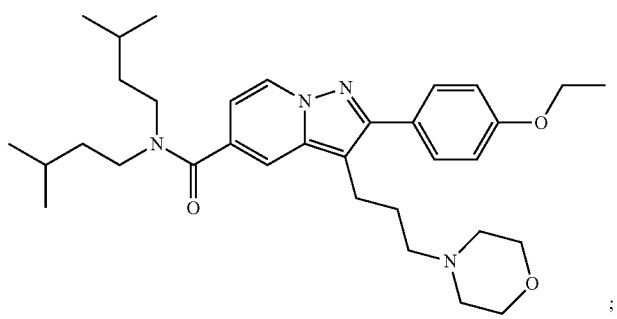 |

| Cpd No | Structure |
|---|---|
| 167 | 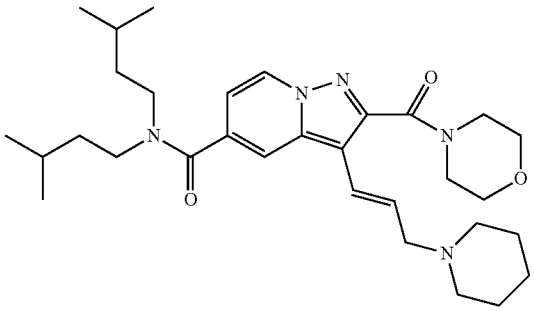 ; |
| 168 | 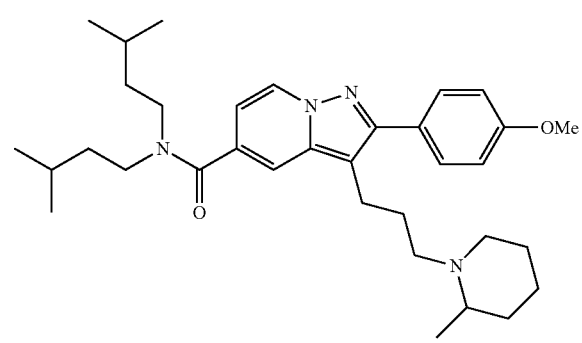 ; and |
| 169 | 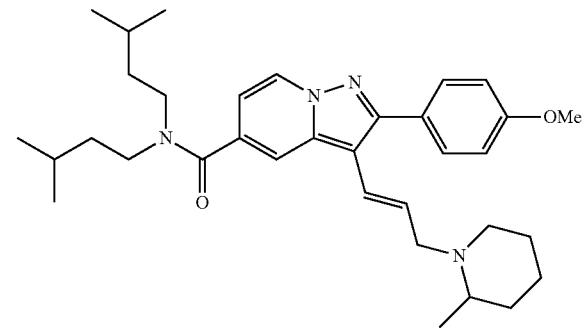 . |
11. A pharmaceutical composition comprising a compound according to claim 1 and a pharmaceutically acceptable carrier.
12. A compound according to claim 1 or a pharmaceutically acceptable salt thereof having the structure of compound 142.
* * * * *